United States Patent
Evarts et al.

(10) Patent No.: US 9,765,060 B2
(45) Date of Patent: Sep. 19, 2017

(54) PHOSPHATIDYLINOSITOL 3-KINASE INHIBITORS

(71) Applicant: Gilead Sciences, Inc., Foster City, CA (US)

(72) Inventors: Jerry Evarts, Seattle, WA (US); Joshua Kaplan, Foster City, CA (US); Musong Kim, Bothell, WA (US); Devan Naduthambi, San Bruno, CA (US); Leena Patel, Mercer Island, WA (US); Stephane Perreault, Brier, WA (US); Gary Phillips, Issaquah, WA (US); Lafe J. Purvis, II, Minneapolis, MN (US); Kirk L. Stevens, Bothell, WA (US); Jennifer A. Treiberg, Redmond, WA (US)

(73) Assignee: GILEAD SCIENCES, INC., Foster City, CA (US)

( * ) Notice: Subject to any disclaimer, the term of this patent is extended or adjusted under 35 U.S.C. 154(b) by 12 days.

(21) Appl. No.: 14/747,931

(22) Filed: Jun. 23, 2015

(65) Prior Publication Data
US 2016/0024054 A1   Jan. 28, 2016

Related U.S. Application Data

(60) Provisional application No. 62/016,194, filed on Jun. 24, 2014.

(51) Int. Cl.
| | | |
|---|---|---|
| C07D 403/12 | (2006.01) | |
| C07D 403/14 | (2006.01) | |
| C07D 409/14 | (2006.01) | |
| C07D 491/107 | (2006.01) | |
| C07D 413/14 | (2006.01) | |
| C07D 401/14 | (2006.01) | |

(52) U.S. Cl.
CPC ......... *C07D 403/12* (2013.01); *C07D 401/14* (2013.01); *C07D 403/14* (2013.01); *C07D 409/14* (2013.01); *C07D 413/14* (2013.01); *C07D 491/107* (2013.01)

(58) Field of Classification Search
CPC .. C07D 403/12; C07D 403/14; C07D 401/14; C07D 409/14; C07D 413/14; C07D 491/107
See application file for complete search history.

(56) References Cited

U.S. PATENT DOCUMENTS

| | | | | |
|---|---|---|---|---|
| 9,029,384 | B2 * | 5/2015 | Evarts ................ | C07D 473/34 514/263.21 |
| 2013/0053362 | A1 * | 2/2013 | Castro ................ | C07D 401/14 514/210.18 |

FOREIGN PATENT DOCUMENTS

| | | |
|---|---|---|
| WO | WO-01/81346 A2 | 11/2001 |
| WO | WO-03/035075 A1 | 5/2003 |
| WO | WO-2011/146882 A1 | 11/2011 |
| WO | WO-2013/032591 A1 | 3/2013 |
| WO | WO-2014/100767 A1 | 6/2014 |
| WO | WO-2014/128612 A1 | 8/2014 |
| WO | WO-2015010641 A | 1/2015 |
| WO | WO 2015168079 * | 4/2015 |
| WO | WO-2015/081127 A2 | 6/2015 |
| WO | WO-2015168079 A1 | 11/2015 |

OTHER PUBLICATIONS

Intl. Search Report—Written Opinion dated Aug. 27, 2015 for PCT/US2015/037234.
Office Action dated May 4, 2017 for New Zealand Appl. No. 727185.

* cited by examiner

*Primary Examiner* — Rebecca Anderson
(74) *Attorney, Agent, or Firm* — Briana R. Barron

(57) ABSTRACT

The present disclosure provides phosphatidylinositol 3-kinase (PI3K) inhibitors of formula (J),

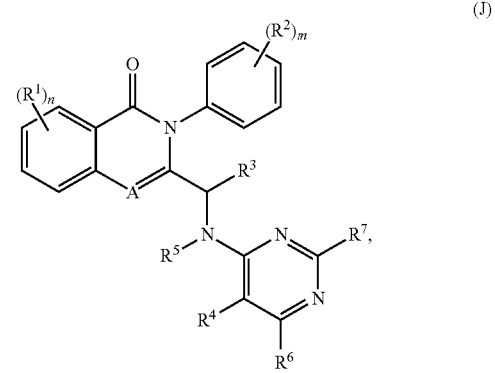

or pharmaceutically acceptable salts thereof, in which A, n, m, $R^1$, $R^2$, $R^3$, $R^4$, $R^5$, $R^6$ and $R^7$ are as defined herein. These compounds are useful for treatment of conditions mediated by one or more PI3K isoforms. The present disclosure further provides pharmaceutical compositions that include a compound of formula (J), or pharmaceutically acceptable salts thereof, and methods of using these compounds and compositions to treat conditions mediated by one or more PI3K isoforms.

2 Claims, No Drawings

PHOSPHATIDYLINOSITOL 3-KINASE INHIBITORS

CROSS REFERENCE TO RELATED APPLICATIONS

This application claims priority to and the benefit under 35 U.S.C. 119(e) of U.S. Provisional Patent Application Ser. No. 62/016,194, filed Jun. 24, 2014, the disclosure of which is hereby incorporated by reference in its entirety.

FIELD

The present disclosure relates generally to inhibitors of phosphatidylinositol 3-kinase (PI3K) activity and, more specifically, to novel compounds that are selective inhibitors of PI3K isoforms.

BACKGROUND

Cell signaling via 3'-phosphorylated phosphoinositides has been implicated in a variety of cellular processes, e.g., malignant transformation, growth factor signaling, inflammation, and immunity. See generally Rameh et al., *J. Biol. Chem.*, 274:8347-8350 (1999). The enzyme responsible for generating these phosphorylated signaling products is phosphatidylinositol 3-kinase (PI 3-kinase; PI3K). PI3K originally was identified as an activity associated with viral oncoproteins and growth factor receptor tyrosine kinases that phosphorylate phosphatidylinositol (PI) and its phosphorylated derivatives at the 3'-hydroxyl of the inositol ring. See Panayotou et al., *Trends Cell Biol* 2:358-60 (1992).

Presently, three classes of the PI 3-kinase (PI3K) enzymes are distinguished, based on their substrate specificities. Class 1 PI3Ks can phosphorylate phosphatidylinositol (PI), phosphatidylinositol-4-phosphate, and phosphatidylinositol-4,5-biphosphate ($PIP_2$) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 summits. See Otsu et al., *Cell*, 65:91-104 (1991); Hiles et al., *Cell*, 70:419-29 (1992). Since then, four distinct Class I PI3Ks have been identified, designated PI3K α, β, δ, and γ, each consisting of a distinct 110 kDa catalytic subunit and a regulatory subunit. More specifically, three of the catalytic sub-units, i.e., p110α, p110β, and p110δ, each interact with the same regulatory subunit, i.e., p85, whereas p110γ interacts with a distinct p101 regulatory subunit. As described below, the patterns of expression of each of these PI3Ks in human cells and tissues also are distinct.

Identification of the p110δ isoform of PI 3-kinase is described in Chantry et al., *J. Biol. Chem.*, 272:19236-41 (1997). It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. Details concerning the p110δ isoform also can be found in U.S. Pat. Nos. 5,858,753; 5,822,910; and 5,985,589, each of which is incorporated herein by reference. See also Vanhaesebroeck et al., *Proc. Natl. Acad. Sci. USA*, 94:4330-5 (1997); and WO 97/46688.

A need remains, however, for additional therapeutic agents useful to treat proliferative disorders or diseases that are mediated by PI3K. The present invention provides novel compounds that are inhibitors of PI3K isoforms.

SUMMARY

The present application provides novel compounds that are inhibitors of PI3K isoforms. The application also provides compositions, including pharmaceutical compositions, kits that include the compounds, and methods of using and making the compounds. The compounds provided herein are useful in treating diseases, disorders, or conditions that are mediated by PI3K isoforms. The application also provides compounds for use in therapy. The application further provides compounds for use in a method of treating a disease, disorder, or condition that is mediated by PI3K isoforms. Moreover, the application provides uses of the compounds in the manufacture of a medicament for the treatment of a disease, disorder or condition mat is mediated by PI3K isoforms.

In one aspect provided is a compound having the structure of formula (J):

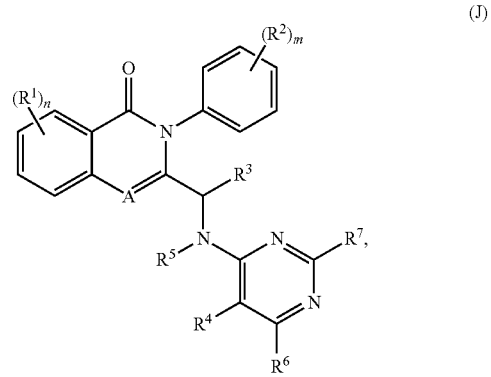

wherein:
A is N or CH;
n is 0, 1, 2, 3, or 4;
m is 0, 1, 2, 3, or 4;
each $R^1$ is independently selected from optionally substituted alkyl, optionally substituted haloalkyl, optionally substituted aryl, optionally substituted heteroaryl, halo, cyano, $NHC(=O)$alkylene-$N(R^{1x})_2$, $NO_2$, $OR^{1x}$, $N(R^{1x})_2$, $OC(=O)R^{1x}$, $C(=O)R^{1x}$, $C(=O)OR^{1x}$, aryl-$OR^{1y}$, optionally substituted cycloalkyl, optionally substituted heterocycloalkyl, $NR^{1x}C(=O)$alkylene-$C(=O)OR^{1x}$, aryl-O-alkylene-$N(R^{1x})_2$, aryl-O—$C(=O)R^{1x}$, alkylene-$C(=O)OR^{1x}$, alkylene-$C(=O)N(R^{1x})_2$, alkylene-$C(=O)$-Het, O-alkylene-$C(=O)OR^{1x}$, alkylene-O-alkylene-$C(=O)OR^{1x}$, $C(=O)NR^{1x}SO_2R^{1x}$, alkylene-$N(R^{1x})_2$, alkenylene-$N(R^{1x})_2$, $C(=O)NR^{1x}$-alkylene-$OR^{1x}$, $C(=O)NR^{1x}$alkylene-Het, O-alkylene-$N(R^{1x})_2$, O-alkylene-$CH(OR^{1y})CH_2N(R^{1x})_2$, O-alkylene-Het, O-alkylene-$C(=O)OR^{1x}$, O-alkylene-$C(=O)$-Het, S-alkylene-$OR^{1x}$, O-alkylene-$OR^{1x}$, O—$C_{1-6}$alkylene-$CH(OR^{1y})C_{1-6}$alkylene-$OR^{1x}$, O-alkylene-$NR^{1x}C(=O)OR^{1x}$, $NR^{1x}$-alkylene-$N(R^{1x})_2$, $NR^{1x}C(=O)R^{1x}$, $NR^{1x}C(=O)N(R^{1x})_2$, $N(SO_2$-alkyl$)_2$, $NR^{1x}(SO_2$-alkyl), $SO_2R^{1x}$, $SO_2N(R^{1x})_2$, alkylene-aryl, alkylene-Het, alkylene-$OR^{1y}$, alkylene-$N(R^{1x})_2$, $C(=O)N(R^{1x})_2$, $NHC(=O)$alkylene-aryl, aryl-O-alkylene-$N(R^{1x})_2$, aryl-$OC(=O)R^{1y}$, $NHC(=O)$alkylene-heterocycloalkyl, $NHC(=O)$alkylene-Het, O-alkylene-O-alkylene-C(=O)OR$^{1y}$, C(=O)alkylene-Het, and NHC(=O)halo-alkyl,
  wherein Het is optionally substituted heteroaryl or optionally substituted heterocycloalkyl wherein R$^{1x}$ is independently hydrogen, optionally substituted alkyl, optionally substituted haloalkyl, optionally substituted cycloalkyl, optionally substituted heterocycloalkyl, and optionally substituted aryl, wherein R$^{1y}$ is independently hydrogen, optionally substituted alkyl, optionally substituted haloalkyl, optionally substituted aryl, and optionally substituted heteroaryl, and wherein R$^{1z}$ is independently optionally substituted alkyl, optionally substituted haloalkyl, optionally substituted cycloalkyl, optionally substituted heterocycloalkyl, and optionally substituted aryl;
each R$^2$ is independently selected from halo, cyano, optionally substituted alkyl, haloalkyl, SO$_2$N(R$^{2x}$)$_2$, and optionally substituted alkoxy,
  wherein R$^{2x}$ is hydrogen, optionally substituted alkyl, or optionally substituted haloalkyl;
R$^3$ is hydrogen, optionally substituted alkyl, optionally substituted haloalkyl, optionally substituted cycloalkyl, optionally substituted aryl, optionally substituted heteroaryl, or optionally substituted heterocycloalkyl;
R$^5$ is hydrogen or alkyl, or R$^5$ and R$^3$ together with the atoms to which they are attached optionally form an optionally substituted four-, five- or six-membered heterocyclic ring;
R$^4$ is cyano, C(=O)NR$^{4x}$R$^{4y}$, SO$_2$-alkyl, halo, haloalkyl, or C(=O)R$^{4x}$,
  wherein each R$^{4x}$ and R$^{4y}$ is independently hydrogen, optionally substituted alkyl, and optionally substituted haloalkyl;
R$^6$ is NH$_2$, halo, optionally substituted alkyl, or optionally substituted haloalkyl; and
R$^7$ is NH$_2$, halo, optionally substituted alkyl, or optionally substituted haloalkyl;
or a pharmaceutically acceptable salt, isomer, or a mixture thereof.

A compound having the structure of formula (J):

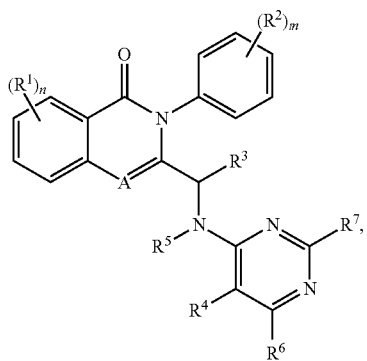

A is N or CH;
n is 0, 1, 2, 3, or 4;
m is 0, 1, 2, 3, or 4;
each R$^1$ is independently selected from optionally substituted alkyl, optionally substituted haloalkyl, optionally substituted aryl, optionally substituted heteroaryl, halo, cyano, NHC(=O)alkylene-N(R$^{1x}$)$_2$, NO$_2$, OR$^{1x}$, N(R$^{1x}$)$_2$, OC(=O)R$^{1x}$, C(=O)R$^{1x}$, C(=O)OR$^{1x}$, aryl-OR$^{1y}$, optionally substituted cycloalkyl, optionally substituted heterocycloalkyl, NR$^{1x}$C(=O)alkylene-C(=O)OR$^{1x}$, aryl-O-alkylene-N(R$^{1x}$)$_2$, aryl-O—C(=O)R$^{1x}$, alkylene-C(=O)OR$^{1x}$, alkylene-C(=O)N(R$^{1x}$)$_2$, alkylene-C(=O)-Het, O-alkylene-C(=O)OR$^{1x}$, alkylene-O-alkylene-C(=O)OR$^{1x}$, C(=O)NR$^{1x}$SO$_2$R$^{1x}$, alkylene-N(R$^{1x}$)$_2$, alkenylene-N(R$^{1x}$)$_2$, C(=O)NR$^{1x}$-alkylene-OR$^{1x}$, C(=O)NR$^{1x}$alkylene-Het, O-alkylene-N(R$^{1x}$)$_2$, O-alkylene-CH(OR$^{1y}$)CH$_2$N(R$^{1x}$)$_2$, O-alkylene-Het, O-alkylene-C(=O)OR$^{1x}$, O-alkylene-C(=O)-Het, S-alkylene-OR$^{1x}$, O-alkylene-OR$^{1x}$, O—C$_{1-6}$alkylene-CH(OR$^{1y}$)C$_{1-6}$alkylene-OR$^{1x}$, O-alkylene-NR$^{1x}$C(=O)OR$^{1x}$, NR$^{1x}$-alkylene-N(R$^{1x}$)$_2$, NR$^{1x}$C(=O)R$^{1x}$, NR$^{1x}$C(=O)N(R$^{1x}$)$_2$, N(SO$_2$-alkyl)$_2$, NR$^{1x}$(SO$_2$-alkyl), SO$_2$R$^{1z}$, SO$_2$N(R$^{1x}$)$_2$, alkylene-aryl, alkylene-Het, alkylene-OR$^{1y}$, alkylene-N(R$^{1x}$)$_2$, C(=O)N(R$^{1x}$)$_2$, NHC(=O)alkylene-aryl, aryl-O-alkylene-N(R$^{1x}$)$_2$, aryl-OC(=O)R$^{1y}$, NHC(=O)alkylene-heterocycloalkyl, NHC(=O)alkylene-Het, O-alkylene-O-alkylene-C(=O)OR$^{1y}$, C(=O)alkylene-Het, and NHC(=O)halo-alkyl,
  wherein Het is optionally substituted heteroaryl or optionally substituted heterocycloalkyl wherein R$^{1x}$ is independently hydrogen, optionally substituted alkyl, optionally substituted haloalkyl, optionally substituted cycloalkyl, optionally substituted heterocycloalkyl, and optionally substituted aryl, wherein R$^{1y}$ is independently hydrogen, optionally substituted alkyl, optionally substituted haloalkyl, optionally substituted aryl, and optionally substituted heteroaryl, and wherein R$^{1z}$ is independently optionally substituted alkyl, optionally substituted haloalkyl, optionally substituted cycloalkyl, optionally substituted heterocycloalkyl, and optionally substituted aryl;
each R$^2$ is independently selected from halo, cyano, optionally substituted alkyl, haloalkyl, SO$_2$N(R$^{2x}$)$_2$, and optionally substituted alkoxy,
  wherein R$^{2x}$ is hydrogen, optionally substituted alkyl, or optionally substituted haloalkyl;
R$^3$ is hydrogen, optionally substituted alkyl, optionally substituted haloalkyl, optionally substituted cycloalkyl, optionally substituted aryl, optionally substituted heteroaryl, or optionally substituted heterocycloalkyl;
R$^5$ is hydrogen or alkyl, or R$^5$ and R$^3$ together with the atoms to which they are attached optionally form an optionally substituted four-, five- or six-membered heterocyclic ring;
R$^4$ is cyano, C(=O)NR$^{4x}$R$^{4y}$, SO$_2$-alkyl, halo, haloalkyl, or C(=O)R$^{4x}$,
  wherein each R$^{4x}$ and R$^{4y}$ is independently hydrogen, optionally substituted alkyl, and optionally substituted haloalkyl;
R$^6$ is NH$_2$, halo, optionally substituted alkyl, or optionally substituted haloalkyl; and
R$^7$ is NH$_2$, halo, optionally substituted alkyl, or optionally substituted haloalkyl;
provided that when R$^5$ and R$^3$ form a 5-membered heterocyclic ring that is optionally substituted with hydroxyl, halo, or methoxy, R$^4$ is cyano, R$^6$ is amino, and R$^7$ is amino;
or a pharmaceutically acceptable salt, isomer, or a mixture thereof.

In one aspect, provided is a compound having the structure of formula (I):

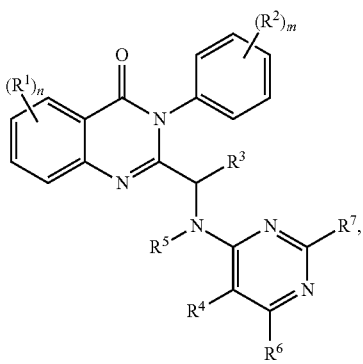

(I)

wherein:
n is 0, 1, 2, 3, or 4;
m is 0, 1, 2, or 3;
  each $R^1$ is independently alkyl, haloalkyl, aryl, heteroaryl, cycloalkyl, heterocycloalkyl halo, cyano, aryl-$OR^{1y}$, alkenylene-$OR^{1y}$, alkenylene-$N(R^{1x})_2$, alkylene-C(=O)$OR^{1x}$, alkylene-C(=O)N($R^{1x})_2$, alkylene-C(=O)-Het, alkylene-O-alkylene-C(=O)$OR^{1x}$, alkylene-$N(R^{1x})_2$, alkylene-aryl, alkylene-Het, alkylene-$OR^{1y}$, alkylene-$N(R^{1x})_2$-alkylene-O-alkylene-C(=O)$OR^{1y}OR^{1x}$, O-alkylene-C(O)$OR^{1x}$, O-alkylene-CH($OR^{1y}$)$CH_2N(R^{1x})_2$, O-alkenylene-$OR^{1y}$, O-alkenylene-$N(R^{1x})_2$, O-alkylene-$OR^{1x}$, O-alkylene-$N(R^{1x})_2$, O-alkylene-CH($OR^{1y}$)alkylene-$OR^{1x}$, O-alkylene-$NR^{1x}$C(=O)$OR^{1x}$, O-alkylene-Het, O-alkylene-C(=O)-Het, S-alkylene-$OR^{1x}$, $SO_2R^{1x}$, and $SO_2N(R^{1x})_2$,
    wherein Het is optionally substituted heteroaryl or optionally substituted heterocycloalkyl, wherein $R^{1x}$ is independently hydrogen, optionally substituted alkyl, optionally substituted haloalkyl, optionally substituted cycloalkyl, optionally substituted heterocycloalkyl, and optionally substituted aryl, wherein $R^{1y}$ is independently hydrogen, optionally substituted alkyl, haloalkyl, optionally substituted aryl, and optionally substituted heteroaryl, and wherein $R^{1z}$ is independently optionally substituted alkyl, optionally substituted haloalkyl, optionally substituted cycloalkyl, optionally substituted heterocycloalkyl, and optionally substituted aryl;
  each $R^2$ is independently halo, cyano, optionally substituted alkyl, optionally substituted haloalkyl, and $SO_2N(R^{2x})_2$, wherein $R^{2x}$ is hydrogen, and optionally substituted alkyl;
  $R^3$ is hydrogen, alkyl, haloalkyl, cycloalkyl, aryl, heteroaryl, or heterocycloalkyl, wherein each of the cycloalkyl, aryl, heteroaryl, and heterocycloalkyl moieties is optionally substituted with halo or alkyl, wherein the alkyl moiety is optionally substituted with —C(=O)$NR^{3x}R^{3y}$, wherein each $R^{3x}$ and $R^{3y}$ is independently hydrogen, alkyl, or haloalkyl;
  $R^5$ is hydrogen or alkyl, or $R^5$ and $R^3$ together with the atoms to which they are attached optionally form a four-, five- or six-membered heterocyclic ring, wherein the heterocyclic ring is optionally substituted with halo, alkyl, haloalkyl, or $NR^{5x}$C(=O)$R^{5y}$,
    wherein $R^{5x}$ is hydrogen or alkyl, and wherein $R^{5y}$ is alkyl, haloalkyl, cycloalkyl, cycloalkylalkyl, or alkyl-$NH_2$;
  $R^4$ is cyano, C(=O)$NR^{4x}R^{4y}$, $SO_2R^{4x}$, halo, haloalkyl or C(=O)$R^{4x}$,
    wherein each $R^{4x}$ and $R^{4y}$ is independently hydrogen, alkyl, and haloalkyl;
  $R^6$ is $NH_2$, halo, alkyl, or haloalkyl; and
  $R^7$ is $NH_2$, halo, alkyl, or haloalkyl;
  or a pharmaceutically acceptable salt, isomer, or a mixture thereof.

In additional embodiments, the PI3K inhibitors are compounds having the structure of formulae (J) or (I) wherein:
n is 1 or 2;
m is 0, 1, or 2;
  each $R^1$ is independently $C_{1-6}$alkyl, $C_{1-6}$haloalkyl, $C_{3-8}$cycloalkyl, $C_{2-8}$heterocycloalkyl, $C_{3-8}$heteroaryl, $C_{6-10}$aryl, halo, cyano, $C_{6-10}$aryl-$OR^{1y}$, $C_{1-6}$alkylene-$C_{6-10}$aryl, $C_{1-6}$alkylene-Het, $C_{1-6}$alkylene-$C_{3-8}$cycloalkyl, $C_{1-6}$alkylene-$OR^{1y}$, $C_{1-6}$alkylene-$N(R^{1x})_2$, $C_{2-6}$alkenylene-$OR^{1y}$, $C_{2-6}$alkenylene-$N(R^{1x})_2$, $C_{1-6}$alkylene-C(=O)$OR^{1x}$, $C_{1-6}$alkylene-C(=O)N($R^{1x})_2$, $C_{1-6}$alkylene-C(=O)-Het, O—$C_{1-6}$alkylene-C(=O)$OR^{1x}$, $C_{1-6}$alkylene-O—$C_{1-6}$alkylene-C(=O)$OR^{1x}$, $C_{1-6}$alkenylene-$N(R^{1x})_2$, $OR^{1x}$, O—$C_{1-6}$alkylene-$N(R^{1x})_2$, O—$C_{1-6}$alkylene-CH($OR^{1y}$)$CH_2N(R^{1x})_2$, $C_{1-6}$alkylene-Het, O—$C_{1-6}$alkylene-C(=O)$OR^{1x}$, O—$C_{1-6}$alkylene-C(=O)-Het, O—$C_{1-6}$alkylene-$OR^{1x}$, O—$C_{1-6}$alkylene-CH($OR^{1y}$)$C_{1-6}$alkylene-$OR^{1x}$, O—$C_{2-6}$alkylene-$OR^{1y}$, O—$C_{2-6}$alkylene-$N(R^{1x})_2$, O—$C_{1-6}$alkylene-$NR^{1x}$C(=O)$OR^{1x}$, O—$C_{1-6}$alkylene-O—$C_{1-6}$alkylene-C(=O)$OR^{1y}$, $SO_2R^{1x}$, S—$C_{1-6}$alkylene-$OR^{1z}$, and $SO_2N(R^{1x})_2$,
    wherein Het is $C_{3-8}$heteroaryl or $C_{2-8}$heterocycloalkyl, wherein $R^{1x}$ is independently hydrogen, $C_{1-6}$alkyl, $C_{1-6}$haloalkyl, $C_{3-8}$cycloalkyl, $C_{6-10}$aryl, $C_{2-8}$heterocycloalkyl, and $C_{3-8}$heteroaryl, wherein $R^{1y}$ is independently hydrogen, $C_{1-6}$alkyl, $C_{1-6}$haloalkyl, $C_{6-10}$aryl, and $C_{3-8}$heteroaryl, wherein $R^{1z}$ is independently $C_{1-6}$alkyl, $C_{1-6}$haloalkyl, $C_{3-8}$cycloalkyl, $C_{6-10}$aryl, $C_{2-8}$heterocycloalkyl, and $C_{3-8}$heteroaryl, and wherein each of Het, $R^{1x}$, $R^{1y}$ and $R^{1z}$ is optionally substituted with one, two, three, or four members independently selected from halo, oxo, $C_{1-6}$alkyl, and $C_{6-10}$aryl;
  each $R^2$ is independently halo, cyano, $C_{1-6}$alkyl, $C_{1-6}$haloalkyl, $SO_2N(R^{2x})_2$, wherein $R^{2x}$ is hydrogen, $C_{1-6}$alkyl, or $C_{1-6}$haloalkyl;
  $R^3$ is hydrogen, $C_{1-6}$alkyl, $C_{1-6}$haloalkyl, $C_{3-8}$cycloalkyl, $C_{6-10}$aryl, wherein the $C_{1-6}$alkyl moiety is optionally substituted with —C(=O)$NR^{3x}R^{3y}$, wherein each $R^{3x}$ and $R^{3y}$ is independently hydrogen, $C_{1-6}$alkyl, or $C_{1-6}$haloalkyl;
  $R^5$ is hydrogen or $C_{1-6}$alkyl, or $R^5$ and $R^3$ together with the atoms to which they are attached optionally form a four-, five- or six-membered heterocyclic ring, wherein the heterocyclic ring is optionally substituted with one, two, or three members independently selected from halo, $C_{1-6}$alkyl, $C_{1-6}$haloalkyl, and $NR^{5x}$C(O)$R^{5y}$ where $R^{5x}$ is hydrogen or $C_{1-6}$alkyl, and $R^{5y}$ is $C_{1-6}$alkylene-$NH_2$, $C_{1-6}$alkylene-$C_{3-8}$cycloalkyl, or $C_{1-6}$haloalkyl;
  $R^4$ is cyano, C(=O)$NR^{4x}R^{4y}$, $SO_2$—$C_{1-6}$alkyl, halo, $C_{1-6}$haloalkyl, or C(=O)$R^{4x}$, wherein each $R^{4x}$ and $R^{4y}$ is independently hydrogen, $C_{1-6}$alkyl, or $C_{1-6}$haloalkyl;
  $R^6$ is $NH_2$, halo, $C_{1-6}$alkyl, or $C_{1-6}$haloalkyl; and
  $R^7$ is $NH_2$, halo, $C_{1-6}$alkyl, or $C_{1-6}$haloalkyl;
  or a pharmaceutically acceptable salt, isomer, or a mixture thereof.

In other embodiments, the PI3K inhibitors are compounds having the structure of formulae (J) or (I) wherein:

n is 1 or 2;

m is 0, 1, or 2;

each $R^1$ is independently $C_{1-6}$alkyl, $C_{1-6}$haloalkyl, $C_{6-10}$aryl, $C_{5-8}$heteroaryl, $C_{3-8}$cycloalkyl, $C_{2-8}$heterocycloalkyl, halo, cyano, $C_{1-6}$alkylene-C(=O)OH, $C_{1-6}$alkylene-C(=O)O$C_{1-6}$alkyl, $C_{1-6}$alkylene-C(=O)—$C_{3-8}$heterocycloalkyl, $C_{1-6}$alkylene-C(=O)—$C_{3-8}$cycloalkyl, $C_{1-6}$alkylene-C(=O)NH$_2$, $C_{1-6}$alkylene-C(=O)N($C_{1-6}$alkyl)$_2$, $C_{1-6}$alkylene-C(=O)NH$C_{1-6}$alkyl, $C_{1-6}$alkylene-O—$C_{1-6}$alkylene-C(=O)OH, $C_{1-6}$alkylene-O—$C_{1-6}$alkylene-C(=O)O$C_{1-6}$alkyl, $C_{1-6}$alkylene-$C_{6-10}$aryl, $C_{1-6}$alkylene-$C_{2-8}$heteroaryl, $C_{1-6}$alkylene-$C_{2-8}$heterocycloalkyl, $C_{1-6}$alkylene-$C_{3-8}$cycloalkyl, $C_{1-6}$alkylene-OH, $C_{1-6}$alkylene-O$C_{1-6}$alkyl, O—$C_{1-6}$alkylene-N($C_{1-6}$alkyl)$_2$, O—$C_{1-6}$alkylene-NH$C_{1-6}$alkyl, O—$C_{1-6}$alkylene-NH$_2$, O—$C_{1-6}$alkylene-CH(OH)$C_{1-6}$alkylNH$_2$, O—$C_{1-6}$alkylene-CH(OH)$C_{1-6}$alkylN($C_{1-6}$alkyl)$_2$, O—$C_{1-6}$alkylene-CH(OH)$C_{1-6}$alkylNH$C_{1-6}$alkyl, O—$C_{1-6}$alkylene-CH(O$C_{1-6}$alkyl)$C_{1-6}$alkylNH$_2$, O—$C_{1-6}$alkylene-CH(O$C_{1-6}$alkyl)$C_{1-6}$alkylN($C_{1-6}$alkyl)$_2$, O—$C_{1-6}$alkylene-CH(O$C_{1-6}$alkyl)$C_{1-6}$alkylNH$C_{1-6}$alkyl, O—$C_{1-6}$alkylene-$C_{2-8}$heterocycloalkyl, O—$C_{1-6}$alkylene-$C_{3-8}$heteroaryl, O—$C_{1-6}$alkylene-C(=O)OH, O—$C_{1-6}$alkylene-C(=O)O$C_{1-6}$alkyl, O—$C_{1-6}$alkylene-C(=O)—$C_{2-8}$heterocycloalkyl, O—$C_{1-6}$alkylene-C(=O)O$C_{3-8}$cycloalkyl, O—$C_{1-6}$alkylene-C(=O)O$C_{6-10}$aryl, O—$C_{1-6}$alkylene-OH, O—$C_{1-6}$alkylene-O$C_{3-8}$-cycloalkyl, O—$C_{1-6}$alkylene-O$C_{1-6}$alkyl, O—$C_{1-6}$alkylene-CH(OH)$C_{1-6}$alkylene-OH, O—$C_{1-6}$alkylene-NHC(=O)OH, O—$C_{1-6}$alkylene-O—$C_{1-6}$alkylene-C(=O)OH, OSO$_2$CF$_3$, S—$C_{1-6}$alkylene-OH, SO$_2$$C_{1-6}$alkylene-$C_{2-8}$heterocycloalkyl, SO$_2$$C_{6-10}$aryl, SO$_2$$C_{3-8}$cycloalkyl, SO$_2$$C_{1-6}$alkylene-OH, SO$_2$N($C_{1-6}$alkyl)$_2$, or SO$_2$NH$_2$;

wherein each of the $C_{6-10}$aryl, $C_{3-8}$cycloalkyl, $C_{2-8}$heterocycloalkyl, and $C_{3-8}$heteroaryl moieties is optionally substituted with one, two, three, or four members independently selected from fluoro, chloro, oxo, methyl, ethyl, fluoromethyl, difluoromethyl, trifluoromethyl, fluoroethyl, difluoroethyl, trifluoroethyl, and phenyl;

each $R^2$ is independently halo, cyano, $C_{1-6}$alkyl, $C_{1-6}$haloalkyl, and SO$_2$NH$_2$;

$R^3$ is $C_{1-6}$alkyl, $C_{1-6}$haloalkyl, $C_{3-8}$cycloalkyl, $C_{6-10}$aryl, $C_{1-6}$alkylene-C(=O)NH$C_{1-6}$alkyl, $C_{1-6}$alkylene-C(=O)NH$_2$, or $C_{1-6}$alkylene-C(=O)N($C_{1-6}$alkyl)$_2$;

$R^5$ is hydrogen or $C_{1-6}$alkyl, or $R^5$ and $R^3$ together with the atoms to which they are attached optionally form a four-, five- or six-membered heterocyclic ring, wherein the heterocyclic ring is optionally substituted with one or two members independently selected from halo, $C_{1-6}$alkyl, NHC(=O)$C_{1-6}$alkylene-NH$_2$, NHC(=O)$C_{1-6}$alkylene-$C_{3-8}$cycloalkyl, NHC(=O)$C_{1-6}$haloalkyl, NC$_{1-6}$alkylC(=O)$C_{1-6}$alkylene-NH$_2$, NC$_{1-6}$alkylC(=O)$C_{1-6}$alkylene-$C_{3-8}$cycloalkyl, and NC$_{1-6}$alkylC(=O)$C_{1-6}$haloalkyl;

$R^4$ is cyano, halo, $C_{1-6}$haloalkyl, C(=O)H, or C(=O)$C_{1-6}$alkyl;

$R^6$ is NH$_2$, halo, or $C_{1-6}$alkyl; and $R^7$ is NH$_2$, halo, or $C_{1-6}$alkyl;

or a pharmaceutically acceptable salt, isomer, or a mixture thereof.

In some embodiments of formulae (J) or (I), each $R^1$ is independently methyl, chloro, fluoro, cyano, tetrahydropyridinyl, —CH$_2$—C(=O)OH, —C$_2$H$_4$—C(=O)OH, —C$_3$H$_6$—C(=O)OH, —CH$_2$—C(=O)NH$_2$, —CH$_2$—C(=O)N(CH$_3$)$_2$, —C$_2$H$_4$—C(=O)NH$_2$, —C$_2$H$_4$—C(=O)N(CH$_3$)$_2$, —C$_3$H$_6$—C(=O)NH$_2$, —C$_3$H$_6$—C(=O)N(CH$_3$)$_2$, —CH$_2$—C(=O)-Het, —C$_2$H$_4$—C(=O)-Het, —C$_3$H$_6$—C(=O)-Het, O—CH$_2$—C(=O)OC$_3$H$_7$, O—C$_2$H$_4$—C(=O)OC$_3$H$_7$, O—C$_3$H$_6$—C(=O)OC$_3$H$_7$, —CH$_2$-Het, —C$_2$H$_4$-Het, —C$_3$H$_6$-Het, —CH$_2$-cyclopropyl, —C$_2$H$_4$-cyclopropyl, —C$_3$H$_6$-cyclopropyl, —CH$_2$-cyclobutyl, —C$_2$H$_4$-cyclobutyl, —C$_3$H$_6$-cyclobutyl, —CH$_2$-cyclopentyl, —C$_2$H$_4$-cyclopentyl, C$_3$H$_6$-cyclopentyl, —CH$_2$-cyclohexyl, —C$_2$H$_4$-cyclohexyl, —C$_3$H$_6$-cyclohexyl, O—CH$_2$—NH$_2$, O—C$_2$H$_4$—NH$_2$, O—C$_3$H$_6$—NH$_2$, O—CH$_2$—N(CH$_3$)$_2$, O—C$_2$H$_4$—N(CH$_3$)$_2$, O—C$_3$H$_6$—N(CH$_3$)$_2$, O—CH$_2$-Het, O—C$_2$H$_4$-Het, O—C$_3$H$_6$-Het, O—CH$_2$—C(=O)OH, O—C$_2$H$_4$—C(=O)OH, O—C$_3$H$_6$—C(=O)OH, O—CH$_2$—C(=O)OCH$_3$, O—C$_2$H$_4$—C(=O)OCH$_3$, O—C$_3$H$_6$—C(=O)OCH$_3$, O—CH$_2$—C(=O)-Het, O—CH$_2$C(CH$_3$)(CH$_2$OH)$_2$, S—C$_2$H$_4$OH, S—C$_3$H$_6$OH, SO$_2$-phenyl, SO$_2$-methylphenyl, —SO$_2$-ethylphenyl, —SO$_2$-cyclopropyl, —SO$_2$-cyclobutyl, —SO$_2$-cyclopentyl, —SO$_2$CH$_3$, —SO$_2$C$_2$H$_5$, —SO$_2$C$_3$H$_7$, —SO$_2$C$_2$H$_4$OH, or —SO$_2$C$_3$H$_6$OH; wherein Het is independently selected from piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl. In some other embodiments of formulae (J) or (I), each $R^2$ is independently fluoro, chloro, bromo, iodo, cyano, methyl, ethyl, propyl, fluoromethyl, difluoromethyl, trifluoromethyl, fluoroethyl, difluoroethyl, trifluoroethyl, and SO$_2$NH$_2$. In certain other embodiments of formulae (J) or (I), $R^3$ is methyl, ethyl, propyl, —CH$_2$—C(=O)NH$_2$, —C$_2$H$_4$—C(=O)NH$_2$, —C$_3$H$_6$—C(=O)NH$_2$, —CH$_2$—C(=O)N(CH$_3$)$_2$, —C$_2$H$_4$—C(=O)N(CH$_3$)$_2$, —C$_3$H$_6$—C(=O)N(CH$_3$)$_2$, cyclopropyl, cyclobutyl, or phenyl. In additional embodiments of formulae (J) or (I), $R^5$ is hydrogen, methyl, ethyl, or propyl. In other additional embodiments, $R^5$ and $R^3$ together with the atoms to which they are attached optionally form a heterocyclic ring, wherein the heterocyclic ring is selected from azetidinyl, morpholinyl or pyrrolidinyl, wherein each of the azetidinyl, morpholinyl, and pyrrolidinyl moieties is optionally substituted with N(CH$_3$)C(=O)CH$_2$NH$_2$, N(CH$_3$)C(=O)CHF$_2$, N(CH$_3$)C(=O)CH$_2$CF$_3$, N(CH$_3$)C(=O)cyclopropyl, NHC(=O)CH$_2$NH$_2$, NHC(=O)CHF$_2$, NHC(=O)CH$_2$CF$_3$, or NHC(=O)cyclopropyl. In another embodiments of formulae (J) or (I), $R^4$ is cyano, chloro, bromo, iodo, or C(=O)CH$_3$. In certain embodiments, $R^6$ is NH$_2$, chloro, fluoro, methyl, ethyl, or propyl. In certain embodiments, $R^7$ is NH$_2$, fluoro, chloro, methyl, ethyl, or propyl. In yet another embodiments of formulae (J) or (I), $R^6$ is NH$_2$, chloro, fluoro, methyl, ethyl, or propyl; and $R^7$ is NH$_2$, fluoro, chloro, methyl, ethyl, or propyl.

Provided are also compounds selected from Table 1, or a pharmaceutically acceptable salt, isomer, or a mixture thereof. In one embodiment, the compound is an (S)-enantiomer. In another embodiment, the compound is an (R)-enantiomer. In some additional embodiment, the compound is an atropisomer.

Provided are also compounds selected from compounds 1-116, or a pharmaceutically acceptable salt, isomer, or a mixture thereof. In one embodiment, the compound is an (S)-enantiomer. In another embodiment, the compound is an (R)-enantiomer. In some additional embodiment, the compound is an atropisomer.

Also provided is a pharmaceutical composition that includes a compound of the present application, or a pharmaceutically acceptable salt, isomer, or a mixture thereof, together with at least one pharmaceutically acceptable vehicle. Examples of pharmaceutically acceptable vehicle may be selected from carriers, adjuvants, and excipients.

Also provided is a method of treating a subject who has or is suspected of having a disease or condition responsive or believed to be responsive to the inhibition of PI3Kδ activity by administering to the subject a compound described herein or a pharmaceutically acceptable salt, isomer, or a mixture thereof. In some embodiments, the subject is a human. In additional embodiments, the disease or condition is leukemia, lymphoma, cancer, or inflammation.

Also provided is a method of inhibiting kinase activity of a phosphatidylinositol 3-kinase delta polypeptide by contacting the polypeptide with a compound described herein or a pharmaceutically acceptable salt, isomer, or a mixture thereof. Further provided is a method of inhibiting excessive or destructive immune reactions, such as asthma, rheumatoid arthritis, multiple sclerosis, and lupus.

Also provided is a method of disrupting leukocyte function, comprising contacting the leukocytes with an effective amount of a compound of formula described herein or a pharmaceutically acceptable salt, isomer, or a mixture thereof.

Also provided is a method of inhibiting a growth or a proliferation of cancer cells, comprising contacting the cancer cells with an effective amount of a compound described herein or a pharmaceutically acceptable salt, isomer, or a mixture thereof. In some embodiments, the cancers cells are of hematopoietic origin.

Also provided is a kit that includes a compound described herein or a pharmaceutically acceptable salt, isomer, or a mixture thereof; and a label and/or instructions for use of the compound in the treatment of a disease or condition mediated by PI3Kδ activity.

Also provided are articles of manufacture that include a compound described herein or a pharmaceutically acceptable salt, isomer, or a mixture thereof; and a container. In one embodiment, the container may be a vial, jar, ampoule, preloaded syringe, or an intravenous bag.

DETAILED DESCRIPTION

The following description sets forth exemplary methods, parameters and the like. It should be recognized, however, that such, description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term, "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all geometric isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH (CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cyclohexylcarbonyl, cyclohexylmethylcarbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{2-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Carboxy" or "carboxy" refers to —COOH or salts thereof.

"Carboxyl ester" or "carboxy ester" refers to the group —C(O)OR, wherein R is hydrogen, alkyl, aryl, arylalkyl heteroalkyl, or heteroaryl, each of which may be optionally substituted. In certain embodiments R is alkyl, aryl, arylalkyl, heteroalkyl, or heteroaryl, each of which may be optionally substituted.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocycloalkyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, aryl alkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. The term "heterocycloalkyl" includes heterocycloalkenyl groups (i.e. the heterocycloalkyl group having at least one double bond). A heterocycloalkyl may be a single ring or multiple rings wherein the multiple rings may be fused, bridged, or spiro. As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-8}$ heterocycloalkyl), 3 to 12 ring carbon atoms (i.e., $C_{3-12}$ heterocycloalkyl), 3 to 8 ring carbon atoms (i.e., $C_{3-8}$ heterocycloalkyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl. As used herein, the term "bridged-heterocycloalkyl" refers to a four- to ten-membered cyclic moiety connected at two non-adjacent atoms of the heterocycloalkyl with one or more (e.g. 1 or 2) four- to ten-membered cyclic moiety having at least one heteroatom where each heteroatom is independently selected from nitrogen, oxygen, and sulfur. As used herein, bridged-heterocycloalkyl includes bicyclic and tricyclic ring systems. Also used herein, the term "spiro-heterocycloalkyl" refers to a ring system in which a three- to ten-membered heterocycloalkyl has one or more additional ring, wherein the one or more additional ring is three- to ten-membered cycloalkyl or three- to ten-membered heterocycloalkyl, where a single atom of the one or more additional ring is also an atom of the three- to ten-membered heterocycloalkyl. Examples of the spiro-heterocycloalkyl include bicyclic and tricyclic ring systems, such as 2-oxa-7-azaspiro[3.5]nonanyl, 2-oxa-6-azaspiro[3,4]octanyl, and 6-oxa-1-azaspiro[3.3]heptanyl. The above definition also encompasses "heterocyclic ring."

"Hydroxy" or "hydroxyl" refers to the group —OH.

"Oxo" refers to the group (=O) or (O).

"Sulfonyl" refers to the group —S(O)$_2$R, where R is alkyl, haloalkyl, heterocycloalkyl, cycloalkyl, heteroaryl, or aryl. Examples of sulfonyl are methylsulfonyl, ethylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted. One or more substituents may include, for example, 1, 2, 3, 4, 5, or 6 substitutents, 1, 2, 3, 4, or 5 substitutents, 1, 2, 3, or 4 substitutents, 1, 2, or 3 substituents, 1 or 2 substituents, or 1 substituent.

In some embodiments, the term "substituted alkyl" refers to an alkyl group having one or more substituents including hydroxyl, halo, alkoxy, cycloalkyl, heterocycloalkyl, aryl and heteroaryl. In additional embodiments, "substituted cycloalkyl" refers to a cycloalkyl group having one or more substituents including alkyl, haloalkyl, cycloalkyl, heterocycloalkyl aryl, heteroaryl, alkoxy, halo, oxo, and hydroxyl; "substituted heterocycloalkyl" refers to a heterocycloalkyl group having one or more substituents including alkyl, haloalkyl, heterocycloalkyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocycloalkyl, heteroaryl, alkoxy, and cyano; "substituted heteroaryl" refers to an heteroaryl group having one or more substituents including halo, alkyl, haloalkyl, heterocycloalkyl, heteroaryl, alkoxy, and cyano and "substituted sulfonyl" refers to a group —S(O)$_2$R, in which R is substituted with one or more substituents including alkyl, cycloalkyl, heterocycloalkyl, aryl, and heteroaryl. In other embodiments, the one or more substituents may be further substituted with halo, alkyl, haloalkyl, hydroxyl, alkoxy, cycloalkyl, heterocycloalkyl, aryl, or heteroaryl, each of which is substituted. In other embodiments, the substituents may be further substituted with halo, alkyl, haloalkyl, alkoxy, hydroxyl, cycloalkyl, heterocycloalkyl, aryl, or heteroaryl each of which is unsubstituted.

The terms "a compound of the present application," "a compound described herein," "a compound of any of the formulae described herein," or variant thereof refer to a compound having the structure of any of the foregoing formulae (J), (I), (I-A1), (IA-2), (I-A3), (IB-1), (IB-2), (IB-3), (IB-4), (IB-5), including at least the compounds of Table 1, 2, or 3, and compounds 1-116 as described herein.

PI3K Inhibitor Compounds

Provided herein are compounds that function as inhibitors of PI3K isoforms, such as PI3Kδ. In one aspect, provided is a compound having structure of formula (J):

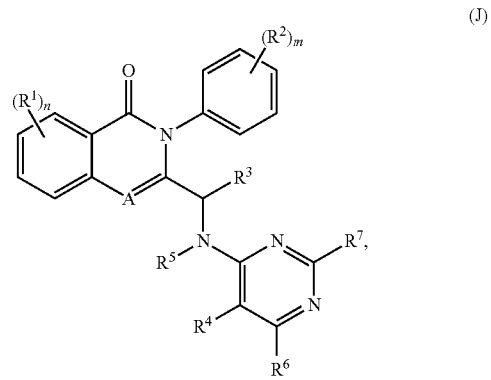

wherein:

A is N or CH;

n is 0, 1, 2, 3, or 4;

m is 0, 1, 2, 3, or 4;

each R$^1$ is independently selected from optionally substituted alkyl, optionally substituted haloalkyl, optionally substituted aryl, optionally substituted heteroaryl, halo, cyano, NHC(=O)alkylene-N(R$^{1x}$)$_2$, NO$_2$, OR$^{1x}$, N(R$^{1x}$)$_2$, OC(=O)R$^{1x}$, C(=O)R$^{1x}$, C(=O)OR$^{1x}$, aryl-OR$^{1y}$, optionally substituted cycloalkyl, optionally substituted heterocycloalkyl, NR$^{1x}$C(=O)alkylene-C(=O)OR$^{1x}$, aryl-O-alkylene-N(R$^{1x}$)$_2$, aryl-O—C(=O)R$^{1x}$, alkylene-C(=O)OR$^{1x}$, alkylene-C(=O)N(R$^{1x}$)$_2$, alkylene-C(=O)-Het, O-alkylene-C(=O)OR$^{1x}$, alkylene-O-alkylene-C(=O)OR$^{1x}$, C(=O)NR$^{1x}$SO$_2$R$^{1x}$, alkylene-N(R$^{1x}$)$_2$, alkenylene-N(R$^{1x}$)$_2$, C(=O)NR$^{1x}$-alkylene-OR$^{1x}$, C(=O)NR$^{1x}$alkylene-Het, O-alkylene-N(R$^{1x}$)$_2$, O-alkylene-CH(OR$^{1y}$)CH$_2$N(R$^{1x}$)$_2$, O-alkylene-Het, O-alkylene-C(=O)OR$^{1x}$, O-alkylene-C(=O)-Het, S-alkylene-OR$^{1x}$, O-alkylene-OR$^{1x}$, O—C$_{1-6}$alkylene-CH(OR$^{1y}$)C$_{1-6}$alkylene-OR$^{1x}$, O-alkylene-NR$^{1x}$C(=O)OR$^{1x}$, NR$^{1x}$-alkylene-N(R$^{1x}$)$_2$, NR$^{1x}$C(=O)R$^{1x}$, NR$^{1x}$C(=O)N(R$^{1x}$)$_2$, N(SO$_2$-alkyl)$_2$, NR$^{1x}$(SO$_2$-alkyl), SO$_2$R$^{1z}$, SO$_2$N(R$^{1x}$)$_2$, alkylene-aryl, alkylene-Het, alkylene-OR$^{1y}$, alkylene-N(R$^{1x}$)$_2$, C(=O)N(R$^{1x}$)$_2$, NHC(=O)alkylene-aryl, aryl-O-alkylene-N(R$^{1x}$)$_2$, aryl-OC(=O)R$^{1y}$, NHC(=O)alkylene-heterocycloalkyl, NHC(=O)alkylene-Het, O-alkylene-O-alkylene-C(=O)OR$^{1y}$, C(=O)alkylene-Het, and NHC(=O)halo-alkyl, wherein Het is optionally substituted heteroaryl or optionally substituted heterocycloalkyl, wherein R$^{1x}$ is independently hydrogen, optionally substituted alkyl, optionally substituted haloalkyl, optionally substituted cycloalkyl, optionally substituted heterocycloalkyl, and optionally substituted aryl, wherein $R^{1y}$ is independently hydrogen, optionally substituted alkyl, optionally substituted haloalkyl, optionally substituted aryl, and optionally substituted heteroaryl, and wherein $R^{1z}$ is independently optionally substituted alkyl, optionally substituted haloalkyl, optionally substituted cycloalkyl, optionally substituted heterocycloalkyl, and optionally substituted aryl;

each $R^2$ is independently selected from halo, cyano, optionally substituted alkyl, haloalkyl, $SO_2N(R^{2x})_2$, and optionally substituted alkoxy,
wherein $R^{2x}$ is hydrogen, optionally substituted alkyl, or optionally substituted haloalkyl;

$R^3$ is hydrogen, optionally substituted alkyl, optionally substituted haloalkyl, optionally substituted cycloalkyl, optionally substituted aryl, optionally substituted heteroaryl, or optionally substituted heterocycloalkyl;

$R^5$ is hydrogen or alkyl, or $R^5$ and $R^3$ together with the atoms to which they are attached optionally form an optionally substituted four-, five- or six-membered heterocyclic ring;

$R^4$ is cyano, $C(=O)NR^{4x}R^{4y}$, $SO_2$-alkyl, halo, haloalkyl, or $C(=O)R^{4x}$,
wherein each $R^{4x}$ and $R^{4y}$ is independently hydrogen, optionally substituted alkyl, and optionally substituted haloalkyl;

$R^6$ is $NH_2$, halo, optionally substituted alkyl, or optionally substituted, haloalkyl; and $R^7$ is $NH_2$, halo, optionally substituted alkyl, or optionally substituted haloalkyl;

or a pharmaceutically acceptable salt, isomer, or a mixture thereof.

Provided herein are compounds that function as inhibitors of PI3K isoforms, such as PI3Kδ. In one aspect, provided is a compound having structure of formula (J):

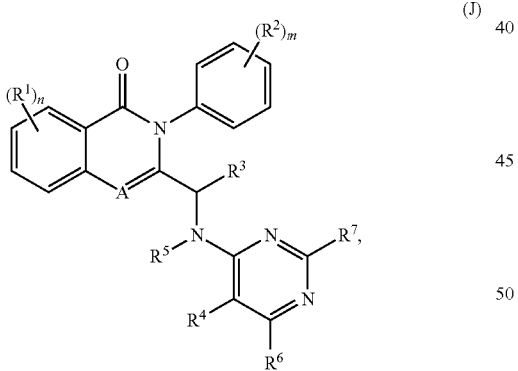

wherein;
A is N or CH;
n is 0, 1, 2, 3, or 4;
m is 0, 1, 2, 3, or 4;
each $R^1$ is independently selected from optionally substituted alkyl, optionally substituted haloalkyl, optionally substituted aryl, optionally substituted heteroaryl, halo, cyano, $NHC(=O)$alkylene-$N(R^{1x})_2$, $NO_2$, $OR^{1x}$, $N(R^{1x})_2$, $OC(=O)R^{1x}$, $C(=O)R^{1x}$, $C(=O)OR^{1x}$, aryl-$OR^{1y}$, optionally substituted cycloalkyl, optionally substituted heterocycloalkyl, $NR^{1x}C(=O)$alkylene-$C(=O)OR^{1x}$, aryl-O-alkylene-$N(R^{1x})_2$, aryl-O—$C(=O)R^{1x}$, alkylene-$C(=O)OR^{1x}$, alkylene-$C(=O)N(R^{1x})_2$, alkylene-$C(=O)$-Het, O-alkylene-$C(=O)OR^{1x}$, alkylene-O-alkylene-$C(=O)OR^{1x}$, $C(=O)NR^{1x}SO_2R^{1x}$, alkylene-$N(R^{1x})_2$, alkenylene-$N(R^{1x})_2$, $C(=O)NR^{1x}$-alkylene-$OR^{1x}$, $C(=O)NR^{1x}$alkylene-Het, O-alkylene-$N(R^{1x})_2$, O-alkylene-$CH(OR^{1y})CH_2N(R^{1x})_2$, O-alkylene-Het, O-alkylene-$C(=O)OR^{1x}$, O-alkylene-$C(=O)$-Het, S-alkylene-$OR^{1x}$, O-alkylene-$OR^{1x}$, O—$C_{1-6}$alkylene-$CH(OR^{1y})C_{1-6}$alkylene-$OR^{1x}$, O-alkylene-$NR^{1x}C(=O)OR^{1x}$, $NR^{1x}$-alkylene-$N(R^{1x})_2$, $NR^{1x}C(=O)R^{1x}$, $NR^{1x}C(=O)N(R^{1x})_2$, $N(SO_2$-alkyl$)_2$, $NR^{1x}(SO_2$-alkyl$)$, $SO_2R^{1z}$, $SO_2N(R^{1x})_2$, alkylene-aryl, alkylene-Het, alkylene-$OR^{1y}$, alkylene-$N(R^{1x})_2$, $C(=O)N(R^{1x})_2$, $NHC(=O)$alkylene-aryl, aryl-O-alkylene-$N(R^{1x})_2$, aryl-$OC(=O)R^{1y}$, $NHC(=O)$alkylene-heterocycloalkyl, $NHC(=O)$alkylene-Het, O-alkylene-O-alkylene-$C(=O)OR^{1y}$, $C(=O)$alkylene-Het, and $NHC(=O)$halo-alkyl, wherein Het is optionally substituted heteroaryl or optionally substituted heterocycloalkyl, wherein $R^{1x}$ is independently hydrogen, optionally substituted alkyl optionally substituted haloalkyl, optionally substituted cycloalkyl, optionally substituted heterocycloalkyl, and optionally substituted aryl, wherein $R^{1y}$ is independently hydrogen, optionally substituted alkyl, optionally substituted haloalkyl optionally substituted aryl, and optionally substituted heteroaryl, and wherein $R^{1z}$ is independently optionally substituted alkyl, optionally substituted haloalkyl, optionally substituted cycloalkyl, optionally substituted heterocycloalkyl, and optionally substituted aryl;

each $R^2$ is independently selected from halo, cyano, optionally substituted alkyl, haloalkyl, $SO_2N(R^{2x})_2$, and optionally substituted alkoxy,
wherein $R^{2x}$ is hydrogen, optionally substituted alkyl, or optionally substituted haloalkyl;

$R^3$ is hydrogen, optionally substituted alkyl, optionally substituted haloalkyl, optionally substituted cycloalkyl, optionally substituted aryl, optionally substituted heteroaryl, or optionally substituted heterocycloalkyl;

$R^5$ is hydrogen or alkyl, or $R^5$ and $R^3$ together with the atoms to which they are attached optionally form an optionally substituted four-, five- or six-membered heterocyclic ring; provided that when $R^5$ and $R^3$ form a 5-membered heterocyclic ring that is optionally substituted with hydroxyl, halo, or methoxy, $R^4$ is cyano, $R^6$ is amino, $R^7$ is amino $R^4$ is cyano, $C(=O)NR^{4x}R^{4y}$, $SO_2$-alkyl, halo, haloalkyl, or $C(=O)R^{4x}$,
wherein each $R^{4x}$ and $R^{4y}$ is independently hydrogen, optionally substituted alkyl, and optionally substituted haloalkyl;

$R^6$ is $NH_2$, halo, optionally substituted alkyl, or optionally substituted, haloalkyl; and $R^7$ is $NH_2$, halo, optionally substituted alkyl, or optionally substituted haloalkyl;

or a pharmaceutically acceptable salt, isomer, or a mixture thereof.

In one aspect, provided is a compound having the structure of formula (I)

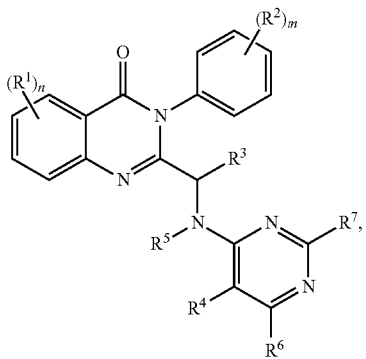

(I)

wherein:

n is 1 or 2;

m is 0, 1, or 2;

each $R^1$ is independently $C_{1-6}$alkyl, $C_{1-6}$haloalkyl, $C_{3-8}$cycloalkyl, $C_{2-8}$heterocycloalkyl, $C_{3-8}$heteroaryl, $C_{6-10}$aryl, halo, cyano, $C_{6-10}$aryl-$OR^{1y}$, $C_{1-6}$alkylene-$C_{6-10}$aryl, $C_{1-6}$alkylene-Het, $C_{1-6}$alkylene-$C_{3-8}$cycloalkyl, $C_{1-6}$alkylene-$OR^{1y}$, $C_{1-6}$alkylene-$N(R^{1x})_2$, $C_{2-6}$alkenylene-$OR^{1y}$, $C_{2-6}$alkenylene-$N(R^{1x})_2$, $C_{1-6}$alkylene-$C(=O)OR^{1x}$, $C_{1-6}$alkylene-$C(=O)N(R^{1x})_2$, $C_{1-6}$alkylene-$C(=O)$-Het, $O-C_{1-6}$alkylene-$C(=O)OR^{1x}$, $C_{1-6}$alkylene-$O-C_{1-6}$alkylene-$C(=O)OR^{1x}$, $C_{1-6}$alkenylene-$N(R^{1x})_2$, $OR^{1x}$, $O-C_{1-6}$alkylene-$N(R^{1x})_2$, $O-C_{1-6}$alkylene-$CH(OR^{1y})CH_2N(R^{1x})_2$, $O-C_{1-6}$alkylene-Het, $O-C_{1-6}$alkylene-$C(=O)OR^{1x}$, $O-C_{1-6}$alkylene-$C(=O)$-Het, $O-C_{1-6}$alkylene-$OR^{1x}$, $O-C_{1-6}$alkylene-$CH(OR^{1y})C_{1-6}$alkylene-$OR^{1x}$, $O-C_{2-6}$alkylene-$OR^{1y}$, $O-C_{2-6}$alkylene-$N(R^{1x})_2$, $O-C_{1-6}$alkylene-$NR^{1x}C(=O)OR^{1x}$, $O-C_{1-6}$alkylene-$O-C_{1-6}$alkylene-$C(=O)OR^{1y}$, $SO_2R^{1x}$, $S-C_{1-6}$alkylene-$OR^{1z}$, and $SO_2N(R^{1x})_2$, wherein Het is $C_{3-8}$heteroaryl or $C_{2-8}$heterocycloalkyl, wherein $R^{1x}$ is independently hydrogen, $C_{1-6}$alkyl, $C_{1-6}$haloalkyl, $C_{3-8}$cycloalkyl, $C_{6-10}$aryl, $C_{2-8}$heterocycloalkyl, and $C_{3-8}$heteroaryl, wherein $R^{1y}$ is independently hydrogen, $C_{1-6}$alkyl, $C_{1-6}$haloalkyl, $C_{6-10}$aryl, and $C_{3-8}$heteroaryl, wherein $R^{1z}$ is independently $C_{1-6}$alkyl, $C_{1-6}$haloalkyl, $C_{3-8}$cycloalkyl, $C_{6-10}$aryl, $C_{2-8}$heterocycloalkyl, and $C_{3-8}$heteroaryl, and wherein each of Het, $R^{1x}$, $R^{1y}$ and $R^{1z}$ is optionally substituted with one, two, three, or four members independently selected from halo, oxo, $C_{1-6}$alkyl, and $C_{6-10}$aryl;

each $R^2$ is independently halo, cyano, $C_{1-6}$alkyl, $C_{1-6}$haloalkyl, $SO_2N(R^{2x})_2$, wherein $R^{2x}$ is hydrogen, $C_{1-6}$alkyl, or $C_{1-6}$haloalkyl;

$R^3$ is hydrogen, $C_{1-6}$alkyl, $C_{1-6}$haloalkyl, $C_{3-8}$cycloalkyl, $C_{6-10}$aryl, wherein the $C_{1-6}$alkyl moiety is optionally substituted with $-C(=O)NR^{3x}R^{3y}$, wherein each $R^{3x}$ and $R^{3y}$ is independently hydrogen, $C_{1-6}$alkyl, or $C_{1-6}$haloalkyl;

$R^5$ is hydrogen or $C_{1-6}$alkyl, or $R^5$ and $R^3$ together with the atoms to which they are attached optionally form a four-, five- or six-membered heterocyclic ring, wherein the heterocyclic ring is optionally substituted with one, two, or three members independently selected from halo, $C_{1-6}$alkyl, $C_{1-6}$alkoxy, $C_{1-6}$haloalkyl, and $NR^{5x}C(O)R^{5y}$ where $R^{5x}$ is hydrogen or $C_{1-6}$alkyl, and $R^{5y}$ is $C_{1-6}$alkylene-$NH_2$, $C_{1-6}$alkylene-$C_{3-8}$cycloalkyl, or $C_{1-6}$haloalkyl;

$R^4$ is cyano, $C(=O)NR^{4x}R^{4y}$, $SO_2-C_{1-6}$alkyl, halo, $C_{1-6}$haloalkyl, or $C(=O)R^{4x}$, wherein each $R^{4x}$ and $R^{4y}$ is independently hydrogen, $C_{1-6}$alkyl, or $C_{1-6}$haloalkyl;

$R^6$ is $NH_2$, halo, $C_{1-6}$alkyl, or $C_{1-6}$haloalkyl; and $R^7$ is $NH_2$, halo, $C_{1-6}$alkyl, or $C_{1-6}$haloalkyl; or a pharmaceutically acceptable salt, isomer, or a mixture thereof.

In one aspect, provided, is a compound having the structure of formula (I):

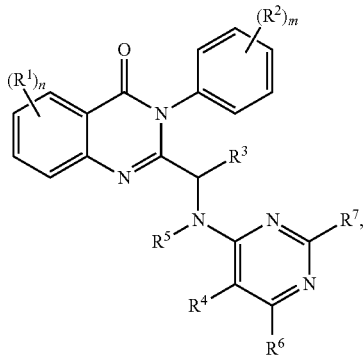

wherein;

n is 0, 1, 2, 3, or 4;

m is 0, 1, 2, or 3;

each $R^1$ is independently alkyl, haloalkyl, aryl, heteroaryl, cycloalkyl, heterocycloalkyl halo, cyano, aryl-$OR^{1y}$, alkenylene-$OR^{1y}$, alkenylene-$N(R^{1x})_2$, alkylene-$C(=O)OR^{1x}$, alkylene-$C(=O)N(R^{1x})_2$, alkylene-$C(=O)$-Het, alkylene-O-alkylene-$C(=O)OR^{1x}$, alkylene-$N(R^{1x})_2$, alkylene-aryl, alkylene-Het, alkylene-$OR^{1y}$, alkylene-$N(R^{1x})_2$, O-alkylene-O-alkylene-$C(=O)OR^{1y}OR^{1x}$, O-alkylene-$C(=O)OR^{1x}$, O-alkylene-$CH(OR^{1y})CH_2N(R^{1x})_2$, O-alkenylene-$OR^{1y}$, O-alkenylene-$N(R^{1x})_2$, O-alkylene-$OR^{1x}$, O-alkylene-$N(R^{1x})_2$, O-alkylene-$CH(OR^{1y})$alkylene-$OR^{1x}$, O-alkylene-$NR^{1x}C(=O)OR^{1x}$, O-alkylene-Het, O-alkylene-$C(=O)$-Het, S-alkylene-$OR^{1x}$, $SO_2R^{1x}$, and $SO_2N(R^{1x})_2$, wherein Het is optionally substituted heteroaryl or optionally substituted heterocycloalkyl, wherein $R^{1x}$ is independently hydrogen, optionally substituted alkyl, optionally substituted haloalkyl, optionally substituted cycloalkyl, optionally substituted heterocycloalkyl, and optionally substituted aryl, wherein $R^{1y}$ is independently hydrogen, optionally substituted alkyl, haloalkyl, optionally substituted aryl, and optionally substituted heteroaryl, and wherein $R^{1z}$ is independently optionally substituted alkyl, optionally substituted haloalkyl, optionally substituted cycloalkyl, optionally substituted heterocycloalkyl, and optionally substituted aryl;

each $R^2$ is independently halo, cyano, optionally substituted alkyl, optionally substituted haloalkyl, and $SO_2N(R^{2x})_2$, wherein $R^{2x}$ is hydrogen, and optionally substituted alkyl;

$R^3$ is hydrogen, alkyl, haloalkyl, cycloalkyl, aryl, heteroaryl, or heterocycloalkyl, wherein each of the cycloalkyl, aryl, heteroaryl, and heterocycloalkyl moieties is optionally substituted with halo or alkyl, wherein the alkyl moiety is optionally substituted with —C(=O)NR$^{3x}$R$^{3y}$, wherein each R$^{3x}$ and R$^{3y}$ is independently hydrogen, alkyl, or haloalkyl;

R$^5$ is hydrogen or alkyl, or R$^5$ and R$^3$ together with the atoms to which, they are attached optionally form a four-, five- or six-membered heterocyclic ring, wherein the heterocyclic ring is optionally substituted with halo, alkyl, haloalkyl, or NR$^{5x}$C(=O)R$^{5y}$,
wherein R$^{5x}$ is hydrogen or alkyl, and wherein R$^{5y}$ is alkyl, haloalkyl, cycloalkyl, cycloalkylalkyl, or alkyl-NH$_2$;

R$^4$ is cyano, C(=O)NR$^{4x}$R$^{4y}$, SO$_2$R$^{4x}$, halo, haloalkyl, or C(=O)R$^{4x}$,
wherein each R$^{4x}$ and R$^{4y}$ is independently hydrogen, alkyl, and haloalkyl;

R$^6$ is NH$_2$, halo, alkyl, or haloalkyl; and
R$^7$ is NH$_2$, halo, alkyl, or haloalkyl;
or a pharmaceutically acceptable salt, isomer, or a mixture thereof.

In additional embodiments, the PI3K inhibitors are compounds having the structure of formulae (J) or (I) wherein:
n is 1 or 2;
m is 0, 1, or 2;
each R$^1$ is independently C$_{1-6}$alkyl, C$_{1-6}$haloalkyl, C$_{3-8}$cycloalkyl, C$_{2-8}$heterocycloalkyl, C$_{3-8}$heteroaryl, C$_{6-10}$aryl, halo, cyano, C$_{6-10}$aryl-OR$^{1y}$, C$_{1-6}$alkylene-C$_{6-10}$aryl, C$_{1-6}$alkylene-Het, C$_{1-6}$alkylene-C$_{3-8}$cycloalkyl, C$_{1-6}$alkylene-OR$^{1y}$, C$_{1-6}$alkylene-N(R$^{1x}$)$_2$, C$_{2-6}$alkenylene-OR$^{1y}$, C$_{2-6}$alkenylene-N(R$^{1x}$)$_2$, C$_{1-6}$alkylene-C(=O)OR$^{1x}$, C$_{1-6}$alkylene-C(=O)N(R$^{1x}$)$_2$, C$_{1-6}$alkylene-C(=O)-Het, O—C$_{1-6}$alkylene-C(=O)OR$^{1x}$, C$_{1-6}$alkylene-O—C$_{1-6}$alkylene-C(=O)OR$^{1x}$, C$_{1-6}$alkenylene-N(R$^{1x}$)$_2$, OR$^{1x}$, O—C$_{1-6}$alkylene-N(R$^{1x}$)$_2$, O—C$_{1-6}$alkylene-CH(OR$^{1y}$)CH$_2$N(R$^{1x}$)$_2$, O—C$_{1-6}$alkylene-Het, O—C$_{1-6}$alkylene-C(=O)OR$^{1x}$, O—C$_{1-6}$alkylene-C(=O)-Het, O—C$_{1-6}$alkylene-OR$^{1x}$, O—C$_{1-6}$alkylene-CH(OR$^{1y}$)C$_{1-6}$alkylene-OR$^{1x}$, O—C$_{2-6}$alkylene-OR$^{1y}$, O—C$_{2-6}$alkylene-N(R$^{1x}$)$_2$, O—C$_{1-6}$alkylene-NR$^{1x}$C(=O)OR$^{1x}$, O—C$_{1-6}$alkylene-O—C$_{1-6}$alkylene-C(=O)OR$^{1y}$, SO$_2$R$^{1x}$, S—C$_{1-6}$alkylene-OR$^{1z}$, and SO$_2$N(R$^{1x}$)$_2$,
wherein Het is C$_{3-8}$heteroaryl or C$_{2-8}$heterocycloalkyl, wherein R$^{1x}$ is independently hydrogen, C$_{1-6}$alkyl, C$_{1-6}$haloalkyl, C$_{3-8}$cycloalkyl, C$_{6-10}$aryl, C$_{2-8}$heterocycloalkyl, and C$_{3-8}$heteroaryl, wherein R$^{1y}$ is independently hydrogen, C$_{1-6}$alkyl, C$_{1-6}$haloalkyl, C$_{6-10}$aryl, and C$_{3-8}$heteroaryl, wherein R$^{1z}$ is independently C$_{1-6}$alkyl, C$_{1-6}$haloalkyl, C$_{3-8}$cycloalkyl, C$_{6-10}$aryl, C$_{2-8}$heterocycloalkyl, and C$_{3-8}$heteroaryl, and wherein each of Het, R$^{1x}$, R$^{1y}$ and R$^{1z}$ is optionally substituted with one, two, three, or four members independently selected from halo, oxo, C$_{1-6}$alkyl, and C$_{6-10}$aryl;

each R$^2$ is independently halo, cyano, C$_{1-6}$alkyl, C$_{1-6}$haloalkyl, SO$_2$N(R$^{2x}$)$_2$, wherein R$^{2x}$ is hydrogen, C$_{1-6}$alkyl, or C$_{1-6}$haloalkyl;

R$^3$ is hydrogen, C$_{1-6}$alkyl, C$_{1-6}$haloalkyl, C$_{3-8}$cycloalkyl, C$_{6-10}$aryl, wherein the C$_{1-6}$alkyl moiety is optionally substituted with —C(=O)NR$^{3x}$R$^{3y}$, wherein each R$^{3x}$ and R$^{3y}$ is independently hydrogen, C$_{1-6}$alkyl, or C$_{1-6}$haloalkyl;

R$^5$ is hydrogen or C$_{1-6}$alkyl, or R$^5$ and R$^3$ together with the atoms to which they are attached optionally form a four-, five- or six-membered heterocyclic ring, wherein the heterocyclic ring is optionally substituted with one, two, or three members independently selected from halo, C$_{1-6}$alkyl, C$_{1-6}$alkoxy, C$_{1-6}$haloalkyl, and NR$^{5x}$C(O)R$^{5y}$ where R$^{5x}$ is hydrogen or C$_{1-6}$alkyl, and R$^{5y}$ is C$_{1-6}$alkylene-NH$_2$, C$_{1-6}$alkylene-C$_{3-8}$cycloalkyl, or C$_{1-6}$haloalkyl;

R$^4$ is cyano, C(=O)NR$^{4x}$R$^{4y}$, SO$_2$—C$_{1-6}$alkyl, halo, C$_{1-6}$haloalkyl, or C(=O)R$^{4x}$, wherein each R$^{4x}$ and R$^{4y}$ is independently hydrogen, C$_{1-6}$alkyl, or C$_{1-6}$haloalkyl;

R$^6$ is NH$_2$, halo, C$_{1-6}$alkyl, or C$_{1-6}$haloalkyl; and
R$^7$ is NH$_2$, halo, C$_{1-6}$alkyl, or C$_{1-6}$haloalkyl;
or a pharmaceutically acceptable salt, isomer, or a mixture thereof.

In some embodiments, the PI3K inhibitors are compounds having the structure of formulae (J) or (I) wherein:
n is 1 or 2;
m is 0, 1, or 2;
each R$^1$ is independently C$_{1-6}$alkyl, C$_{1-6}$haloalkyl, C$_{6-10}$aryl, C$_{5-8}$heteroaryl, C$_{3-8}$cycloalkyl, C$_{2-8}$heterocycloalkyl, halo, cyano, C$_{1-6}$alkylene-C(=O)OH, C$_{1-6}$alkylene-C(=O)OC$_{1-6}$alkyl, C$_{1-6}$alkylene-C(=O)—C$_{3-8}$heterocycloalkyl, C$_{1-6}$alkylene-C(=O)—C$_{3-8}$cycloalkyl, C$_{1-6}$alkylene-C(=O)NH$_2$, C$_{1-6}$alkylene-C(=O)N(C$_{1-6}$alkyl)$_2$, C$_{1-6}$alkylene-C(=O)NHC$_{1-6}$alkyl, C$_{1-6}$alkylene-O—C$_{1-6}$alkylene-C(=O)OH, C$_{1-6}$alkylene-O—C$_{1-6}$alkylene-C(=O)OC$_{1-6}$alkyl, C$_{1-6}$alkylene-C$_{6-10}$-aryl, C$_{1-6}$alkylene-C$_{2-8}$heteroaryl, C$_{1-6}$alkylene-C$_{2-8}$heterocycloalkyl, C$_{1-6}$alkylene-C$_{3-8}$cycloalkyl, C$_{1-6}$alkylene-OH, C$_{1-6}$alkylene-OC$_{1-6}$alkyl, O—C$_{1-6}$alkylene-N(C$_{1-6}$alkyl)$_2$, O—C$_{1-6}$alkylene-NHC$_{1-6}$alkyl, O—C$_{1-6}$alkylene-NH$_2$, O—C$_{1-6}$alkylene-CH(OH)C$_{1-6}$alkylNH$_2$, O—C$_{1-6}$alkylene-CH(OH)C$_{1-6}$alkylN(C$_{1-6}$alkyl)$_2$, O—C$_{1-6}$alkylene-CH(OH)C$_{1-6}$alkylNHC$_{1-6}$alkyl, O—C$_{1-6}$alkylene-CH(OC$_{1-6}$alkyl)C$_{1-6}$alkylNH$_2$, O—C$_{1-6}$alkylene-CH(OC$_{1-6}$alkyl)C$_{1-6}$alkylN(C$_{1-6}$alkyl)$_2$, O—C$_{1-6}$alkylene-CH(OC$_{1-6}$alkyl)C$_{1-6}$alkylNHC$_{1-6}$alkyl, O—C$_{1-6}$alkylene-C$_{2-8}$heterocycloalkyl, O—C$_{1-6}$alkylene-C$_{3-8}$heteroaryl, O—C$_{1-6}$alkylene-C(=O)OH, O—C$_{1-6}$alkylene-C(=O)OC$_{1-6}$alkyl, O—C$_{1-6}$alkylene-C(=O)—C$_{2-8}$heterocycloalkyl, O—C$_{1-6}$alkylene-C(=O)OC$_{3-8}$cycloalkyl, O—C$_{1-6}$alkylene-C(=O)OC$_{6-10}$aryl, O—C$_{1-6}$alkylene-OH, O—C$_{1-6}$alkylene-OC$_{3-8}$-cycloalkyl, O—C$_{1-6}$alkylene-OC$_{1-6}$alkyl, O—C$_{1-6}$alkylene-CH(OH)C$_{1-6}$alkylene-OH, O—C$_{1-6}$alkylene-NHC(=O)OH, O—C$_{1-6}$alkylene-O—C$_{1-6}$alkylene-C(=O)OH, OSO$_2$CF$_3$, S—C$_{1-6}$alkylene-OH, SO$_2$C$_{1-6}$alkylene-C$_{2-8}$heterocycloalkyl, SO$_2$C$_{6-10}$aryl, SO$_2$C$_{3-8}$cycloalkyl, SO$_2$C$_{1-6}$alkylene-OH, SO$_2$N(C$_{1-6}$alkyl)$_2$, or SO$_2$NH$_2$;
wherein each of the C$_{6-10}$aryl, C$_{3-8}$cycloalkyl, C$_{2-8}$heterocycloalkyl, and C$_{3-8}$heteroaryl moieties is optionally substituted with one, two, three, or four members independently selected from fluoro, chloro, oxo, methyl, ethyl, fluoromethyl, difluoromethyl, trifluoromethyl, fluoroethyl, difluoroethyl, trifluoroethyl, and phenyl;

each R$^2$ is independently halo, cyano, C$_{1-6}$alkyl, C$_{1-6}$haloalkyl, and SO$_2$NH$_2$;

R$^3$ is C$_{1-6}$alkyl, C$_{1-6}$haloalkyl, C$_{3-8}$cycloalkyl, C$_{6-10}$aryl, C$_{1-6}$alkylene-C(=O)NHC$_{1-6}$alkyl, C$_{1-6}$alkylene-C(=O)NH$_2$, or C$_{1-6}$alkylene-C(=O)N(C$_{1-6}$alkyl)$_2$;

R$^5$ is hydrogen or C$_{1-6}$alkyl, or R$^5$ and R$^3$ together with the atoms to which they are attached optionally form a four-, live- or six-membered heterocyclic ring, wherein the heterocyclic ring is optionally substituted with one or two members independently selected from halo, C$_{1-6}$alkyl, NHC(=O)C$_{1-6}$alkylene-NH$_2$, NHC(=)C$_{1-6}$alkylene-C$_{3-8}$cycloalkyl, NHC(=O)C$_{1-6}$haloalkyl, $NC_{1-6}alkylC(=O)C_{1-6}alkylene-NH_2$, $NC_{1-6}alkylC(=O)C_{1-6}alkylene-C_{3-8}cycloalkyl$, and $NC_{1-6}alkylC(=O)C_{1-6}haloalkyl$;

$R^4$ is cyano, halo, $C_{1-6}haloalkyl$, $C(=O)H$, or $C(=O)C_{1-6}alkyl$;

$R^6$ is $NH_2$, halo, or $C_{1-6}alkyl$; and $R^7$ is $NH_2$, halo, or $C_{1-6}alkyl$;

or a pharmaceutically acceptable salt, isomer, or a mixture thereof.

In some embodiments of formulae (J) or (I), each $R^1$ is independently methyl, chloro, fluoro, cyano, tetrahydropyridinyl, $—CH_2—C(=O)OH$, $—C_2H_4—C(=O)OH$, $—C_3H_6—C(=O)OH$, $—CH_2—C(=O)NH_2$, $—CH_2—C(=O)N(CH_3)_2$, $—C_2H_4—C(=O)NH_2$, $—C_2H_4—C(=O)N(CH_3)_2$, $—C_3H_6—C(=O)NH_2$, $—C_3H_6—C(=O)N(CH_3)_2$, $—CH_2—C(=O)-Het$, $C_2H_4—C(=O)-Het$, $—C_3H_6—C(=O)-Het$, $O—CH_2—C(=O)OC_3H_7$, $O—C_2H_4—C(=O)OC_3H_7$, $O—C_3H_6—C(=O)OC_3H_7$, $—CH_2-Het$, $—C_2H_4-Het$, $—C_3H_6-Het$, $—CH_2-cyclopropyl$, $—C_2H_4-cyclopropyl$, $—C_3H_6-cyclopropyl$, $—CH_2-cyclobutyl$, $—C_2H_4-cyclobutyl$, $—C_3H_6-cyclobutyl$, $—CH_2-cyclopentyl$, $—C_2H_4-cyclopentyl$, $C_3H_6-cyclopentyl$, $—CH_2-cyclohexyl$, $—C_2H_4-cyclohexyl$, $—C_3H_6-cyclohexyl$, $O—CH_2—NH_2$, $O—C_2H_4—NH_2$, $O—C_3H_6—NH_2$, $O—CH_2—N(CH_3)_2$, $O—C_2H_4—N(CH_3)_2$, $O—C_3H_6—N(CH_3)_2$, $O—CH_2-Het$, $O—C_2H_4-Het$, $O—C_3H_6-Het$, $O—CH_2—C(=O)OH$, $O—C_2H_4—C(=O)OH$, $O—C_3H_6—C(=O)OH$, $O—CH_2—C(=O)OCH_3$, $O—C_2H_4—C(=O)OCH_3$, $O—C_3H_6—C(=O)OCH_3$, $O—CH_2—C(=O)-Het$, $O—CH_2C(CH_3)(CH_2OH)_2$, $S—C_2H_4OH$, $S—C_3H_6OH$, $SO_2$-phenyl, $SO_2$-methylphenyl, $—SO_2$-ethylphenyl, $—SO_2$-cyclopropyl, $—SO_2$-cyclobutyl, $—SO_2$-cyclopentyl, $—SO_2—C_2H_4-Het$, $—SO_2CH_3$, $—SO_2C_2H_5$, $—SO_2C_3H_7$, $—SO_2C_2H_4OH$, or $—SO_2C_3H_6OH$; wherein Het is independently selected from piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl. In some other embodiments of formulae (J) or (I), each $R^2$ is independently fluoro, chloro, bromo, iodo, cyano, methyl, ethyl, propyl, fluoromethyl, difluoromethyl, trifluoromethyl, fluoroethyl, difluoroethyl, trifluoroethyl, and $SO_2NH_2$. In certain other embodiments of formulae (J) or (I), $R^3$ is methyl, ethyl, propyl, $—CH_2—C(=O)NH_2$, $—C_2H_4—C(=O)NH_2$, $—C_3H_6—C(=O)NH_2$, $—CH_2—C(=O)N(CH_3)_2$, $—C_2H_4—C(=O)N(CH_3)_2$, $—C_3H_6—C(=O)N(CH_3)_2$, cyclopropyl, cyclobutyl, or phenyl. In certain embodiments, $R^3$ is methyl, ethyl, or cyclopropyl. In additional embodiments of formulae (J) or (I), $R^5$ is hydrogen, methyl, ethyl, or propyl. In other additional embodiments, $R^5$ and $R^3$ together with the atoms to which they are attached optionally form a heterocyclic ring, wherein the heterocyclic ring is selected from azetidinyl, morpholinyl or pyrrolidinyl, wherein each of the azetidinyl, morpholinyl, and pyrrolidinyl moieties is optionally substituted with $N(CH_3)C(=O)CH_2NH_2$, $N(CH_3)C(=O)CHF_2$, $N(CH_3)C(=O)CH_2CF_3$, $N(CH_3)C(=O)cyclopropyl$, $NHC(=O)CH_2NH_2$, $NHC(=O)CHF_2$, $NHC(=O)CH_2CF_3$, or $NHC(=O)cyclopropyl$. In certain embodiments, $R^5$ and $R^3$ together with the atoms to which they are attached optionally form a heterocyclic ring, wherein the heterocyclic ring is selected from azetidinyl, morpholinyl, or pyrrolidinyl, wherein each of the azetidinyl, morpholinyl, and pyrrolidinyl moities is optionally substituted with $C_{1-4}$ alkyl, halo, $N(CH_3)C(=O)CH_2NH_2$, $N(CH_3)C(=O)CHF_2$, $N(CH_3)C(=O)CH_2CF_3$, $N(CH_3)C(=O)cyclopropyl$, $NHC(=O)CH_2NH_2$, $NHC(=O)CHF_2$, $NHC(=O)CH_2CF_3$, or $NHC(=O)cyclopropyl$ or $NHC(=O)cyclopropyl$. In another embodiments of formulae (J) or (I), $R^4$ is cyano, chloro, bromo, iodo, or $C(=O)CH_3$. In yet another embodiments of formulae (J) or (I), $R^6$ is $NH_2$, chloro, fluoro, methyl, ethyl, or propyl; and $R^7$ is $NH_2$, fluoro, chloro, methyl, ethyl or propyl.

In certain embodiments, $R^5$ and $R^3$ together with the atoms to which they are attached optionally form a heterocyclic ring, wherein the heterocyclic ring is selected from azetidinyl, morpholinyl, or pyrrolidinyl, wherein each of the azetidinyl morpholinyl, and pyrrolidinyl moieties is optionally substituted with 1, 2 or 3 groups which are independently $C_{1-4}$ alkyl, methoxy, ethoxy, halo, $N(CH_3)C(=O)CH_2NH_2$, $N(CH_3)C(=O)CHF_2$, $N(CH_3)C(=O)CH_2CF_3$, $N(CH_3)C(=O)cyclopropyl$, $NHC(=O)CH_2NH_2$, $NHC(=O)CHF_2$, $NHC(=O)CH_2CF_3$, $NHC(=O)CH_2cyclopropyl$ or $NHC(=O)cyclopropyl$; and each $R^1$ is independently chloro, fluoro, cyano, methyl, $SO_2$-phenyl, $—SO_2CH_3$, or $—C_3H_6—C(=O)OH$.

In certain embodiments, $R^5$ and $R^3$ together with the atoms to which they are attached optionally form a heterocyclic ring, wherein the heterocyclic ring is selected from azetidinyl, morpholinyl, or pyrrolidinyl, wherein each of the azetidinyl, morpholinyl, and pyrrolidinyl moieties is optionally substituted with Cm alkyl, halo, $C_{1-4}$ alkyl, halo, $N(CH_3)C(=O)CH_2NH_2$, $N(CH_3)C(=O)CHF_2$, $N(CH_3)C(=O)CH_2CF_3$, $N(CH_3)C(=O)cyclopropyl$, $NHC(=O)CH_2NH_2$, $NHC(=O)CHF_2$, $NHC(=O)CH_2CF_3$, $NHC(=O)CH_2cyclopropyl$ or $NHC(=O)cyclopropyl$; and each $R^1$ is independently chloro, fluoro, cyano, methyl, $SO_2$-phenyl, $—SO_2CH_3$, or $—C_3H_6—C(=O)OH$.

In certain embodiments of a compound of the present application, $R^3$ is methyl; n is 1 or 2; and one $R^1$ is tetrahydropyridinyl, $—CH_2—C(=O)OH$, $—C_2H_4—C(=O)OH$, $—C_3H_6—C(=O)OH$, $—CH_2—C(=O)NH_2$, $—CH_2—C(=O)N(CH_3)_2$, $—C_2H_4—C(=O)NH_2$, $—C_2H_4—C(=O)N(CH_3)_2$, $—C_3H_6—C(=O)NH_2$, $—C_3H_6—C(=O)N(CH_3)_2$, $—CH_2—C(=O)-Het$, $C_2H_4—C(=O)-Het$, $—C_3H_6—C(=O)-Het$, $O—CH_2—C(=O)OC_3H_7$, $O—C_2H_4—C(=O)OC_3H_7$, $O—C_3H_6—C(=O)OC_3H_7$, $—CH_2-Het$, $—C_2H_4-Het$, $—C_3H_6-Het$, $—CH_2-cyclopropyl$, $—C_2H_4-cyclopropyl$, $—C_3H_6-cyclopropyl$, $—CH_2-cyclobutyl$, $—C_2H_4-cyclobutyl$, $—C_3H_6-cyclobutyl$, $—CH_2-cyclopentyl$, $—C_2H_4-cyclopentyl$, $C_3H_6-cyclopentyl$, $—CH_2-cyclohexyl$, $—C_2H_4-cyclohexyl$, $—C_3H_6-cyclohexyl$, $O—CH_2—NH_2$, $O—C_2H_4—NH_2$, $O—C_3H_6—NH_2$, $O—CH_2—N(CH_3)_2$, $O—C_2H_4—N(CH_3)_2$, $O—C_3H_6—N(CH_3)_2$, $O—CH_2-Het$, $O—C_2H_4-Het$, $O—C_3H_6-Het$, $O—CH_2—C(=O)OH$, $O—C_2H_4—C(=O)OH$, $O—C_3H_6—C(=O)OH$, $O—CH_2—C(=O)OCH_3$, $O—C_2H_4—C(=O)OCH_3$, $O—C_3H_6—C(=O)OCH_3$, $O—CH_2—C(=O)-Het$, $O—CH_2C(CH_3)(CH_2OH)_2$, $S—C_2H_4OH$, $S—C_3H_6OH$, $SO_2$-phenyl, $SO_2$-methylphenyl, $—SO_2$-ethylphenyl, $—SO_2$-cyclopropyl, $—SO_2$-cyclobutyl, $—SO_2$-cyclopentyl, $SO_2—C_2H_4-Het$, $—SO_2CH_3$, $—SO_2C_2H_5$, $—SO_2C_3H_7$, $—SO_2C_2H_4OH$, or $—SO_2C_3H_6OH$; wherein Het is independently selected from piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl.

In certain embodiments of a compound of the present application, $R^3$ is methyl; n is 1 or 2; and one $R^1$ is tetrahydropyridinyl, —CH$_2$—C(=O)OH, —C$_2$H$_4$—C(=O)OH, —C$_3$H$_6$—C(=O)OH, —CH$_2$—C(=O)NH$_2$, —CH$_2$—C(=O)N(CH$_3$)$_2$, —C$_2$H$_4$—C(=O)NH$_2$, —C$_2$H$_4$—C(=O)N(CH$_3$)$_2$, —C$_3$H$_6$—C(=O)NH$_2$, —C$_3$H$_6$—C(=O)N(CH$_3$)$_2$, —CH$_2$—C(=O)-Het, C$_2$H$_4$—C(=O)-Het, —C$_3$H$_6$—C(=O)-Het, O—CH$_2$—C(=O)OCH$_3$, O—C$_2$H$_4$—C(=O)OC$_3$H$_7$, O—C$_3$H$_6$—C(=O)OC$_3$H$_7$, —CH$_2$-Het, —C$_2$H$_4$-Het, —C$_3$H$_6$-Het, —CH$_2$-cyclopropyl, —C$_2$H$_4$-cyclopropyl, —C$_3$H$_6$-cyclopropyl, —CH$_2$-cyclobutyl, —C$_2$H$_4$-cyclobutyl, —C$_3$H$_6$-cyclobutyl, —CH$_2$-cyclopentyl, —C$_2$H$_4$-cyclopentyl, C$_3$H$_6$-cyclopentyl, —CH$_2$-cyclohexyl, —C$_2$H$_4$-cyclohexyl, —C$_3$H$_6$-cyclohexyl, O—CH$_2$—NH$_2$, O—C$_2$H$_4$—NH$_2$, O—C$_3$H$_6$—NH$_2$, O—CH$_2$—N(CH$_3$)$_2$, O—C$_2$H$_4$—N(CH$_3$)$_2$, O—C$_3$H$_6$—N(CH$_3$)$_2$, O—CH$_2$-Het, O—C$_2$H$_4$-Het, O—C$_3$H$_6$-Het, O—CH$_2$—C(=O)OH, O—C$_2$H$_4$—C(=O)OH, O—C$_3$H$_6$—C(=O)OH, O—CH$_2$—C(=O)OCH$_3$, O—C$_2$H$_4$—C(=O)OCH$_3$, O—C$_3$H$_6$—C(=O)OCH$_3$, O—CH$_2$—C(=O)-Het, O—CH$_2$C(CH$_3$)(CH$_2$OH)$_2$, S—C$_2$H$_4$OH, S—C$_3$H$_6$OH, SO$_2$-phenyl, SO$_2$-methylphenyl, —SO$_2$-ethylphenyl, —SO$_2$C$_2$H$_4$OH, and —SO$_2$C$_3$H$_6$OH; wherein Het is independently selected from piperidinyl, morpholinyl, piperazinyl azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl.

In certain embodiments, when n is 1, 2, 3, or 4, the $R^1$ substituents may be listed individually as $R^{1a}$, $R^{1b}$, $R^{1c}$, or $R^{1d}$ respectively. In certain embodiments, when m is 1, 2, 3, or 4, the $R^2$ substituents may be listed individually as $R^{2a}$, $R^{2b}$, $R^{2c}$, or $R^{2d}$ respectively In certain embodiments of a compound of the present application, $R^1$ is independently methyl, chloro, fluoro, or cyano; $R^3$ is methyl or ethyl; $R^4$ is cyano or halo; $R^6$ is NH$_2$, halo, or C$_{1-4}$ alkyl; and $R^7$ is NH$_2$, halo, or C$_{1-4}$ alkyl; wherein only one of $R^6$ and $R^7$ is NH$_2$.

In certain embodiments of the compounds of the present application, each $R^1$ is independently methyl, chloro, fluoro, cyano, tetrahydropyridinyl, —CH$_2$—C(=O)OH, —C$_2$H$_4$—C(=O)OH, —C$_3$H$_6$—C(=O)OH, —CH$_2$—C(=O)NH$_2$, —CH$_2$—C(=O)N(CH$_3$)$_2$, —C$_2$H$_4$—C(=O)NH$_2$, —C$_2$H$_4$—C(=O)N(CH$_3$)$_2$, —C$_3$H$_6$—C(=O)NH$_2$, —C$_3$H$_6$—C(=O)N(CH$_3$)$_2$, —CH$_2$—C(=O)-Het, C$_2$H$_4$—C(=O)-Het, —C$_3$H$_6$—C(=O)-Het, O—CH$_2$—C(=O)OC$_3$H$_7$, O—C$_2$H$_4$—C(=O)OC$_3$H$_7$, O—C$_3$H$_6$—C(=O)OC$_3$H$_7$, —CH$_2$-Het, —C$_2$H$_4$-Het, —C$_3$H$_6$-Het, —CH$_2$-cyclopropyl, —C$_2$H$_4$-cyclopropyl, —C$_3$H$_6$-cyclopropyl, —CH$_2$-cyclobutyl, —C$_2$H$_4$-cyclobutyl, —C$_3$H$_6$-cyclobutyl, —CH$_2$-cyclopentyl, —C$_2$H$_4$-cyclopentyl, C$_3$H$_6$-cyclopentyl, —CH$_2$-cyclohexyl, —C$_2$H$_4$-cyclohexyl, —C$_3$H$_6$-cyclohexyl, O—CH$_2$—NH$_2$, O—C$_2$H$_4$—NH$_2$, O—C$_3$H$_6$—NH$_2$, O—CH$_2$—N(CH$_3$)$_2$, O—C$_2$H$_4$—N(CH$_3$)$_2$, O—C$_3$H$_6$—N(CH$_3$)$_2$, O—CH$_2$-Het, O—C$_2$H$_4$-Het, O—C$_3$H$_6$-Het, O—CH$_2$—C(=O)OH, O—C$_2$H$_4$—C(=O)OH, O—C$_3$H$_6$—C(=O)OH, O—CH$_2$—C(=O)OCH$_3$, O—C$_2$H$_4$—C(=O)OCH$_3$, O—C$_3$H$_6$—C(=O)OCH$_3$, O—CH$_2$—C(=O)-Het, O—CH$_2$C(CH$_3$)(CH$_2$OH)$_2$, S—C$_2$H$_4$OH, S—C$_3$H$_6$OH, SO$_2$-phenyl, SO$_2$-methylphenyl, —SO$_2$-ethylphenyl, —SO$_2$-cyclopropyl, —SO$_2$-cyclobutyl, —SO$_2$-cyclopentyl, —SO$_2$—C$_2$H$_4$-Het, —SO$_2$CH$_3$, —SO$_2$C$_2$H$_5$, —SO$_2$C$_3$H$_7$, —SO$_2$C$_2$H$_4$OH, or —SO$_2$C$_3$H$_6$OH; wherein Het is independently selected from piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl.

In one embodiment, n is 0. In other embodiments, n is 1, 2 or 3. In certain embodiments, n is 1 or 2. In one embodiment, n is 1 and the $R^1$ moiety (e.g. $R^{1a}$) may be located on any position of the phenyl of the quinazolinone ring, as depicted below.

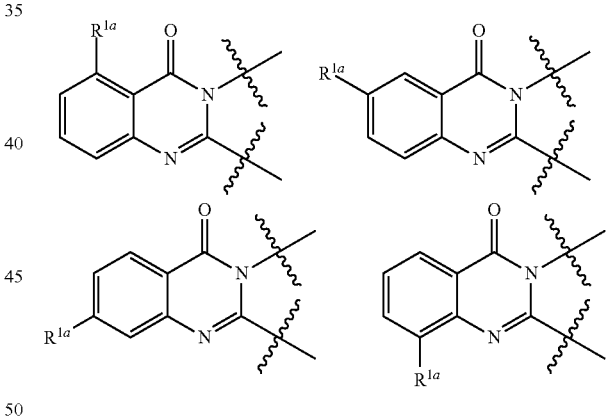

In another embodiment, n is 2. In embodiments where n is 2, both $R^1$ may be the same or different. Two $R^1$ moieties may be located of any two positions of the phenyl of the quinazolinone ring as depicted below. For example, two $R^1$ moieties (e.g. $R^{1a}$ and $R^{1b}$) may be in para-, meta- or ortho-positions to each other.

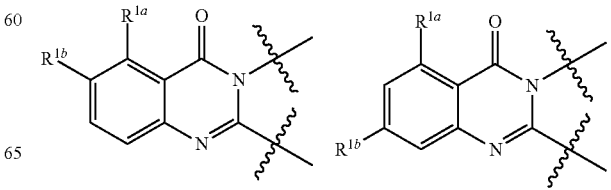

-continued

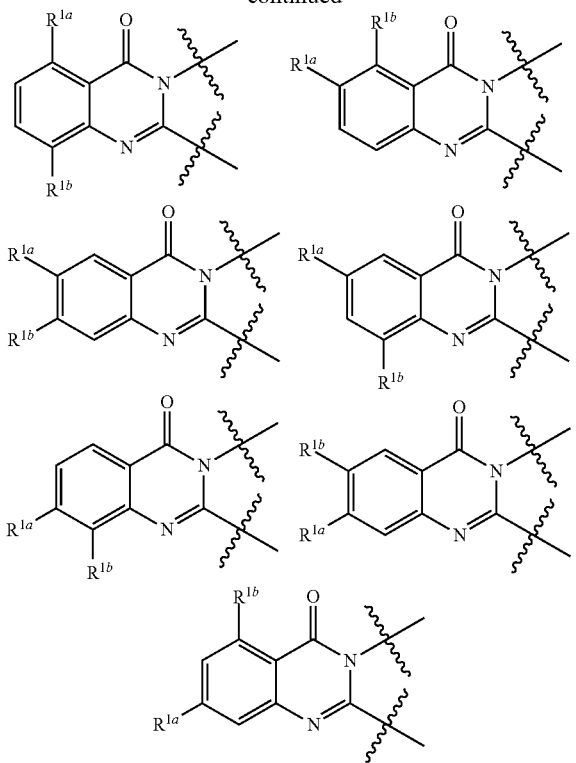

In yet another embodiment, n is 3. In embodiments where n is 3, all $R^1$ may be the same or different, or two $R^1$ may be the same and different from the third $R^1$. Three $R^1$ moieties (e.g. $R^{1a}$, $R^{1b}$, and $R^{1c}$) may be located on any three positions of the phenyl of the quinazolinone ring as depicted below. For example, the first $R^1$ may be ortho to the second $R^1$, and the first $R^1$ may be para to the third $R^1$.

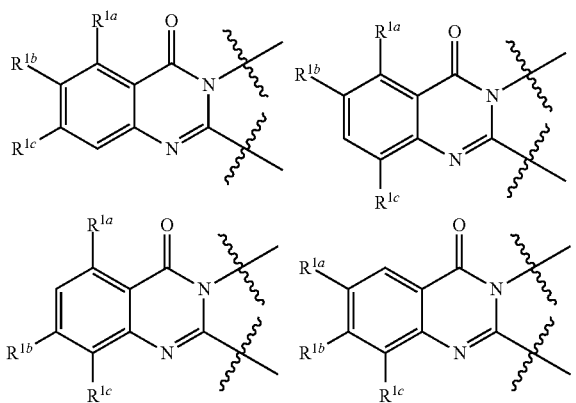

In embodiments where n is 4, all $R^1$ (e.g. $R^{1a}$, $R^{1b}$, $R^{1c}$, and $R^{1d}$) may be the same or different. Also, three $R^1$ moieties may be the same or different from the fourth $R^1$ moiety, or two $R^1$ moieties may be the same or different from the third or fourth R1 moieties. All four $R^1$ moieties (e.g. $R^{1a}$, $R^{1b}$, $R^{1c}$, and $R^{1d}$) may be located at any position of the phenyl of the quinazolinone ring. In any of the foregoing embodiments, each of $R^{1a}$, $R^{1b}$, $R^{1c}$, and $R^{1d}$ is independently selected from the moieties defined as $R^1$ described herein.

In one embodiment, each $R^1$ is independently $C_{1-6}$alkyl, $C_{1-6}$haloalkyl, $C_{3-8}$cycloalkyl, $C_{2-8}$heterocycloalkyl, $C_{3-8}$heteroaryl, $C_{6-10}$aryl, halo, cyano, $C_{6-10}$aryl-$OR^{1y}$, $C_{1-6}$alkylene-$C_{6-10}$aryl, $C_{1-6}$alkylene-Het, $C_{1-6}$alkylene-$C_{3-8}$cycloalkyl, $C_{1-6}$alkylene-$OR^{1y}$, $C_{1-6}$alkylene-$N(R^{1x})_2$, $C_{2-6}$alkenylene-$OR^{1y}$, $C_{2-6}$alkenylene-$N(R^{1x})_2$, $C_{1-6}$alkylene-C(=O)$OR^{1x}$, $C_{1-6}$alkylene-C(=O)$N(R^{1x})_2$, $C_{1-6}$alkylene-C(=O)-Het, O—$C_{1-6}$alkylene-C(=O)$OR^{1x}$, $C_{1-6}$alkylene-O—$C_{1-6}$alkylene-C(=O)$OR^{1x}$, $C_{1-6}$alkenylene-$N(R^{1x})_2$, $OR^{1x}$, O—$C_{1-6}$alkylene-$N(R^{1x})_2$, O—$C_{1-6}$alkylene-CH($OR^{1y}$)$CH_2N(R^{1x})_2$, O—$C_{1-6}$alkylene-Het, O—$C_{1-6}$alkylene-C(=O)$OR^{1x}$, O—$C_{1-6}$alkylene-C(=O)-Het, O—$C_{1-6}$alkylene-$OR^{1x}$, O—$C_{1-6}$alkylene-CH($OR^{1y}$)$C_{1-6}$alkylene-$OR^{1x}$, O—$C_{2-6}$alkylene-$OR^{1y}$, O—$C_{2-6}$alkylene-N$(R^{1x})_2$, O—$C_{1-6}$alkylene-$NR^{1x}$C(=O)$OR^{1x}$, O—$C_{1-6}$alkylene-O—$C_{1-6}$alkylene-C(=O)$OR^{1y}$, $SO_2R^{1x}$, S—$C_{1-6}$alkylene-$OR^{1x}$, and $SO_2N(R^{1x})_2$; wherein Het is heteroaryl or heterocycloalkyl, wherein $R^{1x}$ is independently hydrogen, $C_{1-6}$alkyl, $C_{1-6}$haloalkyl, $C_{3-8}$cycloalkyl, aryl, heterocycloalkyl, and $C_{3-8}$heteroaryl, wherein $R^{1y}$ is independently hydrogen, $C_{1-6}$alkyl, $C_{1-6}$haloalkyl, aryl, and heteroaryl, wherein $R^{1z}$ is independently $C_{1-6}$alkyl, $C_{1-6}$haloalkyl, $C_{3-8}$cycloalkyl, aryl, heterocycloalkyl, and $C_{3-8}$heteroaryl, and wherein each of Het, $R^{1x}$, $R^{1y}$ and $R^{1z}$ is optionally substituted with one, two, three, or four members independently selected from halo, oxo, $C_{1-6}$alkyl, and $C_{6-10}$aryl. In some embodiments, Het is a seven- to nine-membered spiro-heterocycloalkyl which is optionally substituted, wherein the spiro-heterocycloalkyl has at least two heteroatoms which are independently selected from nitrogen, oxygen, or sulfur. In some additional embodiments, Het is a seven- to nine-membered spiro-heterocycloalkyl selected from the group consisting of 2-oxa-7-azaspiro[3.5]nonanyl, 2-oxa-6-azaspiro[3.4]octanyl, and 6-oxa-1-azaspiro[3.3]heptanyl, each of which is optionally substituted one, two, three, or four members independently selected from halo, oxo, $C_{1-6}$alkyl and $C_{6-10}$aryl. In certain embodiments, Het is a four- to seven-membered heterocycloalkyl which is optionally substituted, wherein the heterocycloalkyl is a single ring having at least one heteroatom which is independently selected from nitrogen, oxygen, or sulfur. In certain other embodiments, Het is a four- to eight-membered heterocycloalkyl selected from the group consisting of piperidinyl, morpholinyl, piperazinyl, azepanyl, imidazolyl, oxetanyl, azetidinyl, pyrrolidinyl, and tetrahydropyridinyl, each of which is optionally substituted one, two, three, or four members independently selected from halo, oxo, $C_{1-6}$alkyl, and $C_{6-10}$aryl. In further embodiments, Het is independently selected from 2-oxa-7-azaspiro[3.5]nonanyl, 2-oxa-6-azaspiro[3.4]octanyl, 6-oxa-1-azaspiro[3.3]heptanyl, piperidinyl, morpholinyl, piperazinyl, azepanyl, imidazolyl, oxetanyl, azetidinyl, pyrrolidinyl, and tetrahydropyridinyl, wherein Het is optionally substituted with one, two, three, or four members independently selected from fluoro, chloro, oxo, methyl, ethyl, fluoromethyl, difluoromethyl, trifluoromethyl, fluoroethyl, difluoroethyl, trifluoroethyl, and phenyl.

In certain embodiments of a compound of the present application, n is 1 or 2, and one $R^1$ is tetrahydropyridinyl, —$CH_2$—C(=O)OH, —$C_2H_4$—C(=O)OH, —$C_3H_6$—C(=O)OH, —$CH_2$—C(=O)$NH_2$, —$CH_2$—C(=O)N(CH_3)_2, —$C_2H_4$—C(=O)$NH_2$, —$C_2H_4$—C(=O)N(CH_3)_2, —$C_3H_6$—C(=O)$NH_2$, —$C_3H_6$—C(=O)N(CH_3)_2, —$CH_2$—C(=O)-Het, $C_2H_4$—C(=O)-Het, —$C_3H_6$—C(=O)-Het, O—$CH_2$—C(=O)$OC_3H_7$, O—$C_2H_4$—C(=O)$OC_3H_7$, O—$C_3H_6$—C(=O)$OC_3H_7$, —$CH_2$-Het, —$C_2H_4$-Het, —$C_3H_6$-Het, —$CH_2$-cyclopropyl, —C$_2$H$_4$-cyclopropyl, —C$_3$H$_6$-cyclopropyl, —CH$_2$-cyclobutyl, —C$_2$H$_4$-cyclobutyl, —C$_3$H$_6$-cyclobutyl, —CH$_2$-cyclopentyl, —C$_2$H$_4$-cyclopentyl, —C$_3$H$_6$-cyclopentyl, —CH$_2$-cyclohexyl, —C$_2$H$_4$-cyclohexyl, —C$_3$H$_6$-cyclohexyl, O—CH$_2$—NH$_2$, O—C$_2$H$_4$—NH$_2$, O—C$_3$H$_6$—NH$_2$, O—CH$_2$—N(CH$_3$)$_2$, O—C$_2$H$_4$—N(CH$_3$)$_2$, O—C$_3$H$_6$—N(CH$_3$)$_2$, O—CH$_2$-Het, O—C$_2$H$_4$-Het, O—C$_3$H$_6$-Het, O—CH$_2$—C(=O)OH, O—C$_2$H$_4$—C(=O)OH, O—C$_3$H$_6$—C(=O)OH, O—CH$_2$—C(=O)OCH$_3$, O—C$_2$H$_4$—C(=O)OCH$_3$, O—C$_3$H$_6$—C(=O)OCH$_3$, O—CH$_2$—C(=O)-Het, O—CH$_2$C(CH$_3$)(CH$_2$OH)$_2$, S—C$_2$H$_4$OH, S—C$_3$H$_6$OH, SO$_2$-phenyl, SO$_2$-methylphenyl, —SO$_2$-ethylphenyl, —SO$_2$-cyclopropyl, —SO$_2$-cyclobutyl, —SO$_2$-cyclopentyl, SO$_2$—C$_2$H$_4$-Het, —SO$_2$CH$_3$, —SO$_2$C$_2$H$_5$, —SO$_2$C$_3$H$_7$, —SO$_2$C$_2$H$_4$OH, and —SO$_2$C$_3$H$_6$OH; wherein Het is independently selected from piperidinyl, morpholinyl, piperazinyl azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl.

In certain embodiments of a compound of the present application, n is 1 or 2, and one R$^1$ is tetrahydropyridinyl, —CH$_2$—C(=O)OH, —C$_2$H$_4$—C(=O)OH, —C$_3$H$_6$—C(=O)OH, —CH$_2$—C(=O)NH$_2$, —CH$_2$—C(=O)N(CH$_3$)$_2$, —C$_2$H$_4$—C(=O)NH$_2$, —C$_2$H$_4$—C(=O)N(CH$_3$)$_2$, —C$_3$H$_6$—C(=O)NH$_2$, —C$_3$H$_6$—C(=O)N(CH$_3$)$_2$, —CH$_2$—C(=O)-Het, C$_2$H$_4$—C(=O)-Het, —C$_3$H$_6$—C(=O)-Het, O—CH$_2$—C(=O)OC$_3$H$_7$, O—C$_2$H$_4$—C(=O)OC$_3$H$_7$, O—C$_3$H$_6$—C(=O)OC$_3$H$_7$, —CH$_2$-Het, —C$_2$H$_4$-Het, —C$_3$H$_6$-Het, —CH$_2$-cyclopropyl, —C$_2$H$_4$-cyclopropyl, —C$_3$H$_6$-cyclopropyl, —CH$_2$-cyclobutyl, —C$_2$H$_4$-cyclobutyl, —C$_3$H$_6$-cyclobutyl, —CH$_2$-cyclopentyl, —C$_2$H$_4$-cyclopentyl, C$_3$H$_6$-cyclopentyl, —CH$_2$-cyclohexyl, —C$_2$H$_4$-cyclohexyl, —C$_3$H$_6$-cyclohexyl, O—CH$_2$—NH$_2$, O—C$_2$H$_4$—NH$_2$, O—C$_3$H$_6$—NH$_2$, O—CH$_2$—N(CH$_3$)$_2$, O—C$_2$H$_4$—N(CH$_3$)$_2$, O—C$_3$H$_6$—N(CH$_3$)$_2$, O—CH$_2$-Het, O—C$_2$H$_4$-Het, O—C$_3$H$_6$-Het, O—CH$_2$—C(=O)OH, O—C$_2$H$_4$—C(=O)OH, O—C$_3$H$_6$—C(=O)OH, O—CH$_2$—C(=O)OCH$_3$, O—C$_2$H$_4$—C(=O)OCH$_3$, O—C$_3$H$_6$—C(=O)OCH$_3$, O—CH$_2$—C(=O)-Het, O—CH$_2$C(CH$_3$)(CH$_2$OH)$_2$, S—C$_2$H$_4$OH, S—C$_3$H$_6$OH, SO$_2$-phenyl, —SO$_2$-methylphenyl, —SO$_2$-ethylphenyl, —SO$_2$-cyclopropyl, —SO$_2$-cyclobutyl, —SO$_2$-cyclopentyl, —SO$_2$—C$_2$H$_4$-Het, —SO$_2$C$_2$H$_4$OH, and —SO$_2$C$_3$H$_6$OH; wherein Het is independently selected from piperidinyl, morpholinyl, piperazinyl azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl.

In certain embodiments of a compound of the present application, n is 1 or 2, and one R$^1$ is tetrahydropyridinyl, —C$_2$H$_4$—C(=O)OH, —C$_3$H$_6$—C(=O)OH, —C$_2$H$_4$—C(=O)NH$_2$, —CH$_2$—C(=O)N(CH$_3$)$_2$, —C$_2$H$_4$—C(=O)NH$_2$, —C$_2$H$_4$—C(=O)N(CH$_3$)$_2$, —C$_3$H$_6$—C(=O)NH$_2$, O—CH$_2$—C(=O)OC$_3$H$_7$, —C$_3$H$_6$-Het, —C$_3$H$_6$-cyclohexyl, O—CH$_2$-Het, O—C$_3$H$_6$-Het, O—CH$_2$—C(=O)-Het, O—CH$_2$C(CH$_3$)(CH$_2$OH)$_2$, S—C$_2$H$_4$OH, SO$_2$-phenyl, SO$_2$-methylphenyl, —SO$_2$-cyclopentyl, and —SO$_2$C$_2$H$_4$OH, wherein Het is independently selected from piperidinyl, morpholinyl, piperazinyl, azepanyl, imidazolyl, oxetanyl, azetidinyl, pyrrolidinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, pyrrolidinyl, 2-oxa-7-azaspiro[3.5]nonanyl, 2-oxa-6-azaspiro[3.4]octanyl, 6-oxa-1-azaspiro[3.3]heptanyl, cyclopentyl, and cyclohexyl moieties is optionally substituted with one, two, or three members independently selected from fluoro, chloro, methyl, ethyl, propyl, oxo, or phenyl.

In some embodiments, each R$^1$ is independently C$_{1-6}$alkyl, C$_{1-6}$haloalkyl, C$_{6-10}$aryl, C$_{5-8}$heteroaryl, C$_{3-8}$cycloalkyl, C$_{2-8}$heterocycloalkyl, halo, cyano, C$_{1-6}$alkylene-C(=O)OH, C$_{1-6}$alkylene-C(=O)OC$_{1-6}$alkyl, C$_{1-6}$alkylene-C(=O)—C$_{3-8}$heterocycloalkyl, C$_{1-6}$alkylene-C(=O)—C$_{3-8}$cycloalkyl, C$_{1-6}$alkylene-C(=O)NH$_2$, C$_{1-6}$alkylene-C(=O)N(C$_{1-6}$alkyl)$_2$, C$_{1-6}$alkylene-C(=O)NHC$_{1-6}$alkyl, C$_{1-6}$alkylene-O—C$_{1-6}$alkylene-C(=O)OH, C$_{1-6}$alkylene-O—C$_{1-6}$alkylene-C(=O)OC$_{1-6}$alkyl, C$_{1-6}$alkylene-C$_{6-10}$aryl, C$_{1-6}$alkylene-C$_{2-8}$heteroaryl, C$_{1-6}$alkylene-C$_{2-8}$heterocycloalkyl, C$_{1-6}$alkylene-C$_{3-8}$cycloalkyl, C$_{1-6}$alkylene-OH, C$_{1-6}$alkylene-OC$_{1-6}$alkyl, O—C$_{1-6}$alkylene-N(C$_{1-6}$alkyl)$_2$, O—C$_{1-6}$alkylene-NHC$_{1-6}$alkyl, O—C$_{1-6}$alkylene-NH$_2$, O—C$_{1-6}$alkylene-CH(OH)C$_{1-6}$alkylNH$_2$, O—C$_{1-6}$alkylene-CH(OH)C$_{1-6}$alkylN(C$_{1-6}$alkyl)$_2$, O—C$_{1-6}$alkylene-CH(OH)C$_{1-6}$alkylNHC$_{1-6}$alkyl, O—C$_{1-6}$alkylene-CH(OC$_{1-6}$alkyl)C$_{1-6}$alkylNH$_2$, O—C$_{1-6}$alkylene-CH(OC$_{1-6}$alkylN(C$_{1-6}$alkylN(C$_{1-6}$alkyl)$_2$, O—C$_{1-6}$alkylene-CH(OC$_{1-6}$alkyl)C$_{1-6}$alkylNHC$_{1-6}$alkyl, O—C$_{1-6}$alkylene-C$_{2-8}$heterocycloalkyl, O—C$_{1-6}$alkylene-C$_{3-8}$heteroaryl, O—C$_{1-6}$alkylene-C(=O)OH, O—C$_{1-6}$alkylene-C(=O)OC$_{1-6}$alkyl, O—C$_{1-6}$alkylene-C(=O)—C$_{2-8}$heterocycloalkyl, O—C$_{1-6}$alkylene-C(=O)OC$_{3-8}$cycloalkyl, O—C$_{1-6}$alkylene-C(=O)OC$_{6-10}$aryl, O—C$_{1-6}$alkylene-OH, O—C$_{1-6}$alkylene-OC$_{3-8}$cycloalkyl, O—C$_{1-6}$alkylene-OC$_{1-6}$alkyl, O—C$_{1-6}$alkylene-CH(OH)C$_{1-6}$alkylene-OH, O—C$_{1-6}$alkylene-NHC(=O)OH, O—C$_{1-6}$alkylene-O—C$_{1-6}$alkylene-C(=O)OH, S—C$_{1-6}$alkylene-OH, SO$_2$C$_{1-6}$alkylene-C$_{2-8}$heterocycloalkyl, SO$_2$C$_{6-10}$aryl, SO$_2$C$_{3-8}$cycloalkyl, SO$_2$C$_{1-6}$alkylene-OH, SO$_2$N(C$_{1-6}$alkyl)$_2$, or SO$_2$NH$_2$; wherein each of the C$_{6-10}$aryl, C$_{3-8}$cycloalkyl, C$_{2-8}$heterocycloalkyl, and C$_{3-8}$heteroaryl moieties is optionally substituted with one, two, three, or four members independently selected from fluoro, chloro, oxo, methyl, ethyl, fluoromethyl, difluoromethyl, trifluoromethyl, fluoroethyl, difluoroethyl, trifluoroethyl, and phenyl. In some additional embodiments, each R$^1$ is independently selected from C$_{1-6}$alkyl, C$_{1-6}$haloalkyl, C$_{6-10}$aryl, C$_{5-8}$heteroaryl, C$_{3-8}$cycloalkyl, C$_{2-8}$heterocycloalkyl, halo, cyano, C$_{1-6}$alkylene-C(=O))OH, C$_{1-6}$alkylene-C(=O)—C$_{3-8}$heterocycloalkyl, C$_{1-6}$alkylene-C(=O)NH$_2$, C$_{1-6}$alkylene-C(=O)N(C$_{1-6}$alkyl)$_2$, C$_{1-6}$-alkylene-C$_{2-8}$-heterocycloalkyl, C$_{1-6}$alkylene-C$_{3-8}$cycloalkyl, O—C$_{1-6}$alkylene-N(C$_{1-6}$alkyl)$_2$, C$_{1-6}$alkylene-C$_{2-8}$heterocycloalkyl, O—C$_{1-6}$alkylene-C$_{3-8}$heteroaryl, O—C$_{1-6}$alkylene-C(=O)OC$_{1-6}$alkyl, O—C$_{1-6}$alkylene-C(=O)—C$_{2-8}$heterocycloalkyl, O—C$_{1-6}$alkylene-CH(OH)C$_{1-6}$alkylene-OH, S—C$_{1-6}$alkylene-OH, SO$_2$C$_{1-6}$alkylene-C$_{2-8}$heterocycloalkyl, SO$_2$C$_{6-10}$aryl, SO$_2$C$_{3-8}$cycloalkyl, and SO$_2$C$_{1-6}$alkylene-OH; wherein each of the aryl, cycloalkyl, and heterocycloalkyl moieties is optionally substituted with one, two, three, or four members independently selected from fluoro, chloro, oxo, methyl, ethyl, and phenyl. Each and every variation of n and $R^1$ may be combined with each and every variation of W, m, $R^2$, $R^3$, $R^4$, $R^5$, $R^6$, and $R^7$ as described for any of the foregoing formulae.

In some embodiments, m is 0. In other embodiments, m is 1, 2, 3, or 4. In yet other embodiments, m is 1 or 2. In the embodiment where m is 1, the $R^2$ moiety may be located on any position of the phenyl ring, as depicted below.

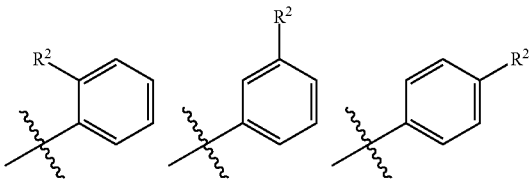

In the embodiment where m is 2, both $R^2$ may be the same or different. The two $R^2$ moieties (e.g. $R^{2a}$ and $R^{2b}$) may be located on any two positions of the phenyl ring, as depicted below.

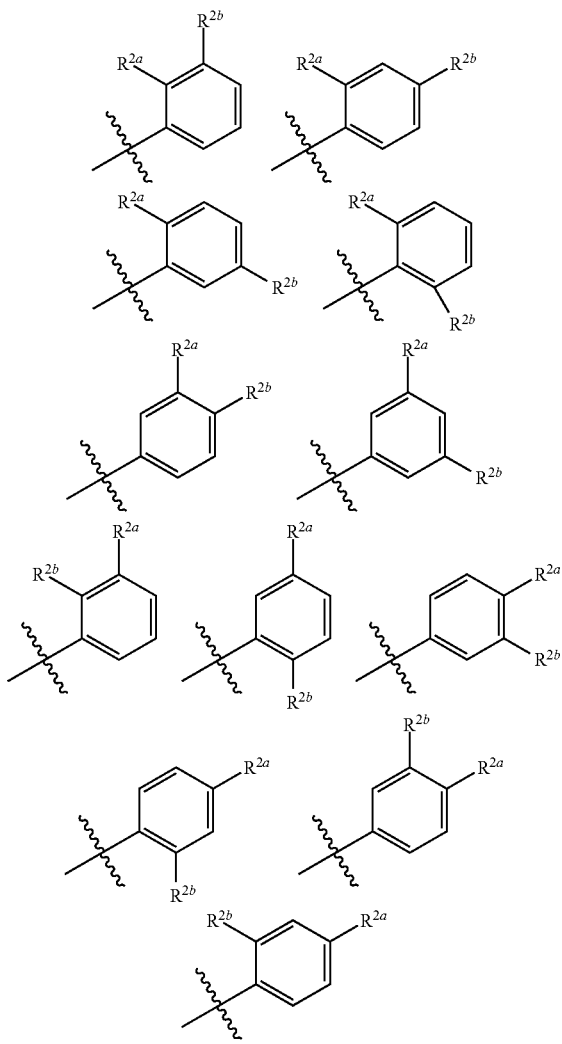

In embodiments where m is 3, all $R^2$ may be the same or different, or two $R^2$ may be the same and different from the third $R^2$. The three $R^2$ moieties (e.g. $R^{2a}$, $R^{2b}$, and $R^{2c}$) may be located on any three positions of the phenyl ring. In embodiments where m is 4, all four $R^2$ may be the same or different, two $R^2$ may be the same and different from the third or fourth $R^2$, or three $R^2$ may be the same and different from the fourth $R^2$. The four $R^2$ moieties (e.g. $R^{2a}$, $R^{2b}$, $R^{2c}$, and $R^{2d}$) may be located on any three positions of the phenyl ring. In any of the foregoing embodiments, each of $R^{2a}$, $R^{2b}$, $R^{2c}$, and $R^{2d}$ is independently selected from the moieties defined as $R^2$ described herein.

In some embodiments, each $R^2$ is independently halo, cyano, $C_{1-6}$alkyl, $C_{1-6}$haloalkyl, and $SO_2N(R^{2x})_2$ where $R^{2x}$ is hydrogen, $C_{1-6}$alkyl, or $C_{1-6}$haloalkyl. In some other embodiments, each $R^2$ is independently fluoro, chloro, bromo, iodo, cyano, methyl, ethyl, propyl, fluoromethyl, difluoromethyl, trifluoromethyl, fluoroethyl, difluoroethyl, trifluoroethyl, and $SO_2NH_2$. Accordingly, for compounds having m is 1, 2, 3, or 4, each $R^{2a}$, $R^{2b}$, $R^{2c}$, or $R^{2d}$ is independently halo, cyano, $C_{1-6}$alkyl, $C_{1-6}$haloalkyl, and $SO_2N(R^{2x})_2$ where $R^{2x}$ is hydrogen, $C_{1-6}$alkyl, or $C_{1-6}$haloalkyl. In certain embodiments where m is 1, each $R^{2a}$ is independently selected from fluoro, chloro, bromo, iodo, cyano, methyl, ethyl, propyl, fluoromethyl, difluoromethyl, trifluoromethyl, fluoroethyl, difluoroethyl, trifluoroethyl, and $SO_2NH_2$. In some embodiments where m is 2, each $R^{2a}$ and $R^{2b}$ is independently selected from fluoro, chloro, bromo, iodo, cyano, methyl, ethyl, propyl, fluoromethyl, difluoromethyl, trifluoromethyl, fluoroethyl, difluoroethyl, trifluoroethyl, and $SO_2NH_2$. In additional embodiments where m is 3, each $R^{2a}$, $R^{2b}$, and $R^{2c}$ is independently selected from fluoro, chloro, bromo, iodo, cyano, methyl, ethyl, propyl, fluoromethyl, difluoromethyl, trifluoromethyl, fluoroethyl, difluoroethyl, trifluoroethyl, and $SO_2NH_2$. In other embodiments where m is 4, each $R^{2a}$, $R^{2b}$, $R^{2c}$, and $R^{2d}$ is independently selected from fluoro, chloro, bromo, iodo, cyano, methyl, ethyl, propyl, fluoromethyl, difluoromethyl, trifluoromethyl, fluoroethyl, difluoroethyl, trifluoroethyl, and $SO_2NH_2$. Each and every variation of m and $R^2$ may be combined with each and every variation of W, n, $R^1$, $R^3$, $R^4$, $R^5$, $R^6$, and $R^7$ as described herein.

In other embodiments of formula (I) where n is 2 and m is 2, the compound has the structure of formula (IA-1):

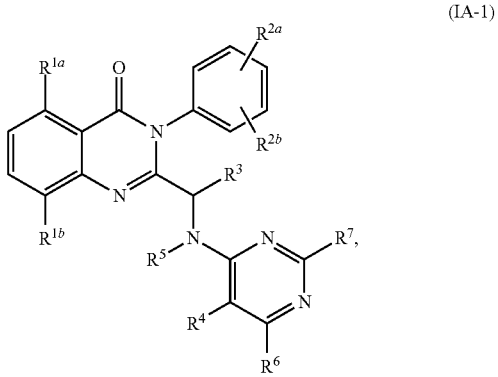

wherein:
$R^{1a}$ and $R^{1b}$ are independently selected from the moieties defined for $R^1$ described herein;
$R^{2a}$ and $R^{2b}$ are independently selected from the moieties defined for $R^2$ described herein; and
$R^3$, $R^4$, $R^5$, $R^6$, and $R^7$ are as defined herein;
or a pharmaceutically acceptable salt, isomer, or a mixture thereof.

In other embodiments of formula (I) where n is 2 and m is 2, the compound is of formula (IA-2):

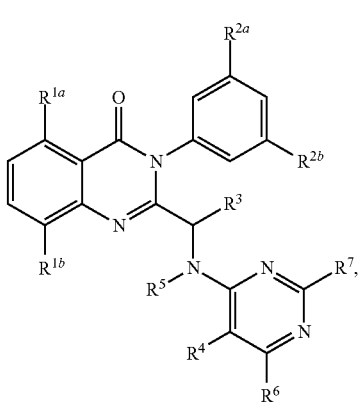

(IA-2)

wherein $R^{1a}$, $R^{1b}$, $R^{2a}$, $R^{2b}$, $R^3$, $R^4$, $R^5$, $R^6$, and $R^7$ are as defined herein;
or a pharmaceutically acceptable salt, isomer, or a mixture thereof.

In other embodiments of formula (I) where n is 2 and m is 2, the compound is of formula (IA-3):

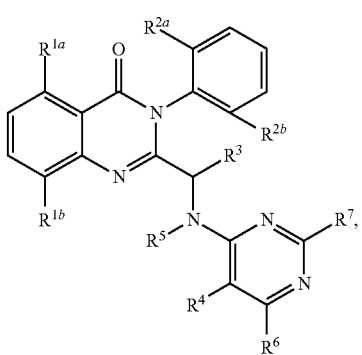

(IA-3)

wherein $R^{1a}$, $R^{1b}$, $R^{2a}$, $R^{2b}$, $R^3$, $R^4$, $R^5$, $R^6$, and $R^7$ are as defined herein;
or a pharmaceutically acceptable salt, isomer, or a mixture thereof.

In yet other embodiments of formula (I) where n is 1 and m is 2, the compound has the structure of formula (IB-1):

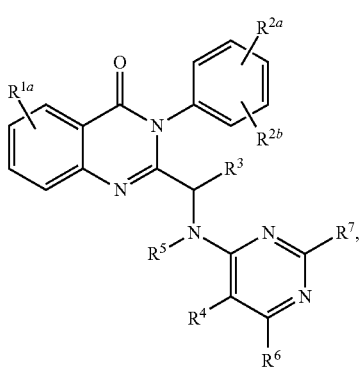

(IB-1)

wherein $R^{1a}$, $R^{1b}$, $R^{2a}$, $R^{2b}$, $R^3$, $R^4$, $R^5$, $R^6$, and $R^7$ are as defined herein;
or a pharmaceutically acceptable salt, isomer, or a mixture thereof.

In yet other embodiments of formula (I) where n is 1 and m is 2, the compound has the structure of formula (IB-2):

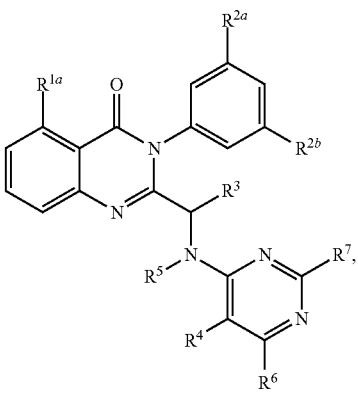

(IB-2)

wherein $R^{1a}$, $R^{1b}$, $R^{2a}$, $R^{2b}$, $R^3$, $R^4$, $R^5$, $R^6$, and $R^7$ are as defined herein;
or a pharmaceutically acceptable salt, isomer, or a mixture thereof.

In yet other embodiments of formula (I) where n is 1 and m is 2, the compound is of formula (IB-3):

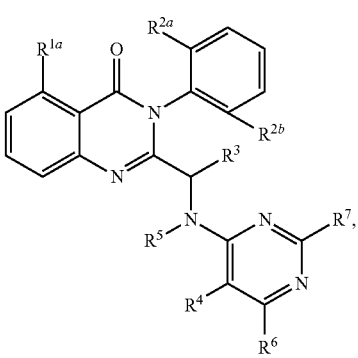

(IB-3)

wherein $R^{1a}$, $R^{1b}$, $R^{2a}$, $R^{2b}$, $R^3$, $R^4$, $R^5$, $R^6$, and $R^7$ are as defined herein;
or a pharmaceutically acceptable salt, isomer, or a mixture thereof.

In yet other embodiments of formula (I) where n is 1 and m is 2, the compound has the structure of formula (IB-4):

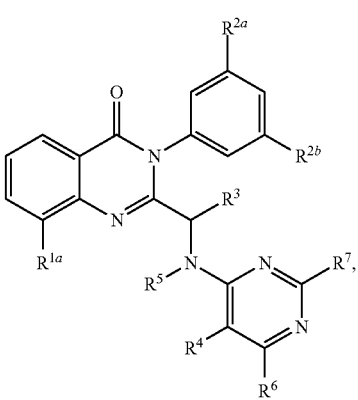

(IB-4)

wherein $R^{1a}$, $R^{2a}$, $R^{2b}$, $R^3$, $R^4$, $R^5$, $R^6$, and $R^7$ are as defined herein;

or a pharmaceutically acceptable salt, isomer, or a mixture thereof.

In yet other embodiments of formula (I) where n is 1 and m is 2, the compound is of formula (IB-5):

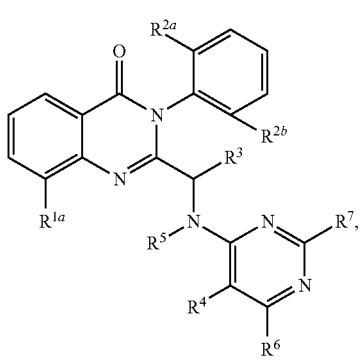

(IB-5)

wherein $R^{1a}$, $R^{2a}$, $R^{2b}$, $R^3$, $R^4$, $R^5$, $R^6$, and $R^7$ are as defined herein;

or a pharmaceutically acceptable salt, isomer, or a mixture thereof.

In the embodiments, the compound has the structure of any of the foregoing formulae (IA-1), (IA-2), (IA-3), (IB-1), (IB-2), (IB-3), (IB-4), or (IB-5), wherein $R^{1a}$ is chloro, fluoro, $SO_2$-phenyl (i.e. $SO_2C_6H_6$), $SO_2$-methyl (i.e. $SO_2CH_3$), $SO_2$-methylphenyl, $SO_2$-cyclopentyl, $SO_2$-ethylene-OH (i.e. $SO_2C_2H_4OH$), $SC_2H_4OH$, $SO_2CH_2$-Het, O—$C_2H_4(CH_3)(CH_2OH)_2$, O—$C_2H_4N(CH_3)_2$, O—$CH_2C(O)OC_3H_7$, O—$CH_2C(O)$-Het, tetrahydropyridinyl, $CH_2COOH$, $C_2H_4COOH$, $C_3H_6COOH$, $CH_2C(O)NH_2$, $C_2H_4C(O)NH_2$, $C_3H_6C(O)NH_2$, $CH_2C(O)N(CH_3)_2$, $C_2H_4C(O)N(CH_3)_2$, $C_3H_6C(O)N(CH_3)_2$, $CH_2C(O)$-Het, $C_2H_4C(O)$-Het, $C_3H_6C(O)$-Het, $CH_2$-Het, $C_2H_4$-Het, $C_3H_6$-Het, O—$CH_2$-Het, O—$C_2H_4$-Het, O—$C_3H_6$-Het; wherein Het is azetidinyl, pyrrolidinyl, piperidinyl, azepanyl, piperazinyl, imidazolyl, oxetanyl, morpholinyl, 2-oxa-7-azaspiro[3.5]nonanyl, 2-oxa-6-azaspiro[3.4]octanyl, 6-oxa-1-azaspiro[3,3]heptanyl, where each of the Het moieties is optionally substituted with one, two, three, or four members independently selected from oxo, fluoro, methyl, and phenyl. In some other embodiments, the compound has the structure of any of the foregoing formulae (IA-1), (IA-2), (IA-3), (IB-1), (IB-2), (IB-3), (IB-4), or (IB-5), wherein $R^{1b}$ is fluoro, chloro, methyl, or cyano. In certain embodiments, the compound has the structure of any of the foregoing formulae (IA-1), (IA-2), (IA-3), (IB-1), (IB-2), (IB-3), (IB-4), or (IB-5), wherein $R^{2a}$ is fluoro, difluoromethyl, fluoromethyl, trifluoromethyl, or $SO_2NH_2$. In certain other embodiments, the compound has the structure of any of the foregoing formulae (IA-1), (IA-2), (IA-3), (IB-1), (IB-2), (IB-3), (IB-4), or (IB-5), wherein $R^{2b}$ is fluoro, or cyano. Each and every variation of $R^{1a}$ and $R^{1b}$ may be combined with each and every variation of $R^{2a}$, $R^{2b}$, $R^3$, $R^4$, $R^5$, $R^6$, and $R^7$ as described herein.

In the embodiments, the compound has the structure of any of the foregoing formulae (IA-1), (IA-2), (IA-3), (IB-1), (IB-2), (IB-3), (IB-4), or (IB-5), wherein $R^{1a}$ is methyl, chloro, fluoro, cyano, tetrahydropyridinyl, —$CH_2$—C(=O)OH, —$C_2H_4$—C(=O)OH, —$C_3H_6$—C(=O)OH, —$CH_2$—C(=O)NH_2$, —$CH_2$—C(=O)N(CH_3)_2$, —$C_2H_4$—C(=O)NH_2, —$C_2H_4$—C(=O)N(CH_3)_2$, —$C_3H_6$—C(=O)NH_2$, —$C_3H_6$—C(=O)N(CH_3)_2$, —$CH_2$—C(=O)-Het, $C_2H_4$—C(=O)-Het, —$C_3H_6$—C(=O)-Het, O—$CH_2$—C(=O)OC_3H_7$, O—$C_2H_4$—C(=O)OC_3H_7$, O—$C_3H_6$—C(=O)OC_3H_7$, —$CH_2$-Het, —$C_2H_4$-Het, —$C_3H_6$-Het, —$CH_2$-cyclopropyl, —$C_2H_4$-cyclopropyl, —$C_3H_6$-cyclopropyl, —$CH_2$-cyclobutyl, —$C_2H_4$-cyclobutyl, —$C_3H_6$-cyclobutyl, —$CH_2$-cyclopentyl, —$C_2H_4$-cyclopentyl, $C_3H_6$-cyclopentyl, —$CH_2$-cyclohexyl, —$C_2H_4$-cyclohexyl, —$C_3H_6$-cyclohexyl, O—$CH_2$—NH_2$, O—$C_2H_4$—NH_2$, O—$C_3H_6$—NH_2$, O—$CH_2$—N(CH_3)_2$, O—$C_2H_4$—N(CH_3)_2$, O—$C_3H_6$—N(CH_3)_2$, O—$CH_2$-Het, O—$C_2H_4$-Het, O—$C_3H_6$-Het, O—$CH_2$—C(=O)OH, O—$C_2H_4$—C(=O)OH, O—$C_3H_6$—C(=O)OH, O—$CH_2$—C(=O)OCH_3$, O—$C_2H_4$—C(=O)OCH_3$, O—$C_3H_6$—C(=O)OCH_3$, O—$CH_2$—C(=O)-Het, NH_2, —$C_2H_4$—C(=O)N(CH_3)_2$, —$C_3H_6$—C(=O)NH_2$, —$C_3H_6$—C(=O)N(CH_3)_2$, —$CH_2$—C(=O)-Het, $C_2H_4$—C(=O)-Het, —$C_3H_6$—C(=O)-Het, O—$CH_2$—C(=O)OC_3H_7$, O—$C_2H_4$—C(=O)OC_3H_7$, O—$C_3H_6$—C(=O)OC_3H_7$, —$CH_2$-Het, —$C_2H_4$-Het, —$C_3H_6$-Het, —$CH_2$-cyclopropyl, —$C_2H_4$-cyclopropyl, —$C_3H_6$-cyclopropyl, —$CH_2$-cyclobutyl, —$C_2H_4$-cyclobutyl, —$C_3H_6$-cyclobutyl, —$CH_2$-cyclopentyl, —$C_2H_4$-cyclopentyl, $C_3H_6$-cyclopentyl, —$CH_2$-cyclohexyl, —$C_2H_4$-cyclohexyl, —$C_3H_6$-cyclohexyl, O—$CH_2$—NH_2$, O—$C_2H_4$—NH_2$, O—$C_3H_6$—NH_2$, O—$CH_2$—N(CH_3)_2$, O—$C_2H_4$—N(CH_3)_2$, O—$C_3H_6$—N(CH_3)_2$, O—$CH_2$-Het, O—$C_2H_4$-Het, O—$C_3H_6$-Het, O—$CH_2$—C(=O)OH, O—$C_2H_4$—C(=O)OH, O—$C_3H_6$—C(=O)OH, O—$CH_2$—C(=O)OCH_3$, O—$C_2H_4$—C(=O)OCH_3$, O—$C_3H_6$—C(=O)OCH_3$, O—$CH_2$—C(=O)-Het, O—$CH_2C(CH_3)(CH_2OH)_2$, S—$C_2H_4OH$, S—$C_3H_6OH$, $SO_2$-phenyl, $SO_2$-methylphenyl, —$SO_2$-ethylphenyl, —$SO_2$-cyclopropyl, —$SO_2$-cyclobutyl, —$SO_2$-cyclopentyl, —$SO_2C_2H_4$-Het, —$SO_2CH_3$, —$SO_2C_2H_5$, —$SO_2C_3H_7$, —$SO_2C_2H_4OH$, or —$SO_2C_3H_6OH$; wherein Het is independently selected from piperidinyl, morpholinyl, piperazinyl, azepanyl, imidazolyl, oxetanyl, azetidinyl, pyrrolidinyl, tetrahydropyridinyl, 2-oxa-7-azaspiro[3,5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3,5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl. In some other embodiments, the compound has the the structure of any of the foregoing formulae (IA-1), (IA-2), (IA-3), (IB-1), (IB-2), (IB-3), (IB-4), or (IB-5), wherein $R^{1b}$ is fluoro, chloro, methyl, or cyano. In certain embodiments, the compound has the structure of any of the foregoing formulae (IA-1), (IA-2), (IA-3), (IB-1), (IB-2), (IB-3), (IB-4), or (IB-5), wherein $R^{2a}$ is fluoro, difluoromethyl, fluoromethyl, trifluoromethyl, or $SO_2NH_2$. In certain other embodiments, the compound has the structure of any of the foregoing formulae (IA-1), (IA-2), (IA-3), (IB-1), (IB-2), (IB-3), (IB-4), or (IB-5), wherein $R^{2b}$ is fluoro, or cyano. Each and every variation of $R^{1a}$ and $R^{1b}$ may be combined with each and every variation of $R^{2a}$, $R^{2b}$, $R^3$, $R^4$, $R^5$, $R^6$, and $R^7$ as described herein.

In the embodiments, the compound has the structure of any of the foregoing formulae (IA-1), (IA-2), (IA-3), (IB-1), (IB-2), (IB-3), (IB-4), or (IB-5), wherein $R^{1a}$ is tetrahydropyridinyl, —$CH_2$—C(=O)OH, —$C_2H_4$—C(=O)OH, —$C_3H_6$—C(=O)OH, —$CH_2$—C(=O)NH_2, —$CH_2$—C(=O)N(CH_3)_2$, —$C_2H_4$—C(=O)NH_2, —$C_2H_4$—C(=O)N(CH_3)_2, —$C_3H_6$—C(=O)NH_2, —$C_3H_6$—C(=O)N(CH_3)_2$, —$CH_2$—C(=O)-Het, $C_2H_4$—C(=O)-Het, —$C_3H_6$—C(=O)-Het, O—$CH_2$—C(=O)OC_3H_7$, O—$C_2H_4$—C(=O)OC_3H_7$, O—$C_3H_6$—C(=O)OC_3H_7$, —$CH_2$-Het, —$C_2H_4$-Het, —$C_3H_6$-Het, —$CH_2$-cyclopropyl, —$C_2H_4$-cyclopropyl, —$C_3H_6$-cyclopropyl, —$CH_2$-cyclobutyl, —$C_2H_4$-cyclobutyl, —$C_3H_6$-cyclobutyl, —$CH_2$-cyclopentyl, —$C_2H_4$-cyclopentyl, $C_3H_6$-cyclopentyl, —$CH_2$-cyclohexyl, —$C_2H_4$-cyclohexyl, —$C_3H_6$-cyclohexyl, O—$CH_2$—NH_2$, O—$C_2H_4$—NH_2$, O—$C_3H_6$—NH_2$, O—$CH_2$—N(CH_3)_2$, O—$C_2H_4$—N(CH_3)_2$, O—$C_3H_6$—N(CH_3)_2$, O—$CH_2$-Het, O—$C_2H_4$-Het, O—$C_3H_6$-Het, O—$CH_2$—C(=O)OH, O—$C_2H_4$—C(=O)OH, O—$C_3H_6$—C(=O)OH, O—$CH_2$—C(=O)OCH_3$, O—$C_2H_4$—C(=O)OCH_3$, O—$C_3H_6$—C(=O)OCH_3$, O—$CH_2$—C(=O)-Het, O—CH$_2$C(CH$_3$)(CH$_2$OH)$_2$, S—C$_2$H$_4$OH, S—C$_3$H$_6$OH, SO$_2$-phenyl, SO$_2$-methylphenyl, —SO$_2$-ethylphenyl, —SO$_2$-cyclopropyl, —SO$_2$-cyclobutyl, —SO$_2$-cyclopentyl, —SO$_2$C$_2$H$_4$-Het, —SO$_2$CH$_3$, —SO$_2$C$_2$H$_5$, —SO$_2$C$_3$H$_7$, —SO$_2$C$_2$H$_4$OH, or —SO$_2$C$_3$H$_6$OH; wherein Het is independently selected from piperidinyl, morpholinyl, piperazinyl, azepanyl, imidazolyl, oxetanyl, azetidinyl, pyrrolidinyl, tetrahydropyridinyl, 2-oxa-7-azaspiro[3.5]nonanyl, 2-oxa-6-azaspiro[3.4]octanyl, and 6-oxa-1-azaspiro[3.3]heptanyl, wherein each of the piperidinyl, morpholinyl, piperazinyl, azepanyl, imidazolyl, oxetanyl, azetidinyl, pyrrolidinyl, tetrahydropyridinyl, 2-oxa-7-azaspiro[3,5]nonanyl, 2-oxa-6-azaspiro[3.4]octanyl, 6-oxa-1-azaspiro[3.3]heptanyl, cyclopropyl, cyclobutyl, cyclopentyl, and cyclohexyl moieties is optionally substituted with one, two, three, or four members independently selected from fluoro, chloro, methyl, ethyl, propyl, oxo, or phenyl. In some other embodiments, the compound has the structure of any of the foregoing formulae (IA-1), (IA-2), (IA-3), (IB-1), (IB-2), (IB-3), (IB-4), or (IB-5), wherein $R^{1b}$ is fluoro, chloro, methyl, or cyano. In certain embodiments, the compound has the structure of any of the foregoing formulae (IA-1), (IA-2), (IA-3), (IB-1), (IB-2), (IB-3), (IB-4), or (IB-5), wherein $R^{2a}$ is fluoro, difluoromethyl, fluoromethyl, trifluoromethyl, or SO$_2$NH$_2$. In certain other embodiments, the compound has the structure of any of the foregoing formulae (IA-1), (IA-2), (IA-3), (IB-1), (IB-2), (IB-3), (IB-4), or (IB-5), wherein $R^{2b}$ is fluoro, or cyano. Each and every variation of $R^{1a}$ and $R^{1b}$ may be combined with each and every variation of $R^{2a}$, $R^{2b}$, $R^3$, $R^4$, $R^5$, $R^6$, and $R^7$ as described herein.

In certain embodiments, $R^3$ is hydrogen, optionally substituted alkyl, optionally substituted $C_{3-8}$ cycloalkyl, or optionally substituted $C_{6-10}$ aryl. In one embodiment, $R^3$ is $C_{3-6}$ cycloalkyl, $C_{6-10}$ aryl, or $C_{1-6}$ alkyl optionally substituted with hydroxy, $C_{6-10}$ aryl $C_{1-6}$ alkoxy, $C_{3-6}$ cycloalkyl, or —C(=O)NR$^{3x}$R$^{3y}$ wherein each $R^{3x}$ and $R^{3y}$ is independently hydrogen, $C_{1-6}$ alkyl, or $C_{1-6}$ haloalkyl. In some embodiments, $R^3$ is methyl, ethyl, propyl, butyl, pentyl, hexyl, cyclopropylmethyl, cyclopropylethyl, cyclobutylmethyl, cyclobutylethyl, cyclopropyl, cyclobutyl, cyclopentyl, cyclohexyl, —CH$_2$OH, —C$_2$H$_4$OH, —C$_3$H$_6$OH, phenyl, —CH$_2$—C(=O)NH$_2$, —C$_2$H$_4$—(=O)NH$_2$, —C$_3$H$_6$—C(=O)NH$_2$, —CH$_2$—C(=O)N(CH$_3$)$_2$, —C$_2$H$_4$—C(=O)N(CH$_3$)$_2$, or —C$_3$H$_6$—C(=O)N(CH$_3$)$_2$. In some other embodiments, $R^3$ is methyl, ethyl, propyl, cyclopropyl, cyclobutyl, phenyl, —CH$_2$—C(=O)N(CH$_3$)$_2$, —C$_2$H$_4$—(=O)N(CH$_3$)$_2$, or —C$_3$H$_6$—C(=O)N(CH$_3$)$_2$.

In additional embodiments, $R^5$ is hydrogen or optionally substituted $C_{1-6}$ alkyl. In some embodiments, $R^5$ is hydrogen or $C_{1-4}$ alkyl. In certain embodiments, $R^5$ is hydrogen, methyl, ethyl, propyl or butyl. In certain other embodiments, $R^5$ is hydrogen.

In further embodiments, $R^3$ and $R^5$ with the atoms to which they are attached (e.g. carbon and nitrogen, respectively) optionally form a heterocyclic ring that is optionally substituted. In other embodiments, the $R^3$-$R^5$ heterocyclic ring is an optionally substituted three- to eight-membered heterocycloalkyl (i.e. heterocycloalkyl having three to eight ring members and at least one ring member is a heteroatom). In other embodiments, the $R^3$-$R^5$ heterocyclic ring is an optionally substituted four- to seven-membered heterocycloalkyl (i.e. heterocycloalkyl having four to seven ring members and at least one ring member is a heteroatom). In certain other embodiments, the $R^3$-$R^5$ heterocyclic ring is $C_{3-8}$ heterocycloalkyl. In certain embodiments, the $R^3$-$R^5$ heterocyclic ring is azepanyl, azetidinyl, piperidinyl, pyrrolidinyl, or morpholinyl; where each of the azepanyl, azetidinyl, piperidinyl, pyrrolidinyl, and morpholinyl moieties is optionally substituted with one or two members independently selected from halo, $C_{1-6}$alkyl, $C_{1-6}$haloalkyl, and NR$^{5x}$C(O)R$^{5y}$ where $R^{5x}$ is hydrogen or $C_{1-6}$alkyl, and $R^{5y}$ is $C_{1-6}$alkylene-NH$_2$, $C_{1-6}$alkylene-$C_{3-8}$cycloalkyl or $C_{1-6}$haloalkyl. In further embodiments, the $R^3$-$R^5$ heterocyclic ring is selected from azetidinyl, morpholinyl, and pyrrolidinyl, each of which is optionally substituted with one member of fluoro, chloro, iodo, methyl, ethyl, propyl, N(CH$_3$)C(=O)CH$_2$NH$_2$, N(CH$_3$)C(=O)CHF$_2$, N(CH$_3$)C(=O)CH$_2$CF$_3$, N(CH$_3$)C(=O))cyclopropyl, NHC(=O)CH$_2$NH$_2$, NHC(=O)CHF$_2$, NHC(=O)CH$_2$CF$_3$, or NHC(=O)cyclopropyl.

In yet other embodiments, $R^4$ is cyano, halo, $C_{1-6}$haloalkyl, C(=O)H, or C(=O)$C_{1-6}$alkyl. In some other embodiments, $R^4$ is cyano, chloro, fluoro, bromo, iodo, methyl, ethyl, propyl, fluoromethyl, difluoromethyl, trifluoromethyl, fluoroethyl, difluoroethyl, trifluoroethyl, or C(=O)CH$_3$. In yet some other embodiments, $R^4$ is cyano, chloro, fluoro, methyl or C(=O)CH$_3$. In certain embodiments, $R^6$ is NH$_2$, halo, or $C_{1-6}$alkyl. In certain other embodiments, $R^6$ is NH$_2$, fluoro, chloro, bromo, iodo, methyl, ethyl, or propyl. In yet certain other embodiments, $R^6$ is NH$_2$, chloro, or methyl. In additional embodiments, $R^7$ is NH$_2$, halo, or $C_{1-6}$alkyl. In some additional embodiments, $R^7$ is NH$_2$, fluoro, chloro, methyl, ethyl, or propyl. In yet some additional embodiments, $R^7$ is NH$_2$, chloro, or methyl. Each and every variation of $R^4$ may be combined with each and every variation of W, n, m, $R^1$, $R^2$, $R^3$, $R^5$, $R^6$, and $R^7$ as described herein.

In certain embodiments of the compounds of the present application, when $R^5$ and $R^3$ form a 5-membered heterocyclic ring that is optionally substituted with hydroxyl, halo, or methoxy, $R^4$ is cyano, $R^6$ is amino, and $R^7$ is amino;

For certain compounds described herein, each unique stereoisomer has a compound number bearing a suffix "a", "b", etc. As an example. Compound 1 bearing one chiral center can be resolved into its individual enantiomers 1a and 1b.

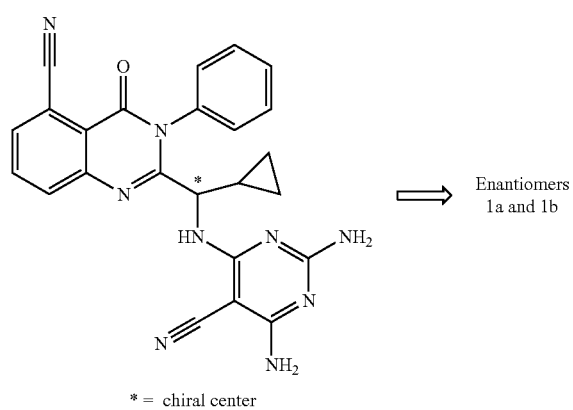 [SMILES: N#Cc1c(N)nc(N)nc1NC(c1nc2cccc(C#N)c2c(=O)n1-c1ccccc1)C1CC1]

* = chiral center

In any one of the foregoing embodiments, the compound described herein or a pharmaceutically acceptable salt thereof is the (S)-enantiomer. It is understood that each compound having a chiral center has enantiomers that correspond with the "a" and "b" example provided above.

A composition containing a mixture of enantiomers of the compound described herein or a pharmaceutically acceptable salt thereof, is also provided herein. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a described herein or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound of formula described herein or a pharmaceutically acceptable salt thereof, may also contain the compound in enantiomeric excess (e.e.). For instance, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%. In some of the foregoing embodiments, the compound is enantiomerically-enriched in the (S)-isomer of compound of formula described herein.

Provided is also a composition comprising a mixture of the (S)-enantiomer and the (R)-enantiomer of a compound of formula described herein or a pharmaceutically acceptable salt thereof. In one embodiment, the mixture is a racemic mixture. In other embodiments, the composition comprises the (S)-enantiomer of a compound described herein or a pharmaceutically acceptable salt thereof wherein the (S)-enantiomer of the compound is present in excess of over the corresponding the (R)-enantiomer of the compound, or a pharmaceutically acceptable salt thereof.

In any one of the foregoing embodiments, the compound described herein or a pharmaceutically acceptable salt thereof, is an atropisomer. A composition containing a mixture of atropisomers of the compound described herein or a pharmaceutically acceptable salt thereof, is also provided herein. "Atropisomers" refers to conformational stereoisomers which occur when rotation about a single bond in the molecule is prevented, or greatly slowed, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers are enantiomers without a single asymmetric atom. As an example, Compound 17 can be resolved into its individual atropisomers as depicted below.

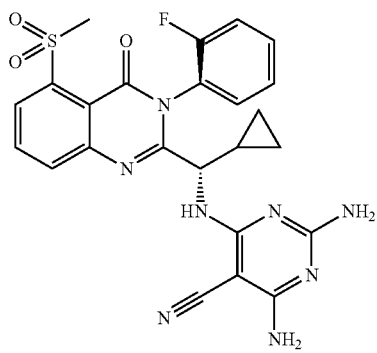

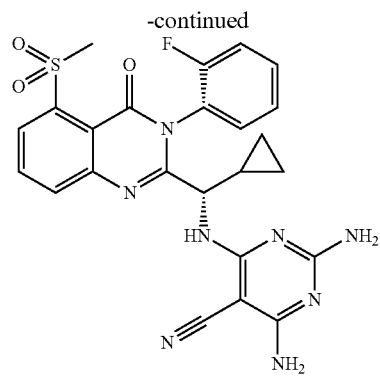

-continued

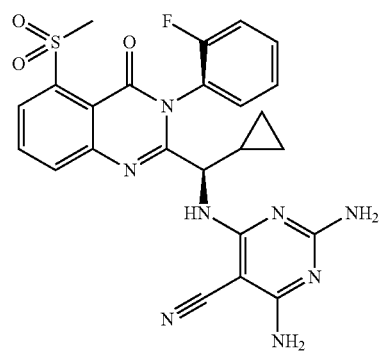

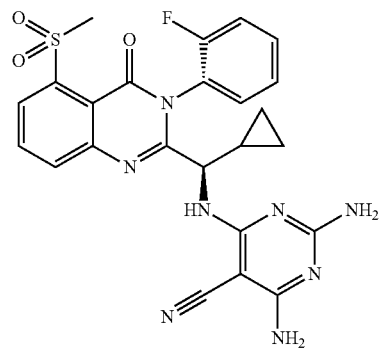

Representative compounds of the invention are listed in Table 1 below in its non-isomeric form. The compounds in Table 1 are named using ChemBioDraw Ultra. Similarly, the Compounds 1-116 (which include certain compounds of Table 1) are named using ChemBioDraw Ultra. It is understood that other names may be used to identity compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC), The naming and numbering of the compounds of the present disclosure is illustrated with representative compounds shown in Table 1 below. The compounds provided in Table 1 may be a single enantiomer (e.g., (S)-enantiomer, (R)-enantiomer), or the compounds may be present in a composition having an enantiomeric mixture.

TABLE 1

| # | Structure | Name |
|---|---|---|
| 1. | 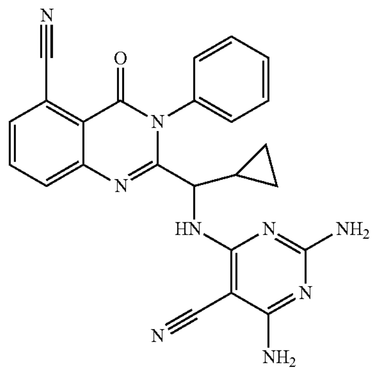 [SMILES: N#Cc1c(N)nc(N)nc1NC(c1nc2cccc(C#N)c2c(=O)n1-c1ccccc1)C1CC1] | 2-(cyclopropyl((2,6-diamino-5-cyanopyrimidin-4-yl)amino)methyl)-4-oxo-3-phenyl-3,4-dihydroquinazoline-5-carbonitrile<br>a: (S)-enantiomer<br>b: (R)-enantiomer |
| 2. | 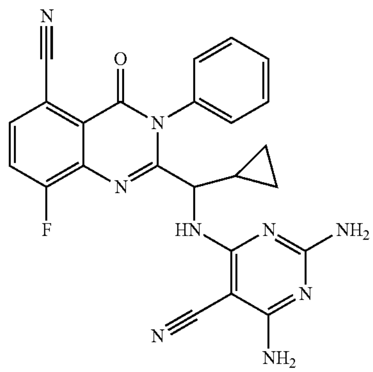 [SMILES: N#Cc1c(N)nc(N)nc1NC(c1nc2c(F)ccc(C#N)c2c(=O)n1-c1ccccc1)C1CC1] | 2-(cyclopropyl((2,6-diamino-5-cyanopyrimidin-4-yl)amino)methyl)-8-fluoro-4-oxo-3-phenyl-3,4-dihydroquinazoline-5-carbonitrile<br>a: (S)-enantiomer<br>b: (R)-enantiomer |
| 3. | 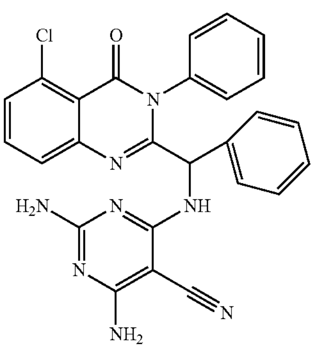 [SMILES: N#Cc1c(N)nc(N)nc1NC(c1ccccc1)c1nc2cccc(Cl)c2c(=O)n1-c1ccccc1] | 2,4-diamino-6-(((5-chloro-4-oxo-3-phenyl-3,4-dihydroquinazolin-2-yl)(phenyl)methyl)amino)pyrimidine-5-carbonitrile<br>a: (S)-enantiomer<br>b: (R)-enantiomer |
| 4. | 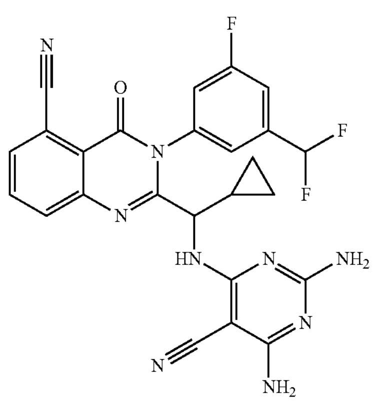 [SMILES: N#Cc1c(N)nc(N)nc1NC(c1nc2cccc(C#N)c2c(=O)n1-c1cc(F)cc(C(F)F)c1)C1CC1] | 2-(cyclopropyl((2,6-diamino-5-cyanopyrimidin-4-yl)amino)methyl)-3-(3-(difluoromethyl)-5-fluorophenyl)-4-oxo-3,4-dihydroquinazoline-5-carbonitrile<br>a: (S)-enantiomer<br>b: (R)-enantiomer |

TABLE 1-continued

Representative Compounds

| # | Structure | Name |
|---|-----------|------|
| 5. | 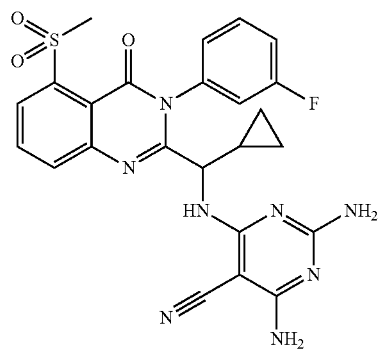 [SMILES: CS(=O)(=O)c1cccc2nc(C(Nc3nc(N)nc(N)c3C#N)C3CC3)n(-c3cccc(F)c3)c(=O)c12] | 2,4-diamino-6-((cyclopropyl(3-(3-fluorophenyl)-5-(methylsulfonyl)-4-oxo-3,4-dihydroquinazolin-2-yl)methyl)amino)pyrimidine-5-catbonitrile<br>a: (S)-enantiomer<br>b: (R)-enantiomer |
| 6. | 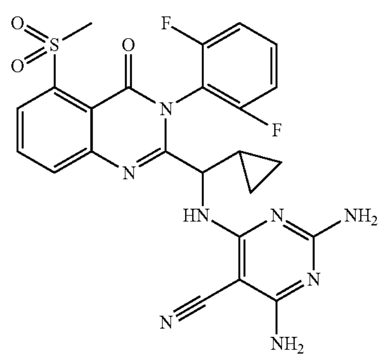 [SMILES: CS(=O)(=O)c1cccc2nc(C(Nc3nc(N)nc(N)c3C#N)C3CC3)n(-c3c(F)cccc3F)c(=O)c12] | 2,4-diamino-6-((cyclopropyl(3-(2,6-difluorophenyl-5-(methylsulfonyl)-4-oxo-3,4-dihydroquniazolin-2-yl)methyl)amino)pyrimidine-5-carbonitrile<br>a: (S)-enantiomer<br>b: (R)-enantiomer |
| 7. | 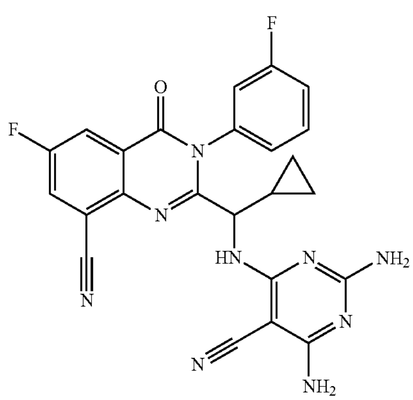 [SMILES: N#Cc1c(N)nc(N)nc1NC(c1nc2c(C#N)cc(F)cc2c(=O)n1-c1cccc(F)c1)C1CC1] | 2-(cyclopropyl((2,6-diamino-5-cyanopyrimidin-4-yl)amino)methyl)-6-fluoro-3-(3-fluorophenyl)-4-oxo-3,4-dihydroquinazoline-8-carbonitrile<br>a: (S)-enantiomer<br>b: (R)-enantiomer |
| 8. | 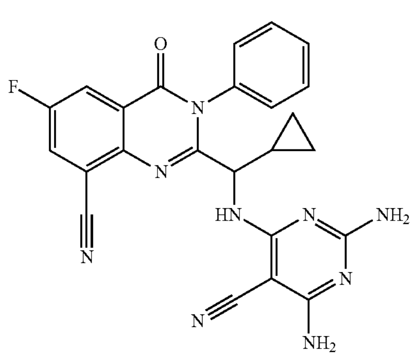 [SMILES: N#Cc1c(N)nc(N)nc1NC(c1nc2c(C#N)cc(F)cc2c(=O)n1-c1ccccc1)C1CC1] | 2-(cyclopropyl((2,6-diamino-5-cyanopyrimidin-4-yl)amino)methyl)-6-fluoro-4-oxo-3-phenyl-3,4-dihydroquinazoline-8-carbonitrile<br>a: (S)-enantiomer<br>b: (R)-enantiomer |

TABLE 1-continued

Representative Compounds

| # | Structure | Name |
|---|---|---|
| 9. | 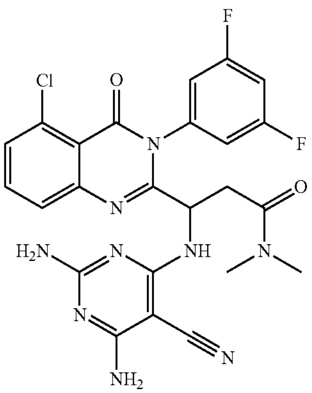 [SMILES: CN(C)C(=O)CC(Nc1nc(N)nc(N)c1C#N)c1nc2cccc(Cl)c2c(=O)n1-c1cc(F)cc(F)c1] | 3-(5-chloro-3-(3,5-difluorophenyl)-4-oxo-3,4-dihydroquinazolin-2-yl)-3-((2,6-diamino-5-cyanopyrimidin-4-yl)amino)-N,N-dimethylpropanamide<br>a: (S)-enantiomer<br>b: (R)-enantiomer |
| 10. | 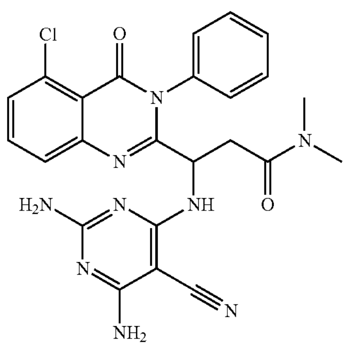 [SMILES: CN(C)C(=O)CC(Nc1nc(N)nc(N)c1C#N)c1nc2cccc(Cl)c2c(=O)n1-c1ccccc1] | 3-(5-chloro-4-oxo-3-phenyl-3,4-dihydroquinazolin-2-yl)-3-((2,6-diamino-5-cyanopyrimidin-4-yl)amino)-N,N-dimethylpropanamide<br>a: (S)-enantiomer<br>b: (R)-enantiomer |
| 11. | 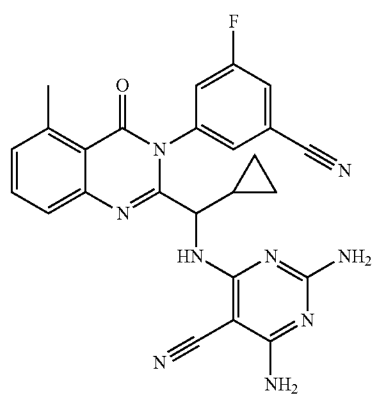 [SMILES: Cc1cccc2nc(C(Nc3nc(N)nc(N)c3C#N)C3CC3)n(-c3cc(F)cc(C#N)c3)c(=O)c12] | 2,4-diamino-6-(((3-(3-cyano-5-fluoroaphenyl)-5-methyl-4-oxo-3,4-dihydroquinazolin-2-yl)(cyclopropyl)methyl)amino)pyrimidine-5-carbonitrile<br>a: (S)-enantiomer<br>b: (R)-enantiomer |
| 12. | 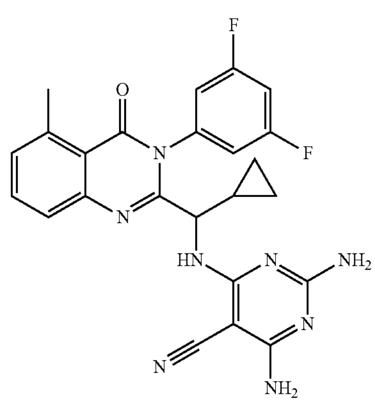 [SMILES: Cc1cccc2nc(C(Nc3nc(N)nc(N)c3C#N)C3CC3)n(-c3cc(F)cc(F)c3)c(=O)c12] | 2,4-diamino-6-((cyclopropyl(3-(3,5-difluorophenyl)-5-methyl-4-oxo-3,4-dihydroquinazolin-2-yl)methyl)amino)pyrimidine-5-carbonitrile<br>a: (S)-enantiomer<br>b: (R)-enantiomer |

TABLE 1-continued

Representative Compounds

| # | Structure | Name |
|---|---|---|
| 13. | 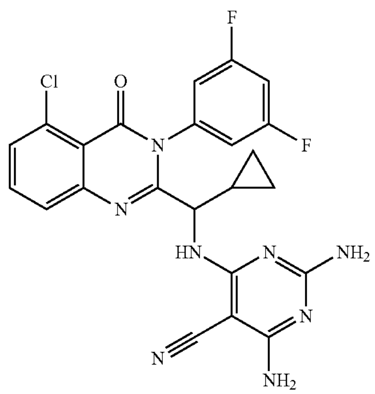 [SMILES: N#Cc1c(N)nc(N)nc1NC(c1nc2cccc(Cl)c2c(=O)n1-c1cc(F)cc(F)c1)C1CC1] | 2,4-diamino-6-(((5-chloro-3-(3,5-difluorophenyl)-4-oxo-3,4-dihydroquinazolin-2-yl)(cyclopropyl)methyl)amino)pyrimidine-5-carbonitrile<br>a: (S)-enantiomer<br>b: (R)-enantiomer |
| 14. | 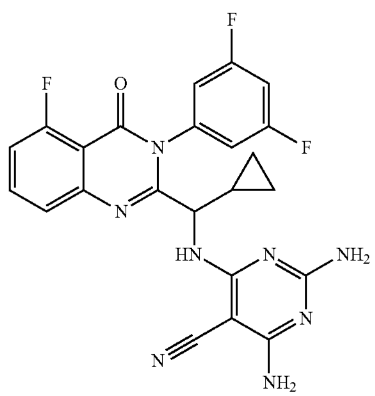 [SMILES: N#Cc1c(N)nc(N)nc1NC(c1nc2cccc(F)c2c(=O)n1-c1cc(F)cc(F)c1)C1CC1] | 2,4-diamino-6-((cyclopropyl(3-(3,5-difluorophenyl)-5-fluoro-4-oxo-3,4-dihydroquinazolin-2-yl)methyl)amino)pyrimidine-5-carbonitrile<br>a: (S)-enantiomer<br>b: (R)-enantiomer |
| 15. | 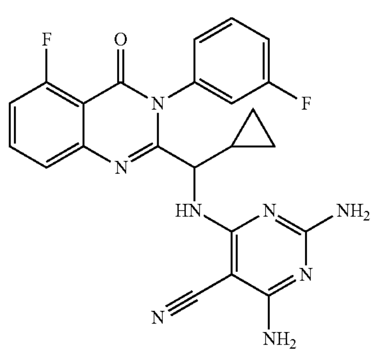 [SMILES: N#Cc1c(N)nc(N)nc1NC(c1nc2cccc(F)c2c(=O)n1-c1cccc(F)c1)C1CC1] | 2,4-diamino-6-((cyclopropyl(5-fluoro-3-(3-fluorophenyl)-4-oxo-3,4-dihydroquinazolin-2-yl)methyl)amino)pyrimidine-5-carbonitrile<br>a: (S)-enantiomer<br>b: (R)-enantiomer |
| 16. | 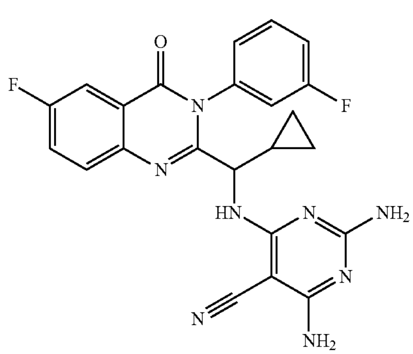 [SMILES: N#Cc1c(N)nc(N)nc1NC(c1nc2ccc(F)cc2c(=O)n1-c1cccc(F)c1)C1CC1] | 2,4-diamino-6-((cyclopropyl(6-fluoro-3-(3-fluorophenyl)-4-oxo-3,4-dihydroquinazolin-2-yl)methyl)amino)pyrimidine-5-carbonitrile<br>a: (S)-enantiomer<br>b: (R)-enantiomer |

TABLE 1-continued

Representative Compounds

| # | Structure | Name |
|---|---|---|
| 17. | 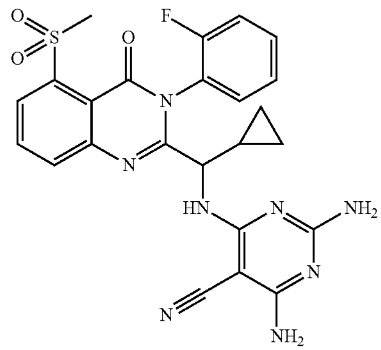 [SMILES: CS(=O)(=O)c1cccc2nc(C(Nc3nc(N)nc(N)c3C#N)C3CC3)n(-c3ccccc3F)c(=O)c12] | 2,4-diamino-6-((cyclopropyl(3-(2-fluorophenyl)-5-(methylsulfonyl)-4-oxo-3,4-dihydroquinazolin-2-yl)methyl)amino)pyrimidine-5-carbonitrile<br>a: (S)-enantiomer<br>a-1 and a-2: atropisomers<br>b: (R)-enantiomer<br>b-1 and b-2: atropisomers |
| 18. | 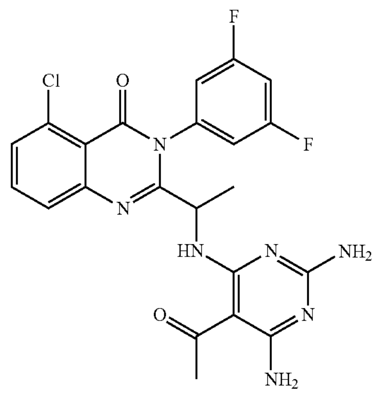 [SMILES: CC(=O)c1c(N)nc(N)nc1NC(C)c1nc2cccc(Cl)c2c(=O)n1-c1cc(F)cc(F)c1] | 2-(1-((5-acetyl-2,6-diaminopyrimidin-4-yl)amino)ethyl)-5-chloro-3-(3,5-difluorophenyl)quinazolin-4(3H)-one<br>a: (S)-enantiomer<br>b: (R)-enantiomer |

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use, "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" includes any compound that becomes a compound described herein when administered to a subject, e.g., upon metabolic processing of the prodrug.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the compounds described herein with carbon-carbon double bonds. Provided are also all tautomeric forms of the compounds of formula described herein.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds described herein or pharmaceutically acceptable salts, isomer, or a mixture thereof.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The compounds described herein or pharmaceutically acceptable salts, isomer, or a mixture thereof may be used for the treatment of diseases and/or conditions mediated by PI3K isomers, such as PI3Kδ. Thus, provided herein are methods for inhibiting one or more PI3K isomers. In one embodiment, provided are methods for inhibiting PI3Kδ activity using a described herein or pharmaceutically acceptable salts, isomer, or a mixture thereof. The PI3K isomers may be selectively or specifically inhibited. Additionally, the compounds may be used to inhibit PI3K activity therapeutically or prophylactically.

In some embodiments, the methods include administering a compound described herein or pharmaceutically acceptable salts, isomer, or a mixture thereof in a therapeutically effective amount to a subject (including a human) in need thereof. The method can be employed to treat a subject who has or is believed to have a disease or condition whose symptoms or pathology is mediated by PI3Kδ expression or activity.

In addition to the therapeutic uses described herein, certain compounds of the present application have one or more properties selected from: (i) selectivity to any PI3K isoforms, such as PI3Kδ; (ii) hepatocyte stability; and (iii) potency in a cellular assay. In one embodiment, certain compounds described herein or pharmaceutically acceptable salts, isomer, or a mixture thereof have selectivity to any PI3K isoforms, such as PI3Kδ. In other embodiments, certain compounds described have selectivity to at least PI3Kδ. In yet other embodiments, certain compounds have one of the properties selected from: (i) selectivity to PI3Kδ; (ii) hepatocyte stability; and (iii) potency in a cellular assay. In yet other embodiments, certain compounds have selectivity to PI3Kδ and hepatocyte stability; or selectivity to PI3Kδ and potency in a cellular assay; or hepatocyte stability and potency in a cellular assay. In some embodiments, certain compounds have selectivity to PI3Kδ, hepatocyte stability, and potency in a cellular assay.

In another embodiment, certain compounds have hepatocyte stability. Hepatocyte stability of a subject can be determined using any methods currently known in the art, including the methods described in the Examples below. For example, hepatocyte stability may be characterized based on clearance or half-life. In some embodiments, the half-life is greater than or about 3 hours, 4 hours, 5 hours, 6 hours, 7 hours, 8 hours, 9 hours, 10 hours, 11 hours, 12 hours, or 15 hours in human, hepatocytes.

In yet another embodiment, certain compounds have potency in a cellular assay. Potency in a cellular assay can be determined using any methods currently known in the art, including the methods described in the Examples below. In some embodiments, the activity in the cellular assay is less than 10 nM, 9 nM, 8 nM, 7 nM, 6 nM, 5 nM, 4 nM, 3 nM, 2 nM, 1 nM, 0.1 nM, or 0.01 nM. For example, certain compounds may have selectivity to at least one PI3K isoform, including PI3Kδ, and have hepatocyte stability based on a half-life of greater than 3 hours. As used herein, the term "potency," "potent," or variants thereof refer to a compound exhibiting an $IC_{50}$ value that is less than 100 nM. When comparing two compounds, the compound that exhibits a lower $IC_{50}$ value is referred to as a more potent inhibitor.

"Treatment" or "treating" is an approach for obtaining beneficial or desired results including clinical results. Beneficial or desired clinical results may include one or more of the following: a) Inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases, or disorders, or conditions that would benefit from certain treatment; for example, being treated with the PI3K inhibitor of the compounds according to the present application. In certain embodiments, the subject may be a human who (i) has not received any treatment including chemotherapy treatment, (ii) is substantially refractory to at least one chemotherapy treatment, (iii) is in relapse after treatment with chemotherapy, or both (I) and (ii). In some of embodiments, the subject is refractory to at least one, at least two, at least three, or at least four chemotherapy treatments (including standard or experimental chemotherapies).

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ activity. The therapeutically effective amount may vary depending on the subject and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process, "Inhibition of activity of PI3K isoforms" or variants thereof refer to a decrease in activity in any PI3K isoform (e.g., alpha, beta, gamma, or delta) as a direct or indirect response to the presence of a compound of the present application relative to the activity of PI3K isoform in the absence of the compound of the present application. "Inhibition of PI3Kδ activity" or variants thereof refer to a decrease in PI3Kδ activity as a direct or indirect response to the presence of a compound described herein relative to the activity of PI3Kδ in the absence of the compound described herein. In some embodiments, the inhibition of PI3Kδ activity may be compared in the same subject prior to treatment, or other subjects not receiving the treatment.

Without wishing to be bound to any theory, the decrease in PI3Kδ activity may be due to the direct interaction of the compound with PI3Kδ, or due to the interaction of the compounds described herein with one or more other factors that in turn affect PI3Kδ activity. For example, the presence of the compounds of any of the foregoing formulae may decrease PI3Kδ activity by directly binding to the PI3Kδ, by causing (directly or indirectly) another factor to decrease PI3Kδ activity, or by (directly or indirectly) decreasing the amount of PI3Kδ present in the cell or organism.

The terms "PI3K isoform selective inhibitor" generally refers to a compound that inhibits the activity of one or more PI3K isoforms more effectively than the other remaining PI3K isoforms. By way of example, the term "PI3Kδ selective inhibitor" generally refers to a compound that inhibits the activity of the PI3Kδ isoform more effectively than other isoforms of the PI3K family (e.g., PI3K α, β, or γ). The term "PI3Kα selective inhibitor" generally refers to a compound that inhibits the activity of the PI3Kα isoform more effectively than other isoforms of the PI3K family (e.g., PI3K β, δ, or γ). The term "PI3Kβ selective inhibitor" generally refers to a compound that inhibits the activity of the PI3Kβ isoform more effectively than other isoforms of the PI3K family (e.g., PI3K α, δ, or γ). The term "dual PI3Kα/β selective inhibitor generally refers to a compound that inhibits the activity of the PI3Kα and PI3Kβ isoforms more effectively than other isoforms of the PI3K family (e.g., PI3K δ or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the concentration that inhibits 50% of the activity in a biochemical assay, i.e., the 50% inhibitory concentration or "$IC_{50}$". $IC_{50}$ determinations can be accomplished using conventional techniques known in the art, including the techniques describes in the Examples below. In general, an $IC_{50}$ can be determined by measuring the activity of a given enzyme in the presence of a range of concentrations of the compound under study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

In one embodiment, a PI3Kδ selective inhibitor is a compound that exhibits a 50% inhibitory concentration ($IC_{50}$) with respect to PI3Kδ that is at least 10-fold, in another aspect at least 20-fold, and in another aspect at least 30-fold, lower than the $IC_{50}$ value with respect to any or all of the other Class I PI3K family members. In another embodiment, a PI3Kδ selective inhibitor is a compound that exhibits an $IC_{50}$ with respect to PI3Kδ that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kδ selective inhibitor is typically administered in an amount such that it selectively inhibits PI3Kδ activity, as described above.

In one embodiment, a PI3Kα selective inhibitor is a compound that exhibits a 50% inhibitory concentration ($IC_{50}$) with respect to PI3Kβ that is at least 10-fold, in another aspect at least 20-fold, and in another aspect at least 30-fold, lower than the $IC_{50}$ value with respect to any or all of the other Class I PI3K family members. In another embodiment, a PI3Kα selective inhibitor is a compound that exhibits an $IC_{50}$ with respect to PI3Kα that is at least 50-fold, in another aspect at least 100-fold, in an additional aspect at least 200-fold, and in yet another aspect at least 500-fold, lower than the $IC_{50}$ with respect to any or all of the other PI3K. Class I family members. A PI3Kα selective inhibitor is typically administered in an amount such that it selectively inhibits PI3Kα activity, as described above In one embodiment, a PI3Kβ selective inhibitor is a compound that exhibits a 50% inhibitory concentration ($IC_{50}$) with respect to PI3Kβ that is at least 10-fold, in another aspect at least 20-fold, and in another aspect at least 30-fold, lower than the $IC_{50}$ value with respect to any or all of the other Class I PI3K family members. In another embodiment, a PI3Kβ selective inhibitor is a compound that exhibits an $IC_{50}$ with respect to PI3Kβ that is at least 50-fold, in another aspect at least 100-fold, in an additional aspect at least 200-fold, and in yet another aspect at least 500-fold, lower than the $IC_{50}$ with respect to any or all of the other PI3K Class I family members. A PI3Kβ selective inhibitor is typically administered in an amount such that it selectively inhibits PI3Kβ activity, as described above.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of a PI3Kδ selective inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds may be further characterized to examine the safety or tolerance dosage in human or non-human subjects. Such properties may be examined using commonly known methods to those skilled in the art.

Compared to other PI3K isoforms, PI3Kδ is generally expressed in hematopoietic cells. Consequently, the direct effects of selective inhibitors of PI3Kδ can be observed in non-hematopoietic cells. Hematopoietic cells typically differentiate into either lymphoid progenitor cells or myeloid progenitor cells, both of which ultimately differentiate into various mature cell types including leukocytes. Aberrant proliferation of hematopoietic cells of one type often interferes with the production or survival of other hematopoietic cell types, which can result in compromised immunity, anemia, and/or thrombocytopenia. The methods described herein may treat aberrant proliferation of hematopoietic cells by inhibiting aberrant proliferation of hematopoietic cells. As a result, these methods may also ameliorate the symptoms and secondary conditions that result from a primary effect such as excessive system or localized levels of leukocytes or lymphocytes.

In some embodiments, the compounds described herein may be used to treat subjects having various disease states, disorders, and conditions (also collectively referred to as "indications") involving aberrant proliferation of hematopoietic cells (including excessive production of lymphoid progenitor cell-derived cells and/or myeloid progenitor cell-derived cells). Such indications may include, for example, leukemias, lymphomas, myeloproliferative disorders, myelodysplastic syndromes, and plasma cell neoplasms. In certain embodiments, the compounds described herein may be used to treat hematologic malignancies, inflammation, autoimmune disorders, allergic conditions, cardiovascular disease, and autoimmune diseases. In certain embodiments, allergic conditions may include all forms of hypersensitivity.

In other embodiments, the compounds described herein may be used to treat cancers that are mediated by, dependent on or associated with PI3K activity, such as PI3Kδ activity. In certain embodiments, the disease is a hematologic malignancy. In certain embodiments, the disease is lymphoma, multiple myeloma, or leukemia. In particular embodiments, the hematologic malignancy is leukemia or lymphoma. In specific embodiments, the disease is acute lymphocytic leukemia (ALL), acute myeloid leukemia (AML), chronic lymphocytic leukemia (CLL), small lymphocytic lymphoma (SLL), myelodysplasia syndrome (MDS), myeloproliferative disease (MPD), chronic myeloid leukemia (CML), juvenile myelomonocytic leukemia (JMML), multiple myeloma (MM), Hodgkin lymphoma, indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), minimal residual disease (MRD), T-cell lymphoma, B-cell lymphoma, diffuse large B-cell lymphoma (DLBCL), T-cell acute lymphoblastic leukemia (T-ALL), B-cell acute lymphoblastic leukemia (B-ALL), lymphoplamacytic lymphoma, marginal zone lymphoma, or Burkitt lymphoma. In one embodiment, the disease is T-cell acute lymphoblastic leukemia (T-ALL), or B-cell acute lymphoblastic leukemia (B-ALL). It should be understood that the non-Hodgkin lymphoma may, in certain embodiments, encompass the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL).

In other embodiments, the disease is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease is an autoimmune disease. In particular embodiments, the autoimmune disease is systemic lupus erythematosus (SLE), myestenia gravis, rheumatoid arthritis (RA), acme disseminated encephalomyelitis, idiopathic thrombocytopenic purpura, multiple sclerosis (MS), psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

Provided is a method for treating a subject, who has or is suspected of having a disease or condition responsive or believed to be responsive to the inhibition of PI3Kδ activity by administering to the subject the compound described herein or pharmaceutically acceptable salts, isomer, or a mixture thereof. Provided is also a method of inhibiting kinase activity of a phosphatidylinositol 3-kinase delta polypeptide by contacting the polypeptide with the compound described herein or pharmaceutically acceptable salts, isomer, or a mixture thereof. Provided is also a method of disrupting leukocyte function comprising contacting the leukocytes with an effective amount of a compound described herein or pharmaceutically acceptable salts, isomer, or a mixture thereof in a subject in need thereof (e.g., a human). Provided is also a method of inhibiting a growth or a proliferation of cancer cells of hematopoietic origin comprising contacting the cancer cells with an effective amount of a compound described herein or pharmaceutically acceptable salts, isomer, or a mixture thereof.

Combination Therapies

The compounds according to the present application may be used in combination with one or more additional therapeutic agents. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In one embodiment, the application provides a product comprising a compound described herein and an additional therapeutic agent as a combined preparation for simultaneous, separate or sequential use in therapy, e.g. a method of treating a disease, disorder, or condition that is mediated by PI3K isoforms.

In one embodiment, the compounds of the present application may be used in combination with one or more additional therapeutic agent that are being used and/or developed to treat cancers or inflammatory disorders. The one or more additional therapeutic agent may be an inhibitor to PI3K such as PI3Kγ, PI3Kδ, and/or PI3Kα, Janus kinase (JAK) such as JAK1, JAK2 and/or JAK3, spleen tyrosine kinase (SYK), Bruton's tyrosine kinase (BTK), bromodomain containing protein inhibitor (BHD) such as BRD4, a lysyl oxidase protein (LOX), lysyl oxidase-like protein (LOXL) such as LOXL1-5, matrix metalloprotease (MMP) such as MMP 1-10, adenosine A2B receptor (A2B), isocitrate dehydrogenase (IDH) such as IDH1, apoptosis signal-regulating kinase (ASK) such as ASK1, serine/threonine kinase TPL2, discoidin domain receptor (DDR) such as DDR1 and DDR2, histone deacetylase (HDAC), protein kinase C (PKC), or any combination thereof.

One, two, three, or more of the therapeutic agents (e.g. a PI3K inhibitor, a JAK inhibitor, a SYK inhibitor, a BTK inhibitor, a BRD4 inhibitor, a LOXL2 inhibitor, a MMP9 inhibitor, a A2B inhibitor, an IDH inhibitor, an ASK inhibitor, a TPL2 inhibitor, a DDR1 inhibitor, a TBK inhibitor, a HDAC inhibitor, a PKC inhibitor) may be further used or combined with a chemotherapeutic agent, an immunotherapeutic agent, a radiotherapeutic agent, an anti-neoplastic agent, an anti-cancer agent, an anti-fibrotic agent, an anti-angiogenic agent, a therapeutic antibody, or any combination thereof.

Also, the therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, matrix metallopeptidase, bromodomain-containing protein, adenosine A2B receptor, isocitrate dehydrogenase, serine/threonine kinase TPL2, discoidin domain receptor, serine/threonine-protein kinases, IKK, MEK, EGFR, histone deacetylase, protein kinase C, or any combination thereof. In certain embodiments, the therapeutic agent may be selected from a PI3K (including PI3Kγ, PI3Kδ, PI3Kβ, PI3Kα, and/or pan-PI3K) inhibitor, a JAK (Janus kinase, including JAK1, JAK2, and/or JAK3) inhibitor, a SYK (spleen tyrosine kinase) inhibitor, a BTK (Bruton's tyrosine kinase) inhibitor, an A2B (adenosine A2B receptor) inhibitor, an ACK (activated CDC kinase, including ACK1) inhibitor, an ASK (apoptosis signal-regulating kinase, including ASK1) inhibitor, Auroa kinase, a BRD (bromodomain-containing protein, including BRD4) inhibitor, a Bcl (B-cell CLL/lymphoma, including Bcl-1 and/or Bcl-2) inhibitor, a CAK (CDK-activating kinase) inhibitor, a CaMK (calmodulin-dependent protein kinases) inhibitor, a CDK (cyclin-dependent kinases, including CDK1, 2, 3, 4, and/or 6) inhibitor, a CK (casein kinase, including CK1 and/or CK2) inhibitor, a DDR (discoidin domain receptor, including DDR1 and/or DDR2) inhibitor, a EGFR inhibitor, a FXR (farnesoid x receptor) inhibitor, a FAK (focal adhesion kinase) inhibitor, a GSK (glycogen synthase kinase) inhibitor, a HDAC (histone deacetylase) inhibitor, an IDO (indoleamine 2,3-dioxygenase) inhibitor, an IDH (isocitrate dehydrogenase, including IDH1) inhibitor, an IKK (1-Kappa-B kinase) inhibitor, a KDM5 (lysine demethylase) inhibitor, a LCK (lymphocyte-specific protein tyrosine kinase) inhibitor, a LOX (lysyl oxidase) inhibitor, a LOXL (lysyl oxidase like protein, including LOXL1, LOXL2, LOXL3, LOXL4, and/or LOXL5) inhibitor, a MTH (mut T homolog) inhibitor, a MEK (mitogen-activated protein kinase kinase) inhibitor, a matrix metalloprotease (MMP, including MMP2 and/or MMP9) inhibitor, a mitogen-activated protein kinases (MAPK) inhibitor, a PD-1 (programmed cell death protein 1) inhibitor, a PD-L1 (programmed death-ligand 1) inhibitor, a PDGF (platelet-derived growth factor) inhibitor, a phosphorylase kinase (PK) inhibitor, a PLK (polo-like kinase, including PLK1, 2, 3) inhibitor, a protein kinase (PK, including protein kinase A, B, C) inhibitor, a STK (serine/threonine kinase) inhibitor, a STAT (signal transduction and transcription) inhibitor, a serine/threonine-protein kinase inhibitor, a TBK (tank-binding kinase) inhibitor, a TLR (toll-like receptor modulators, including TLR-1, TLR-2, TLR-3, TLR-4, TLR-5, TLR-6, TLR-7, TLR-8, TLR-9, TLR-10, TLR-11, TLR-12, and/or TLR-13) inhibitor, a TK (tyrosine kinase) inhibitor, a TPL2 (serine/threonine kinase) inhibitor, a NEK9 inhibitor, an Abl inhibitor, a p38 kinase inhibitor, a PYK inhibitor, a PYK inhibitor, a c-Kit inhibitor, a NPM-ALK inhibitor, a Flt-3 inhibitor, a c-Met inhibitor, a KDR inhibitor, a TIE-2 inhibitor, a VEGFR inhibitor, a SRC inhibitor, a HCK inhibitor, a LYN inhibitor, a FYN inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiments, the JAK inhibitor is N-(cyanomethyl)-4-[2-(4-morpholinoanilino)pyrimidin-4-yl]benzamide as named by ChemDraw (may also be referred to as CYT0387 or momelotinib) and may be synthesized by the methods described in U.S. Pat. No. 8,486,941. In certain embodiment, the SyK inhibitor is 6-(1H-indazol-6-yl)-N-(4-morpholinophenyl) imidazo[1,2-a]pyrazin-8-amine as named by ChemDraw (may also be referred to as 6-(1H-indazol-6-yl)-N-[4-(morpholin-4-yl)phenyl]imidazo[1,2-a]pyrazin-8-amine) and may be synthesized by the methods described in U.S. Pat. No. 8,450,321. In other embodiments, the BTK inhibitor is (S)-6-amine-9-(1-(but-2-ynoyl)pyrrolidin-3-yl)-7-(4-phenoxyphenyl)-7H-purin-8(9H)-one as named by ChemDraw (may also be 6-amino-9-[(3R)-1-(2-butynoyl)-3-pyrrolidinyl]-7-(4-phenoxyphenyl)-7,9-dihydro-8H-purin-8-one) and may be synthesized by the methods in U.S. Pat. No. 8,557,803.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, ammoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothecin), corticosteroids (cortisone, dexamethasone, hydrocortisone, methylprednisolone, prednisone, and prednisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophyeins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformithine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK®; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL® and docetaxel (TAXOTERE®); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine®); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen trioxifene, keoxifene, LY117018, onapristone, and toremifene (Fareston®); inhibitors of the enzyme aromatase, which regulates estrogen production in the adrenal glands, such as, for example, 4(5)-imidazoles, aminoglutethimide, megestrol acetate (Megace®), exemestane, formestane, fadrozole, vorozole (Rivisor®), letrozole (Femara®), and anastrozole (Arimidex®); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2

(3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-2-carboxyphenyl-4-chloroanthronilic acid disodium or "CCA", thalidomide; angiostatic steroid, carboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminopropionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,5059,714; U.S. Pat. No. 5,120,764; U.S. Pat. No. 5,182,297; U.S. Pat. No. 5,252,608 (relating to 2-(1-naphthayloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butenoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients: such as abagovomab, adecatumumab, afutuzumab, alemtuzumab, altumomab, amatuximab, anatumomab, arcitumomab, bavituximab, bectamomab, bevacizumab, bivatuzumab, blinatumomab, brentuximab, cantuzumab, catumaxomab, cetorimab, citatuzumab, cixatumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzurmab, indatuximab, inotuzumab, intetumumab, ipilimumab, iratumumab, labetuzumab, lexatumumab, lintuzumab, lorvotuzumab, lucatumumab, mapatumomab, matuzumab, milatuzumab, minretumomab, mitumomab, moxetumomab, namatumab, naptumomab, necitumumab, nimotuzumab, nofetumomabn, ocaratuzumab, ofatumumab, olaratumab, onarutzumab, oportuzumab, oregovomab, paaitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131. Obinutuzumab is also an example of an immunotherapeutic agent.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" The New England Journal of Medicine 2008, 359(6), p.

613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, Mab-Campath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta aletheine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alia, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCI-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP). An additional example includes ABT-199.

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Kits

Provided herein are also kits that include a compound of the present application or a pharmaceutically acceptable salt, stereoisomer, prodrug, or solvate thereof, and suitable packaging. Provided herein are also kits that include a compound of formula (J), (I), (J-1), (J-1a), (J-1b), (IA-1), (IA-2), (IB-1), (IB-2), (IB-3), or (IB-4), or a pharmaceutically acceptable salt, stereoisomer, prodrug, or solvate thereof, and suitable packaging. In one embodiment, a kit further includes instructions for use. In one aspect, a kit includes a compound of formula (J-1), (J-1a), (J-1b), (IA-1), (IA-2), (IB-1), (IB-2), (IB-3), or (IB-4), or a pharmaceutically acceptable salt, stereoisomer, prodrug, or solvate thereof, and a label and/or instructions for use of the compounds in the treatment of the indications, including the diseases or conditions, described herein. In one aspect, a kit includes a compound selected from Compound 1 to 116, or a pharmaceutically acceptable salt, stereoisomer, prodrug, or solvate thereof, and a label and/or instructions for use of the compounds in the treatment of the indications, including the diseases or conditions, described herein.

Provided herein are also articles of manufacture that include a compound described herein or pharmaceutically acceptable salts, isomer, or a mixture thereof in a suitable container. The container may be a vial, jar, ampoule, pre-loaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds described herein or pharmaceutically acceptable salts, isomer, or a mixture thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa., 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or pharmaceutically acceptable salts, isomer, or a mixture thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or pharmaceutically acceptable salts, isomer, or a mixture thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of formula (J), (J1-a), (J1-b), (IA-1), (IA-2), (IB-1), (IB-2), (IB-3), or (IB-4)) may be between about 1 mg and 4,000 mg, between about 2,000 to 4,000 mg/day, between about 1 to 2,000 mg/day, between about 1 to 1,000 mg/day, between about 1.0 to 500 mg/day, between about 20 to 500 mg/day, between about 50 to 300 mg/day, between about 75 to 200 mg/day, or between about 15 to 150 mg/day. Daily dosage of a compound of the present application (e.g. compounds of formula (J), (I), (IA-1), (IA-2), (IB-1), (IB-2), (IB-3), or (IB-4)) also falls within the ranges described above. Daily dosage of a compound selected from Compounds 1 to 116 also falls within the ranges described above.

When administered orally, the total daily dosage for a human subject may be between 1 mg and 1,000 mg, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

After synthesis, the compounds may be isolated in the form of a free base or a trifluoroacetic acid salt and further characterized by NMR. The resulting compounds and their NMR characterizations may represent either the free base or salt form. The ratio of parent compound and corresponding salt is not determined.

Compounds of Formula I

One method of preparing compounds of formula (I) is shown in Reaction Scheme I.

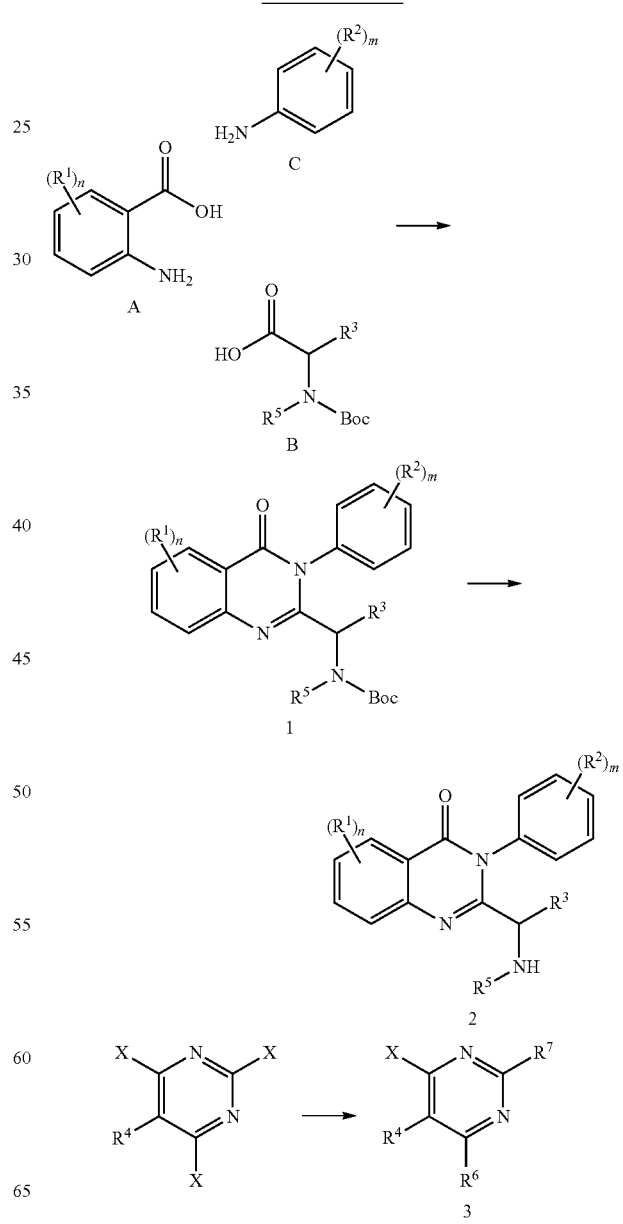

Reaction Scheme I

-continued

2 + 3 ⟶ 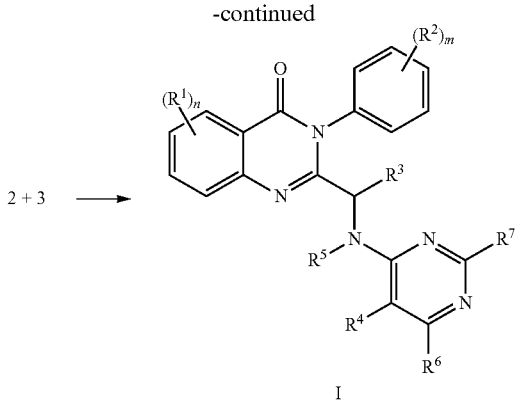

I

Step 1—Preparation of a Compound of Formula (1)

The compound of formula (1) can be made by combining compounds (A), (B) and (C) in the presence of a dehydrating agent. Compounds (A), (B) and (C) are commercially available or can be made by methods known in the art. With respect to compound (A), $R^1$ is as defined herein. With respect to compound (B), $R^3$ and $R^5$ are as defined herein. With respect to compound (C), $R^2$ is as defined herein. Compound (A) can be mixed with Compound (B) in the presence of a coupling agent such as diphenyl phosphite in a solvent such as pyridine. After stirring at a temperature between ambient and 100° C. for between 1 and 5 hours, compound (C) is added. After further stirring at a temperature between ambient and 100° C. for between 5 and 24 hours, the reaction mixture is allowed to cool to room temperature. To extract the compound of formula (1), an organic solvent such as ethyl acetate (EtOAc) may be added, followed by washing with, mild acid, water, and brine. The organic phase can be concentrated to obtain the compound of formula (1). Additional compounds may be prepared by alkylation of compounds of formula (1) in which $R^1$ is OH. For example a compound of formula (1), $R^1$=OH, is mixed with a reagent containing a leaving group, such as a halide or mesylate, in the presence of a base, such as $Cs_2CO_3$ or $K_2CO_3$, in a solvent such as DMF or DMSO. After stirring at a temperature between ambient and 110° C. for between 5 and 24 hours, the reaction mixture is allowed to cool to room temperature and worked up under standard conditions. Additional compounds may be prepared by coupling reactions with compounds of formula (1) in which $R^1$ is halo, such as iodo, bromo, or chloro. For example a compound of formula (1), $R^1$=Br, may be mixed with a double bond containing compound, such as acrylamide, allyl alcohol, allylcyclohexane, or acrolein, in the presence of a base, such as Hunig's base, $Cs_2CO_3$ or $K_2CO_3$, and metal catalyst such as chloro(2-dicyclohexylphosphino-2',4',6'-triisopropyl-1,1'-biphenyl)[2-(2'-amino-1,1'-biphenyl)]palladium(II) in a solvent such as DMF. After stirring at a temperature between ambient and 110° C. for between 5 and 24 hours, the reaction mixture is allowed to cool to room temperature and worked up under standard conditions. If $R^1$ contains a double bond, it can be reduced under standard conditions such as hydrogenation in the presence of a catalyst, such as Pd/C or Pt in a solvent such as EtOAc, EtOH, or MeOH under ambient or elevated pressure. If $R^1$ contains an aldehyde, it can be converted to an amine under standard conditions such as reaction with a primary or secondary amine in the presence of sodium cyanoborohydride or sodium triacetoxyborohydride, in a solvent such as DCM, EtOAc, EtOH, or MeOH under ambient or elevated temperature. Compounds where $R^1$ is $SO_2R$ may be prepared by reaction of a compound (1) where $R^1$ is halo, such as Br, with sodium alkyl or aryl sulfinate in the presence of a base, such as $Cs_2CO_3$ or $K_2CO_3$, and a catalyst such as CuI, in a solvent such as DMSO, and heated at a temperature between ambient and 120° C. Further, compounds where $R^1$ is $SO_2R$ may be prepared by first reacting a compound (1) where $R^1$ is halo, such as Br, with a thiol in the presence of a base such as Hunig's base, a catalyst such as $Pd(dba)_2$, a ligand such as Xantphos, and (S)-proline in a solvent such as dioxane, and heated at a temperature between ambient and 140° C. The resulting thiol can be oxidized by treatment with an oxidizing agent, such as oxone in an aqueous solvent such as a mixture of THF and water. Additionally for compounds that have a latent amine which is desired to be acylated, the amine may be reacted with an acid in the presence of base, such as Hunig's base or triethylamine and a coupling agent such as HATU or HOBT to give the amide. The compound of formula (1) may be purified by any suitable methods known in the art, such as chromatography on silica gel. Alternatively, the compound of formula (1) may be used in the next step without purification.

Step 2—Preparation of a Compound of Formula (2)

The compound of formula (2) can be made by removing the protecting group(s) from the compound of formula (1). The compound of formula (1) is dissolved in a suitable solvent and treated with a suitable acid. Suitable solvents may include, for example, dichloromethane,-dioxane, or other suitable solvents. Suitable acids may include, for example, trifluoroacetic acid, hydrochloric acid, or boron tribromide ($BBr_3$). The reaction can be carried out at temperatures between −78° C. to ambient temperature. On reaction completion, solvent is removed to obtain the compound of formula (2). In the case of a reaction using $BBr_3$ the reaction may first be treated with MeOH before an aqueous work-up to obtain a compound of formula (2).

Step 3—Preparation of a Compound of Formula (3)

The compound of formula (3) can be made by treating 5-substituted-2,4,6-trihalopyrimidine with ammonium hydroxide in a suitable solvent such as dioxane, where the halo is either chloro or fluoro. The reaction is carried out at an elevated temperature between 30 and 80° C. for a suitable time, typically between 2 and 8 hours or when the reaction is complete. Upon completion, water is added to the cooled solution, and the precipitate is collected by filtration. The nitrile can be converted to the carboxamide under standard conditions.

Step 4—Preparation of a Compound of Formula (I)

The compound of formula (I) can generally be prepared by coupling compound of formula (2) and compound of formula (3) in the presence of a suitable base in a suitable solvent. An example of a suitable base is diisopropylethylamine. An example of a suitable solvent is N-methylpyrrolidone (NMP), DMF, DMSO, isopropanol, or ethanol. The reaction is typically performed at a temperature between 30° C. to 150° C. for about 30 minutes to 120 hours. Alternatively the reaction can be performed in a microwave at a temperature between 100° C. to 150° C. for about 30 minutes to 24 hours. Water can be added to quench the reaction upon completion, and the precipitate may be filtered and then dissolved in an organic solvent such as dichloromethane (DCM). The product can be isolated by methods known in the art, for example by removal of solvent under reduced pressure. The product can be purified using any suitable methods known in the art, for example, chromatography of the residue on a silica column.

It should be understood that the compounds of formula (I) can be prepared according to the methods provided in Reaction Scheme 1, starting from materials known to one of skill in the art.

Example 1a. Preparation of a Compound of Formula (1)

A. Preparation of a Compound of Formula (1) in which n is 1, $R^1$ is fluoro, m is 1, $R^2$ is fluoro, $R^5$ is hydrogen, and $R^3$ is cyclopropyl.

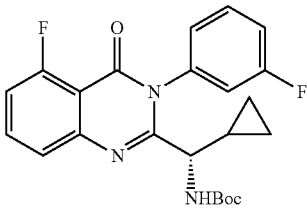 [SMILES: CC(C)(C)OC(=O)N[C@H](c1nc2cccc(F)c2c(=O)n1-c1cccc(F)c1)C1CC1]

Diphenyl phosphite (1.6 mL, 9 mmol) was added to a solution of 2-amino-6-fluorobenzoic acid (380 mg, 2 mmol) and (S)-2-(tert-butoxycarbonylamino)-2-cyclopropylacetic acid (680 mg, 3 mmol) in pyridine (2 mL). The reaction mixture was stirred at 40° C. for 1 hour. 3-Fluoroaniline (330 mg, 3 mmol) was then added to the reaction mixture, which was then stirred at 50° C. for 16 hours. The reaction mixture was cooled to room temperature. This mixture was purified by column chromatography on $SiO_2$ eluting with EtOAc in hexanes (0-75%) to afford (S)-tert-butyl (cyclopropyl(5-fluoro-3-(3-fluorophenyl)-4-oxo-3,4-dihydroquinazolin-2-yl)methyl)carbamate.

B. Following the procedure described in Example 1A and Reaction Scheme I, below compounds of formula (1) were prepared:

(S)-tert-butyl ((5-chloro-4-oxo-3-phenyl-3,4-dihydroquinazolin-2-yl)(phenyl)methylcarbamate;
(S)-tert-butyl ((5-cyano-3-(3-(difluoromethyl)-5-fluorophenyl)-4-oxo-3,4-dihydroquinazolin-2-yl)(cyclopropyl)methyl)carbamate;
(S)-tert-butyl cyclopropyl(3-(3-fluorophenyl)-5-(methylsulfonyl)-4-oxo-3,4-dihydroquinazolin-2-yl)methyl)carbamate;
(S)-tert-butyl (cyclopropyl(3-(2,6-difluorophenyl)-5-(methylsulfonyl)-4-oxo-3,4-dihydroquinazolin-2-yl)methyl)carbamate;
(S)-tert-butyl (cyclopropyl(3-(2-fluorophenyl)-5-(methylsulfonyl)-4-oxo-3,4-dihydroquinazolin-2-yl)methyl)carbamate;
(S)-tert-butyl (cyclopropyl(6-fluoro-3-(3-fluorophenyl)-8-iodo-4-oxo-3,4-dihydroquinazolin-2-yl)methyl)carbamate;
(S)-tert-butyl (cyclopropyl(6-fluoro-3-phenyl-8-iodo-4-oxo-3,4-dihydroquinazolin-2-yl)methyl)carbamate;
(S)-tert-butyl (1-(5-chloro-3-(3,5-difluorophenyl-4-oxo-3,4-dihydroquinazolin-2-yl)-3-(dimethylamino)-3-oxopropyl)carbamate;
(S)-tert-butyl (1-(5-chloro-4-oxo-3-phenyl-3,4-dihydroquinazolin-2-yl)-3-(dimethylamino)-3-oxopropyl)carbamate;
(S)-tert-butyl ((3-(3-cyano-5-fluorophenyl)-5-methyl-4-oxo-3,4-dihydroquinazolin-2-yl)(cyclopropyl)methyl)carbamate;
(S)-tert-butyl (cyclopropyl(3-(3,5-difluorophenyl)-5-methyl-4-oxo-3,4-dihydroquinazolin-2-yl)methyl)carbamate;
(S)-tert-butyl ((5-chloro-3-(3,5-difluorophenyl)-4-oxo-3,4-dihydroquinazolin-2-yl)(cyclopropyl)methyl)carbamate;
(S)-tert-butyl ((5-fluoro-3-(3,5-difluorophenyl)-4-oxo-3,4-dihydroquinazolin-2-yl)(cyclopropyl)methyl)carbamate;
(S)-tert-butyl (cyclopropyl(6-fluoro-3-(3-fluorophenyl)-4-oxo-3,4-dihydroquinazolin-2-yl)methyl)carbamate;
(2S,4S)-tert-butyl 2-(5-chloro-3-(3,5-difluorophenyl)-4-oxo-3,4-dihydroquinazolin-2-yl)-4-methoxypyrrolidine-1-carboxylate;
(S)-tert-butyl 2-(5-chloro-3-(3,5-difluorophenyl)-4-oxo-3,4-dihydroquinazolin-2-yl)azetidine-1-carboxylate;
(S)-tert-butyl 2-(5-bromo-4-oxo-3-phenyl-3,4-dihydroquinazolin-2-yl)pyrrolidine-1-carboxylate;
(S)-tert-butyl 2-(5-chloro-3-(3,5-difluorophenyl)-4-oxo-3,4-dihydroquinazolin-2-yl)pyrrolidine-1-carboxylate;
(S)-tert-butyl 2-(5-chloro-3-(3,5-difluorophenyl)-8-methyl-4-oxo-3,4-dihydroquinazolin-2-yl)pyrrolidine-1-carboxylate;
(S)-tert-butyl 2-(8-chloro-3-(3,5-difluorophenyl)-4-oxo-3,4-dihydroquinazolin-2-yl)pyrrolidine-1-carboxylate;
(S)-tert-butyl 2-(3-(3,5-difluorophenyl)-8-methyl-4-oxo-3,4-dihydroquinazolin-2-yl)pyrrolidine-1-carboxylate;
(S)-tert-butyl 2-(3-(3,5-difluorophenyl)-5-fluoro-4-oxo-3,4-dihydroquinazolin-2-yl)pyrrolidine-1-carboxylate;
(S)-tert-butyl 2-(5-chloro-3-(3-cyano-5-fluorophenyl-4-oxo-3,4-dihydroquinazolin-2-yl)pyrrolidine-1-carboxylate;
(S)-tert-butyl 2-(5,8-dichloro-4-oxo-3-(3-sulfamoylphenyl)-3,4-dihydroquinazolin-2-yl)pyrrolidine-1-carboxylate;
(S)-tert-butyl 2-(3-(3-(difluoromethyl)phenyl)-8-iodo-3,4-dihydroquinazolin-2-yl)pyrrolidine-1-carboxylate;
(S)-tert-butyl 2-(8-iodo-4-oxo-3-phenyl-3,4-dihydroquinazolin-2-yl)pyrrolidine-1-carboxylate;
(2S,4S)-tert-butyl 2-(5-chloro-3-(3,5-difluorophenyl)-4-oxo-3,4-dihydroquinazolin-2-yl)-4-fluoropyrrolidine-1-carboxylate;
(2S,4S)-tert-butyl 2-(5-chloro-4-oxo-3-phenyl-3,4-dihydroquinazolin-2-yl)-4-methylpyrrolidine-1-carboxylate;
(S)-tert-butyl (1-(5-chloro-3-(3,5-difluorophenyl)-4-oxo-3,4-dihydroquinazolin-2-yl)ethyl)carbamate;
(S)-tert-butyl (1-(5-chloro-4-oxo-3-phenyl-3,4-dihydroquinazolin-2-yl)ethyl)carbamate;
(R)-tert-butyl 3-(5-chloro-4-oxo-3-phenyl-3,4-dihydroquinazolin-2-yl)morpholine-4-carboxylate;
(S)-tert-butyl (1-(3-(3,5-difluorophenyl)-5-fluoro-4-oxo-3,4-dihydroquinazolin-2-yl)methyl)carbamate;
(2S,4R)-tert-butyl 4-amino-2-(5-chloro-4-oxo-3-phenyl-3,4-dihydroquinazolin-2-yl)pyrrolidine-1-carboxylate;
(2S,4R)-tert-butyl 4-amino-2-(5-chloro-3-(3,5-difluorophenyl)-4-oxo-3,4-dihydroquinazolin-2-yl)pyrrolidine-1-carboxylate;
(2S,4R)-tert-butyl 4-amino-2-(3-(3,5-difluorophenyl)-5-fluoro-4-oxo-3,4-dihydroquinazolin-2-yl)pyrrolidine-1-carboxylate;
(2S,4R)-tert-butyl 4-amino-2-(3-(3-(difluoromethyl)-5-fluorophenyl)-5-fluoro-4-oxo-3,4-dihydroquinazolin-2-yl)pyrrolidine-1-carboxylate;
(2S,4R)-tert-butyl 4-amino-2-(5-chloro-3-(3-(difluoromethyl)-5-fluorophenyl)-4-oxo-3,4-dihydroquinazolin-2-yl)pyrrolidine-1-carboxylate; and
(2S,4R)-tert-butyl 4-amino-2-(5-chloro-3-(3-(difluoromethyl)-5-fluorophenyl)-4-oxo-3,4-dihydroquinazolin-2-yl)pyrrolidine-1-carboxylate.

Example 1b. Preparation of Compound of Formula (1b)

A. Preparation of a Compound of Formula (1) in which n is 1, $R^1$ is cyano, m is 0, $R^5$ is hydrogen, and $R^3$ is cyclopropyl.

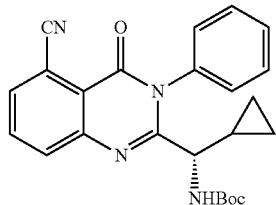

1b (S)-tert-butyl (1-(chloro-bromo-4-oxo-3-phenyl-3,4-dihydroquinazolin-2-yl)(cyclopropyl)methyl)carbamate (230 mg, 0.5 mmol), zinc cyanide (70 mg, 0.6 mmol), and tetrakis(triphenylphosphine)Pd(0) (63 mg, 0.05 mmol) were combined in NMP (2 mL). The mixture was degassed under Ar and heated to 80° C. for 72 h. The reaction was poured into EtOAc, washed with aqueous $NaHCO_3$ (2×) and brine. The solvent was removed in vacuo and the residue was purified by chromatography to give (S)-tert-butyl ((5-cyano-4-oxo-3-phenyl-3,4-dihydroquinazolin-2-yl)(cyclopropyl)methyl)carbamate. ES/MS 417.1 (M+H+).

B. Following the procedure described in Example 1b and Reaction Scheme I, below compound of formula (1) were prepared:
(S)-tert-butyl ((5-cyano-8-fluoro-4-oxo-3-phenyl-3,4-dihydroquinazolin-2-yl)(cyclopropyl)methyl)carbamate.

Example 1c. Preparation of Compound of Formula (1c)

A. Preparation of a Compound of Formula (1) in which n is 1, $R^1$ is 2-(morpholin-4-yl)ethoxy, m is 0, $R^5$ is hydrogen, and $R^3$ is methyl

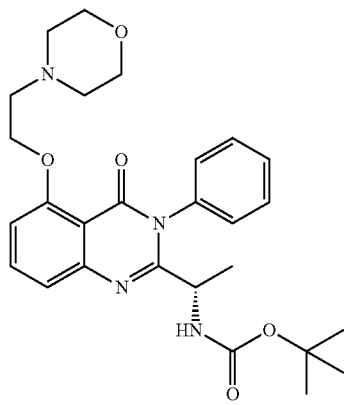

1c

To a suspension of (S)-tert-butyl (1-(5-hydroxy-4-oxo-3-phenyl-3,4-dihydroquinazolin-2-yl)ethyl)carbamate (75 mg, 0.197 mmol) and cesium carbonate (256 mg, 0.786 mmol) in DMF (0.75 mL) was added 4-(2-chloroethyl)morpholine hydrochloride (52 mg, 0.279 mmol). The reaction was heated to 50° C. and stirred for 18 hours, then poured into EtOAc and washed with $H_2O$ (3×). The organic phase was dried over $Na_2SO_4$, filtered, and concentrated to give (S)-tert-butyl (1-(5-(2-morpholinoethoxy)-4-oxo-3-phenyl-3,4-dihydroquinazolin-2-yl)ethyl)carbamate, which was taken on without further purification.

B. Following the procedure described in Example 1c and Reaction Scheme I, below compound of formula (1) were prepared:
(S)-tert-butyl (1-(5-(2-morpholinoethoxy)-4-oxo-3-phenyl-3,4-dihydroquinazolin-2-yl)ethyl)carbamate;
(S)-tert-butyl (1-(5-(2-(azepan-1-yl)ethoxy)-4-oxo-3-phenyl-3,4-dihydroquinazolin-2-yl)ethyl)carbamate;
(S)-tert-butyl (1-(4-oxo-3-phenyl-5-(2-(pyrrolidin-1-yl)ethoxy)-3,4-dihydroquinazolin-2-yl)ethyl)carbamate;
(S)-isopropyl 2-((2-(1-((tert-butoxycarbonyl)amino)ethyl)-4-oxo-3-phenyl-3,4-dihydroquinazolin-5-yl)oxy)acetate;
(S)-tert-butyl (1-(4-oxo-5-(2-(2-oxopyrrolidin-1-yl)ethoxy)-3-phenyl-3,4-dihydroquinazolin-2-yl)ethyl)carbamate;
(S)-tert-butyl (1-(5-(2-(dimethylamino)ethoxy)-4-oxo-3-phenyl-3,4-dihydroquinazolin-2-yl)ethyl)carbamate;
(S)-tert-butyl (1-(4-oxo-5-(2-oxo-2-(piperidin-1-yl)ethoxy)-3-phenyl-3,4-dihydroquinazolin-2-yl)ethyl)carbamate;
(S)-tert-butyl (1-(5-(3-hydroxy-2-(hydroxymethyl)-2-methylpropoxy)-4-oxo-3-phenyl-3,4-dihydroquinazolin-2-yl)ethyl)carbamate;
(S)-tert-butyl (1-(4-oxo-3-phenyl-5-(2-(piperidin-1-yl)ethoxy)-3,4-dihydroquinazolin-2-yl)ethyl)carbamate;
(S)-tert-butyl (1-(4-oxo-3-phenyl-5-(2-(4-phenylpiperazin-1-yl)ethoxy)-3,4-dihydroquinazolin-2-yl)ethyl)carbamate;
(S)-tert-butyl (1-(5-(2-(2-methyl-1H-imidazol-1-yl)ethoxy)-4-oxo-3-phenyl-3,4-dihydroquinazolin-2-yl)ethyl)carbamate;
tert-butyl ((1S)-1-(5-(2-(1-methylpyrrolidin-2-yl)ethoxy)-4-oxo-3-phenyl-3,4-dihydroquinazolin-2-yl)ethyl)carbamate; and
(S)-tert-butyl (1-(5-((3-methyloxetan-3-yl)methoxy)-4-oxo-3-phenyl-3,4-dihydroquinazolin-2-yl)ethyl)carbamate.

Example 1d. Preparation of Compound of Formula (1d)

A. Preparation of a Compound of Formula (1) in which n is 1. $R^1$ is 2-(morpholin-4-yl)-2-oxoethoxy, m is 0, $R^3$ is hydrogen, and $R^3$ is methyl

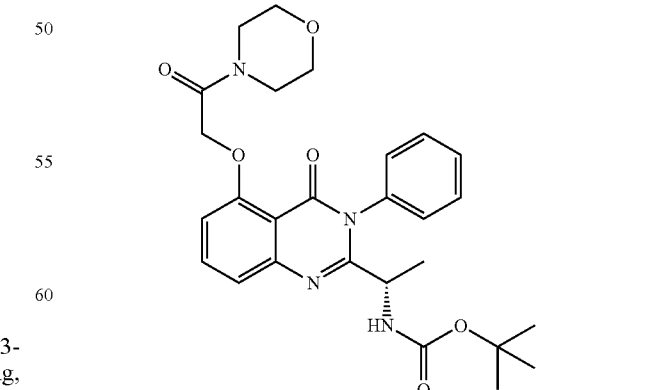

1d

To a solution of (S)-tert-butyl (1-(5-fluoro-4-oxo-3-phenyl-3,4-dihydroquinazolin-2-yl)ethyl)carbamate (500 mg, 1.30 mmol) in DMF (2 mL) was added 2-hydroxy-1-(morpholin-4-yl)ethan-1-one (283 mg, 1.95 mmol) and freshly ground K₂CO₃ (198 mg, 1.43 mmol). The mixture was heated to 80° C. and allowed to stir for 12 days. The reaction was adsorbed directly onto isolate and purified on ISCO (40 g silica, 0-100% EtOAc/hexane) to give (S)-tert-butyl (1-(5-(2-morpholino-2-oxoethoxy)-4-oxo-3-phenyl-3,4-dihydroquinazolin-2-yl)ethyl)carbamate.

Example 1e. Preparation of Compound of Formula (1e)

A. Preparation of a Compound of Formula (1) in which n is 1, R¹ is 2-(4-methylpiperidin-4-yl)-2-oxoethoxy, m is 0, R⁵ is hydrogen, and R³ is methyl

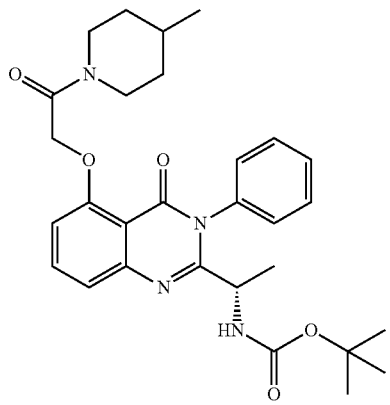

1e

To a suspension of (S)-tert-butyl (1-(5-hydroxy-4-oxo-3-phenyl-3,4-dihydroquinazolin-2-yl)ethyl)carbamate (150 mg, 0.393 mmol), 2-hydroxy-1-(4-methylpiperidin-1-yl)ethan-1-one (124 mg, 0.787 mmol), and triphenyl phosphine (206 mg, 0.787 mmol) in DCM (2 mL) was added di-tert-butyl azodicarboxylate (181 mg, 0.787 mmol). The reaction was stirred at ambient temperature, with more reagents added as needed to drive the reaction. The reaction was poured into H₂O (20 mL), extracted into DCM (3×10 mL), and the combined extracts were purified by flash chromatography (12 g silica, 0-50% EtOAc/DCM) to give (S)-tert-butyl (1-(5-(2-(4-methylpiperidin-1-yl)-2-oxoethoxy)-4-oxo-3-phenyl-3,4-dihydroquinazolin-2-yl)ethyl)carbamate.

Example 1f. Preparation of Compound of Formula (1f)

A. Preparation of a Compound of Formula (1) in which n is 1, R¹ is 3-amino-3-oxopropyl, m is 0, R⁵ is hydrogen, and R³ is methyl

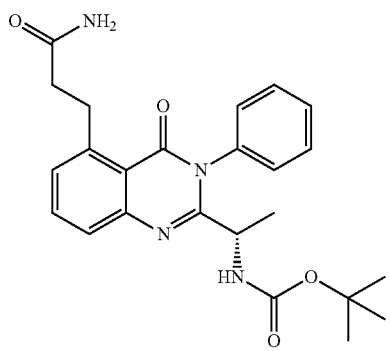

1f

To a solution of (S)-tert-butyl (1-(5-bromo-4-oxo-3-phenyl-3,4-dihydroquinazolin-2-yl)ethyl)carbamate (300 mg, 0.675 mmol) in DMF (3 mL) was added chloro(2-dicyclohexylphosphino-2',4',6'-triisopropyl-1,1'-biphenyl)[2-(2'-amino-1,1'-biphenyl)]palladium(II) (16 mg, 0.023 mmol), acrylamide (72 mg, 1.01 mmol) and DIEA (0.35 mL, 2.03 mmol). The mixture was degassed and heated to 80° C. for 6 hours. The reaction was poured into EtOAc and washed with H₂O. The resulting solution was dried over Na₂SO₄, filtered, and concentrated to an orange oil. Purification by flash chromatography (25 g silica, 0-100% EtOAc/DCM) provided the unsaturated intermediate as a white solid. This material was dissolved in EtOAc (5 mL) and hydrogenated over 10% Pd/C to give (S)-tert-butyl (1-(5-(3-amino-3-oxopropyl)-4-oxo-3-phenyl-3,4-dihydroquinazolin-2-yl)ethyl)carbamate.

B. Following the procedure described in Example 1f and Reaction Scheme I, below compound of formula (1) were prepared:
(S)-tert-butyl 1-(5-(3-amino-3-oxopropyl)-8-fluoro-4-oxo-3-phenyl-3,4-dihydroquinazolin-2-yl)ethyl)carbamate;
(S)-tert-butyl (1-(5-(3-amino-3-oxopropyl)-3-(3,5-difluorophenyl)-8-fluoro-4-oxo-3,4-dihydroquinazolin-2-yl)ethyl)carbamate;
(S)-tert-butyl (1-(5-(3-amino-3-oxopropyl)-3-(3,5-difluorophenyl)-4-oxo-3,4-dihydroquinazolin-2-yl)ethyl)carbamate.

Example 1g. Preparation of Compound of Formula (1g)

A. Preparation of a Compound of Formula (1) in which n is 1, R¹ is 3-oxopropenyl, m is 0, R⁵ is hydrogen, and R³ is methyl

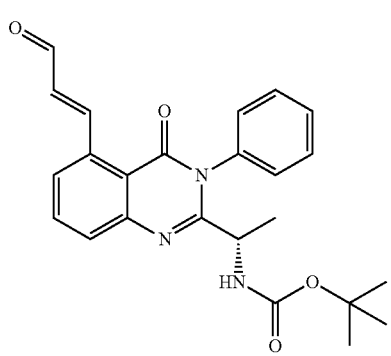

1g

To a solution of (S)-tert-butyl (1-(5-bromo-4-oxo-3-phenyl-3,4-dihydroquinazolin-2-yl)ethyl)carbamate (250 mg, 0.563 mmol) in DMF (3 mL) was chloro(2-dicyclohexylphosphino-2',4',6'-triisopropyl-1,1'-biphenyl)[2-(2'-amino-1,1'-biphenyl)]palladium(II) (38 mg, 0.055 mmol) and DIEA (0.29 mL, 1.69 mmol). The mixture was degassed under Ar₂. Acrolein (0.076 mL, 1.13 mmol) was added, and the mixture heated to 80° C. for 10 hours. The reaction was poured into EtOAc and washed with H₂O (2×). Purified by flash chromatography (25 g silica, 0-30% EtOAc/hexane) to provide (S,E)-tert-butyl (1-(4-oxo-5-(3-oxoprop-1-en-1-yl)-3-phenyl-3,4-dihydroquinazolin-2-yl)ethyl)carbamate.

Example 1h. Preparation of Compound of Formula (1h)

A. Preparation of a Compound of Formula (1) in which n is 1, R¹ is 3-(pyrrolidin-1-yl)propyl, m is 0, R⁵ is hydrogen, and R³ is methyl 1h

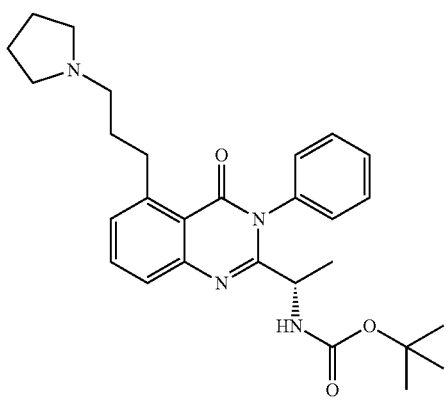

A solution of (S,E)-tert-butyl (1-(4-oxo-5-(3-oxoprop-1-en-1-yl)-3-phenyl-3,4-dihydroquinazolin-2-yl)ethyl)carbamate (84 mg, 0.200 mmol) and pyrrolidine (excess) in EtOAc (1.5 mL) was charged to a flask containing 10% Pd/C. The mixture was hydrogenated under ambient pressure for 1.5 hours. The catalyst was removed by filtration and the filtrate purified by flash chromatography (12 g silica column, 0-100% EtOAc/hexane followed by 0-50% MeOH/DCM) to provide (S)-tert-butyl (1-(4-oxo-3-phenyl-5-(3-(pyrrolidin-1-yl)propyl)-3,4-dihydroquinazolin-2-yl)ethyl) carbamate.

Example 1i. Preparation of Compound of Formula (1i)

A. Preparation of a Compound of Formula (1) in which n is 1, $R^1$ is 3-oxopropyl, m is 0, $R^5$ is hydrogen, and $R^3$ is methyl 1i

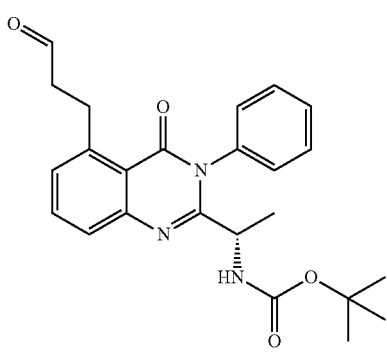

To a solution of (S)-tert-butyl (1-(5-bromo-4-oxo-3-phenyl-3,4-dihydroquinazolin-2-yl)ethyl)carbamate (1.5 g, 3.38 mmol) in DMF (10 mL) was added chloro(2-dicyclohexylphosphino-2',6'-dimethoxy-1,1'-biphenyl)[2-(2'-amino-1,1'-biphenyl)]palladium(II) (205 mg, 0.284 mmol) and DIEA (0.88 mL, 5.07 mmol). The mixture was degassed under $Ar_2$. Allyl alcohol (0.25 mL, 3.71 mmol) was added, and the mixture heated to 120° C. in microwave for 2 hours. The reaction was poured into EtOAc and washed with aq. NaCl (3x). Purification by flash chromatography (0-40% EtOAc/hexane) provided (S)-tert-butyl (1-(4-oxo-5-(3-oxopropyl)-3-phenyl-3,4-dihydroquinazolin-2-yl)ethyl)carbamate.

Example 1j. Preparation of Compound of Formula (1j)

A. Preparation of a Compound of Formula (1) in which n is 1, $R^1$ is 3-(3,3-difluoroazetidin-1-yl)propyl, m is 0, $R^5$ is hydrogen, and $R^3$ is methyl 1j

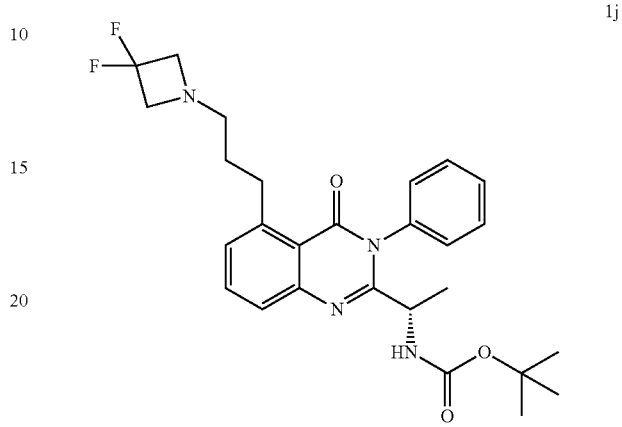

To a solution of (S)-tert-butyl (1-(4-oxo-5-(3-oxopropyl)-3-phenyl-3,4-dihydroquinazolin-2-yl)ethyl)carbamate (99 mg, 0.235 mmol) in DCM (3 mL) was added 3,3-difluoroazetidin hydrochloride (40 mg, 0.305 mmol). Allowed to stir at ambient temperature for one hour, then sodium triacetoxyborohydride (65 mg, 0.305 mmol) was added. Additional sodium triacetoxyborohydride added as necessary until reaction was deemed complete by LCMS. Aq. NaHCO₃ was added, and the mixture extracted into DCM (3x). The combined organics were concentrated in vacuo and purified by flash chromatography (4 g silica column, 0-100% EtOAc/hexane) to provide (S)-tert-butyl (1-(5-(3-(3,3-difluoroazetidin-1-yl)propyl)-4-oxo-3-phenyl-3,4-dihydroquinazolin-2-yl)ethyl)carbamate.

B. Following the procedure described in Example 1j and Reaction Scheme I, below compound of formula (1) were prepared:

(S)-tert-butyl (1-(4-oxo-3-phenyl-5-(3-(piperidin-1-yl)propyl)-3,4-dihydroquinazolin-2-yl)ethyl)carbamate;

(S)-tert-butyl (1-(5-(3-(3,3-difluoropyrrolidin-1-yl)propyl)-4-oxo-3-phenyl-3,4-dihydroquinazolin-2-yl)ethyl)carbamate;

(S)-tert-butyl (1-(5-(3-(4,4-difluoropiperidin-1-yl)propyl)-4-oxo-3-phenyl-3,4-dihydroquinazolin-2-yl)ethyl)carbamate;

tert-butyl ((1S)-1-(5-(3-(3,5-(dimethylmorpholino)propyl)-4-oxo-3-phenyl-3,4-dihydroquinazolin-2-yl)ethyl)carbamate;

(S)-tert-butyl (1-(3-(3,5-difluorophenyl)-4-oxo-5-(3-(pyrrolidin-1-yl)propyl)-3,4-dihydroquinazolin-2-yl)ethyl)carbamate;

(S)-tert-butyl (1-(5-(3-(2,2-dimethylmorpholino)propyl)-4-oxo-3-phenyl-3,4-dihydroquinazolin-2-yl)ethyl)carbamate;

(S)-tert-butyl (1-(5-(3-(3,3-dimethylmorpholino)propyl)-4-oxo-3-phenyl-3,4-dihydroquinazolin-2-yl)ethyl)carbamate;

(S)-tert-butyl (1-(8-fluoro-4-oxo-3-phenyl-5-(3-(pyrrolidin-1-yl)propyl)-3,4-dihydroquinazolin-2-yl)ethyl)carbamate;

(S)-tert-butyl (1-(4-oxo-3-phenyl-5-(3-(2,2,6,6-tetrafluoromorpholino)propyl)-3,4-dihydroquinazolin-2-yl)ethyl)carbamate;

(S)-tert-butyl (1-(5-(3-(3,3-difluoropyrrolidin-1-yl)propyl)-8-fluoro-4-oxo-3-phenyl-3,4-dihydroquinazolin-2-yl)ethyl)carbamate;

(S)-tert-butyl (cyclopropyl(4-oxo-3-phenyl-5-(3-(piperidin-1-yl)propyl)-3,4-dihydroquinazolin-2-yl)methyl)carbamate;

(S)-tert-butyl (cyclopropyl(4-oxo-3-phenyl-5-(3-(pyrrolidin-4-yl)propyl)-3,4-dihydroquinazolin-2-yl)methyl)carbamate;

(S)-tert-butyl (cyclopropyl(8-fluoro-4-oxo-3-phenyl-5-(3-(piperidin-1-yl)propyl)-3,4-dihydroquinazolin-2-yl)methyl)carbamate;

(S)-tert-butyl (cyclopropyl(8-fluoro-4-oxo-3-phenyl-5-(3-(pyrrolidin-1-yl)propyl)-3,4-dihydroquinazolin-2-yl)methyl)carbamate.

Example 1k. Preparation of Compound of Formula (1k)

A. Preparation of a Compound of Formula (1) in which n is 1, $R^1$ is 3-cyclohexylprop-1-en-1-yl, m is 0, $R^5$ is hydrogen, and $R^3$ is methyl

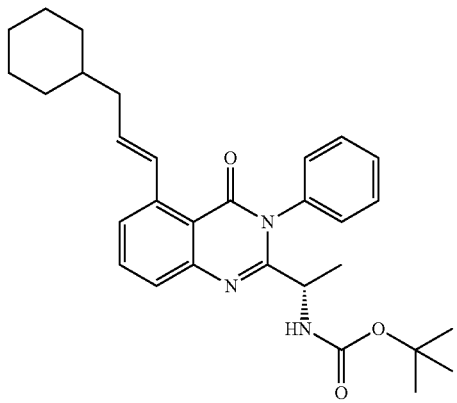

1k

To a solution of (S)-tert-butyl (1-(5-bromo-4-oxo-3-phenyl-3,4-dihydroquinazolin-2-yl)ethyl)carbamate (300 mg, 0.675 mmol) in DMF (3 mL) was added Chloro(2-dicyclohexylphosphino-2',6'-dimethoxy-1,1'-biphenyl)[2-(2-amino-1,1'-biphenyl)]palladium(II) (50 mg, 0.0069 mmol) and DIEA (0.59 mL, 3.38 mmol). The mixture was degassed under Ar₂. Allyl cyclohexane (0.21 mL, 1.35 mmol) was added, and the mixture heated to 80° C. for 18 hours. The reaction was poured into EtOAc and washed with aq. NaCl (3×). The organic phase was adsorbed to isolate and purified by flash chromatography (25 g silica, 0-30% EtOAc/hexane) to provide (S,E)-tert-butyl (1-(5-(3-cyclohexylprop-1-en-1-yl)-4-oxo-3-phenyl-3,4-dihydroquinazolin-2-yl)ethyl)carbamate.

B. Following the procedure described in Example 1k and Reaction Scheme I, below compound of formula (1k) were prepared:
(S,E)-tert-butyl 4-(2-(1-((tert-butoxycarbonyl)amino)ethyl)-4-oxo-3-phenyl-3,4-dihydroquinazolin-5-yl)but-3-enoate;
(S,E)-tert-butyl 2-(5-(4-(tert-butoxy)-4-oxobut-1-en-1-yl)-4-oxo-3-phenyl-3,4-dihydroquinazolin-2-yl)pyrrolidine-1-carboxylate;
(S,E)-tert-butyl 4-(2-(1-((tert-butoxycarbonyl)amino)ethyl)-3-(3,5-difluorophenyl)-4-oxo-3,4-dihydroquinazolin-5-yl)but-3-enoate.

Example 1l. Preparation of Compound of Formula (1l)

A. Preparation of a Compound of Formula (1) in which n is 1, $R^1$ is 3-cyclohexylpropyl, m is 0, $R^5$ is hydrogen, and $R^3$ is methyl

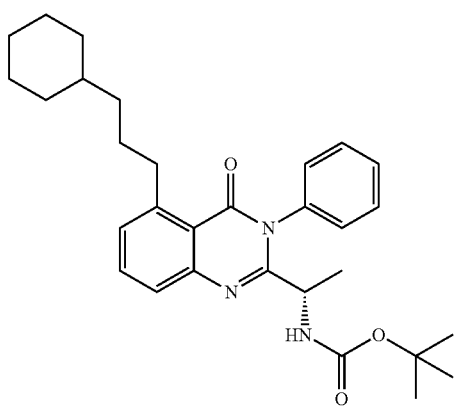

1l

A solution of (S,E)-tert-butyl (1-(5-(3-cyclohexylprop-1-en-1-yl)-4-oxo-3-phenyl-3,4-dihydroquinazolin-2-yl)ethyl)carbamate (274 mg, 0.562 mmol) in EtOAc (5 mL) was added to a flask charged with 10% Pd/C. The mixture was hydrogenated at atmospheric pressure for 10 hours. Filtration provided (S)-tert-butyl (1-(5-(3-cyclohexylpropyl)-4-oxo-3-phenyl-3,4-dihydroquinazolin-2-yl)ethyl)carbamate.

B. Following the procedure described in Example 1l and Reaction Scheme I, below compound of formula (1) were prepared:
(S)-tert-butyl 4-(2-(1-((tert-butoxycarbonyl)amino)ethyl)-4-oxo-3-phenyl-3,4-dihydroquinazolin-5-yl)butanoate;
(S)-tert-butyl 2-(5-(4-(tert-butoxy)-4-oxobutyl)-4-oxo-3-phenyl-3,4-dihydroquinazolin-2-yl)pyrrolidine-1-carboxylate;
(S)-tert-butyl 4-(2-(1-((tert-butoxycarbonyl)amino)ethyl)-3-(3,5-difluorophenyl)-4-oxo-3,4-dihydroquinazolin-5-yl)butanoate.

Example 1m. Preparation of Compound of Formula (1m)

A. Preparation of a Compound of Formula (1) in which n is 1, $R^1$ is $SO_2Me$, m is 1, $R^2$ is F, $R^5$ and $R^3$ together with the atoms to which they are attached optionally term a pyrrolidine 1m To a solution of (S)-tert-butyl 2-(5-bromo-3-(3-fluorophenyl)-4-oxo-3,4-dihydroquinazolin-2-yl)pyrrolidine-1-carboxylate (460 mg, 0.94 mmol) in DMSO (5 mL) was added sodium methanesulfinate (375 mg, 3.7 mmol), cesium carbonate (153 mg, 0.47 mmol), copper iodide (72 mg, 0.38 mmol) and (S)-proline (87 mg, 0.75 mmol). The resulting mixture was degassed under Ar, sealed, and heated to 95° C. After 18 hours the reaction was cooled, poured into EtOAc, and washed with H₂O (3×). The organic phase was dried over MgSO4, concentrated, and purified by column chromatography on silica eliding with EtOAc in hexanes (5-80%) to afford (S)-tert-butyl 2-(3-(3-fluorophenyl)-5-(methylsulfonyl)-4-oxo-3,4-dihydroquinazolin-2-yl)pyrrolidine-1-carboxylate, ES/MS m/z=488.1 (M+H⁺).

B. Following the procedure described in Example 1g and Reaction Scheme I, below compound of formula (1) were prepared:
(S)-tert-butyl 2-(3-(2-fluorophenyl)-5-(methylsulfonyl)-4-oxo-3,4-dihydroquinazolin-2-yl)pyrrolidine-1-carboxylate
(S)-tert-butyl 2-(3-(2,6-difluorophenyl)-5-(methylsulfonyl)-4-oxo-3,4-dihydroquinazolin-2-yl)pyrrolidine-1-carboxylate
(S)-tert-butyl (1-(3-(3-fluorophenyl)-4-oxo-5-(phenylsulfonyl)-3,4-dihydroquinazolin-2-yl)ethyl)carbamate
(S)-tert-butyl 2-(3-(3-fluorophenyl)-4-oxo-5-(phenylsulfonyl)-3,4-dihydroquinazolin-2-yl)pyrrolidine-1-carboxylate Example 1n. Preparation of Compound of Formula (1n)

A. Preparation of a Compound of Formula (1) in which n is 1, R¹ is S(CH₂)₂OH, m is 1, R² is F, R⁵ is H, and R³ is Me

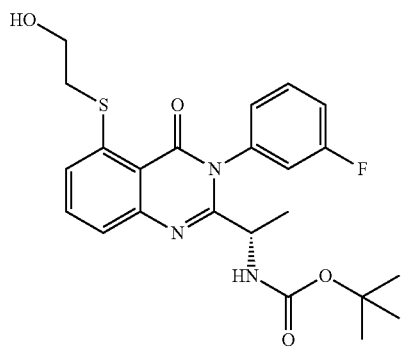

To a solution of (S)-tert-butyl (1-(5-bromo-3-(3-fluorophenyl)-4-oxo-3,4-dihydroquinazolin-2-yl)ethyl)carbamate (1100 mg, 2.38 mmol) and mercaptoethanol (0.20 mL, 2.9 mmol) in dioxane (12 mL) was added diisopropylethylamine (1.25 mL, 7.1 mmol), Xantphos (193 mg, 0.34 mmol), Pd(dba)₂ (96 mg, 0.17 mmol) and (S)-proline (87 mg, 0.75 mmol). The resulting mixture was sealed and heated to 100° C. After 18 hours the reaction was cooled, poured into EtOAc, and washed with H₂O. The organic phase was dried over MgSO4, concentrated, and purified by column chromatography on silica eluting with EtOAc in hexanes (5-100%) to afford (S)-tert-butyl (1-(3-(3-fluorophenyl)-5-((2-hydroxyethyl)thio)-4-oxo-3,4-dihydroquinazolin-2-yl)ethyl)carbamate. ES/MS m/z=460.1 (M+H⁺).

B. Following the procedure described in Example 1n and Reaction Scheme I, below compound of formula (1) were prepared:
(S)-tert-butyl (1-(5-(cyclopentylthio)-3-(3-fluorophenyl)-4-oxo-3,4-dihydroquinazolin-2-yl)ethyl)carbamate
(S)-tert-butyl (1-(3-(3-fluorophenyl)-4-oxo-5-(o-tolylthio)-3,4-dihydroquinazolin-2-yl)ethyl)carbamate Example 1o. Preparation of Compound of Formula (1o)

A. Preparation of a Compound of Formula (1) in which n is 1, R¹ is SO₂(CH₂)₂OH, m is 1, R² is F, R⁵ is H, and R³ is Me

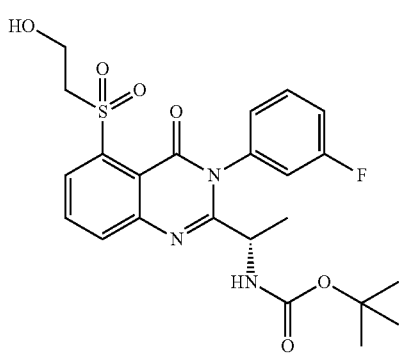

To a solution of (S)-tert-butyl (1-(3-(3-fluorophenyl)-5-((2-hydroxyethyl)thio)-4-oxo-3,4-dihydroquinazolin-2-yl)ethyl)carbamate (1050 mg, 2.29 mmol) in THF (12 mL) and water (6 mL) was added Oxone (4.9 g). The resulting mixture was stirred at room temperature overnight. The reaction was poured into EtOAc and washed with H₂O. The organic phase was dried over MgSO4 and concentrated to afford (S)-tert-butyl (1-(3-(3-fluorophenyl)-5-((2-hydroxyethyl)thio)-4-oxo-3,4-dihydroquinazolin-2-yl)ethyl)carbamate, ES/MS m/z=492.1 (M+H⁺).

B. Following the procedure described in Example 1o and Reaction Scheme I, below compound of formula (1) were prepared:
(S)-tert-butyl (1-(5-(cyclopentylsulfonyl)-3-(3-fluorophenyl)-4-oxo-3,4-dihydroquinazolin-2-yl)ethyl)carbamate
(S)-tert-butyl (1-(3-(3-fluorophenyl)-4-oxo-5-(o-tolylsulfonyl)-3,4-dihydroquinazolin-2-yl)ethyl)carbamate Example 1p. Preparation of Compound of Formula (1p)

A. Preparation of a Compound of Formula (1) in which n is 1, R¹ is Cl, m is 0, R³ and R⁵ together are 4-(2,2-difluoroacetamido)pyrrolidine-1-yl attached at the 2-position of the pyrrolidine to the quinazolinone

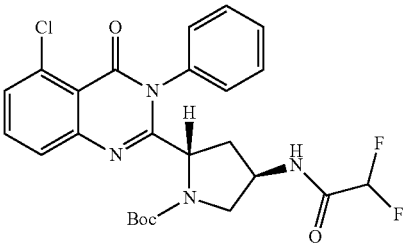

HATU (724 mg, 1.9 mmol), difluoroacetic acid (0.11 mL, 1.75 mmol), and DIEA (0.83 mL, 4.77 mmol) were added to a stirring solution of (2S,4R)-tert-butyl 4-amino-2-(5-chloro-4-oxo-3-phenyl-3,4-dihydroquinazolin-2-yl)pyrrolidine-1-carboxylate (700 mg, 1.59 mmol) in ACN (15 mL) at rt. After stirring for 3 h the resulting mixture was quenched with NaHCO₃ (sat) and the aqueous layer was extracted with. The combined organic layers were washed with brine, dried over Na₂SO₄, and concentrated to give crude acetamide. Chromatography (1:1, Hexanes/EtOAc) afforded the pure acetamide (2S,4R)-tert-butyl 2-(5-chloro-4-oxo-3-phenyl-3,4-dihydroquinazolin-2-yl)-4-(2,2-difluoroacetamido)pyrrolidine-1-carboxylate.

B. Following the procedure described in Example 1p and Reaction Scheme I, below compound of formula (1) were prepared:

(2S,4R)-tert-butyl 2-(5-chloro-3-(3,5-difluorophenyl)-4-oxo-3,4-dihydroquinazolin-2-yl)-4-(2,2-difluoroacetamido)pyrrolidine-1-carboxylate;

(2S,4S)-tert-butyl 2-(5-chloro-4-oxo-3-phenyl-3,4-dihydroquinazolin-2-yl)-4-(2,2,2-trifluoroacetamido)pyrrolidine-1-carboxylate;

(2S,4R)-tert-butyl 2-(5-chloro-3-(3-(difluoromethyl)-5-fluorophenyl)-4-oxo-3,4-dihydroquinazolin-2-yl)-4-(2,2-difluoroacetamido)pyrrolidine-1-carboxylate;

(2S,4R)-tert-butyl 4-(2,2-difluoroacetamido)-2-(3-(3,5-dihydroquinazolin-2-yl)pyrrolidine-1-carboxylate;

(2S,4R)-tert-butyl 4-(2,2-difluoroacetamido)-2-(3-(3-(difluoromethyl)-5-fluorophenyl)-5-fluoro-4-oxo-3,4-dihydroquinazolin-2-yl)pyrrolidine-1-carboxylate;

(2S,4R)-tert-butyl 2-(5-chloro-3-(3-(difluoromethyl)-5-fluorophenyl)-4-oxo-3,4-dihydroquinazolin-2-yl)-4-(2,2-difluoroacetamido)pyrrolidine-1-carboxylate;

(2S,4R)-tert-butyl 2-(5-chloro-4-oxo-3-phenyl-3,4-dihydroquinazolin-2-yl)-4-(2-cyclopropylacetamido)pyrrolidine-1-carboxylate;

Example 1q. Preparation of Compound of Formula (1q)

A. Preparation of a Compound of Formula (1) in which n is 1, R¹ is Cl, m is 0, R³ and R⁵ together are 4-(2,2-difluoro-N-methylacetamido)pyrrolidine-1-yl attached at the 2-position of the pyrrolidine to the quinazolinone

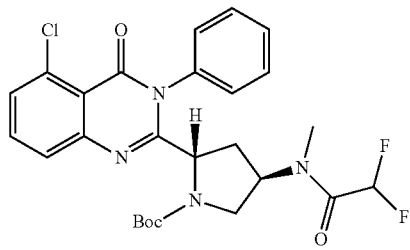 [SMILES: CN(C(=O)C(F)F)[C@@H]1C[C@@H](c2nc3cccc(Cl)c3c(=O)n2-c2ccccc2)N(C(=O)OC(C)(C)C)C1]

Solid NaH (60%, 29 mg, 0.72 mmol) was added to a stirring solution of (2S,4R)-tert-butyl 2-(5-chloro-4-oxo-3-phenyl-3,4-dihydroquinazolin-2-yl)-4-(2,2-difluoroacetamido)pyrrolidine-1-carboxylate (200 mg, 0.36 mmol) in THF (5 mL) at 0° C. After stirring for 5 min., iodomethane (77 mg, 0.54 mmol) was added. The resulting solution was allowed to warm to rt and stirred for an additional 4 d. The reaction mixture was quenched with NaHCO₃ (sat) and the aqueous layer was extracted with EtOAc. The combined organic layers were washed with brine, dried over Na₂SO₄, and concentrated to give (2S,4R)-tert-butyl 2-(5-chloro-4-oxo-3-phenyl-3,4-dihydroquinazolin-2-yl)-4-(2,2-difluoro-N-methylacetamido)pyrrolidine-1-carboxylate that was used in the next step without further purification.

Example 2. Preparation of a Compound of Formula (2)

A. Preparation of a Compound of Formula (2) in which n is 1, R¹ is fluoro, m is 1, R² is fluoro, R⁵ is hydrogen, and R³ is cyclopropyl

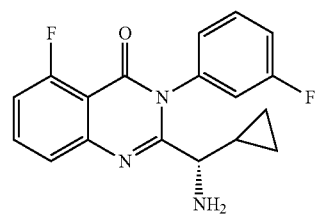

Trifluoroacetic acid (2 mL) was added to a solution of (S)-tert-butyl (cyclopropyl(5-fluoro-3-(3-fluorophenyl)-4-oxo-3,4-dihydroquinazolin-2-yl)methyl)carbamate (0.5 g, 1 mmol) in dichloromethane (2 mL). The resulting solution was stirred at room temperature for 2 hours. The mixture was poured into saturated aqueous NaHCO₃ and extracted with DCM. The organic layer was dried (Na₂SO₄) and the solvent was removed in vacuo to afford (S)-2-(amino(cyclopropyl)methyl)-5-fluoro-3-(3-fluorophenyl)quinazolin-4(3H)-one.

B. Following the procedure described in Example 2A and Reaction Scheme I, below compounds of formula (2) were prepared:

(S)-2-(amino(cyclopropyl)methyl-3,4-dihydroquinazolin-5-carbonitrile;

(S)-2-(amino(cyclopropyl)methyl)-8-fluoro-4-oxo-3-phenyl-3,4-dihydroquinazolin-5-carbonitrile;

(S)-2-(amino(phenyl)methyl)-5-chloro-3-phenylquinazolin-4(3H)-one;

(S)-2-(amino(cyclopropyl)methyl)-3-(3-(difluoromethyl)-5-fluorophenyl)-4-oxo-3,4-dihydroquinazolin-5-carbonitrile;

(S)-2-(amino(cyclopropyl)methyl)-3-(3-fluoromethyl)-5-(methylsulfonyl)quinazolin-4(3H)-one;

(S)-2-(amino(cyclopropyl)methyl)-3-(2,6-difluorophenyl)-5-(methylsulfonyl)quinazolin-4(3H)-one;

(S)-2-(amino(cyclopropyl)methyl)-3-(2-fluorophenyl)-5-(methylsulfonyl)quinazolin-4(3H)-one;

(S)-2-(amino(cyclopropyl)methyl)-6-fluoro-3-(3-fluorophenyl)-8-iodoquinazolin-4(3H)-one;

(S)-2-(amino(cyclopropyl)methyl)-6-fluoro-3-phenyl-8-iodoquinazolin-4(3H)-one;

(S)-3-amino-3-(5-chloro-3-(3,5-difluorophenyl)-4-oxo-3,4-dihydroquinazolin-2-yl)-N,N-dimethylpropanamide;

(S)-3-amino-3-(5-chloro-4-oxo-3-phenyl-3,4-dihydroquinazolin-2-yl)-N,N-dimethylpropanamide;

(S)-3-(2-(amino(cyclopropyl)methyl)-5-methyl-4-oxoquinazolin-3(4H)-yl)-5-fluorobenzonitrile;

(S)-2-(amino(cyclopropyl)methyl)-3-(3,5-difluorophenyl)-5-methylquinazolin-4(3H)-one;

(S)-2-(amino(cyclopropyl)methyl)-5-chloro-3-(3,5-difluorophenyl)quinazolin-4(3H)-one;

(S)-2-(amino(cyclopropyl)methyl)-5-fluoro-3-(3,5-difluorophenyl)quinazolin-4(3H)-one;
(S)-2-(amino(cyclopropyl)methyl)-6-fluoro-3-(3-fluorophenyl)quinazolin-4(3H)-one;
5-chloro-3-(3,5-difluorophenyl)-2-((2S,4S)-4-methoxypyrrolidin-2-yl)quinazolin-4(3H)-one;
(S)-2-(1-aminoethyl)-5-(2-morpholinoethoxy)-3-phenylquinazolin-4(3H)-one;
(S)-2-(1-aminoethyl)-5-(2-(azepan-1-yl)ethoxy)-3-phenylquinazolin-4(3H)-one
(S)-2-(1-aminoethyl)-3-phenyl-5-(2-(pyrrolidin-1-yl)ethoxy)quinazolin-4(3H)-one;
(S)-isopropyl 2-((2-(1-aminoethyl)-4-oxo-3-phenyl-3,4-dihydroquinazolin-5-yl)oxy)acetate;
(S)-2-(1-aminoethyl)-5-(2-(2-oxopyrrolidin-1-yl)ethoxy)-3-phenylquinazolin-4(3H)-one;
(S)-2-(1-aminoethyl)-5-(2-(dimethylamino)ethoxy)-3-phenylquinazolin-4(3H)-one;
(S)-2-(1-aminoethyl)-5-(2-oxo-2-(piperidin-1-yl)ethoxy)-3-phenylquinazolin-4(3H)-one;
(S)-2-(1-aminoethyl)-5-(3-hydroxy-2-(hydroxymethyl)-2-methylpropoxy)-3-phenylquinazolin-4(3H)-one;
(S)-2-(1-aminoethyl)-3-phenyl-5-(2-(piperidin-1-yl)ethoxy)quinazolin-4(3H)-one;
(S)-2-(1-aminoethyl)-3-phenyl-5-(2-(4-phenylpiperazin-1-yl)ethoxy)-quinazolin-4(3H)-one;
(S)-2-(1-aminoethyl)-5-(2-(2-methyl-1H-imidazol-1-yl)ethoxy)-3-phenylquinazolin-4(3H)-one;
2-((S)-1-aminoethyl)-5-(2-(1-methylpyrrolidin-2-yl)ethoxy)-3-phenylquinazolin-4(3H)-one;
(S)-2-(1-aminoethyl)-5-((3-methyloxetan-3-yl)methoxy)-3-phenylquinazolin-4(3H)-one;
(S)-2-(1-aminoethyl)-5-(2-morpholino-2-oxoethoxy)-3-phenylquinazolin-4(3H)-one;
(S)-2-(1-aminoethyl)-5-(2-(4-methylpiperidin-1-yl)-2-oxoethoxy)-3-phenylquinazolin-4(3H)-one;
(S)-3-(2-(1-aminoethyl)-4-oxo-3-phenyl-3,4-dihydroquinazolin-5-yl)propanamide;
(S)-3-(2-(1-aminoethyl)-8-fluoro-4-oxo-3-phenyl-3,4-dihydroquinazolin-5-yl)propanamide;
(S)-3-(2-(1-aminoethyl)-3-(3,5-difluorophenyl)-8-fluoro-4-oxo-3,4-dihydroquinazolin-5-yl)propanamide;
(S)-3-(2-(1-aminoethyl)-3-(3,5-difluorophenyl)-4-oxo-3,4-dihydroquinazolin-5-yl)propanamide;
(S)-2-(1-aminoethyl)-3-phenyl-5-(3-(pyrrolidin-1-yl)propyl)quinazolin-4(3H)-one;
(S)-2-(1-aminoethyl)-5-(3-(3,3-difluoroazetidin-1-yl)propyl)-3-phenylquinazolin-4(3H)-one;
(S)-2-(1-aminoethyl)-3-(3-phenyl-5-(3-piperidin-1-yl)propyl)quinazolin-4(3H)-one;
(S)-2-(1-aminoethyl)-5-(3-(3,3-difluoropyrrolidin-1-yl)propyl)-3-phenylquinazolin-4(3H)-one;
(S)-2-(1-aminoethyl)-5-(3-(4,4-difluoropiperidin-1-yl)propyl)-3-phenylquinazolin-4(3H)-one;
2-((S)-1-aminoethyl)-5-(3-(3,5-dimethylmorpholino)propyl)-3-phenylquinazolin-4(3H)-one;
(S)-2-(1-aminoethyl)-3-(3,5-difluorophenyl)-5-(3-(pyrrolidin-1-yl)propyl)quinazolin-4(3H)-one;
(S)-2-(1-aminoethyl)-5-(3-(2,2-dimethylmorpholino)propyl)-3-phenylquinazolin-4(3H)-one;
(S)-2-(1-aminoethyl)-5-(3-(3,3-dimethylmorpholino)propyl)-3-phenylquinazolin-4(3H)-one;
(S)-2-(1-aminoethyl)-8-fluoro-3-phenyl-5-(3-(pyrrolindin-1-yl)propyl)quinazolin-4(3H)-one;
(S)-2-(1-aminoethyl)-3-phenyl-5-(3-(2,2,6,6-tetrafluoromorpholino)propyl)quinazolin-4(3H)-one;
(S)-2-(amino(cyclopropyl)methyl)-3-phenyl-5-(3-(piperidin-1-yl)propyl)quinazolin-4(3H)-one;
(S)-2-(amino(cyclopropyl)methyl)-3-phenyl-5-(3-(pyrrolidin-1-yl)propyl)quinazolin-4(3H)-one; 4(3H)-one;
(S)-2-(1-aminoethyl)-5-(3-(3,3-difluoropyrrolidin-1-yl)propyl)-8-fluoro-3-phenylquinazolin-4(3H)-one;
(S)-2-(amino(cyclopropyl)methyl)-8-fluoro-3-phenyl-5-(3-(piperidin-1-yl)propyl)quinazolin-4(3H)-one;
(S)-2-(amino(cyclopropyl)methyl)-8-fluoro-3-phenyl-5-(3-(piperidin-1-yl)propyl)quinazolin-4(3H)-one;
(S)-2-(1-aminoethyl)-5-(3-cyclohexlpropyl)-3-phenylquinazolin-4(3H)-one
(S)-2-(azetidin-2-yl)-5-chloro-3-(3,5-difluorophenyl)quinazolin-4(3H)-one;
(S)-2-(azetidin-2-yl)-5-chloro-3-(3,5-phenylquinazolin-4(3H)-one;
(S)-4-(2-(1-aminoethyl)-4-oxo-3-phenyl-3,4-dihydroquinazolin-5-yl)butanoic acid;
(S)-4-(4-oxo-3-phenyl-2-(pyrrolidin-2-yl)-3,4-dihydroquinazolin-5-yl)butanoic acid;
(S)-4-(2-(1-aminoethyl)-3-(3,5-difluorophenyl)-4-oxo-3,4-dihydroquinazolin-5-yl)butanoic acid;
(S)-2-(1-aminoethyl)-3-(3-fluorophenyl)-5-(phenylsulfonyl)quinazolin-4(3H)-one;
(S)-3-(2,6-difluorophenyl)-5-(methylsulfonyl)-2-(pyrrolindin-2-yl)quinazolin-4(3H)-one;
(S)-3-(2-fluorophenyl)-5-(methylsulfonyl)-2-(pyrrolindin-2-yl)quinazolin-4(3H)-one;
(S)-3-(3-fluorophenyl)-5-(methylsulfonyl)-2-(pyrrolindin-2-yl)quinazolin-4(3H)-one;
(S)-3-(3-fluorophenyl)-5-(phenylsulfonyl)-2-(pyrrolindin-2-yl)quinazolin-4(3H)-one;
(S)-2-(1-aminoethyl)-3-(3-fluorophenyl)-5-((2-hydroxyethyl)sulfonyl)quinazolin-4(3H)-one;
(S)-2-(1-aminoethyl)-3-(3-fluorophenyl)-5-((2-hydroxyethyl)thio)quinazolin-4(3H)-one;
(S)-2-(1-aminoethyl)-3-(3-fluorophenyl)-5-(o-tolylsulfonyl)quinazolin-4(3H)-one;
(S)-2-(1-aminoethyl)-5-(cyclopentylsulfonyl)-3-(3-fluorophenyl)quinazolin-4(3H)-one;
(S)-5-chloro-3-(3,5-difluorophenyl)-2-(pyrrolindin-2-yl)quinazolin-4(3H)-one;
(S)-5-chloro-3-(3,5-difluorophenyl)-8-methyl-2-(pyrrolindin-2-yl)quinazolin-4(3H)-one;
(S)-8-chloro-3-(3,5-difluorophenyl)-2-(pyrrolindin-2-yl)quinazolin-4(3H)-one;
(S)-3-(3,5-difluorophenyl)-8-methyl-2-(pyrrolindin-2-yl)quinazolin-4(3H)-one;
(S)-3-(3-(difluoromethyl)phenyl)-8-iodo-2-(pyrrolindin-2-yl)quinazolin-4(3H)-one;
(S)-8-iodo-3-phenyl-2-(pyrrolidin-2-yl)quinazolin-4(3H)-one;
(S)-3-(5-chloro-4-oxo-2-(pyrrolindin-2-yl)quinazolin-3(4H)-yl)-5-fluorobenzonitrile;
(S)-3-(3,5-difluorophenyl)-5-fluoro-2-(pyrrolidin-2-yl)quinazolin-4(3H)-one;
(S)-3-(5,8-(chloro-4-oxo-2-(pyrrolindin-2-yl)quinazolin-3(4H)-yl)benzenesulfonamide;
5-chloro-2-((2S,4R)-4-methylpyrrolidin-2-yl)-3-phenylquinazolin-4(3H)-one;
5-chloro-3-(3,5-difluorophenyl)-2-((2S,4R)-4-methylpyrrolidin-2-yl)quinazolin-4(3H)-one;
(S)-2-(1-aminoethyl)-5-chloro-3-(3,5-difluorophenyl)quinazolin-4(3H)-one;
(R)-5-chloro-2-(morpholin-3-yl)-3-phenylquinazolin-4(3H)-one;

(S)-2-(1-aminoethyl)-3-(3,5-difluorophenyl)-5-fluoroquinazolin-4(3H)-one; N-((3R,5S)-5-(5-chloro-3-(3,5-difluorophenyl)-4-oxo-3,4-dihydroquinazolin-2-yl)pyrrolindin-3-yl)-2,2-difluoroacetamide;
N-((3R,5S)-5-(5-chloro-4-oxo-3-phenyl-3,4-dihydroquinazolin-2-yl)pyrrolindin-3-yl)-2,2-difluoroacetamide;
N-((3S,5S)-5-(5-chloro-4-oxo-3-phenyl-3,4-dihydroquinazolin-2-yl)pyrrolindin-3-yl)-2,2,2-trifluoroacetamide;
N-((3R,5S)-5-(3-(3,5-difluorophenyl)-5-fluoro-4-oxo-3,4-dihydroquinazolin-2-yl)pyrrolidin-3-yl)-2,2-difluoroacetamide;
N-((3R,5S)-5-(3-(3-(difluoromethyl)-5-fluorophenyl)-5-fluoro-4-oxo-3,4-dihydroquinazolin-2-yl)pyrrolidin-3-yl)-2,2-difluoroacetamide;
N-((3R,5S)-5-(5-chloro-3-(3-(difluoromethyl)-5-fluorophenyl)-4-oxo-3,4-dihydroquinazolin-2-yl)pyrrolidin-3-yl)-2,2-difluoroacetamide;
N-((3R,5S)-5-(5-chloro-3-(3,5-difluorophenyl)-4-oxo-3,4-dihydroquinazolin-2-yl)pyrrolidin-3-yl)-2,2-difluoroacetamide;
N-((3R,5S)-5-(5-chloro-3-(3-(difluoromethyl)-5-fluorophenyl)-4-oxo-3,4-dihydroquinazolin-2-yl)pyrrolidin-3-yl)-2,2-difluoroacetamide; and
N-((3R,5S)-5-(5-chloro-4-oxo-3-phenyl-3,4-dihydroquinazolin-2-yl)pyrrolidin-3-yl)-2,2-difluoroacetamide;

Example 3. Preparation of a Compound of Formula (3)

A. Preparation of a Compound of Formula (3) in which $R^4$ is CN, $R^6$ and $R^7$ are $NH_2$, and X is Cl (2,4-diamino-6-chloropyrimidine-5-carbonitrile)

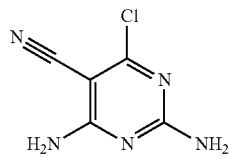 [SMILES: N#Cc1c(N)nc(N)nc1Cl]

Ammonium hydroxide (20 mL) was added to a solution of 2,4,6-trichloropyrimidine-5-carbonitrile (5.0 g, 24 mmol) in dioxane (20 mL) at room temperature. The solution was warmed to 50° C. and stirred for 3 hrs. The reaction mixture was cooled to 10° C. and water (50 mL) was added. The resulting solid was filtered, washed with water, and dried under high vacuum to afford the above compound. $^{13}$H NMR (100 MHz, DMSO) 164.8, 162.6, 161.9, 115.8, 77.6. ES/MS m/z=169.9 (M+H)$^+$.

B. Following the procedure described in Example 3 and Reaction Scheme I, below compounds of formula (3) were prepared:
5-chloro-6-fluoropyrimidine-2,4-diamine;
6-chloro-5-(methylsulfonyl)pyrimidine-2,4-diamine;
2-amino-4,6-dichloropyrimidine-5-carbonitrile;
2-amino-4-chloro-6-methylpyrimidine-5-carbonitrile;
4-amino-2,6-dichloropyrimidine-5-carbonitrile;
4-amino-6-chloro-2-methylpyrimidine-5-carbonitrile;
4-chloro-5-iodo-6-methylpyrimidine-2-amine;
6-chloro-5-(trifluoromethyl)pyrimidine-2,4-diamine; and
2,4-diamino-6-chloropyrimidine-5-carboxamide.

C. Preparation of a Compound of Formula (3) in which $R^4$ is Cl, $R^6$ and $R^7$ are $NH_2$, and X is F

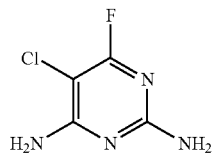

To 2,4,6-trifluoropyrimidine (10 g, 75 mmol) in acetonitrile (100 mL) cooled to 0° C. is added conc $NH_4OH$ (50 mL) in three portions. Remove the cooling bath and allow to stir at room temperature for 6 h followed by heating at 40° C. overnight. Remove the solvent in vacuo to give 2,4-diamino-6-fluoropyrimidine. MeOH/EtOH (250 mL, 1:1) is added to the 2,4-diamino-6-fluoropyrimidine and the mixture is cooled with an ice bath. NCS (13 g, 97 mmol) was added in portions. The ice bath was removed and the mixture stirred for 6 h, followed by heating to 5° C. overnight. Approximately 75 mL of the solvent is removed in vacuo and the reaction vessel is cooled to −10° C. The solid is collected by filtration and added to water (100 mL) and stirred. The solid is collected by filtration and added to 0.1M NaOH (100 mL) and stirred. The solid is collected by filtration to give 2,4-diamino-5-chloro-6-fluoropyrimidine.

Example 4. Preparation of a Compound of Formula (I)

A. Preparation of a Compound of Formula (I) in which n is 1, $R^1$ is fluoro, m is 1, $R^2$ is fluoro, $R^3$ is cyclopropyl, $R^4$ is cyano, $R^5$ is hydrogen, $R^6$ is $NH_2$, and $R^7$ is $NH_2$

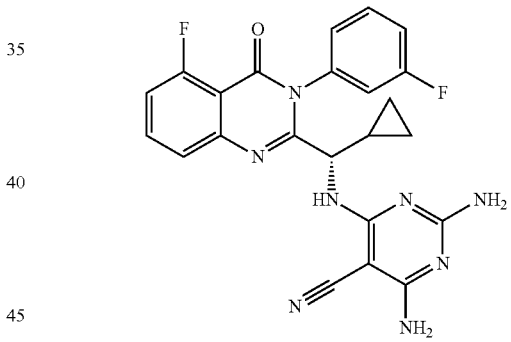

(S)-2-(amino(cyclopropyl)methyl)-5-fluoro-3-(3-fluorophenyl)quinazolin-4(3H)-one (270 mg, 0.8 mmol) and 2,4-diamino-6-chloropyrimidine-5-carbonitrile (120 mg, 0.7 mmol) were dissolved in diisopropylethylamine (0.7 mL, 4.0 mmol) and iPA (2 mL). The resultant mixture was heated using a microwave to 130° C. for 14 hours, after which time the reaction was cooled to room temperature, and the solvent removed in vacuo. The residue was purified by chromatography elating with 0-100% EtOAc/hexanes followed by 0-20% MeOH in EtOAc to afford 2,4-diamino-6-((cyclopropyl(5-fluoro-3-(3-fluorophenyl)-4-oxo-3,4-dihydroquinazolin-2-yl)methyl)amino)pyrimidine-5-carbonitrile (Compound 15a). $^1$H NMR (400 MHz, DMSO-$d_6$) δ 7.96-7.68 (m, 2H), 7.64-7.04 (m, 3H), 6.72-6.33 (m, 2H), 6.16 (s, 2H), 4.61 (dt, J=21.5, 7.6 Hz, 1H), 1.49-1.21 (m, 1H), 0.39 (dtd, J=11.7, 7.0, 2.0 Hz, 3H), 0.12 (m, 1H). ES/MS 461.2 (M+H$^+$).

B. Following the procedure described in Example 4 and Reaction Scheme I, below compounds of formula (I) were prepared:

(S)-2-(cyclopropyl((2,6-diamino-5-cyanopyrimidin-4-yl)amino)methyl)-4-oxo-3-phenyl-3,4-dihydroquinazoline-5-carbonitrile (Compound 1a). $^1$H NMR (400 MHz, DMSO-d$_6$) δ 8.13-7.94 (m, 2H), 7.62-7.37 (m, 4H), 6.59 (s, 2H), 6.46 (d, J=7.6 Hz, 1H), 6.20 (s, 2H), 4.74-4.55 (m, 1H), 1.36-1.22 (m, 1H), 0.49-0.30 (m, 3H), 0.07-0.07 (m, 1H). ES/MS 450.1 ((M+H$^+$).

(S)-2-(cyclopropyl((2,6-diamino-5-cyanopyrimidin-4-yl)amino)methyl)-8-fluoro-4-oxo-3-phenyl-3,4-dihydroquinazoline-5-carbonitrile (Compound 2a). $^1$H NMR (400 MHz, DMSO-d$_6$) δ 8.16 (dd, J=8.4, 4.5 Hz, 1H), 7.99 (dd, J=9.6, 8.4 Hz, 1H), 7.93-7.58 (m, 4H), 7.57-7.49 (m, 2H), 7.48-7.33 (m, 2H), 7.33-7.23 (m, 1H), 4.65 (t, J=8.0 Hz, 1H), 1.48 (ddt, J=13.0, 7.9, 4.0 Hz, 1H), 0.57-0.35 (m, 3H), 0.16-0.03 (m, 1H). ES/MS 468.1 (M+H$^+$).

(S)-2,4-diamino-6-(((5-chloro-4-oxo-3-phenyl-3,4-dihydroquinazoline-2-yl)(phenyl)methyl)amino)pyrimidine-5-carbonitrile (Compound 3a). $^1$H NMR (400 MHz, DMSO-d$_6$) δ 7.99-6.97 (m, 14H), 6.60-6.51 (m, 1H), 5.91 (dd, J=6.8, 1.2 Hz, 1H), 4.54-3.39 (br m, 4H). ES/MS 495.1 (M+H$^+$);

(S)-2-(cyclopropyl((2,6-diamino-5-cyanopyrimidin-4-yl)amino)methyl)-3-(3-(difluoromethyl)-5-fluorophenyl)-4-oxo-3,4-dihydroquinazoline-5-carbonitrile (Compound 4a); $^1$H NMR (400 MHz, DMSO) δ 8.17-8.00 (m, 3H), 7.95-7.47 (m, 6H), 7.47-7.28 (m, 2H), 7.26-6.79 (m, 1H), 4.60 (q, J=8.3 Hz, 1H), 1.65-1.44 (m, 1H), 0.65-0.40 (m, 3H), 0.31-0.07 (m, 1H), ES/MS 518.1 (M+H$^+$):

(S)-2,4-diamino-6-((cyclopropyl(3-(3-fluorophenyl)-5-(methylsulfonyl)-4-oxo-3,4-dihydroquinazolin-2-yl)methyl)amino)pyrimidine-5-carbonitrile (Compound 5a): $^1$H NMR (400 MHz, DMSO) δ 8.36-8.30 (m, 1H), 8.14-8.08 (m, 2H), 7.91 (br s, 4H), 7.61-7.47 (m, 1H), 7.47-7.31 (m, 1H), 7.24-7.14 (m, 1H), 7.13-7.05 (m, 1H), 4.65-4.66 (m, 1H), 3.49 (s, 3H), 1.60-1.48 (m, 1H), 0.60-0.38 (m, 3H), 0.23-0.12 (m, 1H). ES/MS 521.1 (M+H$^+$);

(S)-2,4-diamino-6-((cyclopropyl(3-(2-fluorophenyl)-5-(methylsulfonyl)-4-oxo-3,4-dihydroquinazolin-2-yl)methyl)amino)pyrimidine-5-carbonitrile (Compound 17a-1): $^1$H NMR (400 MHz, DMSO) δ 8.34 (dd, J=6.7, 2.3 Hz, 1H), 8.16-8.08 (m, 2H), 7.90-7.56 (m, 4H), 7.50-7.38 (m, 4H), 7.21 (ddd, J=8.2, 6.3, 2.3 Hz, 1H), 4.55-4.48 (m, 1H), 3.49 (s, 3H), 1.46 (dt, J=8.9, 5.0 Hz, 1H), 0.59-0.50 (m, 1H), 0.49-0.35 (m, 2H), −0.04-−0.12 (m, 1H). ES/MS 521.1 (M+H$^+$).

(S)-2,4-diamino-6-((cyclopropyl(3-(2-fluorophenyl)-5-(methylsulfonyl)-4-oxo-3,4-dihydroquinazolin-2-yl)methyl)amino)pyrimidine-5-carbonitrile (Compound 17a-2): $^1$H NMR (400 MHz, DMSO) δ 8.44 (br s, 2H), 8.36-8.32 (m, 2H), 8.20-8.06 (m, 2H), 7.85 (br s, 2H), 7.65 (tt, J=7.6, 1.4 Hz, 1H), 7.39-7.22 (m, 2H), 7.13 (ddt, J=9.5, 8.0, 1.3 Hz, 1H), 4.78-4.56 (m, 1H), 3.48 (s, 3H), 1.65 (qt, J=8.9, 5.0 Hz, 1H), 0.62 (tt, J=8.7, 4.9 Hz, 1H), 0.44 (ddp, J=13.1, 9.0, 4.7 Hz, 2H), 0.30 (dq, J=10.1, 4.9 Hz, 1H), ES/MS 521.1 (M+H$^+$);

(S)-2,4-diamino-6-((cyclopropyl(3-(2,6-difluorophenyl)-5-(methylsulfonyl)-4-oxo-3,4-dihydroquinazolin-2-yl)methyl)amino)pyrimidine-5-carbonitrile (Compound 6a): $^1$H NMR (400 MHz, DMSO) δ 8.46 (br s, 1H), 8.36 (dd, J=5.1, 3.7 Hz, 1H), 8.19-8.19-8.13 (m, 2H), 7.71 (br s, 3H), 7.46-7.38 (m, 1H), 7.28 (t, J=9.1 Hz, 1H), 7.08 (t, J=8.8 Hz, 1H), 4.62 (t, J=8.7 Hz, 1H), 3.49 (s, J=3H), 1.74-1.62 (m, 1H), 0.72-0.63 (m, 1H), 0.46 (m, 2H), 0.14 (m, 1H). ES/MS 539.1 (M+H$^+$);

(S)-2,4-diamino-6-((cyclopropyl(6-fluoro-3-(3-fluorophenyl)-8-iodo-4-oxo-3,4-dihydroquinazolin-2-yl)methyl)amino)pyrimidine-5-carbonitrile;

(S)-2,4-diamino-6-((cyclopropyl(6-fluoro-3-phenyl-8-iodo-4-oxo-3,4-dihydroquinazolin-2-yl)methyl)amino)pyrimidine-5-carbonitrile;

(S)-3-(5-chloro-3-(3,5-difluorophenyl)-4-oxo-3,4-dihydroquinazolin-2-yl)-3-((2,6-diamino-5-cyanopyrimidin-4-yl)amino)-N,N-dimethylpropanamide (Compound 9a): $^1$H NMR (400 MHz, DMSO) δ 7.89 (bs, 1H), 7.82 (t, J=8 Hz, 1H), 7.66-7.62 (m, 2H), 7.38-7.32 (m, 1H), 7.29-7.26 (m, 1H), 7.18-7.14 (m, 1H), 5.26 (m, 1H), 3.02 (s, 3H), 2.76 (s, 3H), 2.69 (d, J=4.4 Hz, 2H), 2.65 (d, J=4.8 Hz, 2H), ES/MS 540.2 (M+H$^+$);

(S)-3-(5-chloro-4-oxo-3-phenyl-3,4-dihydroquinazolin-2-yl)-3-((2,6-diamino-5-cyanopyrimidin-4-yl)amino)-N,N-dimethylpropanamide (Compound 10a): $^1$H NMR (400 MHz, DMSO) δ 7.89 (bs, 1H), 7.80 (t, J=8 Hz, 1H), 7.65-7.59 (m, 2H), 7.55-7.51 (m, 1H), 7.42-7.31 (m, 4H), 5.25 (m, 1H), 3.00 (s, 3H), 2.75 (s, 3H), 2.66 (d, J=4.8 Hz, 2H), 2.62 (d, J=4.8 Hz, 2H). ES/MS 504.2 (M+H$^+$);

(S)-2,4-diamino-6-(((3-(3-cyano-5-fluorophenyl)-5-methyl-4-oxo-3,4-dihydroquinazolin-2-yl)(cyclopropyl)methyl)amino)pyrimidine-5-carbonitrile (Compound 11a). $^1$H NMR (400 MHz, DMSO-d$_6$) δ 8.33-7.94 (m, 3H), 7.98-7.70 (m, 3H), 7.68-7.59 (m, 1H), 7.55-7.43 (m, 1H), 7.45-7.29 (m, 1H), 4.44 (dt, J=20.0, 8.2 Hz, 1H), 2:72 (d, J=1.1 Hz, 3H), 1.56 (dt, J=13.3, 6.5 Hz, 1H), 0.64-0.38 (m, 3H), 0.30-0.16 (m, 1H). ES/MS 482.3 (M+H$^+$).

(S)-2,4-diamino-6-((cyclopropyl(3-(3,5-difluorophenyl)-5-methyl-4-oxo-3,4-dihydroquinazolin-2-yl)methyl)amino)pyrimidine-5-carbonitrile (Compound 12a). $^1$H NMR (400 MHz, DMSO-d$_6$) δ 7.73 (dd, J=8.1, 7.4 Hz, 2H), 7.68-7.52 (m, 2H), 7.48-7.29 (m, 1H), 7.32-7.09 (m, 2H), 6.99 (d, J=9.4 Hz, 2H), 4.55 (t, J=8.0 Hz, 1H), 2.72 (d, J=0.8 Hz, 3H), 1.53 (d, J=8.8 Hz, 1H), 0.68-0.38 (m, 3H), 0.33-0.11 (m, 1H). ES/MS 475.6 (M+H$^+$);

(S)-2,4-diamino-6-(((5-chloro-3-(3,5-difluorophenyl)-4-oxo-3,4-dihydroquinazolin-2-yl)(cyclopropyl)methyl)amino)pyrimidine-5-carbonitrile (Compound 13a). $^1$H NMR (400 MHz, DMSO-d$_6$) δ 7.89-7.78 (m, 1H), 7.71 (dd, J=8.2, 1.2 Hz, 1H), 7.62 (dd, J=7.8, 1.2 Hz, 1H), 7.55-7.36 (m, 1H), 7.22 (tt, J=9.3, 2.4 Hz, 1H), 6.98 (dd, J=9.0, 2.6 Hz, 1H), 4.54 (t, J=8.1 Hz, 1H), 1.52 (dq, J=8.1, 4.2, 3.3 Hz, 1H), 0.64-0.36 (m, 3H), 0.34-0.06 (m, 1H), ES/MS 495.9 (M+H$^+$);

(S)-2,4-diamino-6-((cyclopropyl(3-(3,5-difluorophenyl)-5-fluoro-4-oxo-3,4-dihydroquinazolin-2-yl)methyl)amino)pyrimidine-5-carbonitrile (Compound 14a). $^1$H NMR (400 MHz, DMSO-d$_6$) δ 7.91 (td, J=8.2, 5.5 Hz, 1H), 7.86-7.52 (m, 2H), 7.52-7.33 (m, 2H), 7.24 (tt, J=9.3, 2.4 Hz, 1H), 7.13-6.87 (m, 1H), 4.58 (t, J=8.0 Hz, $^1$H), 1.53 (ddd, J=13.1, 8.8, 5.2 Hz, 1H), 0.66-0.29 (m, 3H), 0.31-0.17 (m, 1H). ES/MS 479.2 (M+H$^+$); and (S)-2,4-diamino-6-((cyclopropyl(6-fluoro-3-(3-fluorophenyl)-4-oxo-3,4-dihydroquinazolin-2-yl)methyl)amino)pyrimidine-5-carbonitrile (Compound 16a). $^1$H NMR (400 MHz, DMSO-d$_6$) δ 8.01-7.63 (m, 3H), 7.61-7.43 (m, 2H), 7.43-7.24 (m, 2H), 7.27-6.81 (m, 3H), 4.55 (dt, J=18.0, 8.0 Hz, 1H), 1.47 (dd, J=15.0, 7.8 Hz, 1H), 0.64-0.23 (m, 3H), 0.23-0.04 (m, 1H). ES/MS 461.1 (M+H$^+$); (S)-2 (1-((5-acetyl-2,6-diaminopyrimidin-4-yl)amino)ethyl)-5-chloro-3-(3,5-difluorophenyl)quinazolin-4(3H)-one (Compound 18a).

(19)

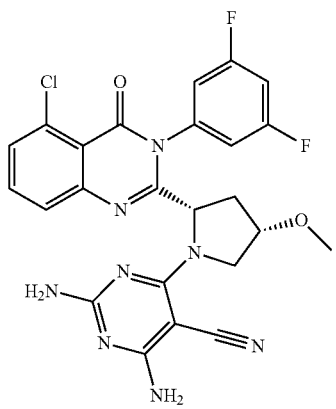

2,4-diamino-6-((2S)-2-(5-chloro-3-(3,5-difluorophenyl)-4-oxo-3,4-dihydroquinazolin-2-yl)-4-methoxypyrrolidin-1-yl)pyrimidine-5-carbonitrile (Compound 19) $^1$H NMR (400 MHz, DMSO-d$_6$) δ 7.73-7.69 (m, 3H), 7.54-7.47 (m, 3H), 7.21 (broad s, 2H), 4.67 (br s, 1H), 4.34-4.29 (m, 1H), 3.99-3.94 (m, 1H), 3.72-3.70 (m, 1H), 3.19 (s, 3H) 2.18-2.13 (m, 1H), 1.97-1.92 (m, 1H). ES/MS 525.3 (M+H$^+$)

(20)

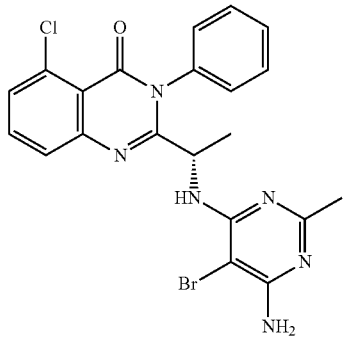

(S)-2-(1-((6-amino-5-bromo-2-methylpyrimidin-4-yl)amino)ethyl)-5-chloro-3-phenylquinazolin-4(3H)-one (Compound 20). $^1$H NMR (400 MHz, DMSO-d$_6$) δ 7.82-7.75 (m, 1H), 7.65 (dd, J=8.2, 1.2 Hz, 1H), 7.61-7.55 (m, 3H), 7.49-7.39 (m, 3H), 4.91 (d, J=7.3 Hz, 1H), 2.19 (s, 3H), 1.37 (d, J=6.7 Hz, 3H).

(21)

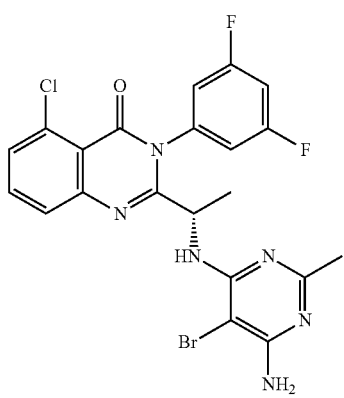

(S)-2-(1-((6-amino-5-bromo-2-methylpyrimidin-4-yl)amino)ethyl)-5-chloro-3-(3,5-difluorophenyl)quinazolin-4(3H)-one (Compound 21). $^1$H NMR (400 MHz, DMSO-d$_6$) δ 7.85-7.78 (m, 1H), 7.69 (dd, J=8.2, 1.2 Hz, 1H), 7.62 (dd, J=7.8, 1.2 Hz, 1H), 7.57-7.51 (m, 1H), 7.43-7.33 (m, 1H), 7.16-7.10 (m, 1H), 5.09 (dd, J=7.8, 6.4 Hz, 1H), 2.20 (s, 3H), 1.42 (d, J=6.7 Hz, 3H).

(22)

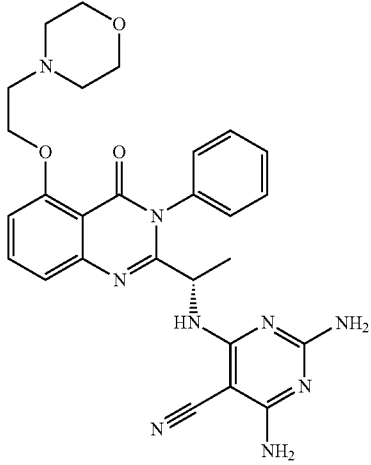

(S)-2,4-diamino-6-((1-(5-(2-morpholinoethoxy)-4-oxo-3-phenyl-3,4-dihydroquinazolin-2-yl)ethyl)amino)pyrimidine-5-carbonitrile (Compound 22). $^1$H NMR (400 MHz, DMSO-d$_6$) δ 9.59 (s, 1H), 7.82 (t, J=8.2 Hz, 1H), 7.60-7.12 (br m, 2H), 7.57-7.39 (m, 5H), 7.35 (dd, J=8.2, 0.9 Hz, 1H), 7.21 (dd, J=8.3, 1.0 Hz, 1H), 7.09-6.74 (br m, 2H), 4.89-4.75 (m, 1H), 4.46 (q, J=4.9 Hz, 2H), 3.87 (d, J=12.9 Hz, 2H), 3.62-3.41 (m, 6H), 3.27-3.10 (m, 2H), 1.30 (d, J=6.6 Hz, 3H). ES/MS 528.2 (M+H$^+$).

(23)

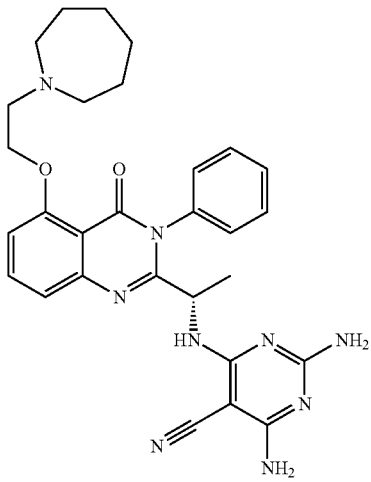

(S)-2,4-diamino-6-((1-(5-(2-(azepan-1-yl)ethoxy)-4-oxo-3-phenyl-3,4-dihydroquinazolin-2-yl)ethyl)amino)pyrimidine-5-carbonitrile (Compound 23). $^1$H NMR (400 MHz, DMSO-d$_6$) δ 9.12 (s, 1H), 7.82 (t, J=8.2 Hz, 1H), 7.63-7.22 (br m, 2H), 7.56-7.37 (m, 5H), 7.34 (dd, J=8.2, 1.0 Hz, 1H), 7.21-6.84 (br m, 2H), 7.19 (dd, J=8.3, 1.0 Hz, 1H), 4.90-4.78 (m, 1H), 4.46 (q, J=5.1, 4.5 Hz, 2H), 3.54 (q, J=4.8 Hz, 2H), 3.52-3.40 (m, 2H), 3.35-3.21 (m, 2H), 1.81-1.67 (m, 2H), 1.67-1.53 (m, 2H), 1.53-1.40 (m, 4H), 1.31 (d, J=6.6 Hz, 3H). ES/MS 540.3 (M+H⁺).

(24)

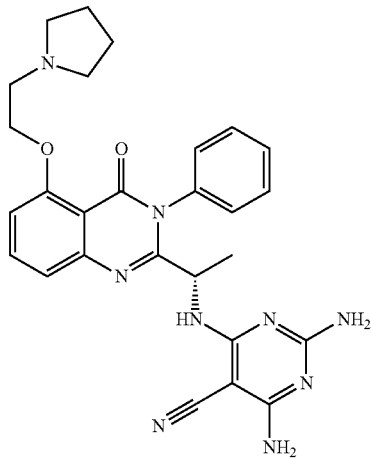

(S)-2,4-diamino-6-((1-(4-oxo-3-phenyl-5-(2-(pyrrolidin-1-yl)ethoxy)-3,4-dihydroquinazolin-2-yl)ethyl)amino)pyrimidine-5-carbonitrile (Compound 24). ¹H NMR (400 MHz, DMSO-d₆) δ 9.56 (s, 1H), 7.80 (t, J=8.3 Hz, 1H), 7.59-7.08 (br m, 2H), 7.55-7.38 (m, 5H), 7.32 (d, J=8.3 Hz, 1H), 7.20-7.14 (m, 1H), 7.02-6.64 (br m, 2H), 4.85-4.74 (m, 1H), 4.44-4.30 (m, 2H), 3.64-3.53 (m, 4H), 3.23-3.08 (m, 2H), 2.01-1.85 (m, 2H), 1.83-1.65 (m, 2H), 1.29 (d, J=6.6 Hz, 3H). ES/MS 512.2 (M+H⁺).

(25)

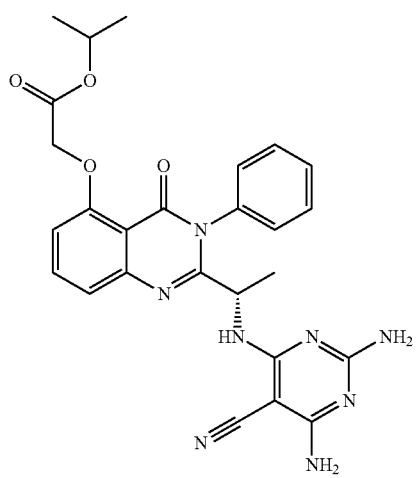

(S)-isopropyl 2-((2-(1-(((2,6-diamino-5-cyanopyrimidin-4-yl)amino)ethyl)-4-oxo-3-phenyl-3,4-dihydroquinazolin-5-yl)oxy)acetate (Compound 25), ¹H NMR (400 MHz, DMSO-d₆) δ 7.70 (t, J=8.2 Hz, 1H), 7.57-7.31 (m, 7H), 7.24 (dd, J=8.2, 1.0 Hz, 1H), 6.91 (dd, J=8.4, 1.1 Hz, 1H), 5.02-4.89 (m, 1H), 4.83-4.74 (m, 3H), 1.29 (d, J=6.6 Hz, 3H), 1.18 (d, J=6.2 Hz, 6H). ES/MS 515.2 (M+H⁺).

(26)

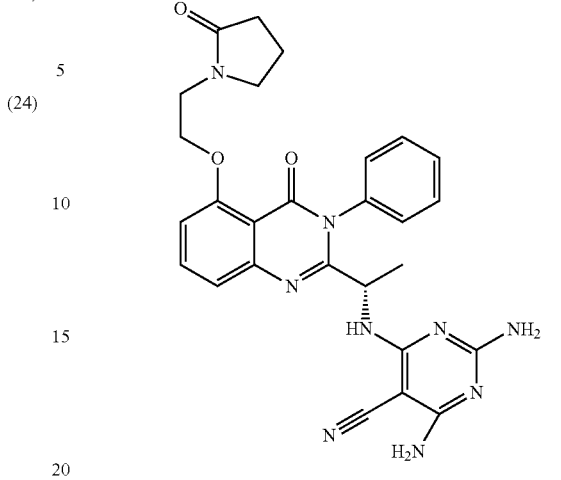

(S)-2,4-diamino-6-((1-(4-oxo-(5-(2-(2-oxopyrrolidin-1-yl)ethoxy)-3-phenyl-3,4-dihydroquinazolin-2-yl)ethyl)amino)pyrimidine-5-carbonitrile (Compound 26). ¹H NMR (400 MHz, DMSO-d₆) δ 7.97-7.12 (br m, 4H), 7.72 (t, J=8.2 Hz, 1H), 7.55-7.35 (m, 5H), 7.21 (dd, J=8.1, 0.9 Hz, 1H), 7.07 (dd, J=8.4, 1.1 Hz, 1H), 4.87-4.75 (m, 1H), 4.13 (t, J=5.3 Hz, 2H), 3.55-3.47 (m, 4H), 2.14 (t, J=8.1 Hz, 2H), 1.81 (p, J=7.5 Hz, 2H), 1.30 (d, J=6.5 Hz, 3H). ES/MS 526.2 (M+H⁺).

(27)

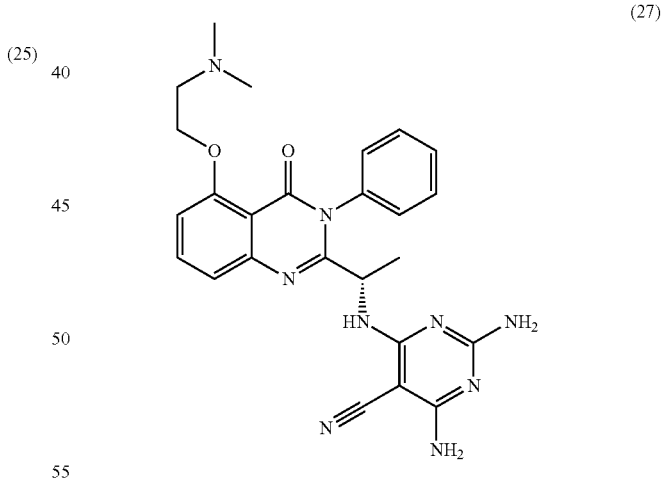

(S)-2,4-diamino-6-((1-(5-(2-(dimethylamino)ethoxy)-4-oxo-3,4-dihydroquinazolin-2-yl)ethyl)amino)pyrimidine-5-carbonitrile (Compound 27). ¹H NMR (400 MHz, DMSO-d₆) δ 9.49 (br s, 1H), 7.79 (t, J=8.2 Hz, 1H), 7.58-7.38 (m, 5H), 7.48-7.16 (br m, 2H), 7.30 (dd, J=8.1, 0.9 Hz, 1H), 7.14 (dd, J=8.4, 1.0 Hz, 1H), 6.90 (br s, 2H), 4.84-4.71 (m, 1H), 4.44-4.36 (m, 2H), 3.50 (q, J=4.6 Hz, 2H), 2.89 (s, 3H), 2.88 (s, 3H), 1.29 (d, J=6.8 Hz, 3H). ES/MS 486.2 (M+H⁺).

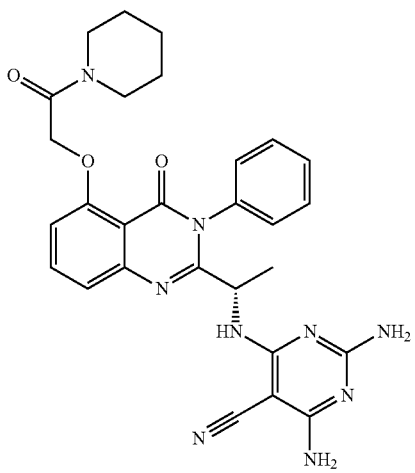

(28)

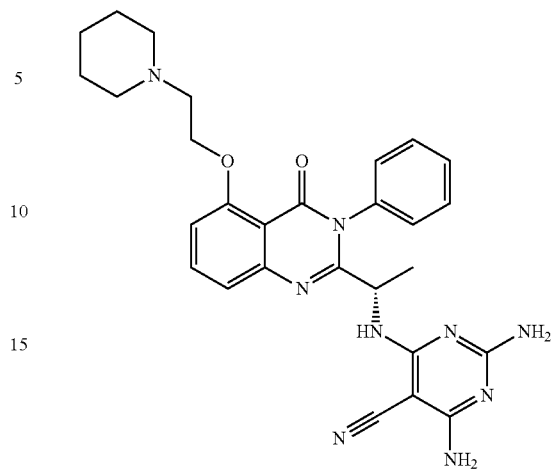

(30)

(S)-2,4-diamino-6-((1-(4-oxo-5-(2-oxo-2-(piperidin-1-yl)ethoxy)-3-phenyl-3,4-dihydroquinazolin-2-yl)ethyl)amino)pyrimidine-5-carbonitrile (Compound 28). $^1$H NMR (400 MHz, DMSO-$d_6$) δ 7.91-6.81 (br m, 4H), 7.69 (ddd, J=8.2, 7.4, 1.0 Hz, 1H), 7.45 (dt, J=21.8, 9.9 Hz, 5H), 7.20 (dt, J=8.1, 1.1 Hz, 1H), 6.90 (d, J=8.3 Hz, 1H), 4.88 (s, 2H), 4.85-4.77 (m, 1H), 3.44-3.33 (m, 4H), 1.58-1.34 (m, 6H), 1.30 (d, J=6.5 Hz, 3H). ES/MS 540.2 (M+H$^+$).

(S)-2,4-diamino-6-((1-(4-oxo-3-phenyl-5-(2-(piperidin-1-yl)ethoxy)-3,4-dihydroquinazolin-2-yl)ethyl)amino)pyrimidine-5-carbonitrile (Compound 30). $^1$H NMR (400 MHz, DMSO-$d_6$) δ 9.06 (br s, 1H), 7.82 (t, J=8.2 Hz, 1H), 7.63-7.24 (br m, 2H), 7.56-7.39 (m, 5H), 7.34 (dd, J=8.2, 0.9 Hz, 1H), 7.20 (dd, J=8.3, 1.0 Hz, 1H), 7.01 (br s, 2H), 4.90-4.78 (m, 1H), 4.50-4.38 (m, 2H), 3.56 (d, J=12.2 Hz, 2H), 3.48 (q, J=4.9 Hz, 2H), 2.99 (q, J=11.3 Hz, 2H), 1.70 (d, J=14.3 Hz, 2H), 1.62-1.41 (m, 3H), 1.37-1.26 (m, 1H), 1.31 (d, J=6.7 Hz, 3H). ES/MS 526.3 (M+H$^+$).

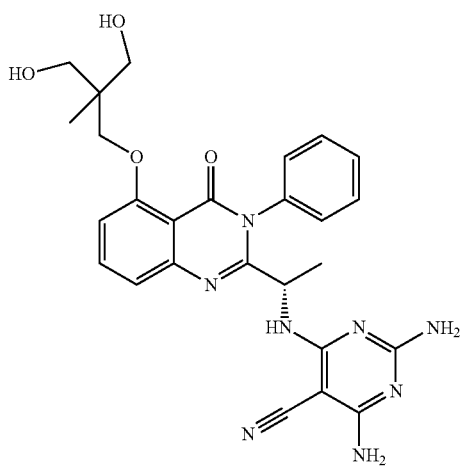

(29)

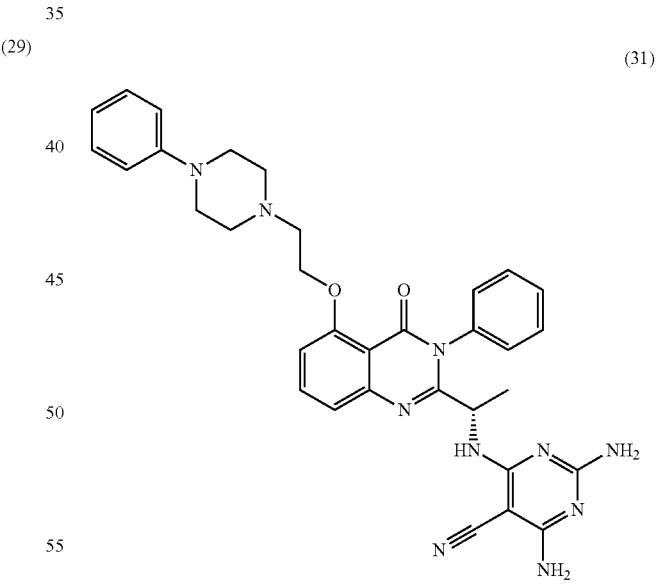

(31)

(S)-2,4-diamino-6-((1-(5-(3-hydroxy-2-(hydroxymethyl)-2-methylpropoxy)-4-oxo-3-phenyl-3,4-dihydroquinazolin-2-yl)ethyl)amino)pyrimidine-5-carbonitrile (Compound 29). $^1$H NMR (400 MHz, DMSO-$d_6$) δ 7.93-6.91 (br m, 4H), 7.73 (t, J=8.2 Hz, 1H), 7.55-7.36 (m, 5H), 7.19 (dd, J=8.2, 0.9 Hz, 1H), 7.04 (dd, J=8.5, 1.1 Hz, 1H), 4.84-4.72 (m, 1H), 3.88 (s, 2H), 3.46-3.31 (m, 4H), 1.30 (d, J=6.6 Hz, 3H), 0.87 (s, 3H). ES/MS 51.7.2 (M+H$^+$).

(S)-2,4-diamino-6-((1-(4-oxo-3-phenyl-5-(2-(4-phenylpiperazin-1-yl)ethoxy)-3,4-dihydroquinazolin-2-yl)ethyl)amino)pyrimidine-5-carbonitrile (Compound 31). $^1$H NMR (400 MHz, DMSO-$d_6$) δ 9.50 (s, 1H), 7.85 (t, J=8.2 Hz, 1H), 7.79-7.29 (m, 8H), 7.29-7.19 (m, 3H), 7.03 (br s, 2H), 6.92 (dd, J=8.4, 1.2 Hz, 2H), 6.87 (t, J=7.3 Hz, 1H), 4.91-4.79 (m, 1H), 4.58-4.44 (m, 2H), 3.77-3.56 (m, 6H), 3.38-3.21 (m, 2H), 2.90-2.74 (m, 2H), 1.31 (d, J=6.8 Hz, 3H). ES/MS 603.3 (M+H$^+$).

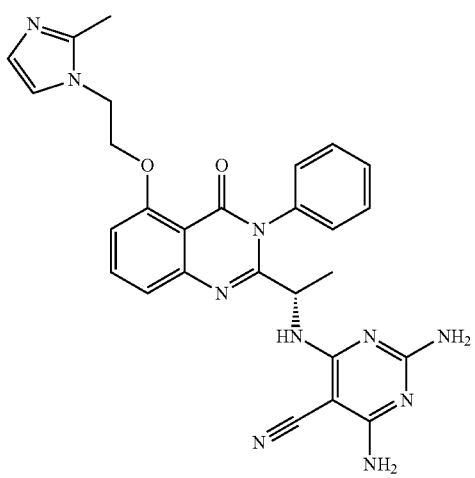

(32)

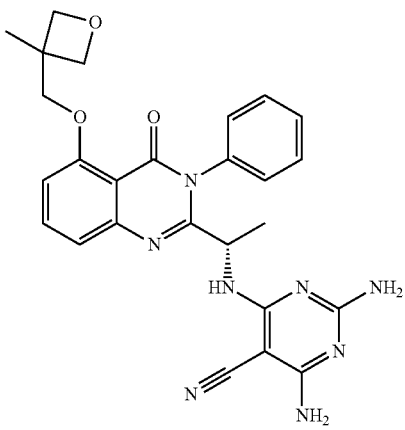

(34)

(S)-2,4-diamino-6-((1-(5-(2-(2-methyl-1H-imidazol-1-yl)ethoxy)-4-oxo-3-phenyl-3,4-dihydroquinazolin-2-yl)ethyl)amino)pyrimidine-5-carbonitrile (Compound 32). $^1$H NMR (400 MHz, DMSO-d$_6$) δ 7.87 (d, J=2.1 Hz, 1H), 7.84-7.55 (br m, 2H), 7.77 (t, J=8.2 Hz, 1H), 7.55-7.38 (m, 6H), 7.40-7.08 (br m, 2H), 7.26 (dd, J=8.2, 0.9 Hz, 1H), 7.04 (dd, J=8.5, 1.0 Hz, 1H), 4.88-4.76 (m, 1H), 4.56-4.47 (m, 2H), 4.45-4.36 (m, 2H), 2.62 (s, 3H), 1.30 (d, J=6.6 Hz, 3H). ES/MS 523.2 (M+H$^+$).

(S)-2,4-diamino-6-((1-(5-((3-methyloxetan-3-yl)methoxy)-4-oxo-3-phenyl-3,4-dihydroquinazolin-2-yl)ethyl)amino)pyrimidine-5-carbonitrile (Compound 34), $^1$H NMR (400 MHz, DMSO-d$_6$) δ 7.70 (t, J=8.2 Hz, 1H), 7.55-7.39 (m, 5H), 7.16 (dd, J=8.2, 0.9 Hz, 1H), 7.06 (d, J=8.1 Hz, 1H), 6.74 (d, J=7.0 Hz, 1H), 6.53 (s, 2H), 6.23 (s, 2H), 4.68-4.58 (m, 1H), 4.46 (d, J=5.7 Hz, 2H), 4.21 (dd, J=5.7, 1.0 Hz, 2H), 4.11 (s, 2H), 1.34 (s, 3H), 1.22 (d, J=6.7 Hz, 3H). ES/MS 499.2 (M+H$^+$).

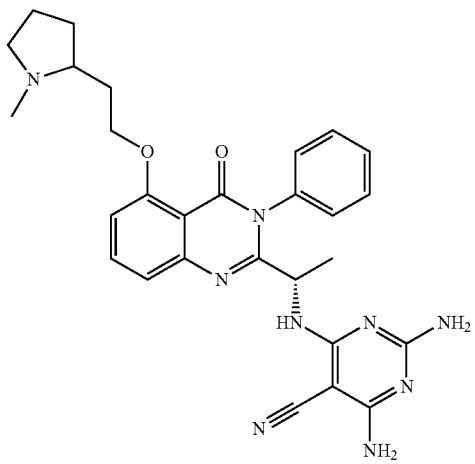

(33)

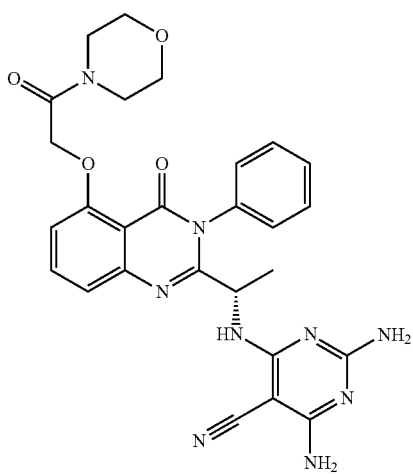

(35)

2,4-diamino-6-(((1S)-1-(5-(2-(1-methylpyrrolidin-2-yl)ethoxy)-4-oxo-3-phenyl-3,4-dihydroquinazolin-2-yl)ethyl)amino)pyrimidine-5-carbonitrile (Compound 33). $^1$H NMR (400 MHz, DMSO-d$_6$) δ 9.54-9.30 (m, 1H), 7.83-7.69 (m, 1H), 7.57-7.39 (m, 5H), 7.29-6.51 (br m, 4H), 7.27-7.08 (m, 2H), 5.13-4.93 (m, 1H), 4.86-4.71 (m, 1H), 3.84-3.29 (m, 2H), 3.29-3.13 (m, 1H), 3.13-2.96 (m, 1H), 2.76-2.70 (m, 3H), 2.29-1.57 (m, 6H), 1.34-1.24 (m, 3H). ES/MS 526.3 (M+H$^+$).

(S)-2,4-diamino-6-((1-(5-(2-morpholino-2-oxoethoxy)-4-oxo-3-phenyl-3,4-dihydroquinazolin-2-yl)ethyl)amino)pyrimidine-5-carbonitrile (Compound 35), $^1$H NMR (400 MHz, DMSO-d$_6$) δ 7.97 (br s, 1H), 7.77 (br s, 1H), 7.74-7.64 (m, 1H), 7.63-7.09 (br m, 2H), 7.62-7.26 (m, 5H), 7.25-7.15 (m, 1H), 6.97-6.88 (m, 1H), 4.98-4.88 (m, 2H), 4.89-4.45 (m, 1H), 3.61-3.31 (m, 8H), 1.36-1.16 (m, 3H). ES/MS 542.2 (M+H$^+$).

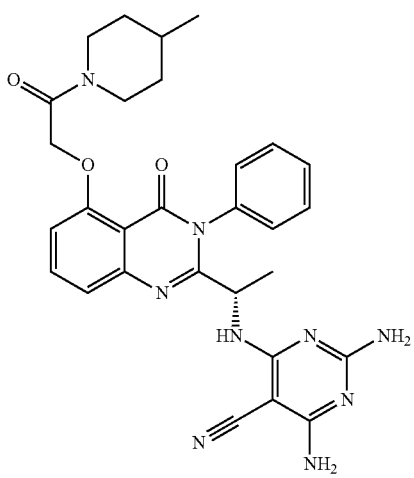

(36)

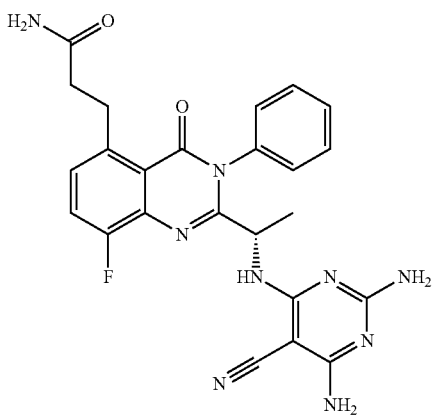

(38)

(S)-2,4-diamino-6-((1-(5-(2-(4-methylpiperidin-1-yl)-2-oxoethoxy)-4-oxo-3-phenyl-3,4-dihydroquinazolin-2-yl)ethyl)amino)pyrimidine-5-carbonitrile (Compound 36). $^1$H NMR (400 MHz, DMSO-d$_6$) δ 8.02-7.54 (br m, 2H), 7.69 (t, J=8.2 Hz, 1H), 7.58-7.31 (m, 5H), 7.49-6.92 (br m, 2H), 7.20 (dd, J=8.1, 0.9 Hz, 1H), 6.89 (dd, J=8.5, 1.0 Hz, 1H), 4.89 (s, 2H), 4.86-4.78 (m, 1H), 4.23 (d, J=13.0 Hz, 1H), 3.82 (d, =13.6 Hz, 1H), 2.96 (t, J=12.8 Hz, 1H), 2.59-2.49 (m, 1H), 1.64-1.48 (m, 3H), 1.30 (d, J=6.6 Hz, 3H), 1.16-0.88 (m, 2H), 0.85 (d, J=6.1 Hz, 3H). ES/MS 554.3 (M+H$^+$).

(S)-3-(2-(1-((2,6-diamino-5-cyanopyrimidin-4-yl)amino)ethyl)-8-fluoro-4-oxo-3-phenyl-3,4-dihydroquinazoline-5-yl)propanamide (Compound 38). $^1$H NMR (400 MHz, DMSO-d$_6$) δ 7.89-7.45 (br m, 3H), 7.62 (dd, J=10.0, 8.4 Hz, 2H), 7.52-7.44 (m, 2H), 7.44-7.33 (m, 3H), 7.30 (dd, J=8.4, 5.0 Hz, 1H), 7.13 (s, 1H), 6.67 (s, 1H), 4.93-4.82 (m, 1H), 3.27 (t, J=7.5 Hz, 2H), 2.33-2.24 (m, 2H), 1.32 (d, J=6.7 Hz, 3H). ES/MS 488.2 (M+H$^+$).

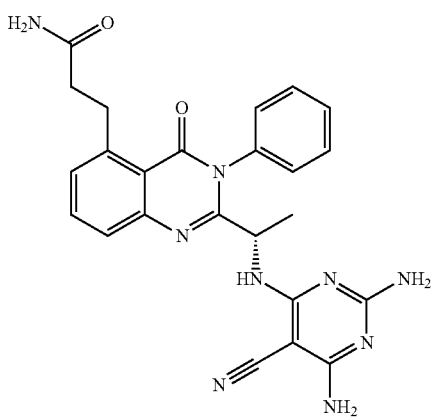

(37)

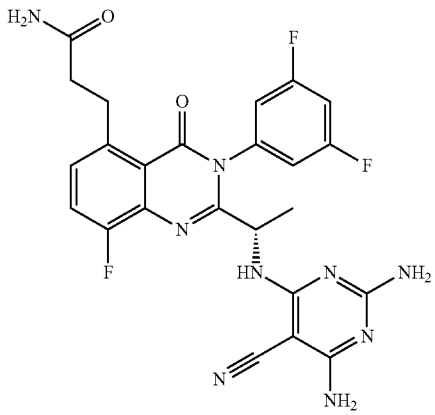

(39)

(S)-3-(2-(1-((2,6-diamino-5-cyanopyrimidin-4-yl)amino)ethyl)-4-oxo-3-phenyl-3,4-dihydroquinazolin-2-yl)propanamide (Compound 37). $^1$H NMR (400 MHz, DMSO-d$_6$) δ 8.04-6.99 (br m, 4H), 7.73 (dd, J=8.1, 7.4 Hz, 1H), 7.55 (dd, J=8.2, 1.2 Hz, 1H), 7.53-7.37 (m, 5H), 7.34 (dd, J=7.6, 1.3 Hz, 1H), 7.15 (s, 1H), 6.69 (s, 1H), 4.94-4.82 (m, 1H), 3.34 (t, J=7.6 Hz, 2H), 2.37-2.28 (m, 2H), 1.33 (d, J=6.6 Hz, 3H). ES/MS 470.2 (M+H$^+$).

(S)-3-(2-(1-((2,6-diamino-5-cyanopyrimidin-4-yl)amino)ethyl)-3-(3,5-difluorophenyl)-8-fluoro-4-oxo-3,4-dihydroquinazoline-5-yl)propanamide (Compound 39). $^1$H NMR (400 MHz, DMSO-d$_6$) δ 7.76-6.79 (br m, 4H), 7.65 (dd, J=10.0, 8.4 Hz, 1H), 7.44 (d, J=9.2 Hz, 1H), 7.36-7.23 (m, 2H), 7.21-7.07 (m, 2H), 6.68 (s, 1H), 5.03-4.91 (m, 1H), 3.27 (t, J=7.6 Hz, 2H), 2.30 (t, J=7.6 Hz, 3H), 1.37 (d, J=6.5 Hz, 3H). ES/MS 524.1 (M+H$^+$).

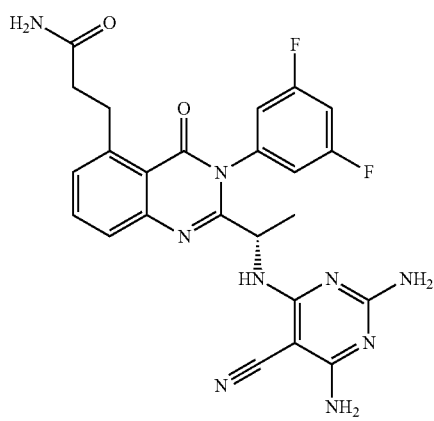

(40)

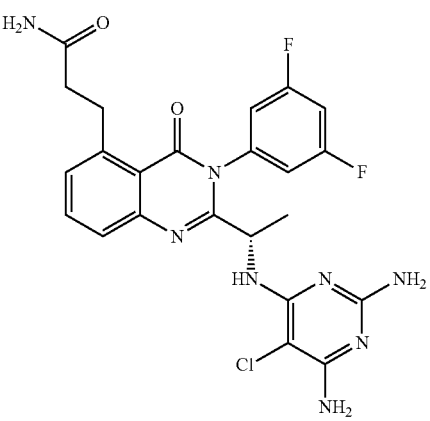

(42)

(S)-3-(2-(1-(((2,6-diamino-5-cyanopyrimidin-4-yl)amino)ethyl)-3-(3,5-difluorophenyl)-4-oxo-3,4-dihydroquinazoline-5-yl)propanamide (Compound 40). ¹H NMR (400 MHz, DMSO-d₆) δ 7.95-6.82 (br m, 4H), 7.77-7.67 (m, 1H), 7.59-7.52 (m, 1H), 7.44 (d, J=9.0 Hz, 1H), 7.34 (dd, J=7.7, 1.3 Hz, 1H), 7.27 (tt, J=9.2, 2.5 Hz, 1H), 7.21-7.09 (m, 2H), 6.68 (s, 1H), 5.03-4.89 (m, 1H), 3.32 (t, J=7.6 Hz, 2H), 2.31 (t, J=7.6 Hz, 2H), 1.36 (d, J=6.6 Hz, 3H). ES/MS 506.1 (M+H⁺).

(S)-3-(2-(1-((2,6-diamino-5-chloropyrimidin-4-yl)amino)ethyl)-3-(3,5-difluorophenyl)-4-oxo-3,4-dihydroquinazoline-5-yl)propanamide (Compound 42). ¹H NMR (400 MHz, DMSO-d₆) δ 11.54 (br s, 1H), 7.86-7.71 (m, 2H), 7.62 (dd, J=8.1, 1.3 Hz, 1H), 7.52 (s, 2H), 7.51-7.47 (m, 1H), 7.39 (dd, J=7.5, 1.3 Hz, 1H), 7.31 (tt, J=9.4, 2.4 Hz, 1H), 7.19 (s, 1H), 7.14-7.02 (m, 1H), 6.73 (s, 1H), 5.08-4.93 (m, 1H), 2.54-2.48 (m, 2H), 2.42-2.29 (m, 2H), 2.08 (s, 0H), 1.43 (d, J=6.6 Hz, 3H). ES/MS 515.1 (M+H⁺).

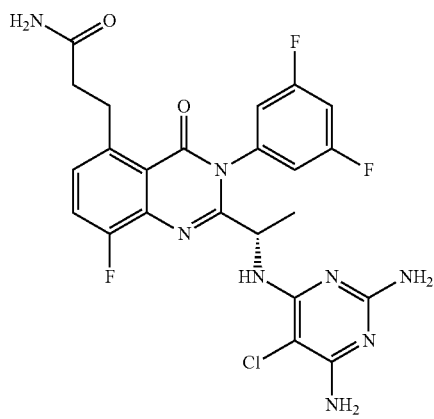

(41)

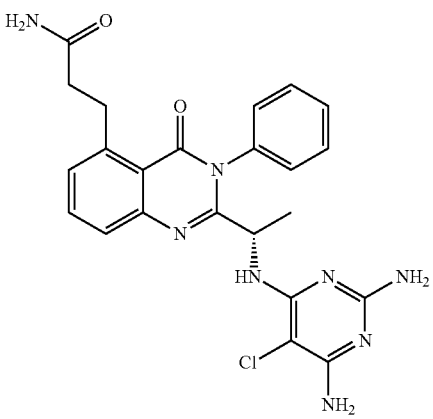

(43)

(S)-3-(2-(1-((2,6-diamino-5-chloropyrimidin-4-yl)amino)ethyl)-3-(3,5-difluorophenyl)-8-fluoro-4-oxo-3,4-dihydroquinazoline-5-yl)propanamide (Compound 41). ¹H NMR (400 MHz, DMSO-d₆) δ 11.39 (br s, 1H), 7.76 (s, 1H), 7.70 (dd, J=10.0, 8.4 Hz, 1H), 7.57-7.41 (m, 3H), 7.39-7.23 (br m, 1H), 7.38 (dd, J=8.5, 5.0 Hz, 1H), 7.31 (tt, J=9.3, 2.4 Hz, 1H), 7.18 (s, 1H), 7.07 (d, J=8.8 Hz, 1H), 6.73 (s, 1H), 5.08-4.95 (m, 1H), 3.37-3.25 (m, 2H), 2.34 (dd, J=8.5, 6.8 Hz, 2H), 1.44 (d, J=6.6 Hz, 3H). ES/MS 533.1 (M+H⁺).

(S)-3-(2-(1-((2,6-diamino-5-chloropyrimidin-4-yl)amino)ethyl)-4-oxo-3-phenyl-3,4-dihydroquinazoline-5-yl)propanamide (Compound 43). ¹H NMR (400 MHz, DMSO-d₆) δ 11.38 (s, 1H), 7.79 (d, J=7.3 Hz, 1H), 7.75 (dd, J=8.1, 7.4 Hz, 1H), 7.59 (dd, J=8.2, 1.2 Hz, 1H), 7.57-7.45 (m, 4H), 7.45-7.38 (m, 3H), 7.36 (dd, J=7.6, 1.3 Hz, 1H), 7.17 (s, 1H), 6.71 (s, 1H), 4.95-4.83 (m, 1H), 3.42-3.29 (m, 2H), 2.34 (dd, J=8.4, 6.8 Hz, 2H), 1.37 (d, J=6.7 Hz, 3H). ES/MS 479.2 (M+H⁺).

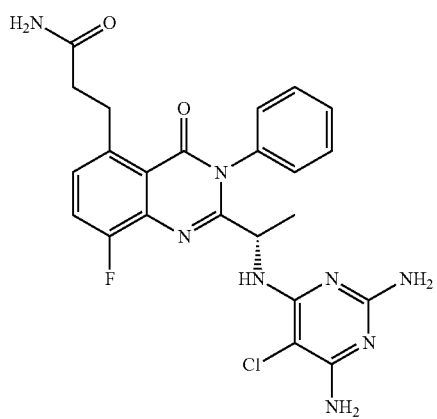

(44)

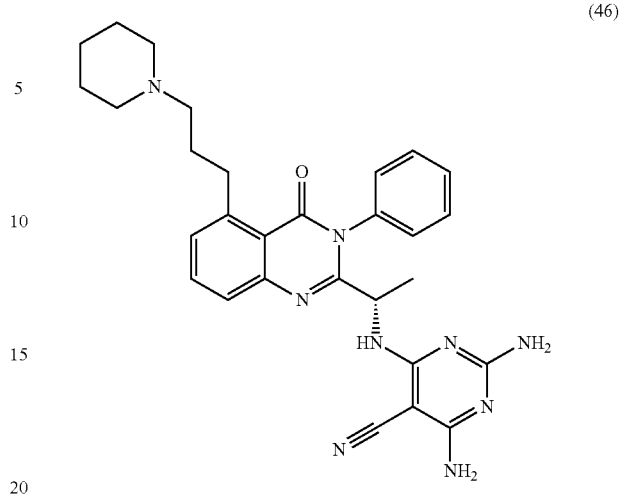

(46)

(S)-3-(2-(1-((2,6-diamino-5-chloropyrimidin-4-yl)amino)ethyl)-8-fluoro-4-oxo-3-phenyl-3,4-dihydroquinazolin-2-yl)propanamide (Compound 44). $^1$H NMR (400 MHz, DMSO-d$_6$) δ 7.71-7.63 (m, 2H), 7.59-7.51 (m, 2H), 7.51-7.38 (m, 5H), 7.35 (dd, J=8.4, 5.0 Hz, 1H), 7.25 (br s, 2H), 7.18 (s, 1H), 6.72 (s, 1H), 4.95-4.85 (m, 1H), 3.37-3.19 (m, 2H), 2.38-2.29 (m, 2H), 1.38 (d, J=6.6 Hz, 3H). ES/MS 497.1 (M+H$^+$).

(S)-2,4-diamino-6-((1-(4-oxo-3-phenyl-5-(3-(piperidin-1-yl)propyl)-3,4-dihydroquinazolin-2-yl)ethyl)amino)pyrimidine-5-carbonitrile (Compound 46). $^1$H NMR (400 MHz, DMSO-d$_6$) δ 8.82 (br s, 1H), 7.78 (dd, J=8.1, 7.4 Hz, 1H), 7.58 (dd, J=8.2, 1.2 Hz, 1H), 7.56-7.40 (m, 5H), 7.37 (d, J=7.5 Hz, 1H), 7.35-6.49 (br m, 4H), 4.90-4.76 (m, 1H), 3.38 (d, J=12.2 Hz, 2H), 3.24-3.10 (m, 2H), 3.10-2.98 (m, 2H), 2.88-2.73 (m, 2H), 1.98-1.83 (m, 2H), 1.74 (d, J=13.6 Hz, 2H), 1.69-1.44 (m, 4H), 1.30 (d, J=6.6 Hz, 3H). ES/MS 524.3 (M+H$^+$).

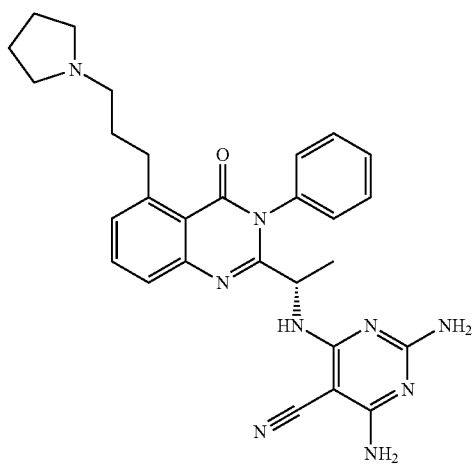

(45)

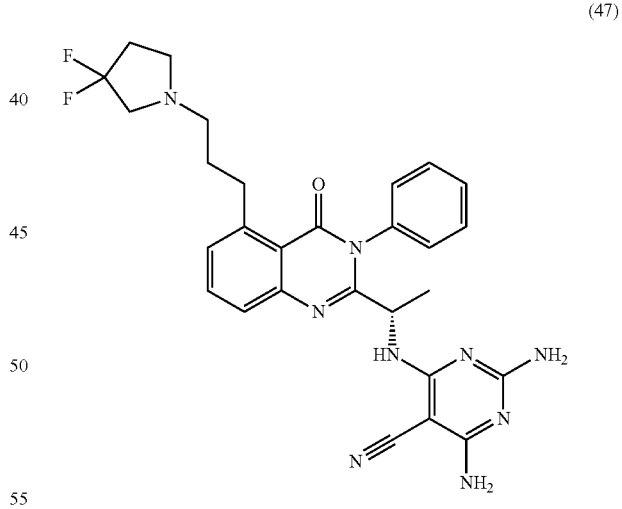

(47)

(S)-2,4-diamino-6-((1-(4-oxo-3-phenyl-5-(2-(pyrrolidin-1-yl)propyl)-3,4-dihydroquinazolin-2-yl)ethyl)amino)pyrimidine-5-carbonitrile (Compound 45). $^1$H NMR (400 MHz, DMSO-d$_6$) δ 9.37 (br s, 1H), 7.78 (dd, J=8.2, 7.4 Hz, 1H), 7.69-7.35 (br m, 2H), 7.59 (dd, J=8.1, 1.2 Hz, 1H), 7.57-7.40 (m, 5H), 7.37 (dd, J=7.5, 1.2 Hz, 1H), 7.20-6.84 (br m, 2H), 4.92-4.80 (m, 1H), 3.55-3.43 (m, 2H), 3.25-3.09 (m, 4H), 2.99-2.85, (m, 2H), 2.03-1.69 (m, 6H), 1.32 (d, J=6.6 Hz, 3H). ES/MS 510.2 (M+H$^+$).

(S)-2,4-diamino-6-((1-(5-(3-(3,3-difluoropyrrolidin-1-yl)propyl)-4-oxo-3-phenyl-3,4-dihydroquinazolin-2-yl)ethyl)amino)pyrimidine-5-carbonitrile (Compound 47). $^1$H NMR (400 MHz, DMSO-d$_6$) δ 7.71 (t, J=7.8 Hz, 1H), 7.60-7.43 (m, 6H), 7.30 (dd, J=7.6, 1.3 Hz, 1H), 6.78 (d, J=7.2 Hz, 1H), 6.55 (s, 2H), 6.25 (s, 2H), 4.78-4.66 (m, 1H), 3.19-3.08 (m, 2H), 2.80 (i, J=13.5 Hz, 2H), 2.61 (t, J=6.9 Hz, 2H), 2.40 (t, J=7.3 Hz, 2H), 2.25-2.08 (m, 2H), 1.73-1.59 (m, 2H), 1.26 (d, J=6.6 Hz, 3H). ES/MS 546.2 (M+H$^+$).

(48)

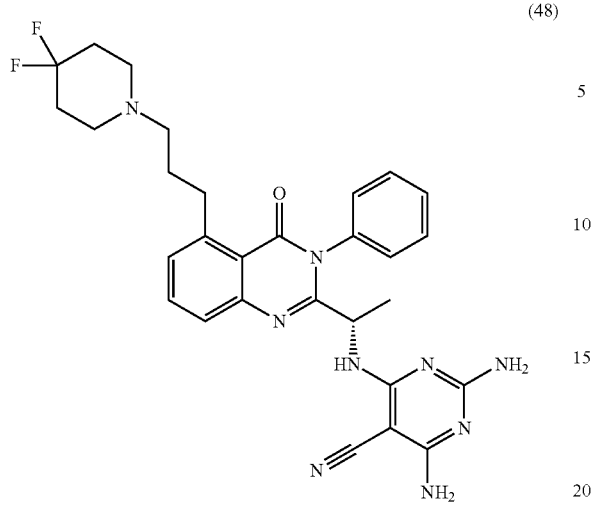

(S)-2,4-diamino-6-((1-(5-(3-(4,4-difluoropiperidin-1-yl)propyl)-4-oxo-3-phenyl-3,4-dihydroquinazolin-2-yl)ethyl)amino)pyrimidine-5-carbonitrile (Compound 48). $^{1}$H NMR (400 MHz, DMSO-d$_6$) δ 9.34 (s, 1H), 7.80 (d, J=7.8 Hz, 1H), 7.59 (dd, J=8.2, 1.2 Hz, 1H), 7.57-7.40 (m, 5H), 7.37 (dd, J=7.5, 1.2 Hz, 1H), 7.40-6.52 (br m, 4H), 4.9-4.80 (m, 1H), 3.64-3.51 (m, 2H), 3.28-3.00 (m, 6H), 2.38-2.23 (m, 2H), 2.23-2.00 (m, 2H), 1.98-1.85 (m, 2H), 1.31 (d, J=6.6 Hz, 3H). ES/MS 560.2 (M+H$^+$).

(50)

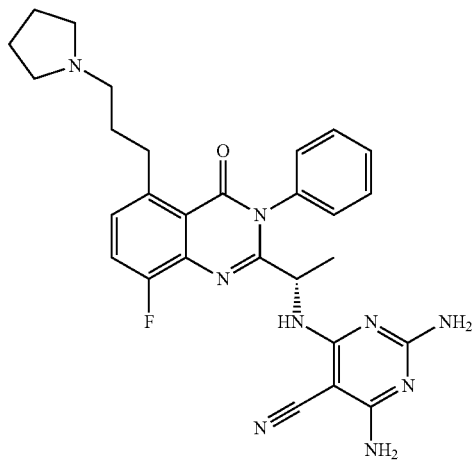

(S)-2,4-diamino-6-((1-(8-fluoro-4-oxo-3-phenyl-5-(3-(pyrrolidin-1-yl)propyl)-3,4-dihydroquinazolin-2-yl)ethyl)amino)pyrimidine-5-carbonitrile (Compound 50). $^{3}$H NMR (400 MHz, DMSO-d$_6$) δ 9.36 (s, 1H), 7.67 (dd, J=9.9, 8.3 Hz, 1H), 7.59-7.37 (m, 5H), 7.33 (dd, J=8.4, 4.9 Hz, 1H), 7.30-6.61 (m, 4H), 4.92-4.78 (m, 1H), 3.55-3.39 (m, 2H), 3.20-3.03 (m, 4H), 2.97-2.83 (m, 2H), 2.03-1.65 (m, 6H), 1.31 (d, J=6.7 Hz, 3H). ES/MS 528.2 (M+H$^+$).

(49)

(51)

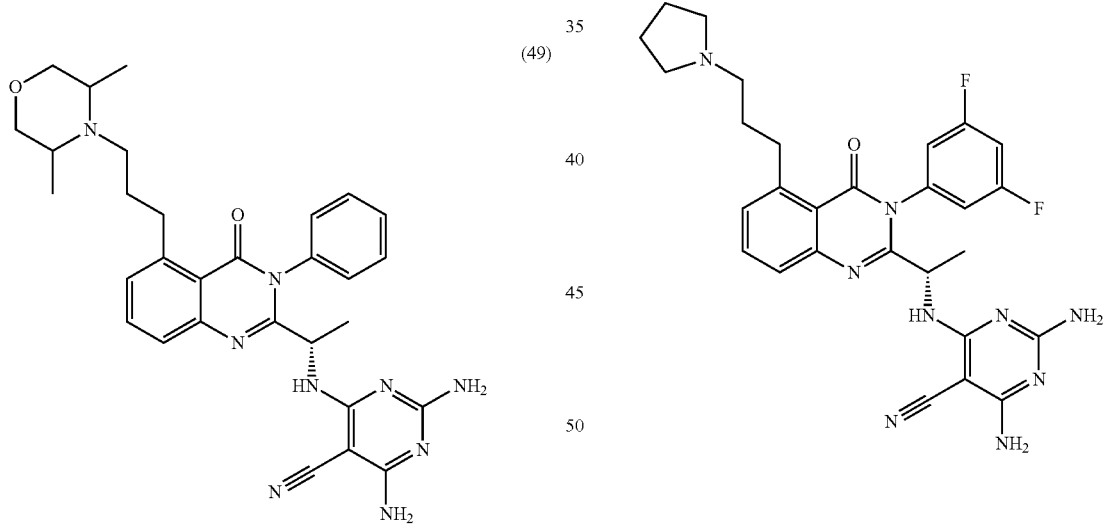

2,4-diamino-6-(((1S)-1-(5-(3-(3,5-dimethylmorpholino)propyl)-4-oxo-3-phenyl-3,4-dihydroquinazolin-2-yl)ethyl)amino)pyrimidine-5-carbonitrile (Compound 49). $^{1}$H NMR (400 MHz, DMSO-d$_6$) δ 9.70-9.12 (br m, 1H), 7.79 (dd, 8.2, 7.4 Hz, 1H), 7.72-7.26 (m, 9H), 7.08 (br s, 2H), 4.88 (t, J=6.8 Hz, 1H), 4.29-3.62 (m, 2H), 3.51-2.91 (m, 6H), 2.65-2.53 (m, 2H), 2.03-1.82 (m, 2H), 1.40-1.18 (m, 3H), 1.13-0.96 (m, 6H). ES/MS 554.3 (M+H$^+$).

(S)-2,4-diamino-6-((1-(3-(3,5-difluorophenyl)-4-oxo-5-(3-(pyrrolidin-1-yl)propyl)-3,4-dihydroquinazolin-2-yl)ethyl)amino)pyrimidine-5-carbonitrile (Compound 51). $^{1}$H NMR (400 MHz, DMSO-d$_6$) δ 9.37 (br s, 1H), 7.78 (dd, J=8.2, 7.4 Hz, 1H), 7.69-6.65 (br m, 4H), 7.60 (dd, J=8.1, 1.2 Hz, 1H), 7.48-7.41 (m, 1H), 7.37 (dd, J=7.5, 1.3 Hz, 1H), 7.29 (tt, J=9.3, 2.3 Hz, 1H), 7.15 (d, J=9.0 Hz, 1H), 5.00-4.90 (m, 1H), 3.54-3.40 (m, 2H), 3.24-3.06 (m, 4H), 2.99-2.84 (m, 2H), 2.02-1.67 (m, 6H), 1.36 (d, J=6.5 Hz, 3H), ES/MS 546.2 (M+H$^+$).

(52)

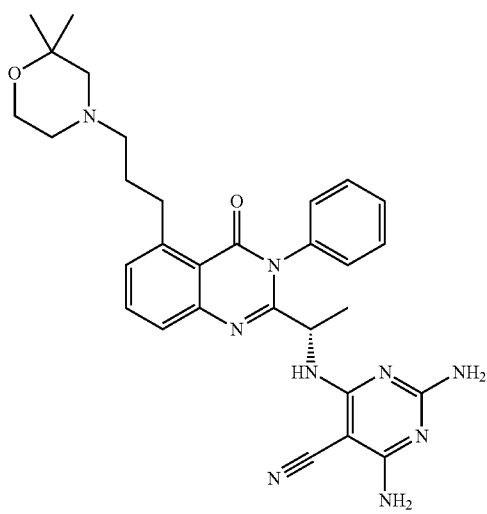

(S)-2,4-diamino-6-((1-(5-(3-(2,2-dimethylmorpholino)propyl)-4-oxo-3-phenyl-3,4-dihydroquinazolin-2-yl)ethyl)amino)pyrimidine-5-carbonitrile (Compound 52), $^1$H NMR (400 MHz, DMSO-d$_6$) δ 9.11 (br s, 1H), 7.76 (dd, J=8.2, 7.4 Hz, 1H), 7.68-7.31 (m, 7H), 7.57 (dd, J=8.2, 1.2 Hz, 1H), 7.35 (dd, J=7.5, 1.3 Hz, 1H), 7.09 (br s, 2H), 4.92-4.78 (m, 1H), 3.78-3.63 (m, 2H), 3.45-3.15 (m, 3H), 3.15-2.93 (m, 3H), 2.93-2.77 (m, 1H), 2.77-2.65 (m, 1H), 1.98-1.81 (m, 2H), 1.37-1.26 (m, 3H), 1.22-1.13 (m, 3H), 1.08 (s, 3H), ES/MS 554.3 (M+H$^+$).

(53)

(S)-2,4-diamino-6-((1-(5-(3-(3,3-dimethylmorpholino)propyl)-4-oxo-3-phenyl-3,4-dihydroquinazolin-2-yl)ethyl)amino)pyrimidine-5-carbonitrile (Compound 53). $^1$H NMR (400 MHz, DMSO-d$_6$) δ 9.26 (s, 1H), 7.91-7.60 (m, 3H), 7.61-7.53 (m, 1H), 7.53-7.12 (m, 8H), 4.94-4.81 (m, 1H), 3.94-3.84 (m, 1H), 3.65-3.48 (m, 2H), 3.40 (d, J=12.6 Hz, 1H), 3.37-2.99 (m, 5H), 2.92-2.76 (m, 1H), 2.02-1.74 (m, 2H), 1.34-1.28 (m, 3H), 1.26 (s, 3H), 1.20 (s, 3H). ES/MS 554.3 (M+H$^+$).

(54)

(S)-2,4-diamino-6-((1-(4-oxo-3-phenyl-5-(3-(2,2,6,6-tetrafluoromorpholino)propyl)-3,4-dihydroquinazolin-2-yl)ethyl)amino)pyrimidine-5-carbonitrile (Compound 54). $^1$H NMR (400 MHz, DMSO-d$_6$) δ 8.04 (br s, 2H), 7.90 (br s, 3H), 7.72 (t, J=7.8 Hz, 1H), 7.53 (dd, J=8.2, 1.2 Hz, 1H), 7.52-7.34 (m, 5H), 7.31 (dd, J=7.5, 1.3 Hz, 1H), 4.93-4.82 (m, 1H), 3.20-3.02 (m, 6H), 2.51 (t, J=7.3 Hz, 2H), 1.69 (p, J=7.6 Hz, 2H), 1.31 (d, J=6.6 Hz, 3H). ES/MS 598.2 (M+H$^+$).

(55)

(S)-2,4-diamino-6-((1-(5-(3-(3,3-difluoropyrrolidin-1-yl)propyl)-8-fluoro-4-oxo-3-phenyl-3,4-dihydroquinazolin-2-yl)ethyl)amino)pyrimidine-5-carbonitrile (Compound 55). $^1$H NMR (400 MHz, DMSO-d$_6$) δ 10.46 (br s, 1H), 7.72 (dd, J=9.9, 8.3 Hz, 1H), 7.63-7.41 (m, 6H), 7.41-7.13 (br m, 2H), 7.37 (dd, J=8.4, 4.9 Hz, 1H), 7.09 (br m, 2H), 4.96-4.84 (m, 1H), 4.09 (s, 1H), 3.71 (s, 3H), 3.46-2.98 (m, 4H), 2.79-2.35 (m, 2H), 1.94-1.73 (m, 2H), 1.35 (d, J=6.6 Hz, 3H). ES/MS 564.2 (M+H$^+$).

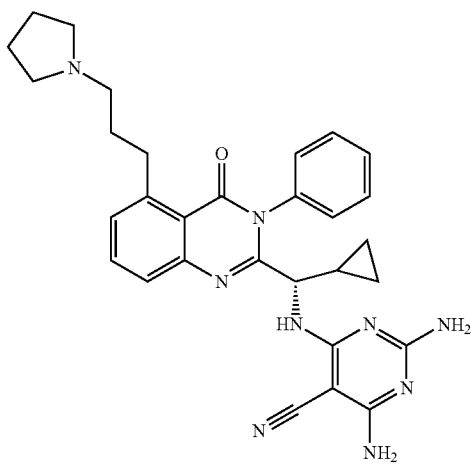

(56)

(S)-2,4-diamino-6-((cyclopropyl(4-oxo-3-phenyl-5-(3-(pyrrolidin-1-yl)propyl)-3,4-dihydroquinazolin-2-yl)methyl)amino)pyrimidine-5-carbonitrile (Compound 56). $^1$H NMR (400 MHz, DMSO-d$_6$) δ 9.45 (s, 1H), 7.81 (i, J=7.8 Hz, 1H), 7.63 (dd, J=8.2, 1.2 Hz, 1H), 7.59-7.33 (m, 5H), 7.32-6.73 (br m, 5H), 4.68 (t, J=7.7 Hz, 1H), 3.47-3.26 (m, 2H), 3.25-3.08 (m, 4H), 2.94 (br p, J=8.0 Hz, 2H), 2.06-1.69 (m, 6H), 1.44-1.29 (m, 1H), 0.51-0.31 (m, 3H), 0.08-0.01 (m, 1H). ES/MS 536.3 (M+H$^+$).

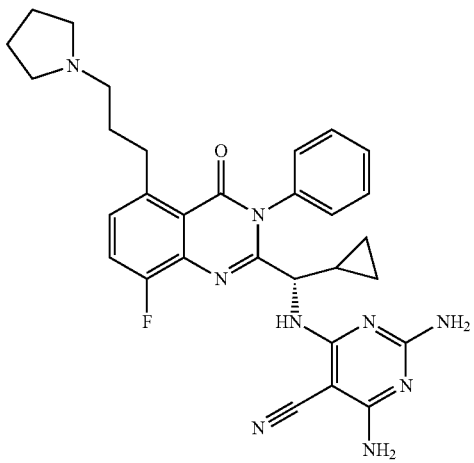

(58)

(S)-2,4-diamino-6-((cyclopropyl(8-fluoro-4-oxo-3-phenyl-5-(3-(pyrrolidin-1-yl)propyl)-3,4-dihydroquinazolin-2-yl)methyl)amino)pyrimidine-5-carbonitrile (Compound 58). $^1$H NMR (400 MHz, DMSO-d$_6$) δ 9.43 (s, 1H), 7.69 (d, J=8.8 Hz, 1H), 7.62-7.15 (m, 7H), 6.94 (br s, 2H), 4.71-4.58 (m, 1H), 3.99-3.30 (m, 2H); 3.11 (s, 4H), 2.99-2.82 (m, 2H), 2.03-1.67 (m, 6H), 1.47-130 (m, 1H), 0.52-0.29 (m, 3H), 0.12-0.08 (m, 1H). ES/MS 554.3 (M+H$^+$).

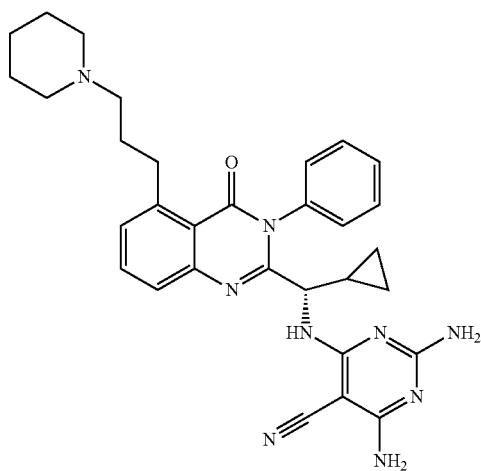

(57)

(S)-2,4-diamino-6-((cyclopropyl(4-oxo-3-phenyl-5-(3-(piperidin-1-yl)propyl)-3,4-dihydroquinazolin-2-yl)methyl)amino)pyrimidine-5-carbonitrile (Compound 57), $^1$H NMR (400 MHz, DMSO-d$_6$) δ 9.22 (s, 1H), 7.79 (t, J=7.8 Hz, 1H), 7.64-7.43 (m, 6H), 7.39 (d, J=7.4 Hz, 1H), 6.63 (s, 2H), 6.45 (d, J=7.9 Hz, 1H), 6.24 (br s, 2H), 4.72 (t, J=7.5 Hz, 1H), 3.46-3.30 (m, 2H), 3.18 (t, J=7.8 Hz, 2H), 3.04 (s, 2H), 2.89-2.74 (m, 2H), 2.03-1.86 (m, 2H), 1.82-1.47 (m, 5H), 1.43-1.18 (m, 2H), 0.44-0.29 (m, 3H), 0.04-0.08 (m, 1H). ES/MS 550.3 (M+H$^+$)

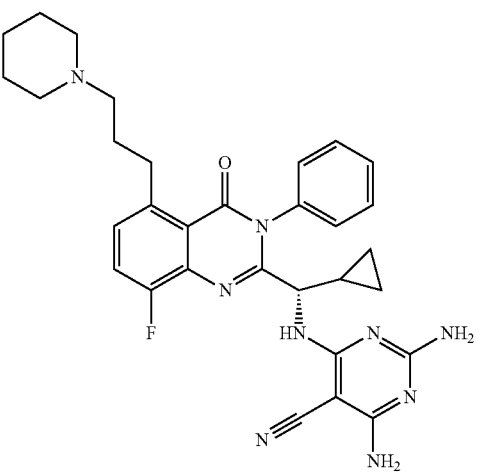

(59)

(S)-2,4-diamino-6-((cyclopropyl(8-fluoro-4-oxo-3-phenyl-5-(3-(piperidin-1-yl)propyl)-3,4-dihydroquinazolin-2-yl)methyl)amino)pyrimidine-5-carbonitrile (Compound 59). $^1$H NMR (400 MHz, DMSO-d$_6$) δ 9.05-8.90 (m, 1H), 7.75-7.65 (m, 1H), 7.65-7.41 (m, 6H), 7.35 (s, 2H), 7.28 (s, 1H), 7.13 (br s, 2H), 4.70-4.58 (m, 1H), 3.42-3.30 (m, 2H), 3.22-2.94 (m, 4H), 2.85-2.68 (m, 2H), 1.93-1.78 (m, 2H), 1.78-1.66 (m, 2H), 1.66-1.12 (m, 6H), 0.52-0.31 (m, 3H), 0.11-0.02 (m, 1H), ES/MS 568.3 (M+H$^+$).

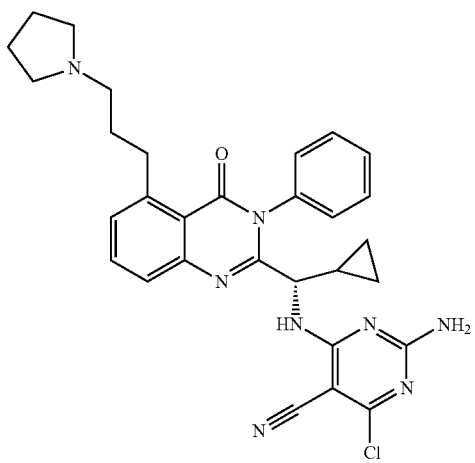

(60)

(S)-2-amino-4-chloro-6-((cyclopropyl(4-oxo-3-phenyl-5-(3-(pyrrolidin-1-yl)propyl)-3,4-dihydroquinazolin-2-yl)methyl)amino)pyrimidine-5-carbonitrile (Compound 60). $^1$H NMR (400 MHz, DMSO-$d_6$) δ 9.38 (s, 1H), 7.77 (dd, J=8.2, 7.4 Hz, 1H), 7.64-7.58 (m, 2H), 7.43 (tddd, J=7.9, 5.9, 3.4, 1.5 Hz, 3H), 7.36 (dd, J=7.5, 1.3 Hz, 1H), 7.32-7.18 (m, 3H), 7.08 (s, 1H), 4.59 (t, J=7.9 Hz, 1H), 3.96-3.62 (m, 2H), 3.23-3.07 (m, 4H), 2.97-2.83 (m, 2H), 2.01-1.69 (m, 6H), 1.51-1.35 (m, 1H), 0.53-0.33 (m, 3H), 0.10-0.01 (m, 1H). ES/MS 555.2 (M+H$^+$).

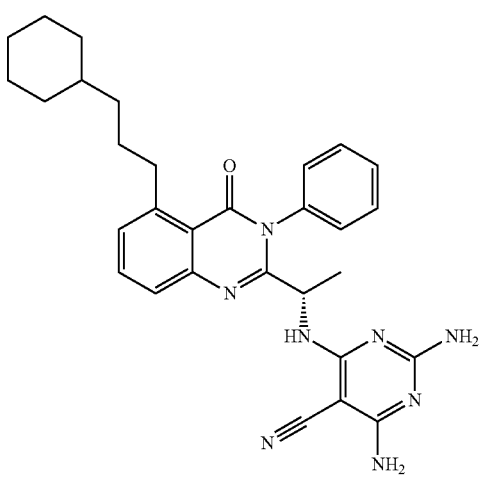

(65)

(S)-2,4-diamino-6-((1-(5-(3-cyclohexylpropyl)-4-oxo-3-phenyl-3,4-dihydroquinazolin-2-yl)ethyl)amino)pyrimidine-5-carbonitrile (Compound 65). $^1$H NMR (400 MHz, DMSO-$d_6$) δ 8.13 (br s, 2H), 7.98 (br s, 2H), 7.77-7.69 (m, 1H), 7.57-7.47 (m, 3H), 7.47-7.36 (m, 3H), 7.32 (dd, J=7.5, 1.3 Hz, 1H), 4.91 (p, J=6.7 Hz, 1H), 3.12 (t, J=7.7 Hz, 2H), 1.68-1.46 (m, 7H), 1.34 (d, J=6.6 Hz, 3H), 1.24-1.00 (m, 6H), 0.88-0.72 (m, 2H). ES/MS 523.3 (M+H$^+$).

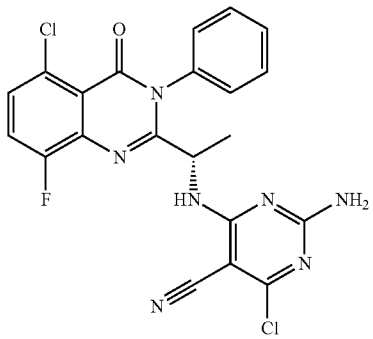

(66)

(S)-2-amino-4-chloro-6-((1-(5-chloro-8-fluoro-4-oxo-3-phenyl-3,4-dihydroquinazolin-2-yl)ethyl)amino)pyrimidine-5-carbonitrile (Compound 66). $^1$H NMR (400 MHz, DMSO-$d_6$) δ 7.83 (d, J=6.9 Hz, 1H), 7.76 (dd, J=9.6, 8.7 Hz, 1H), 7.60 (dd, J=8.8, 4.5 Hz, 1H), 7.56-7.46 (m, 2H), 7.46-7.33 (m, 3H), 7.26 (s, 1H), 4.94-4.84 (m, 1H), 1.37 (d, J=6.6 Hz, 3H). ES/MS 470.0 (M+H$^+$).

(67)

(S)-2,4-diamino-6-(2-(5-chloro-3-(3,5-difluorophenyl)-4-oxo-3,4-dihydroquinazolin-2-yl)azetidin-1-yl)pyrimidine-5-carbonitrile (Compound 67). $^1$H NMR (400 MHz, DMSO-$d_6$) δ 7.86-7.73 (m, 1H), 7.65 (d, J=8.2 Hz, 1H), 7.56 (dd, J=22.3, 9.1 Hz, 2H), 7.45-7.22 (m, 2H), 4.10 (s, 5H), 2.56-2.50 (m, 2H), 2.34-2.08 (m, 2H). ES/MS 48.1.1 (M+H$^+$).

(68)

(S)-2,4-diamino-6-(2-(5-chloro-4-oxo-3-phenyl-3,4-dihydroquinazolin-2-yl)azetidin-1-yl)pyrimidine-5-carbonitrile (Compound 68). ¹H NMR (400 MHz, DMSO-d₆) δ 8.02-7.65 (m, 2H), 7.72-7.49 (m, 4H), 7.42 (s, 2H), 5.25-5.20 (m, 1H), 4.45-4.15 (m, 4H), 2.79-2.49 (m, 1H), 2.39-1.70 (m, 1H). ES/MS 445.1 (M+H⁺).

(m, 1H), 4.70 (s, 3H), 4.27-3.60 (m, 4H), 3.11 (dtd, J=28.3, 13.0, 7.5 Hz, 3H), 2.30-1.95 (m, 3H), 1.98-1.28 (m, 4H). ES/MS 511.1 (M+H⁺).

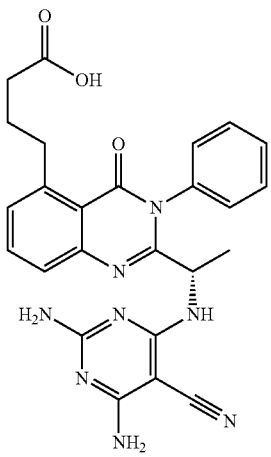

(69)

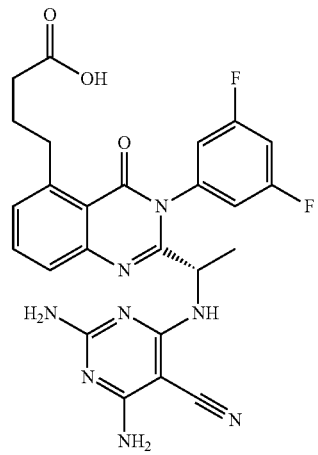

(71)

(S)-4-(2-(1-((2,6-diamino-5-cyanopyrimidin-4-yl)amino)ethyl)-4-oxo-3-phenyl-3,4-dihydroquinazolin-5-yl)butanoic acid (Compound 69). ¹H NMR (400 MHz, DMSO-d₆) δ 8.02 (s, 1H), 7.84 (s, 1H), 7.77-7.65 (m, 1H), 7.61-7.40 (m, 4H), 7.29 (dd, J=7.3, 1.3 Hz, 1H), 4.87 (p, J=6.7 Hz, 2H), 3.13 (dd, J=8.8, 6.4 Hz, 2H), 2.17 (t, J=7.6 Hz, 2H), 1.73 (p, J=7.7 Hz, 3H), 1.32 (d, J=6.6 Hz, 3H). (ES/MS 485.1 (M+H⁺).

(S)-4-(2-(1-((2,6-diamino-5-cyanopyrimidin-4-yl)amino)ethyl)-3-(3,5-difluorophenyl)-4-oxo-3,4-dihydroquinazolin-5-yl)butanoic acid (Compound 71). ¹H NMR (400 MHz, DMSO-d₆) δ 8.15-7.66 (m, 4H), 7.57 (dd, J=8.2, 1.2 Hz, 1H), 7.49-7.40 (m, 1H), 7.36-7.20 (m, 2H), 7.17-6.91 (m, 2H) 4.96 (p, J=6.7 Hz, 1H), 3.14 (dd, J=8.8, 6.0 Hz, 3H), 2.18 (t, J=7.6 Hz, 2H), 1.74 (p, J=7.6 Hz, 2H), 1.37 (d, J=6.6 Hz, 3H). ES/MS 521.1 (M+H⁺).

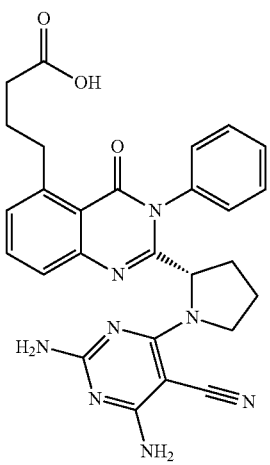

(70)

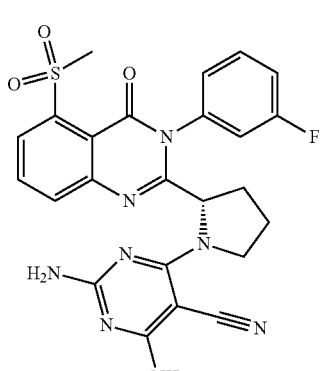

(72)

(S)-4-(2-(1-(2,6-diamino-5-cyanopyrimidin-4-yl)pyrrolidin-2-yl)-4-oxo-3-phenyl-3,4-dihydroquinazolin-5-yl)butanoic acid (Compound 70). ¹H NMR (400 MHz, DMSO-d₆) δ 7.84 (d, J=7.7 Hz, 1H), 7.79-7.35 (m, 5H), 7.30-6.77

(S)-2,4-diamino-6-(2-(3-(3-fluorophenyl)-5-(methylsulfonyl)-4-oxo-3,4-dihydroquinazolin-2-yl)pyrrolidin-1-yl)pyrimidine-5-carbonitrile (Compound 72): ¹H NMR (400 MHz, DMSO) δ 8.27 (dd, J=7.6, 1.4 Hz, 1H), 8.04-7.88 (m, 3H), 7.79-7.39 (m, 4H), 4.84-4.66 (m, 1H), 4.05 (br s, 1H), 3.90 (dt, J=10.1, 7.5 Hz, 1H), 3.48 (s, 3H), 2.09 (br s, 2H), 1.91 (br s, 1H), 1.85-1.70 (m, 1H). ES/MS 521.1 (M+H⁺);

(73)

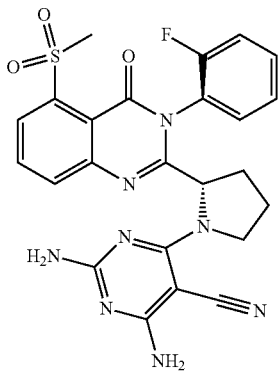

(S)-2,4-diamino-6-(2-(3-(2-fluorophenyl)-5-(methylsulfonyl)-4-oxo-3,4-dihydroquinazolin-2-yl)pyrrolidin-1-yl)pyrimidine-5-carbonitrile (Compound 73): $^1$H NMR (400 MHz, DMSO) δ 8.27 (dd, J=7.6, 1.5 Hz, 1H), 8.05-7.94 (m, 2H), 7.77-7.56 (m, 3H), 7.46 (td, J=7.6, 1.6 Hz, 1H), 7.25 (br s, 2H), 4.69-4.60 (m, 1H), 4.14-4.02 (m, 1H), 3.95-3.83 (m, 1H), 3.48 (s, 3H), 2.29-2.18 (m, 2H), 2.03-1.90 (m, 2H). ES/MS 521.1 (M+H$^+$);

(74)

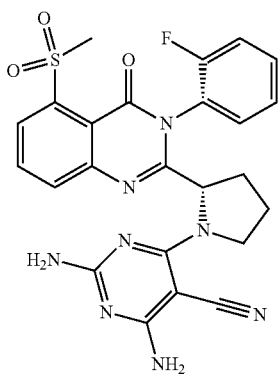

(S)-2,4-diamino-6-(2-(3-(2-fluorophenyl)-5-(methylsulfonyl)-4-oxo-3,4-dihydroquinazolin-2-yl)pyrrolidin-1-yl)pyrimidine-5-carbonitrile (Compound 74): $^1$H NMR (400 MHz, DMSO) δ 8.29 (dd, J=7.6, 1.4 Hz, 1H), 8.06-7.94 (m, 3H), 7.73-7.64 (m, 1H), 7.56 (ddd, J=9.9, 8.4, 1.3 Hz, 1H), 7.48 (td, J=7.7, 1.3 Hz, 1H), 4.93 (br s, 1H), 4.01 (br s, 1H), 3.94-3.85 (m, 1H), 3.48 (s, 3H), 1.98-1.66 (m, 4H). ES/MS 521.1 (M+H$^+$);

(75)

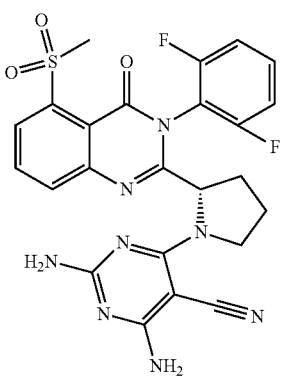

(S)-2,4-diamino-6-(2-(3-(2,6-difluorophenyl)-5-(methylsulfonyl)-4-oxo-3,4-dihydroquinazolin-2-yl)pyrrolidin-1-yl)pyrimidine-5-carbonitrile (Compound 75): $^1$H NMR (400 MHz, DMSO) δ 8.29 (dd, J=7.6, 1.4 Hz, 1H), 8.06 (dd, J=8.2, 7.6 Hz, 1H), 7.99 (dd, J=8.2, 1.4 Hz, 1H), 7.78 (ddd, J=15.0, 8.6, 6.4 Hz, 1H), 7.58-7.47 7.18 (m, 3H), 7.18 (br s, 2H) 4.89-4.84 (m, 1H), 4.05-3.97 (m, 1H), 3.94-3.83 (m, 1H), 3.48 (s, 3H), 2.25-2.09 (m, 1H), 2.09-1.82 (m, 3H). ES/MS 539.1 (M+H$^+$);

(76)

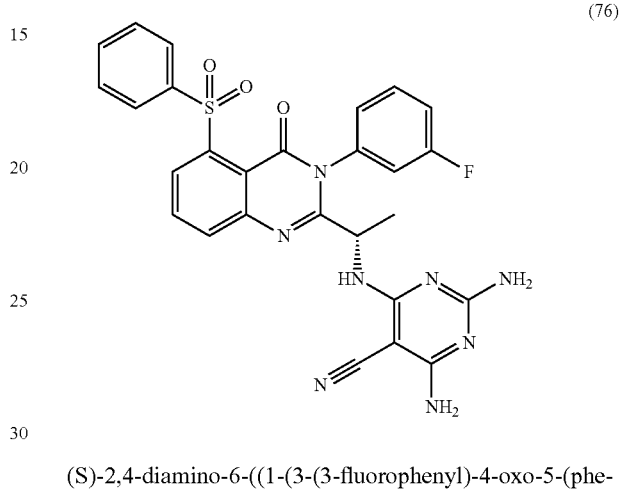

(S)-2,4-diamino-6-((1-(3-(3-fluorophenyl)-4-oxo-5-(phenylsulfonyl)-3,4-dihydroquinazolin-2-yl)ethyl)amino)pyrimidine-5-carbonitrile (Compound 76); $^1$H NMR (400 MHz, DMSO) δ 8.54 (dt, J=7.6, 1.3 Hz, 1H), 8.18-8.04 (m, 2H), 7.72-7.67 (m, 2H), 7.59-7.32 (m, 5H), 7.27-7.01 (m, 3H), 4.89 (q, J=6.7 Hz, 1H), 1.32 (d, J=6.6 Hz, 3H). ES/MS 567.1 (M+H$^+$);

(77)

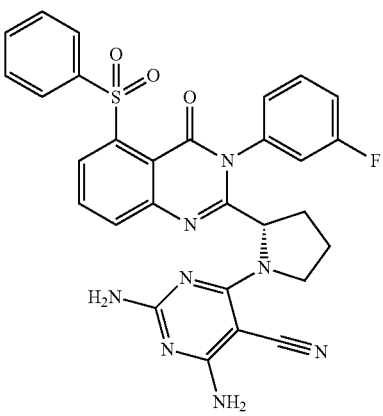

(S)-2,4-diamino-6-(2-(3-(3-fluorophenyl)-5-(methylsulfonyl)-4-oxo-3,4-dihydroquinazolin-2-yl)pyrrolidin-1-yl)pyrimidine-5-carbonitrile (Compound 77): $^1$H NMR (400 MHz, DMSO) δ 8.47 (dt, J=7.7, 1.1 Hz, 1H), 8.08-7.99 (m, 1H), 7.94 (dq, J=8.3, 1.1 Hz, 1H), 7.84-7.67 (m, 3H), 7.67-7.19 (m, 8H), 4.70-4.59 (m, 1H), 4.06-3.95 (m, 1H), 3.99-3.81 (m, 1H), 2.13-1.93 (m, 2H), 1.92-1.80 (m, 1H), 1.72-1.61 (m, 1H), ES/MS 583.1 (M+H$^+$);

(78)

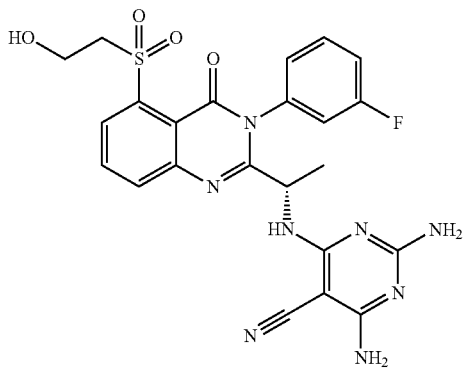

(S)-2,4-diamino-6-((1-(3-(3-fluorophenyl)-5-((2-hydroxyethyl)sulfonyl)-4-oxo-3,4-dihydroquinazolin-2-yl)ethyl)amino)pyrimidine-5-carbonitrile (Compound 78): ¹H NMR (400 MHz, DMSO) δ 8.44-8.34 (m, 1H), 8.22-8.13 (m, 2H), 7.75-7.59 (m, 2H), 7.57-7.48 (m, 1H), 7.41 (dddd, J=17.5, 8.9, 6.1, 2.4 Hz, 1H), 7.03 (dd, J=11.3, 7.1 Hz, 1H), 6.66 (br s, 2H), 6.44-6.32 (m, 2H), 4.99 (td, J=7.1, 5.9 Hz, 1H), 4.93 (td, J=5.5, 1.1 Hz, 1H), 4.09-3.97 (m, 2H), 3.84 (q, J=6.0 Hz, 2H), 1.50-1.46 (m, 3H). ES/MS 525.1 (M+H⁺);

(79)

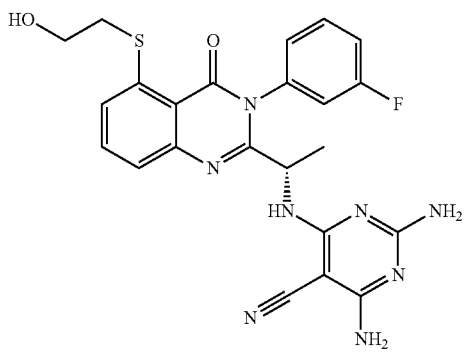

(S)-2,4-diamino-6-((1-(3-(3-fluorophenyl)-5-((2-hydroxyethyl)thio)-4-oxo-3,4-dihydroquinazolin-2-yl)ethyl)amino)pyrimidine-5-carbonitrile (Compound 79): ¹H NMR (400 MHz, DMSO) δ 7.88-7.82 (m, 1H), 7.71-7.60 (m, 2H), 7.59-7.34 (m, 4H), 6.96 (dd, J=15.5, 7.0 Hz, 1H), 6.70-6.63 (m, 2H), 6.45-6.31 (m, 2H), 5.10 (td, J=5.6, 0.7 Hz, 1H), 4.94-4.81 (m, 1H), 3.76 (q, J=6.5 Hz, 2H), 3.15 (t, J=6.7 Hz, 2H), 1.45-1.41 (m, 3H). ES/MS 493.1 (M+H⁺).

(80)

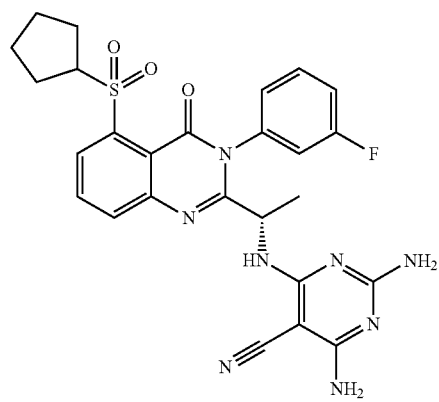

(S)-2,4-diamino-6-((1-(5-(cyclopentylsulfonyl)-3-(3-fluorophenyl)-4-oxo-3,4-dihydroquinazolin-2-yl)ethyl)amino)pyrimidine-5-carbonitrile (Compound 80): ¹H NMR (400 MHz, DMSO) δ 8.31-8.25 (m, 1H), 8.06-8.02 (m, 2H), 7.94-7.36 (m, 6H), 7.27-7.21 (m, 2H), 4.97 (q, J=6.8 Hz, 1H), 4.76 (tt, J=8.9, 6.3 Hz, 1H), 1.98-1.43 (m, 9H), 1.37 (d, J=6.7 Hz, 3H). ES/MS 549.1 (M+H⁺);

(81)

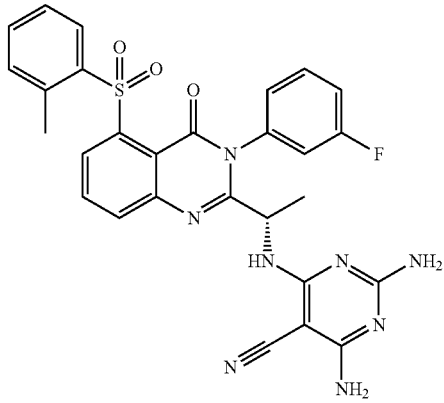

(S)-2,4-diamino-6-((1-(3-(3-fluorophenyl)-4-oxo-5-(o-tolylsulfonyl)-3,4-dihydroquinazolin-2-yl)ethyl)amino)pyrimidine-5-carbonitrile (Compound 81): ¹H NMR (400 MHz, DMSO) δ 8.55 (dt, J=7.6, 1.3 Hz, 1H), 8.20-8.10 (m, 2H), 7.82 (dt, J=8.1, 1.8 Hz, 1H), 7.51-7.37 (m, 3H), 7.37-7.02 (m, 4H), 4.96-4.87 (m, 1H), 2.30 (s, 3H), 1.36 (d, J=6.7 Hz, 3H). ES/MS 571.1 (M+H⁺);

(83)

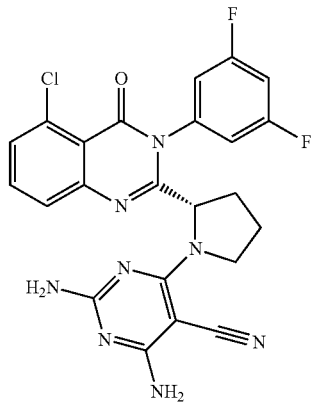

(S)-2,4-diamino-6-(2-(5-chloro-3-(3,5-difluorophenyl)-4-oxo-3,4-dihydroquinazolin-2-yl)pyrrolidin-1-yl)pyrimidine-5-carbonitrile (Compound 83). ¹H NMR (400 MHz, DMSO-d₆) δ 7.83 (m, 1H), 7.76 (t, J=8.0 Hz, 1H), 7.59 (m, 1H), 7.58 (m, 1H), 7.56-7.51 (m, 2H), 7.44 (bs, 2H), 7.03 (bs, 2H), 4.68 (m, 1H), 4.07 (d, J=7.5 Hz, 1H), 3.94 (m, 1H), 2.26-2.05 (m, 2H), 2.00 (m, 1H), 1.92-1.80 (m, 1H). ES/MS 495.2 (M+H⁺);

(84)

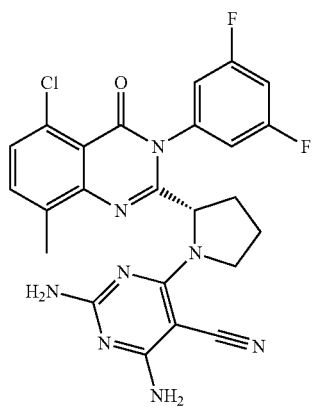

(S)-2,4-diamino-6-(2-(5-chloro-3-(3,5-difluorophenyl)-8-methyl-4-oxo-3,4-dihydroquinazolin-2-yl)pyrrolidin-1-yl)pyrimidine-5-carbonitrile (Compound 84). $^1$H NMR (400 MHz, DMSO-d$_6$) δ 7.83 (m, 1H), 7.67 (d, J=8.0, 1.0 Hz, 1H), 7.55 (m, 2H), 7.48 (d, J=8.0 Hz, 1H), 7.45 (bs, 2H), 7.01 (bs, 2H), 4.77 (m, 1H), 4.07 (m, 1H), 4.00 (m, 1H), 2.42 (s, 3H), 2.30-2.06 (m, 2H), 2.06-1.94 (m, 1H), 1.88 (m, 8.7 Hz, 1H). ES/MS 509.1 (M+H$^+$);

(86)

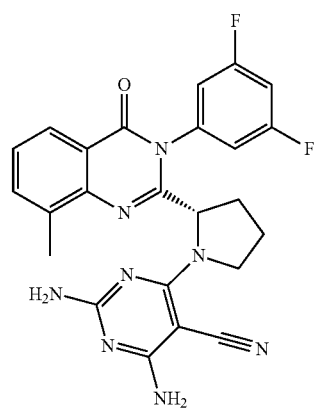

(S)-2,4-diamino-6-(2-(3-(3,5-difluorophenyl)-8-methyl-4-oxo-3,4-dihydroquinazolin-2-yl)pyrrolidin-1-yl)pyrimidine-5-carbonitrile (Compound 86). $^1$H NMR (400 MHz, DMSO-d$_6$) δ 7.99 (ddd, J=8.0, 1.6, 0.7 Hz, 1H), 7.86 (d, J=9.1 Hz, 1H), 7.74 (m, 1H), 7.78 (bs, 2H), 7.56 (m, 2H), 7.46 (t, J=7.6 Hz, 1H), 7.21 (bs, 2H), 4.84 (m, 1H), 4.11 (m, 1H), 4.02 (m, 1H), 2.49 (s, 3H), 2.21 (m, 1H), 2.17-2.08 (m, 1H), 2.01 (m, 1H), 1.89 (m, 1H). ES/MS 475.2 (M+H$^+$);

(85)

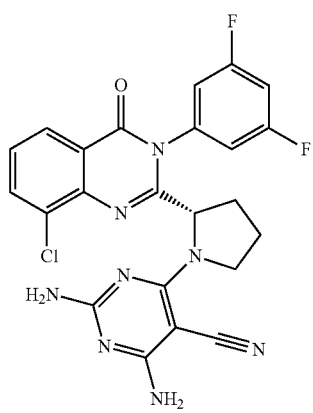

(S)-2,4-diamino-6-(2-(8-chloro-3-(3,5-difluorophenyl)-4-oxo-3,4-dihydroquinazolin-2-yl)pyrrolidin-1-yl)pyrimidine-5-carbonitrile (Compound 85). $^1$H NMR (400 MHz, DMSO-d$_6$) δ 8.09 (dd, J=8.0, 1.4 Hz, 1H), 8.00 (dd, J=7.8, 1.4 Hz, 1H), 7.82 (d, J=9.0 Hz, 1H), 7.66-7.44 (m, 3H), 7.08 (bs, 2H), 4.75 (m, 1H), 4.06 (m, 1H), 3.98 (m, 1H), 2.21 (m, 1H), 2.15-2.05 (m, 1H), 1.98 (m, 1H), 1.86 (m, 1H). ES/MS 495.1 (M+H$^+$);

(87)

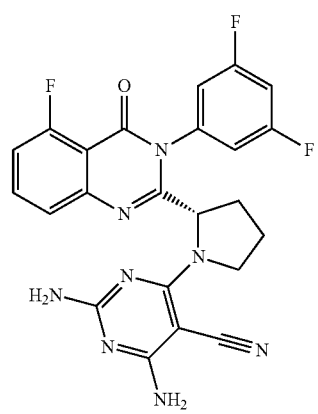

(S)-2,4-diamino-6-(2-(3-(3,5-difluorophenyl)-5-fluoro-4-oxo-3,4-dihydroquinazolin-2-yl)pyrrolidin-1-yl)pyrimidine-5-carbonitrile (Compound 87). $^1$H NMR (400 MHz, DMSO-d$_6$) δ 7.96-7.79 (m, 2H), 7.72 (bs, 2H), 7.56 (m, 2H), 7.46 (m, 1H), 7.34 (m, 1H), 7.25 (bs, 2H), 4.69 (m, 1H), 4.08 (m, 1H), 3.95 (m, 1H), 2.25-2.06 (m, 2H), 1.98 (m, 1H), 1.89 (m, 1H). ES/MS 479.1 (M+H$^+$);

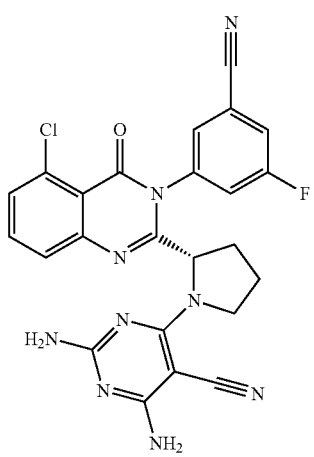

(88)

(S)-2,4-diamino-6-(2-(5-chloro-3-(3-cyano-5-fluorophenyl)-4-oxo-3,4-dihydroquinazolin-2-yl)pyrrolidin-1-yl)pyrimidine-5-carbonitrile (Compound 88). $^1$H NMR (400 MHz, DMSO-d$_6$) δ 8.38 (m, 0.5H), 8.32 (dt, J=9.3, 2.2 Hz, 6.5H), 8.24-8.15 (m, 1H), 8.12 (m, 0.5H), 8.08 (dt, J=9.3, 2.1 Hz, 0.5H), 7.78 (t, J=8.0 Hz, 1H), 7.60 (m, 2H), 7.58 (bs, 2H), 7.17 (bs, 2H), 4.61 (m, 1H), 4.07 (m, 1H), 4.00-3.87 (m, 1H), 2.24-2.04 (m, 2H), 1.98 (m, 1H), 1.86 (m, 1H). ES/MS 502.1 (M+H$^+$);

(S)-2,4-diamino-6-(2-(2-(3-(3-(difluoromethyl)phenyl)-8-iodo-4-oxo-3,4-dihydroquinazolin-2-yl)pyrrolidin-1-yl)pyrimidine-5-carbonitrile;

(S)-2,4-diamino-6-(2-(8-iodo-4-oxo-3-phenyl-3,4-dihydroquinazolin-1-yl)pyrimidine-5-carbonitrile;

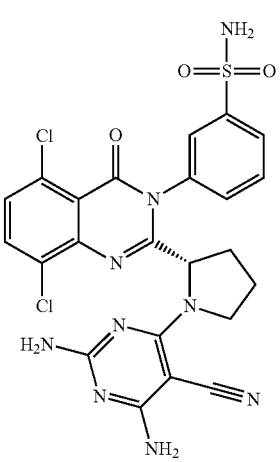

(91)

(S)-3-(5,8-dichloro-2-(1-(2,6-diamino-5-cyanopyrimidin-4-yl)pyrrolidin-2-yl)-4-oxoquinazolin-3(4H)-yl)benzenesulfonamide, mixture of atropisomers (Compound 91). $^1$H NMR (400 MHz, DMSO-d$_6$) δ 8.31 (td, J=1.8, 0.7 Hz, 0.1H), 8.26 (s, 0.1H), 8.25-8.21 (m, 0.1H), 8.14 (m, 0.2H), 8.11-8.08 (m, 0.2H), 8.08-8.02 (m, 0.75H), 8.00 (s, 0.1H), 7.99-7.95 (m, 0.4H), 7.94 (s, 0.1H), 7.91-7.81 (m, 0.75H), 7.62 (s, 0.8H), 7.60-7.55 (m, 0.5H), 7.24-7.15 (m, 0.4H), 6.96 (bs, 2H), 6.82-6.75 (m, 0.5H), 6.52 (bs, 2H), 4.79-4.42 (m, 1H), 4.27-4.05 (m, 0.5H), 4.05-3.93 (m, 0.5H), 3.93-3.75 (m, 0.5H), 3.70-3.53 (m, 0.5H), 2.34-2.05 (m, 2H), 2.05-1.66 (m, 2H). ES/MS 572.1 (M+H$^+$);

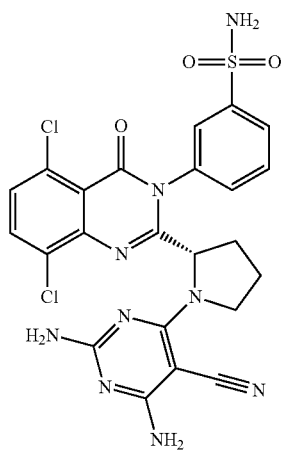

(92)

(S)-3-(5,8-dichloro-2-(1-(2,6-diamino-5-cyanopyrimidin-4-yl)pyrrolidin-2-yl)-4-oxoquinazolin-3(4H)-yl)benzenesulfonamide, single atropisomer of unknown configuration (Compound 92). $^1$H NMR (400 MHz, DMSO-d$_6$) δ 8.26 (s, 1H), 8.14 (ddd, J=7.9, 2.1, 1.1 Hz, 1H), 8.11-8.02 (m, 2H), 7.98 (dd, J=8.5, 6.0 Hz, 1H), 7.92-7.84 (m, 2H), 7.64 (s, 2H), 7.58 (dd, J=8.5, 3.4 Hz, 1H), 7.48 (bs, 1H), 7.14 (bs, 1H), 4.73 (m, 1H), 4.15 (m, 1H), 3.99 (m, 1H), 2.35-2.17 (m, 1H), 2.17-2.06 (m, 1H), 2.00 (m, 1H), 1.90-1.73 (m, 1H). ES/MS 572.0 (M+H$^+$);

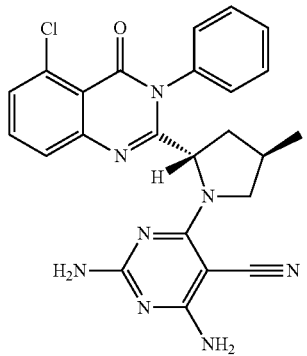

(94)

2,4-diamino-6-((2S,4R)-2-(5-chloro-4-oxo-3-phenyl-3,4-dihydroquinazolin-2-yl)-4-methylpyrrolidin-1-yl)pyrimidine-5-carbonitrile (Compound 94). $^1$H NMR (400 MHz, DMSO-d$_6$) δ 7.90-7.83 (m, 1H), 7.75-7.66 (m, 1H), 7.64-7.45 (m, 10H), 7.11 (brs, 2H), 4.68 (d, J=8.5 Hz, 1H), 4.22 (t, J=8.8 Hz, 1H), 2.64 (s, 1H), 2.23-2.13 (m, 1H), 1.41 (td, J=11.9, 8.8 Hz, 1H), 0.96 (d, J=6.6 Hz, 3H). ES/MS 473.1 (M+H$^+$).

(95)

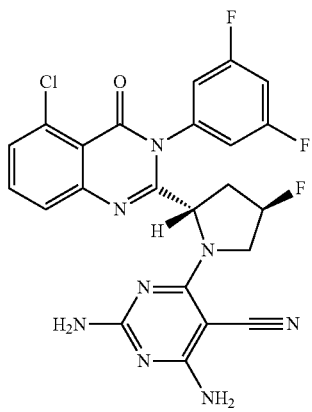

2,4-diamino-6-((2S,4R)-2-(5-chloro-3-(3,5-difluorophenyl)-4-oxo-3,4-dihydroquinazolin-2-yl)-4-fluoropyrrolidin-1-yl)pyrimidine-5-carbonitrile (Compound 95). $^1$H NMR (400 MHz, DMSO-d$_6$) δ 7.85-7.69 (m, 2H), 7.65-7.41 (m, 3H), 7.10 (brs, 4H), 5.51 (d, J=4.1 Hz, 1H), 5.38 (s, 1H), 4.72 (s, 2H), 2.41 (m, 1H), 2.33 (m, $^1$H), 2.13 (m, 2H). ES/MS 513.1 (M+H$^+$).

(96)

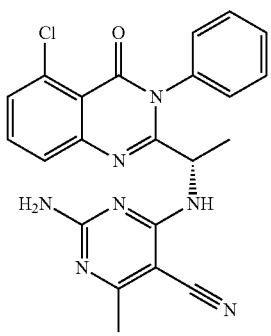

(S)-2-amino-4-((1-(5-chloro-4-oxo-3-phenyl-3,4-dihydroquinazolin-2-yl)ethyl)amino)-6-methylpyrimidine-5-carbonitrile (Compound 96). $^1$H NMR (400 MHz, DMSO-d$_6$) δ 8.14 (s, 1H), 7.85-7.31 (m, 10H), 7.21 (s, 1H), 4.95-4.83 (m, 1H), 2.40-2.29 (m, 3H), 1.37 (dt, J=6.7, 1.6 Hz, 3H). ES/MS 532.1 (M+H$^+$).

(97)

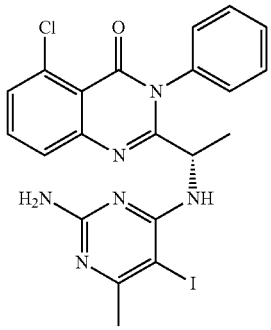

(S)-2-(1-((2-amino-5-iodo-6-methylpyrimidin-4-yl)amino)ethyl)-5-chloro-3-phenylquinazolin-4(3H)-one (Compound 97). $^1$H NMR (400 MHz, DMSO-d$_6$) δ 8.09 (s, 1H), 7.89-7.80 (m, 1H), 7.77 (s, 1H), 7.74-7.49 (m, 6H), 7.49-7.40 (m, 3H), 4.96-4.84 (m, 1H), 2.41 (d, J=1.2 Hz, 3H), 1.36 (d, J=6.5 Hz, 3H). ES/MS 533.1 (M+H$^+$).

(98)

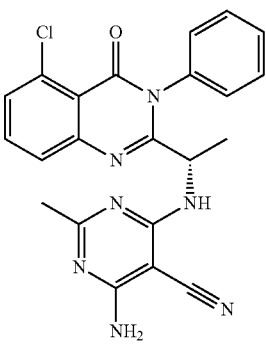

(S)-4-amino-6-((1-(5-chloro-4-oxo-3-phenyl-3,4-dihydroquinazolin-2-yl)ethyl)amino)-2-methylpyrimidine-5-carbonitrile (Compound 98). $^1$H NMR (400 MHz, DMSO-d$_6$) δ 8.00 (d, J=7.2 Hz, 1H), 7.79 (td, J=8.0, 1.1 Hz, 1H), 7.73-7.62 (m, 3H), 7.62-7.52 (m, 3H), 7.49-7.37 (m, 3H), 5.03-4.91 (m, 1H), 2.16 (d, J=1.1 Hz, 3H), 1.38 (d, J=6.7 Hz, 3H). ES/MS 432.1 (M+H$^+$).

(99)

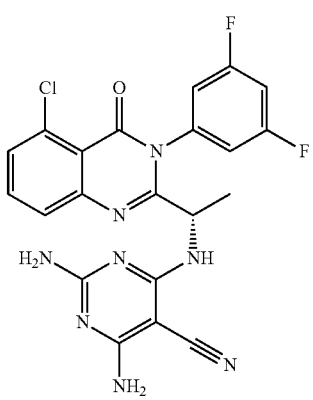

(S)-4-amino-6-((1-(5-chloro-3-(3,5-difluorophenyl)-4-oxo-3-phenyl-3,4-dihydroquinazolin-2-yl)ethyl)amino)-2-methylpyrimidine-5-carbonitrile (Compound 99). $^1$H NMR (400 MHz, DMSO-d$_6$) δ 7.89-7.45 (m, 7H), 7.33 (tt, J=9.3, 2.5 Hz, 1H), 7.16-7.08 (m, 1H), 5.19-5.07 (m, 1H), 2.13 (d, 1.2 Hz, 3H), 1.41 (d, J=6.4 Hz, 3H). ES/MS 468.1 (M+H$^+$).

(100)

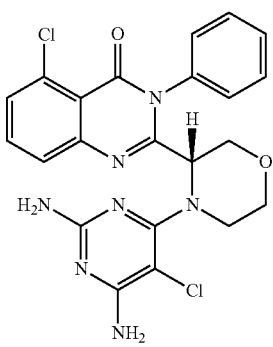

(R)-5-chloro-2-(4-(2,6-diamino-5-chloropyrimidin-4-yl)morpholin-3-yl)-3-phenylquinazolin-4(3H)-one (Compound 100). $^1$H NMR (400 MHz, DMSO-d$_6$) δ 9.47 (brs, 1H), 8.14-7.20 (m, 12H), 4.66 (m, 1H), 4.27-3.08 (m, 6H). ES/MS 484.1 (M+H$^+$).

(101)

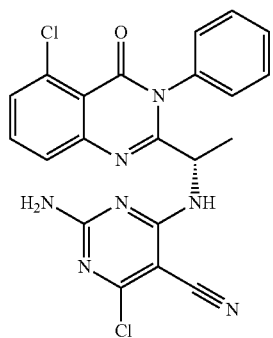

(S)-2-amino-4-chloro-6-((1-(5-chloro-4-oxo-3-phenyl-3,4-dihydroquinazolin-2-yl)ethyl)amino)pyrimidine-5-carbonitrile (Compound 101). $^1$H NMR (400 MHz, DMSO-d$_6$) δ 8.01-7.11 (m, 12H), 4.86 (p, J=6.7 Hz, 1H), 1.36 (d, J=6.6 Hz, 3H). ES/MS 452.1 (M+H$^+$).

(102)

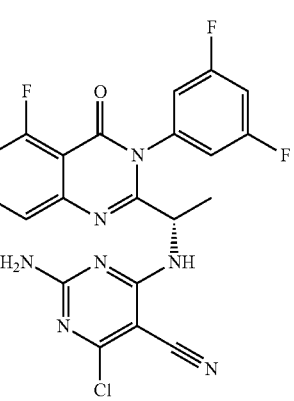

(S)-2-amino-4-chloro-6-((1-(3-(3,5-difluorophenyl)-5-chloro-4-oxo-3-phenyl-3,4-dihydroquinazolin-2-yl)ethyl)amino)pyrimidine-5-carbonitrile (Compound 102). $^1$H NMR (400 MHz, DMSO-d$_6$) δ 8.08-7.00 (m, 9H), 6.30-5.09 (brs, 2H), 5.12-4.86 (m, 1H), 1.41 (dd, J=6.4, 1.2 Hz, 3H). ES/MS 472.1 (M+H$^+$).

(103)

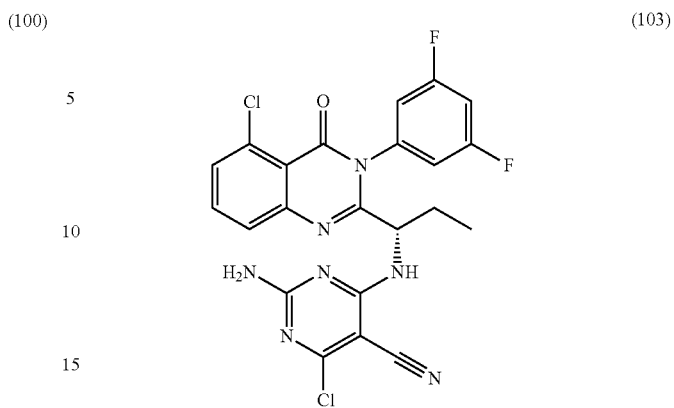

(S)-2-amino-4-chloro-6-((1-(5-chloro-3-(3,5-difluorophenyl)-4-oxo-3-phenyl-3,4-dihydroquinazolin-2-yl)ethyl)amino)pyrimidine-5-carbonitrile (Compound 103). $^1$H NMR (400 MHz, DMSO-d$_6$) δ 7.95-7.07 (m, 7H), 5.9-4.93 (brs, 2H), 4.80 (td, J=7.4, 5.3 Hz, 1H), 2.02 (ddd, J=13.5, 7.5, 5.7 Hz, 1H), 1.82 (dp, J=14.5, 7.3 Hz, 1H), 0.96-0.76 (m, 3H). ES/MS 502.1 (M+H$^+$).

(104)

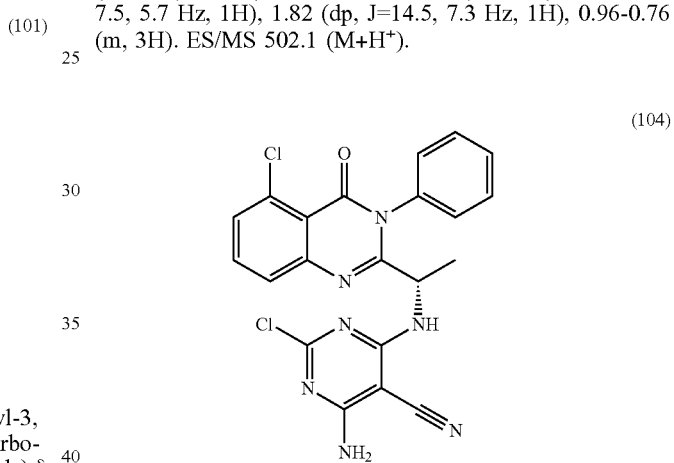

(S)-4-amino-2-chloro-6-((1-(5-chloro-4-oxo-3-phenyl-3,4-dihydroquinazolin-2-yl)ethyl)amino)pyrimidine-5-carbonitrile (Compound 104). $^1$H NMR (400 MHz, DMSO-d$_6$) δ 8.36 (d, J=6.7 Hz, 1H), 7.88-7.33 (m, 10H), 4.57-4.42 (m, 1H), 1.40-1.18 (m, 3H), ES/MS 452.1 (M+H$^+$)

(105)

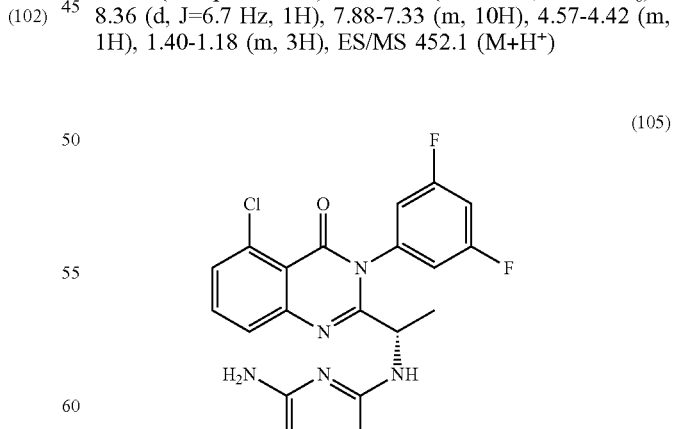

(S)-2-amino-4-chloro-6-((1-(5-chloro-3-(3,5-difluorophenyl)-4-oxo-3,4-dihydroquinazolin-2-yl)ethyl)amino)pyrimidine-5-carbonitrile (Compound 105). ¹H NMR (400 MHz, DMSO-d₆) δ 7.99-6.55 (m, 10H), 5.34-4.64 (m, 1H), 1.42 (dd, J=6.5, 1.1 Hz, 3H). ES/MS 488.1 (M+H⁺).

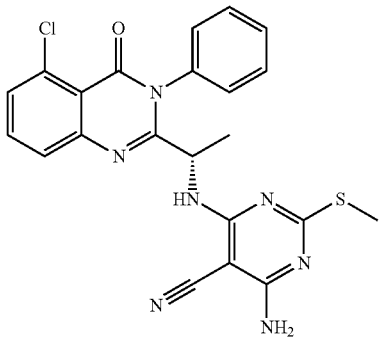 [SMILES: CSc1nc(N)c(C#N)c(N[C@@H](C)c2nc3cccc(Cl)c3c(=O)n2-c2ccccc2)n1]

(S)-4-amino-6-((1-(5-chloro-4-oxo-3-phenyl-3,4-dihydroquinazolin-2-yl)ethyl)amino)-2-(methylthio)pyrimidine-5-carbonitrile.

(107)

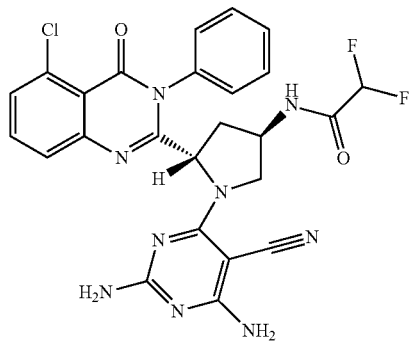

N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2,2-difluoroacetamide (Compound 107). ¹H NMR (400 MHz, DMSO-d₆) δ 9.09 (d, J=7.3 Hz, 1H), 7.92-7.66 (m, 4H), 7.65-7.43 (m, 7H), 7.23 (brs, 2H), 6.38-5.94 (m, 1H), 4.76 (s, 1H), 4.66 (d, J=10.9 Hz, ¹H), 4.29 (d, J=9.0 Hz, 1H), 3.90-3.81 (m, 1H), 2.42-2.31 (m, 1H), 1.82 (dt, J=12.9, 8.4 Hz, 1H). ES/MS 552.2 (M+H⁺).

(108)

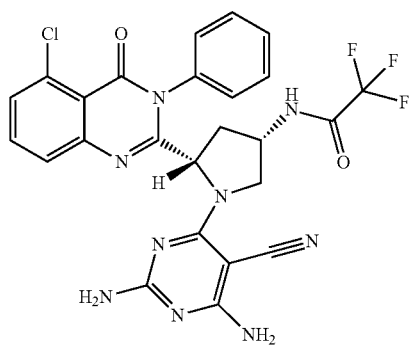

N-((3S,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2,2,2-trifluoroacetamide (Compound 108). ¹H NMR (400 MHz, DMSO-d₆) δ 9.39 (d, J=6.9 Hz, 1H), 7.88 (dt, J=8.1, 1.7 Hz, 1H), 7.77-7.37 (m, 8H), 7.37-7.15 (m, 3H), 4.69 (t, J=7.0 Hz, 1H), 4.40 (q, J=6.7 Hz, 1H), 4.25 (dd, J=10.6, 6.9 Hz, 1H), 4.04 (dd, J=10.6, 5.8 Hz, 1H), 2.27-2.04 (m, 3H). ES/MS 570.1 (M+H⁺).

(109)

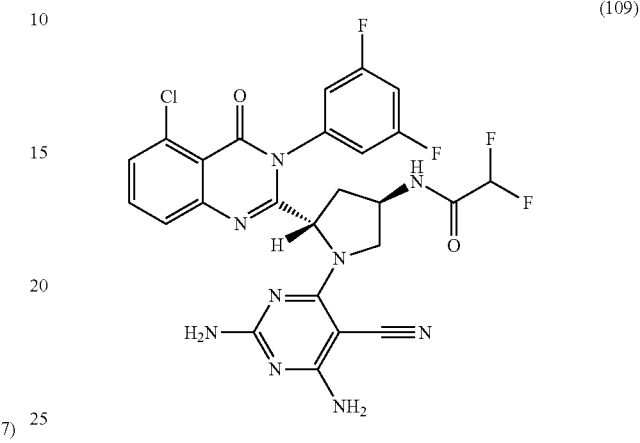

N-((3R,5S)-5-(5-chloro-3-(3,5-difluorophenyl)-4-oxo-3,4-dihydroquinazolin-2-yl)-1-(2,6-diamino-5-cyanopyrimidin-4-yl)pyrrolidin-3-yl)-2,2-difluoroacetamide (Compound 109). ¹H NMR (400 MHz, DMSO-d₆) δ 9.12 (d, J=7.3 Hz, 1H), 8.02-7.66 (m, 4H), 7.63-7.44 (m, 5H), 7.26 (brs, 2H), 6.18 (td, J=53.6, 1.2 Hz, 1H), 4.88-4.51 (m, 2H), 4.29 (t, J=8.6 Hz, 1H), 3.86 (dd, J=10.4, 5.9 Hz, 1H), 2.39 (dt, J=11.6, 5.2 Hz, 1H), 1.92 (dt, J=12.8, 8.2 Hz, 1H). ES/MS 588.1 (M+H⁺).

(110)

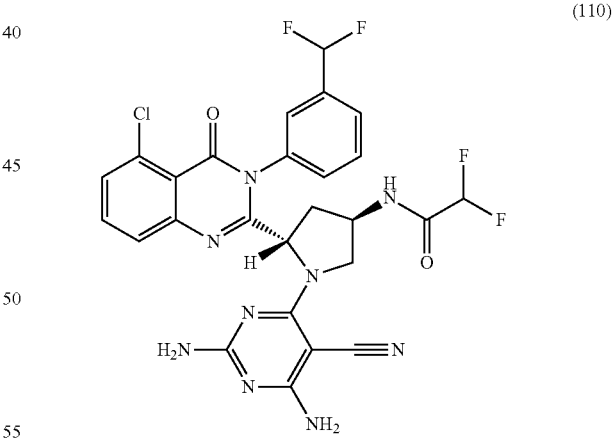

N-((3R,5S)-5-(5-chloro-3-(3-(difluorophenyl)-5-fluorophenyl)-4-oxo-3,4-dihydroquinazolin-2-yl)-1-(2,6-diamino-5-cyanopyrimidin-4-yl)pyrrolidin-3-yl)-2,2-difluoroacetamide (Compound 110). ¹H NMR (400 MHz, DMSO-d₆) δ 9.10 (t, J=6.8 Hz, 1H), 8.08 (d, J=14.9 Hz, 1H), 7.86-7.62 (m, 4H), 7.57 (m, 4H), 7.12 (td, J=55.4, 8.6 Hz, 3H), 6.17 (td, J=53.6, 5.8 Hz, 1H), 4.68 (d, J=13.6 Hz, 2H), 4.39-4.18 (m, 1H), 3.83 (q, J=8.0, 7.5 Hz, 1H), 2.40 (p, J=6.6, 6.0 Hz, 1H), 1.88 (ddt, J=28.3, 12.5, 8.3 Hz, 1H). ES/MS 620.1 (M+H⁺).

(111)

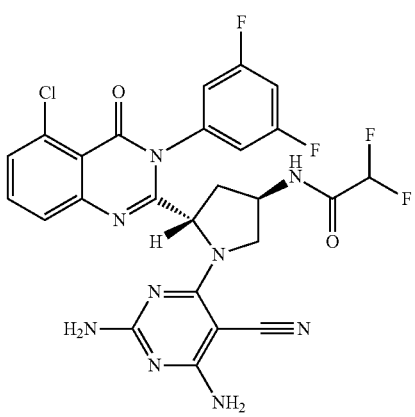

N-((3R,5S)-1-(2,6-diamino-5-cyanopyrimidin-4-yl)-5-(3-(3,5-difluorophenyl)-5-fluoro-4-oxo-3,4-dihydroquinazolin-2-yl)pyrrolidin-3-yl)-2,2-difluoroacetamide (Compound 111). $^1$H NMR (400 MHz, DMSO-d$_6$) δ 9.10 (d, J=7.3 Hz, 1H), 7.92-7.69 (m, 2H), 7.64-7.39 (m, 4H), 7.31 (dd, J=10.9, 8.2 Hz, 1H), 7.09 (brs, 4H), 6.41-5.91 (m, 1H), 4.70 (dd, J=22.0, 8.5 Hz, 2H), 4.28 (t, J=8.8 Hz, 1H), 3.84 (dd, J=10.3, 5.8 Hz, 1H), 2.38 (dt, J=11.5, 5.4 Hz, 1H), 1.92 (dt, J=12.7, 8.3 Hz, 1H). ES/MS 572.2 (M+H$^+$).

(112)

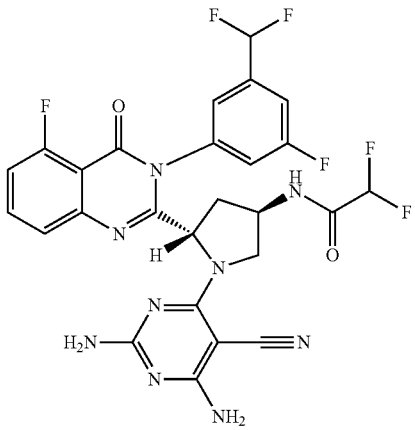

N-((3R,5S)-1-(2,6-diamino-5-cyanopyrimidin-4-yl)-5-(3-(3-(difluorophenyl)-5-fluorophenyl)-5-fluoro-4-oxo-3,4-dihydroquinazolin-2-yl)pyrrolidin-3-yl)-2,2-difluoroacetamide (Compound 112). $^1$H NMR (400 MHz, DMSO-d$_6$) δ 9.10 (t, J=6.7 Hz, 1H), 8.07 (d, J=14.5 Hz, 1H), 7.88-7.62 (m, 3H), 7.62-7.38 (m, 3H), 7.38-7.21 (m, 1H), 7.05 (m, 4H), 6.36-5.94 (m, 1H), 4.67 (m, 2H), 4.27 (m, 1H), 3.91-3.70 (m, 1H), 2.39 (m, 1H), 1.95-1.71 (m, 1H). ES/MS 604.2 (M+H$^+$)

(114)

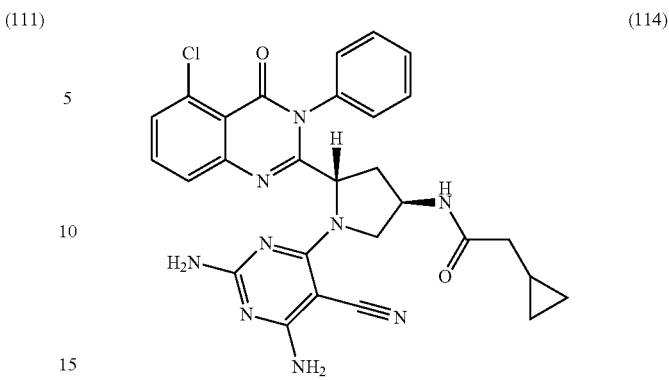

N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2,2-cyclopropylacetamide (Compound 114). $^1$H NMR (400 MHz, DMSO-d$_6$) δ 7.96 (d, 7.2 Hz, 1H), 7.86 (d, J=7.5 Hz, 1H), 7.72 (t, J=8.0 Hz, 1H), 7.64-7.46 (m, 8H), 6.69 (m, 1H), 4.58 (m, 1H), 4.24 (m, 1H), 3.68 (s, 1H), 2.70-2.62 (m, 1H), 2.33 (d, J=3.5 Hz, 1H), 2.26 (m, 1H), 1.89 (dd, J=10.1, 7.0 Hz, 2H), 1.73 (m, 1H), 1.24 (s, 1H), 1.14 (d, J=0.7 Hz, 1H), 0.86 (s, 1H), 0.42-0.30 (m, 2H). ES/MS 556.1 (M+H$^+$).

Example 5. Preparation of a Compound of Formula (I)

A. Preparation of a Compound of Formula (I) in which n is 2, $R^{1a}$ is F, $R^{1b}$=CN, m is 1, $R^2$=F, $R^3$ is cyclopropyl, $R^4$ is cyano, $R^5$ is hydrogen, $R^6$ is $NH_2$, and $R^7$ is $NH_2$

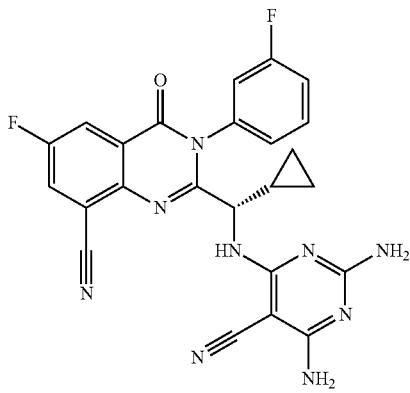

To a solution of (S)-2,4-diamino-6-((cyclopropyl(6-fluoro-3-(3-fluorophenyl)-8-iodo-4-oxo-3,4-dihydroquinazolin-2-yl)methyl)amino)pyrimidine-5-carbonitrile (720 mg, 1.2 mmol) in NMP (4 mL) was added cuprous cyanide (220 mg, 2.4 mmol) and tetrakis(triphenylphosphine)Pd(0) (140 mg, 0.12 mmol). The mixture was irradiated in microwave reactor at 150° C. for one hour. Purification by flash chromatography (40 g flash silica, 30% EtOAc/Hexanes to 20% MeOH/EtOAc), followed by HPLC during with 5%-95% water/acetonitrile (0.1% v/v trifluoroacetic acid) provided (S)-2-(cyclopropyl((2,6-diamino-5-cyanopyrimidin-4-yl)amino)methyl)-6-fluoro-3-(3-fluorophenyl)-4-oxo-3,4-dihydroquinazoline-5-carbonitrile (Compound 7a). $^1$H NMR (400 MHz, DMSO) δ 8.56 (dd, J=3.2, 8.4 Hz, 1H), 8.20 (dd, J=3.2, 8.0 Hz, 1H), 7.80 (bs, 4H), 7.57-7.02 (m, 5H), 4.70 (m, 1H), 1.59 (m, 1H), 0.54 (m, 3H), 0.22 (m, 1H). ES/MS 486.2 (M+H$^+$).

B. Following the procedure described in Example 5 and Reaction Scheme I, below compound of formula (I) were prepared:

(S)-2-(cyclopropyl((2,6-diamino-5-cyanopyrimidin-4-yl)amino)methyl)-6-fluoro-4-oxo-3-phenyl-3,4-dihydroquinazoline-5-carbonitrile (Compound 8a): $^1$H NMR (400 MHz, DMSO) δ 8.55 (dd, J=3.2, 8.4 Hz, 1H), 8.19 (dd, J=2.8, 8.0 Hz, 1H), 7.73 (bs, 4H), 7.50 (m, 2H), 7.32 (m, 2H), 7.23 (m, 1H), 4.71 (m, 1H), 1.57 (m, 1H), 0.52 (m, 3H), 0.19 (m, 1H). ES/MS 468.1 (M+H$^+$)

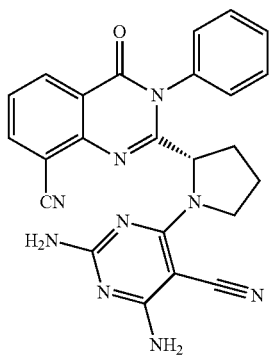 [SMILES: N#Cc1c(N)nc(N)nc1N1CCC[C@H]1c1nc2c(C#N)cccc2c(=O)n1-c1ccccc1]

(S)-2-(1-(2,6-diamino-5-cyanopyrimidin-4-yl)pyrrolidin-2-yl)-4-oxo-3-phenyl-3,4-dihydroquinazoline-5-carbonitrile (Compound 89). $^1$H NMR (400 MHz, DMSO-d$_6$) δ 8.38 (dd, J=8.0, 1.5 Hz, 1H), 8.34 (dd, J=7.6, 1.5 Hz, 1H), 7.89 (m, 1H), 7.63 (m, 2H), 7.60 (bs, 2H), 7.57 (m, 3H), 7.07 (bs, 2H), 4.75 (m, 1H), 4.06 (m, 1H), 3.99 (m, 1H), 2.19 (m, 1H), 2.10 (m, 1H), 1.9 (m, 1H), 1.76 (m, 1H). ES/MS 450.1 (M+H$^+$);

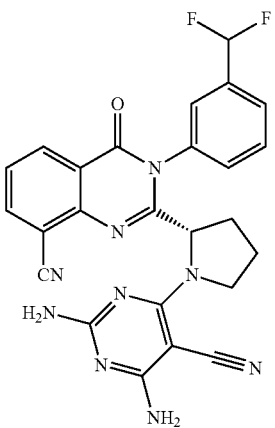 [SMILES: N#Cc1c(N)nc(N)nc1N1CCC[C@H]1c1nc2c(C#N)cccc2c(=O)n1-c1cccc(C(F)F)c1]

(S)-2-(1-(2,6-diamino-5-cyanopyrimidin-4-yl)pyrrolidin-2-yl)-3-(3-(difluoromethyl)phenyl)-4-oxo-3,4-dihydroquinazoline-8-carbonitrile (Compound 90). $^1$H NMR (400 MHz, DMSO-d$_6$) δ 8.42 (ddd, J=8.0, 3.5, 1.5 Hz, 1H), 8.39 (dt, J=7.6, 1.3 Hz, 1H), 8.22 (d, J=1.7 Hz, 0.5H), 8.12 (m, 0.5H), 7.89 (d, J=1.6 Hz, 0.5H), 7.85-7.78 (m, 2.5H), 7.70 (t, J=7.8 Hz, 1H), 7.60 (bs, 2H), 7.38 (td, J=55.7, 14.4 Hz, 1H), 7.09 (bs, 2H), 4.70 (m, 1H), 4.11 (m, 1H), 4.07-3.99 (m, 1H), 2.35-2.09 (m, 2H), 2.02 (m, 1H), 1.80 (m, 1H). ES/MS 500.1 (M+H$^+$);

Example 6. Preparation of a Compound of Formula (I)

A. Preparation of a Compound of Formula (I) in which n is 1, R$^1$ is 3-oxopropyl, m is 0, R$^3$ is methyl, R$^4$ is cyano, R$^5$ is hydrogen, R$^6$ is NH$_2$, and R$^7$ is NH$_2$

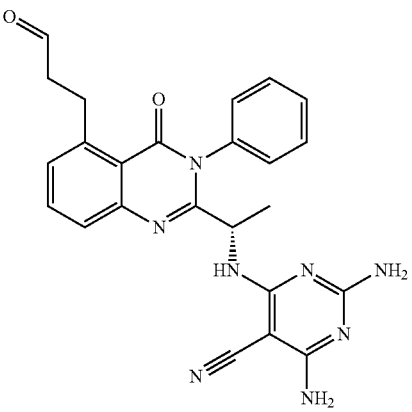 [SMILES: C[C@H](Nc1nc(N)nc(N)c1C#N)c1nc2cccc(CCC=O)c2c(=O)n1-c1ccccc1]

To a solution of (S)-2,4-diamino-6-((1-(5-bromo-4-oxo-3-phenyl-3,4-dihydroquinazolin-2-yl)ethyl)amino)pyrimidine-5-carbonitrile (50 mg, 0.105 mmol) in DMF (0.5 mL) was added chloro(2-dicyclohexylphosphino-2',6'-dimethoxy-1,1'-biphenyl)[2-(2'-amino-1,1'-biphenyl)]palladium (II) (8 mg, 0.011 mmol) and dicyclohexylmethylamine (67 μL, 0.315 mmol). The mixture was degassed under Ar. Allyl alcohol (9 μL, 0.126 mmol) was added, and the mixture heated to 120° C. in microwave for 1 hour. The reaction was poured into EtOAc and washed with H$_2$O (2×). Purified by flash chromatography (4 g silica, 0-100% EtOAc/hexane) to provide (S)-2,4-diamino-6-((1-(4-oxo-5-(3-oxopropyl)-3-phenyl-3,4-dihydroquinazolin-2-yl)ethyl)amino)pyrimidine-5-carbonitrile.

Example 7. Preparation of a Compound of Formula (I)

A. Preparation of a Compound of Formula (I) in which n is 1, R$^1$ is 3-morpholinopropyl, m is 0, R$^3$ is methyl, R$^4$ is cyano, R$^5$ is hydrogen, R$^6$ is NH$_2$, and R$^7$ is NH$_2$ (61)

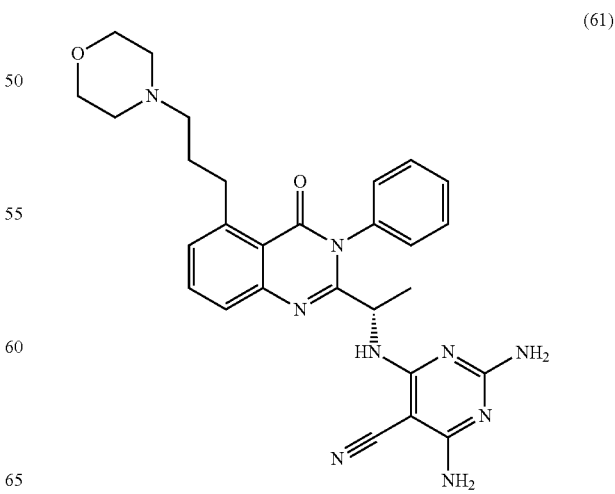

A solution of (S)-2,4-diamino-6-((1-(4-oxo-5-(3-oxopropyl)-3-phenyl-3,4-dihydroquinazolin-2-yl)ethyl)amino)pyrimidine-5-carbonitrile (99 mg, 0.24 mmol) in DCM (2 mL) was treated with morpholine and sodium triacetoxyborohydride. The reaction was filtered and the filtrate purified by prep LC to give (S)-2,4-diamino-6-((1-(5-(3-morpholinopropyl)-4-oxo-3-phenyl-3,4-dihydroquinazoline-2-yl)ethyl)amino)pyrimidine-5-carbonitrile. (Compound 61). $^1$H NMR (400 MHz, DMSO-$d_6$) δ 9.47 (s, 1H), 7.79 (dd, J=8.1, 7.4 Hz, 1H), 7.59 (dd, J=8.2, 1.2 Hz, 4H), 7.58-7.40 (m, 5H), 7.38 (dd, J=7.5, 1.2 Hz, 1H), 6.99 (s, 4H), 4.92-4.80 (m, 1H), 3.91 (d, J=12.6 Hz, 2H), 3.54 (t, J=12.7 Hz, 2H), 3.38 (d, J=12.3 Hz, 2H), 3.26-3.08 (m, 4H), 3.07-2.93 (m, 2H), 1.96-1.84 (m, 2H), 1.32 (d, J=6.6 Hz, 3H). ES/MS 526.3 (M+H$^+$).

B. Following the procedure described in Example 7 and Reaction Scheme I, below compound of formula (I) were prepared:

(62)

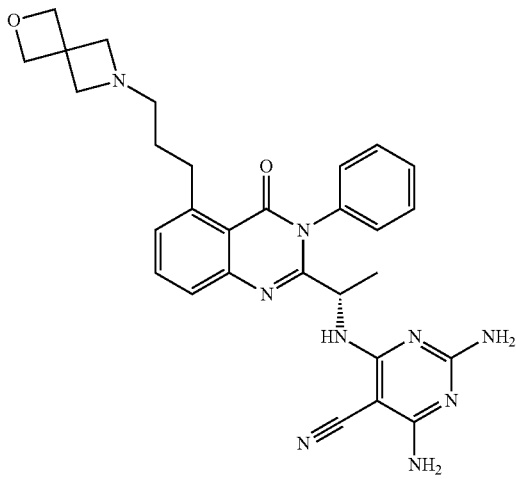

(S)-4-((1-(5-(3-(2-oxa-6-azaspiro[3.3]heptan-6-yl)propyl)-4-oxo-3-phenyl-3,4-dihydroquinazolin-2-yl)ethyl)amino)-2,6-diaminopyrimidine-5-carbonitrile (Compound 62). $^1$H NMR (400 MHz, DMSO-$d_6$) δ 7.71-7.64 (m, 1H), 7.58-7.40 (m, 6H), 7.24 (dd, J=7.5, 1.3 Hz, 1H), 6.76 (d, J=7.2 Hz, 1H), 6.52 (s, 2H), 6.23 (s, 2H), 4.76-4.65 (m, 1H), 4.51 (s, 4H), 3.18 (br s, 4H), 3.10-3.03 (m, 2H), 2.54-2.47 (m, 2H), 1.52-1.38 (m, 2H), 1.24 (d, J=6.7 Hz, 3H). ES/MS 538.2 (M+H$^+$).

(63)

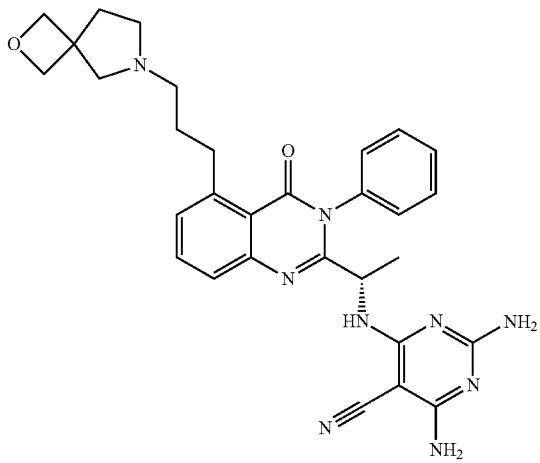

(S)-4-((1-(5-(3-(2-oxa-6-azaspiro[3.4]octan-6-yl)propyl)-4-oxo-3-phenyl-3,4-dihydroquinazolin-2-yl)ethyl)amino)-2,6-diaminopyrimidine-5-carbonitrile (Compound 63). $^1$H NMR (400 MHz, DMSO-$d_6$) δ 7.68 (t, J=7.8 Hz, 1H), 7.56-7.40 (m, 6H), 7.31-7.24 (m, 1H), 6.76 (d, J=7.1 Hz, 1H), 6.52 (s, 2H), 6.22 (s, 2H), 4.75-4.65 (m, 1H), 4.39 (s, 4H), 3.11 (t, J=7.6 Hz, 2H), 2.63 (s, 2H), 2.41-2.24 (m, 4H), 2.01-1.89 (m, 2H), 1.71-1.55 (m, 2H), 1.24 (d, J=6.6 Hz, 3H). ES/MS 552.2 (M+H$^+$).

(64)

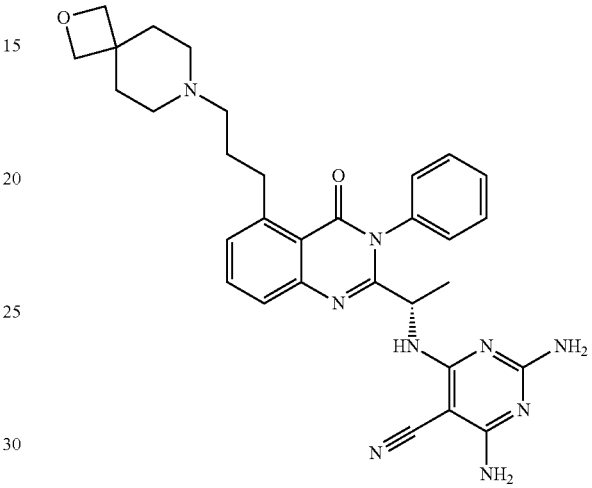

(S)-4-((1-(5-(3-(2-oxa-7-azaspiro[3.5]nonan-7-yl)propyl)-4-oxo-3-phenyl-3,4-dihydroquinazolin-2-yl)ethyl)amino)-2,6-diaminopyrimidine-5-carbonitrile (Compound 64). $^1$H NMR (400 MHz, DMSO-$d_6$) δ 9.63 (s, 1H), 7.75-7.68 (m, 1H), 7.64-7.42 (m, 6H), 7.40-7.15 (m, 2H), 7.15-6.60 (br m, 3H), 4.61-4.50 (m, 1H), 3.87 (dd, J=10.6, 6.4 Hz, 2H), 3.78-3.69 (m, 2H), 3.45 (t, J=5.2 Hz, 2H), 3.37 (t, J=5.3 Hz, 2H), 3.21-3.02 (m, 4H), 1.66 (dt, J=11.1, 5.8 Hz, 6H), 1.19 (d, J=6.8 Hz, 3H). ES/MS 566.3 (M+H$^+$).

Example 8. Preparation of a Compound of Formula (I)

A. Preparation of a Compound of Formula (I) in which, n is 1, R$^1$ is vinylsulfonyl, m is 1, R$^2$ is F, R$^3$ is methyl, R$^4$ is cyano, R$^5$ is hydrogen, R$^6$ is NH$_2$, and R$^7$ is NH$_2$

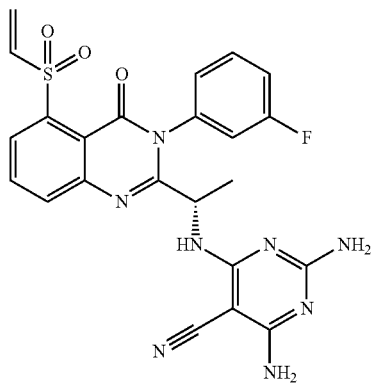 [SMILES: C=CS(=O)(=O)c1cccc2nc([C@H](C)Nc3nc(N)nc(N)c3C#N)n(-c3cccc(F)c3)c(=O)c12]

To a solution of (S)-2,4-diamino-6-((1-(3-(3-fluorophenyl)-5-((2-hydroxyethyl)sulfonyl)-4-oxo-3,4-dihydroquinazolin-2-yl)ethyl)amino)pyrimidine-5-carbonitrile (127 mg, 0.24 mmol) in dichloromethane (1 mL) was added p-toluenesulfonyl chloride (55 mg, 0.29 mmol), 4-dimethylaminopyridine (3 mg, 0.024 mmol) and triethylamine (0.051 mL, 0.36 mmol). The resulting mixture was stirred at room temperature for 2 days. The reaction was poured into saturated NaHCO3 and extracted with EtOAc (2×). The organic phase was dried over MgSO4, concentrated, and purified by column chromatography on silica eluting with EtOAc in hexanes (10-100%) to afford (S)-2,4-diamino-6-((1-(3-(3-fluorophenyl)-4-oxo-5-(vinylsulfonyl)-3,4-dihydroquinazolin-2-yl)ethyl)amino)pyrimidine-5-carbonitrile. ES/MS m/z=507.1 (M+H$^+$).

Example 9. Preparation of a Compound of Formula (I)

A. Preparation of a Compound of Formula (I) in which n is 1, R$^1$ is 2-(pyrrolidin-1-yl)ethyl)sulfonyl, m is 1, R$^2$ is F, R$^3$ is methyl, R$^4$ is cyano, R$^5$ is hydrogen, R$^6$ is NH$_2$, and R$^7$ is NH$_2$

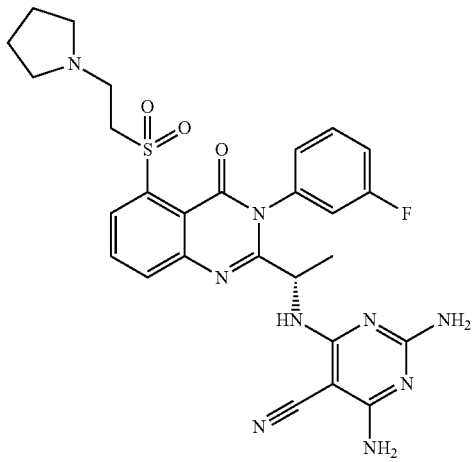

(82)

To a solution of (S)-2,4-diamino-6-((1-(3-(3-fluorophenyl)-4-oxo-5-(vinylsulfonyl)-3,4-dihydroquinazolin-2-yl)ethyl)amino)pyrimidine-5-carbonitrile (33 mg, 0.065 mmol) in THF (1 mL) was added pyrrolidine (0.021 mL, 0.26 mmol). The resulting mixture was stirred at room temperature for 1 h. The reaction was concentrated followed by lyophilization in acetonitrile-water to afford (S)-2,4-diamino-6-((1-(3-(3-fluorophenyl)-4-oxo-5-((2-(pyrrolidin-1-yl)ethyl)sulfonyl)-3,4-dihydroquinazolin-2-yl)ethyl)amino)pyrimidine-5-carbonitrile (Compound 82): $^1$H NMR (400 MHz, DMSO) δ 8.34-8.27 (m, 1H), 8.15-8.05 (m, 2H), 7.65-7.55 (m, 2H), 7.47-7.29 (m, 2H), 6.99-6.90 (m, 1H), 6.59 (br s, 2H), 6.27 (br s, 2H), 4.97-4.88 (m, 1H), 4.07-3.90 (m, 2H), 2.81-2.70 (m, 2H), 2.39-2.20 (m, 4H), 1.55-1.48 (m, 4H), 1.41 (d, J=6.8 Hz, 3H). ES/MS 578.2 (M+H$^+$).

Example 10. Preparation of a Compound of Formula (I)

A. Preparation of a Compound of Formula (I) in which n is 1, R$^1$ is 1,2,3,6-tetrahydropyridin-4-yl, m is 0, R$^3$ is methyl, R$^4$ is cyano, R$^5$ is hydrogen, R$^6$ is NH$_2$, and R$^7$ is NH$_2$

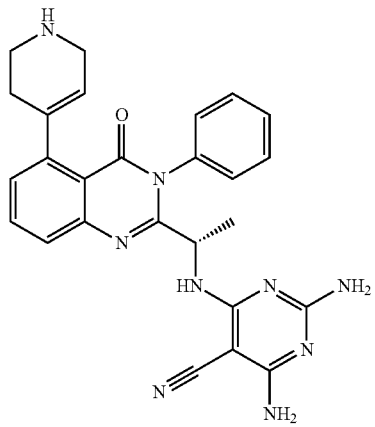 [SMILES: C[C@H](Nc1nc(N)nc(N)c1C#N)c1nc2cccc(C3=CCNCC3)c2c(=O)n1-c1ccccc1]

Tert-butyl 4-(4,4,5,5-tetramethyl-1,3,22-dioxaborolan-2-yl)-5,6-dihydropyridine-1(2H)-carboxylate (0.29 g, 0.93 mmol), (S)-2,4-diamino-6-((1-(5-bromo-4-oxo-3-phenyl-3,4-dihydroquinazolin-2-yl)ethyl)amino)pyrimidine-5-carbonitrile (0.22 g, 0.47 mmol). [1,1'bis(diphenylphosphino)ferrocene]dichloropalladium(II) dichloromethane complex (34 mg, 10 mol %) were taken up in 1,4-dioxanes (5 mL.). A solution of saturated aqueous sodium hydrogen carbonate (2.5 mL) was added. The mixture was heated with magnetic stirring for 90 minutes at 120° C. before being allowed to cool to room temperature. The mixture, diluted, with dichloromethane and water, was filtered through a pad of Celite diatomaceous earth. The aqueous phase was extracted twice with dichloromethane. The combined organics were dried over anhydrous magnesium, sulfate, filtered, and concentrated under reduced pressure to provide (S)-tert-butyl 4-(2-(1-((2,6-diamino-5-cyanopyrimidin-4-yl)amino)ethyl)-4-oxo-3-phenyl-3,4-dihydroquinazolin-5-yl)-5,6-dihydropyridine-1(2H)-carboxylate, which was carried forward without further purification. ES/MS 580.3 (M+H$^+$). A solution of crude (S)-tert-butyl 4-(2-(1-((2,6-diamino-5-cyanopyrimidin-4-yl)amino)ethyl)-4-oxo-3-phenyl-3,4-dihydroquinazolin-5-yl)-5,6-dihydropyridine-1(2H)-carboxylate (assumed 0.47 mmol) in dichloromethane (5 mL) was treated with trifluoroacetic acid (0.89 mL, 12 mmol). After stirring overnight, the mixture was concentrated to dryness under reduced pressure. The residue was purified on a Gilson HPLC system, eluting 5% acetonitrile/95% water (0.1% TFA modifier in both solvents) to 70% acetonitrile over 30 minutes. Fractions were concentrated to furnish (S)-2,4-diamino-6-((1-(4-oxo-3-phenyl-5-(1,2,3,6-tetrahydropyridin-4-yl)-3,4-dihydroquinazolin-2-yl)ethyl)amino)pyrimidine-5-carbonitrile, trifluoroacetic acid salt (Compound 93). $^1$H NMR (400 MHz, DMSO-d$_6$) δ 8.90 (s, 2H), 7.90 (dd, J=8.2, 7.3 Hz, 1H), 7.75 (dd, J=8.3, 1.2 Hz, 1H), 7.65 (bs, 2H), 7.59-7.49 (m, 5H), 7.47 (m, 1H), 7.23 (dd, J=7.4, 1.3 Hz, 1H), 7.19 (bs, 2H), 5.49 (s, 1H), 4.92 (m, 1H), 3.72 (m, 2H), 3.27 (m, 2H), 2.47 (m, 2H), 1.39 (d, J=6.6 Hz, 3H), ES/MS 480.2 (M+H$^+$).

Example 11. Preparation of a Compound of Formula (I)

A. Preparation of a Compound of Formula (I) in which n is 1, $R^1$ is Cl, m is 0, $R^3$ is methyl, $R^4$ is cyano, $R^5$ is hydrogen, $R^6$ is $NH_2$, and $R^7$ is F (106)

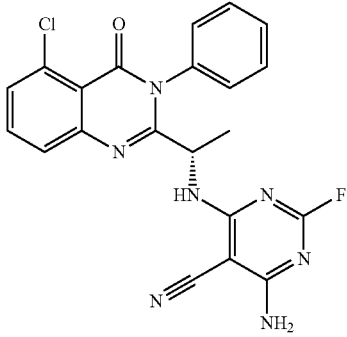

To (S)-4-amino-6-((1-(5-chloro-4-oxo-3-phenyl-3,4-dihydroquinazolin-2-yl)ethyl)amino)-2-(methylthio)pyrimidine-5-carbonitrile (0.98 g) and sodium bicarbonate (1.6 g, 1.9 mmol) in THF (10 mL) was added potassium peroxymonosulfate (0.91 g, 1 mmol) in water (10 mL) dropwise. When the reaction is complete, water and methylene chloride are added. The layers are separated and the solvent was removed in vacuo to give 4-amino-6-(((S)-1-(5-chloro-4-oxo-3-phenyl-3,4-dihydroquinazolin-2-yl)ethyl)amino)-2-(methylsulfinyl)pyrimidine-5-carbonitrile. To 4-amino-6-(((S)-1-(5-chloro-4-oxo-3-phenyl-3,4-dihydroquinazolin-2-yl)ethyl)amino)-2-(methylsulfinyl)pyrimidine-5-carbonitrile in THF (5 mL) was added tetrabutylammonium fluoride in THF (1 M THF, 46 mg, 0.19 mmol). After stirring for 24 h, a few drops of water were added, the reaction was filtered, the solvent was removed in vacuo, and the residue was purified on a Gilson HPLC system, eluting with acetonitrile/water (0.1% TFA modifier). Fractions were concentrated to furnish (S)-4-amino-6-((1-(5-chloro-4-oxo-3-phenyl-3,4-dihydroquinazolin-2-yl)ethyl)amino)-2-fluoropyrimidine-5-carbonitrile Compound 106).

Example 12. Preparation of a Compound of Formula (I)

A. Preparation of a Compound of Formula (I) in which n is 1, $R^1$ is Cl, m is 0, $R^3$ and $R^5$ together are 4-(2-aminoacetamido)pyrrolidine-1-yl attached at the 2-position of the pyrrolidine to the quinazolinone, $R^4$ is cyano, $R^6$ is $NH_2$, and $R^7$ is $NH_2$ (115)

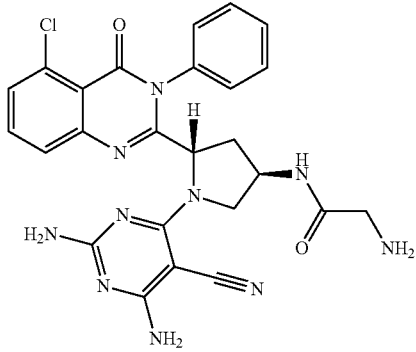

Solid $K_2CO_3$ (39 mg, 0.28 mmol) was added to stirring solution of N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2,2,2-trifluoroacetamide (160 mg, 0.28 mmol) in MeOH/Water (2:1, 15 mL) at rt. After stirring overnight the resulting mixture was concentrated then purified on a silica column to give 2,4-diamino-6-((2S,4R)-4-amino-2-(5-chloro-4-oxo-3-phenyl-3,4-dihydroquinazolin-2-yl)pyrrolidin-1-yl)pyrimidine-5-carbonitrile. HATU (60 mg, 0.16 mmol), DMAP (1 mg, 0.01 mmol), and DIEA (0.028 mL, 0.16 mmol) were added to a stirring solution of N-Boc glycine (18 mg, 0.16 mmol) in NMP (2 mL) at rt. After 5 min 2,4-diamino-6-((2S,4R)-4-amino-2-(5-chloro-4-oxo-3-phenyl-3,4-dihydroquinazolin-2-yl)pyrrolidin-4-yl)pyrimidine-5-carbonitrile (50 mg, 0.11 mmol) was added, and stirred for an additional 15 min. The resulting mixture was loaded directly on to silica column and purified to give tert-butyl (2-(((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2-oxoethyl)carbamate. TFA (2 mL) was added to a stirring solution of tert-butyl (2-(((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2-oxoethyl)carbamate (67 mg, 0.11 mmol) in DCM (2 mL) at rt. After 30 min the reaction mixture was concentrated and purified by HPLC to give 2-amino-N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)acetamide (Compound 115). $^1$H NMR (400 MHz, DMSO-$d_6$) δ 8.53 (d, J=7.2 Hz, 1H), 7.86 (d, J=24.0 Hz, 4H), 7.68 (t, J=8.0 Hz, 1H), 7.63-7.43 (m, 5H), 6.74 (m, 1H), 6.42 (m, 1H), 4.85-4.47 (m, 2H), 4.11-3.28 (m, 5H), 2.67-2.60 (m, 1H), 2.44-2.24 (m, 1H), 1.67 (s, 1H). ES/MS 531.1 (M+H$^+$).

B. Following the procedure described in Example 12 and Reaction Scheme I, below compound of formula (I) was prepared:

(116)

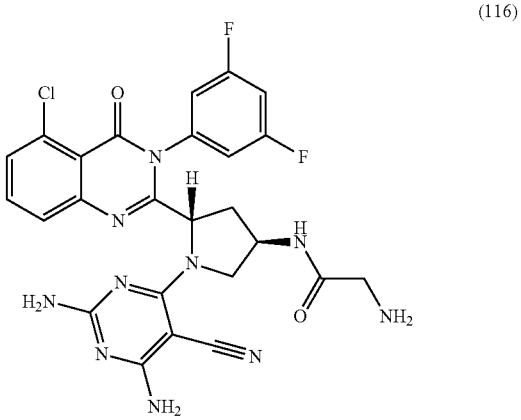 [SMILES: N#Cc1c(N)nc(N)nc1N1C[C@H](NC(=O)CN)C[C@H]1c1nc2cccc(Cl)c2c(=O)n1-c1cc(F)cc(F)c1]

2-amino-N-((3R,5S)-5-(5-chloro-3-(3,5-difluorophenyl)-4-oxo-3,4-dihydroquinazolin-2-yl)-1-(2,6-diamino-5-cyanopyrimidin-4-yl)pyrrolidin-3-yl)acetamide (Compound 116). 1H NMR (400 MHz, DMSO-$d_6$) δ 8.56 (d, J=7.3 Hz, 1H), 7.91 (s, 3H), 7.77 (d, J=9.0 Hz, 1H), 7.70 (t, J=8.0 Hz, 1H), 7.56-7.40 (m, 4H), 6.89-6.70 (m, 2H), 4.77-4.54 (m, 2H), 4.28-4.12 (m, 1H), 3.80-3.65 (m, 1H), 3.52-3.39 (m, 2H), 2.43-2.23 (m, 2H), 1.84-1.69 (m, 1H). ES/MS 567.1 (M+H$^+$).

Biological Examples

Activity testing was conducted in the Examples below using methods described herein and those well known in the art. Enzymatic activity of PI3K isoforms were measured to compare the PI3K isoform activity and selectivity of the compounds tested, including selectivity to PI3Kδ. A cellular assay measuring basophil activation was used to assess the potency of the compounds tested.

Enzymatic activity of the class I PI3K isoforms in the presence of certain compounds of the present application and compounds X and Y was measured using a time-resolved fluorescence resonance energy transfer (TR-FRET) assay. Compounds X and Y have the following structures:

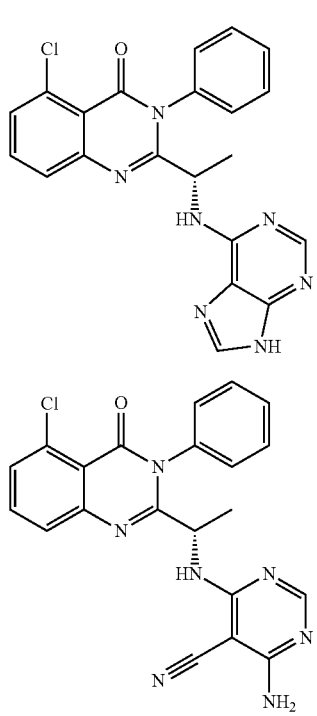

Compound X

Compound Y

TR-FRET monitored the formation of 3,4,5-inositol triphosphate molecule that competed with fluorescently labeled PIP3 for binding to the GRP-1 pleckstrin homology domain protein. An increase in phosphatidylinositide 3-phosphate product resulted in a decrease in TR-FRET signal as the labeled fluorophore was displaced from the GRP-1 protein binding site. Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2× Km ATP (75-500 μM), 2 μM PIP2, 5% glycerol 5 mM $MgCl_2$, 50 mM NaCl, 0.05% (v/v) Chaps, 1 mM dithiothreitol, and 1% (v/v) DMSO at the following concentrations for each isoform: PI3Kα, PI3Kβ, and PI3Kδ between 25 and 50 pM, and PI3Kγ at 2 nM. The compounds of Table 1, Compound X ((S)-2-(1-((9H-purin-6-yl)amino)ethyl)-5-chloro-3-phenylquinazolin-4(3H)-one) and Compound Y ((S)-4-amino-6-((1-(5-chloro-4-oxo-3-phenyl-3,4-dihydroquinazolin-2-yl)ethyl)amino)pyrimidine-5-carbonitrile), were added to the assay solution and incubated for 30 minutes at 25° C. Additionally, compounds 19 to 116 were added to the assay solution and incubated for 30 minutes at 25° C. The reactions were terminated with a final concentration of 10 mM EDTA, 10 nM labeled-PIP3, and 35 nM Europium labeled GRP-1 detector protein before reading TR-FRET on an Envision plate reader (Ex: 340 nm; Em: 615/665 nm; 100 μs delay and 500 μs read window).

The results were normalized based on positive (1 μM wortmanin) and negative (DMSO) controls, and the $IC_{50}$ values for PI3K α, β, δ, and γ were calculated from the fit of the dose-response curves to a four-parameter equation. These assays generally produced results within 3-fold of the reported mean.

Table 2 summarizes the $IC_{50}$ (nM) values for PI3K isoform δ ($IC_{50}$ for PI3K β, α, and γ are not shown). Table 3 summarizes the $IC_{50}$ (nM) values for PI3K isoform δ ($IC_{50}$ for PI3K β, α, and γ are not shown). The results indicate that certain compounds of present application inhibit PI3Kδ.

TABLE 2

The $IC_{50}$ values (nM) for PI3K isoform δ.

| Compound | $IC_{50}$ (nM) |
| --- | --- |
| 1a | 5 |
| 2a | 10 |
| 3a | 0.3 |
| 4a | 49 |
| 5a | 5 |
| 6a | 41 |
| 7a | 6 |
| 8a | 2 |
| 9a | 61 |
| 10a | 2 |
| 11a | 14 |
| 12a | 1 |
| 13a | 1 |
| 14a | 19 |
| 15a | 6 |
| 16a | 4 |
| 17a-1 | 6 |
| 17a-2 | 8 |
| 18a | 6 |
| X | 1 |
| Y | 0.4 |

TABLE 3

The $IC_{50}$ values (nM) for PI3K isoform δ.

| Compound | $IC_{50}$ (nM) |
| --- | --- |
| 19 | 9 |
| 20 | 21 |
| 21 | 30 |
| 22 | 22 |
| 23 | 10 |
| 24 | 10 |
| 25 | 36 |
| 26 | 21 |
| 27 | 57 |
| 28 | 2 |
| 29 | 220 |
| 30 | 6 |
| 31 | 4 |
| 32 | 85 |
| 33 | 24 |
| 34 | 46 |
| 35 | 7 |
| 36 | 2 |
| 37 | 0.5 |
| 38 | 0.5 |
| 39 | 2 |
| 40 | 4 |
| 41 | 25 |
| 42 | 20 |
| 43 | 9 |
| 44 | 15 |
| 45 | 0.7 |
| 46 | 0.4 |

TABLE 3-continued

The IC$_{50}$ values (nM) for PI3K isoform δ.

| Compound | IC$_{50}$ (nM) |
| --- | --- |
| 47 | 2 |
| 48 | 0.5 |
| 49 | 1.4 |
| 50 | 1.3 |
| 51 | 3 |
| 52 | 0.7 |
| 53 | 0.7 |
| 54 | 0.5 |
| 55 | 0.4 |
| 56 | 3 |
| 57 | 1.4 |
| 58 | 3 |
| 59 | 2 |
| 60 | 6 |
| 61 | 0.6 |
| 62 | 0.8 |
| 63 | 0.8 |
| 64 | 30 |
| 65 | 15 |
| 66 | 0.7 |
| 67 | 110 |
| 68 | 30 |
| 69 | 1 |
| 70 | 3 |
| 71 | 2 |
| 72 | 4 |
| 73 | 4 |
| 74 | 3 |
| 75 | 1.2 |
| 76 | 1.3 |
| 77 | 2 |
| 78 | 9 |
| 79 | 51 |
| 80 | 61 |
| 81 | 6 |
| 82 | 2 |
| 83 | 2 |
| 84 | 4 |
| 85 | 10 |
| 86 | 12 |
| 87 | 23 |
| 88 | 17 |
| 89 | 2 |
| 90 | 5 |
| 91 | 17 |
| 92 | 7 |
| 93 | 17 |
| 94 | 2 |
| 95 | 160 |
| 96 | 0.1 |
| 97 | 0.6 |
| 98 | 10 |
| 99 | 14 |
| 100 | 8400 |
| 101 | 1 |
| 102 | 30 |
| 103 | 9 |
| 104 | 4 |
| 105 | 2 |
| 106 | 0.8 |
| 107 | 0.4 |
| 108 | 2 |
| 109 | 0.7 |
| 110 | 2 |
| 111 | 9 |
| 112 | 17 |
| 113 | 7 |
| 114 | 0.9 |
| 115 | 64 |
| 116 | 7 |

All of the U.S. patents, U.S. patent application publications, U.S. patent applications, foreign patents, foreign patent applications and non-patent publications referred to in this specification are incorporated herein by reference, in their entirety to the extent not inconsistent with the present description. From the foregoing it will be appreciated that, although specific embodiments of the invention have been described herein for purposes of illustration, various modifications may be made without deviating from the spirit and scope of the present application.

What is claimed is:
1. A compound selected from the group consisting of:
    (S)-2-(cyclopropyl((2,6-diamino-5-cyanopyrimidin-4-yl)amino)methyl)-4-oxo-3-phenyl-3,4-dihydroquinazoline-5-carbonitrile;
    (S)-2-(cyclopropyl((2,6-diamino-5-cyanopyrimidin-4-yl)amino)methyl)-8-fluoro-4-oxo-3-phenyl-3,4-dihydroquinazoline-5-carbonitrile;
    (S)-2,4-diamino-6-(((5-chloro-4-oxo-3-phenyl-3,4-dihydroquinazolin-2-yl)(phenyl)methyl)amino)pyrimidine-5-carbonitrile;
    (S)-2-(cyclopropyl((2,6-diamino-5-cyanopyrimidin-4-yl)amino)methyl)-3-(3-(difluoromethyl)-5-fluorophenyl)-4-oxo-3,4-dihydroquinazoline-5-carbonitrile;
    (S)-2,4-diamino-6-((cyclopropyl(3-(3-fluorophenyl)-5-(methylsulfonyl)-4-oxo-3,4-dihydroquinazolin-2-yl)methyl)amino)pyrimidine-5-carbonitrile;
    (S)-2,4-diamino-6-((cyclopropyl(3-(2-fluorophenyl)-5-(methylsulfonyl)-4-oxo-3,4-dihydroquinazolin-2-yl)methyl)amino)pyrimidine-5-carbonitrile;
    (S)-2,4-diamino-6-((cyclopropyl(3-(2-fluorophenyl)-5-(methylsulfonyl)-4-oxo-3,4-dihydroquinazolin-2-yl)methyl)amino)pyrimidine-5-carbonitrile;
    (S)-2,4-diamino-6-((cyclopropyl(3-(2,6-difluorophenyl)-5-(methylsulfonyl)-4-oxo-3,4-dihydroquinazolin-2-yl)methyl)amino)pyrimidine-5-carbonitrile;
    (S)-2-(cyclopropyl((2,6-diamino-5-cyanopyrimidin-4-yl)amino)methyl)-6-fluoro-3-(3-fluorophenyl)-4-oxo-3,4-dihydroquinazoline-8-carbonitrile;
    (S)-2-(cyclopropyl((2,6-diamino-5-cyanopyrimidin-4-yl)amino)methyl)-6-fluoro-4-oxo-3-phenyl-3,4-dihydroquinazoline-8-carbonitrile;
    (S)-3-(5-chloro-3-(3,5-difluorophenyl)-4-oxo-3,4-dihydroquinazolin-2-yl)-3-((2,6-diamino-5-cyanopyrimidin-4-yl)amino)-N,N-dimethylpropanamide
    (S)-3-(5-chloro-4-oxo-3-phenyl-3,4-dihydroquinazolin-2-yl)-3-((2,6-diamino-5-cyanopyrimidin-4-yl)amino)-N,N-dimethylpropanamide;
    (S)-2,4-diamino-6-(((3-(3-cyano-5-fluorophenyl)-5-methyl-4-oxo-3,4-dihydroquinazolin-2-yl)(cyclopropyl)methyl)amino)pyrimidine-5-carbonitrile;
    (S)-2,4-diamino-6-((cyclopropyl(3-(3,5-difluorophenyl)-5-methyl-4-oxo-3,4-dihydroquinazolin-2-yl)methyl)amino)pyrimidine-5-carbonitrile;
    (S)-2,4-diamino-6-(((5-chloro-3-(3,5-difluorophenyl)-4-oxo-3,4-dihydroquinazolin-2-yl)(cyclopropyl)methyl)amino)pyrimidine-5-carbonitrile;
    (S)-2,4-diamino-6-((cyclopropyl(3-(3,5-difluorophenyl)-5-fluoro-4-oxo-3,4-dihydroquinazolin-2-yl)methyl)amino)pyrimidine-5-carbonitrile;
    (S)-2,4-diamino-6-((cyclopropyl(5-fluoro-3-(3-fluorophenyl)-4-oxo-3,4-dihydroquinazolin-2-yl)methyl)amino)pyrimidine-5-carbonitrile;
    (S)-2,4-diamino-6-((cyclopropyl(6-fluoro-3-(3-fluorophenyl)-4-oxo-3,4-dihydroquinazolin-2-yl)methyl)amino)pyrimidine-5-carbonitrile;
    (S)-2-(1-((5-acetyl-2,6-diaminopyrimidin-4-yl)amino)ethyl)-5-chloro-3-(3,5-difluorophenyl)quinazolin-4(3H)-one,

2,4-diamino-6-((2S)-2-(5-chloro-3-(3, 5-difluorophenyl)-4-oxo-3,4-dihydroquinazolin-2-yl)-4-methoxypyrrolidin-1-yl)pyrimidine-5-carbonitrile;

(S)-2-(1-((6-amino-5-bromo-2-methylpyrimidin-4-yl)amino)ethyl)-5-chloro-3-phenylquinazolin-4(3H)-one;

(S)-2-(1-((6-amino-5-bromo-2-methylpyrimidin-4-yl)amino)ethyl)-5-chloro-3-(3,5-difluorophenyl)quinazolin-4(3H)-one;

(S)-2,4-diamino-6-((1-(5-(2-morpholinoethoxy)-4-oxo-3-phenyl-3,4-dihydroquinazolin-2-yl)ethyl)amino)pyrimidine-5-carbonitrile;

(S)-2,4-diamino-6-((1-(5-(2-(azepan-1-yl)ethoxy)-4-oxo-3-phenyl-3,4-dihydroquinazolin-2-yl)ethyl)amino)pyrimidine-5-carbonitrile;

(S)-2,4-diamino-6-((1-(4-oxo-3-phenyl-5-(2-(pyrrolidin-1-yl)ethoxy)-3,4-dihydroquinazolin-2-yl)ethyl)amino)pyrimidine-5-carbonitrile;

(S)-isopropyl 2-((2-(1-((2,6-diamino-5-cyanopyrimidin-4-yl)amino)ethyl)-4-oxo-3-phenyl-3,4-dihydroquinazolin-5-yl)oxy)acetate;

(S)-2,4-diamino-6-((1-(4-oxo-5-(2-(2-oxopyrrolidin-1-yl)ethoxy)-3-phenyl-3,4-dihydroquinazolin-2-yl)ethyl)amino)pyrimidine-5-carbonitrile;

(S)-2,4-diamino-6-((1-(5-(2-(dimethylamino)ethoxy)-4-oxo-3-phenyl-3,4-dihydroquinazolin-2-yl)ethyl)amino)pyrimidine-5-carbonitrile;

(S)-2,4-diamino-6-((1-(4-oxo-5-(2-oxo-2-(piperidin-1-yl)ethoxy)-3-phenyl-3,4-dihydroquinazolin-2-yl)ethyl)amino)pyrimidine-5-carbonitrile;

(S)-2,4-diamino-6-((1-(5-(3-hydroxy-2-(hydroxymethyl)-2-methylpropoxy)-4-oxo-3-phenyl-3,4-dihydroquinazolin-2-yl)ethyl)amino)pyrimidine-5-carbonitrile;

(S)-2,4-diamino-6-((1-(4-oxo-3-phenyl-5-(2-(piperidin-1-yl)ethoxy)-3,4-dihydroquinazolin-2-yl)ethyl)amino)pyrimidine-5-carbonitrile;

(S)-2,4-diamino-6-((1-(4-oxo-3-phenyl-5-(2-(4-phenylpiperazin-1-yl)ethoxy)-3,4-dihydroquinazolin-2-yl)ethyl)amino)pyrimidine-5-carbonitrile;

(S)-2,4-diamino-6-((1-(5-(2-(2-methyl-1H-imidazol-1-yl)ethoxy)-4-oxo-3-phenyl-3,4-dihydroquinazolin-2-yl)ethyl)amino)pyrimidine-5-carbonitrile;

2,4-diamino-6-(((1 S)-1-(5-(2-(1-methylpyrrolidin-2-yl)ethoxy)-4-oxo-3-phenyl-3,4-dihydroquinazolin-2-yl)ethyl)amino)pyrimidine-5-carbonitrile;

(S)-2,4-diamino-6-((1-(5-((3-methyloxetan-3-yl)methoxy)-4-oxo-3-phenyl-3,4-dihydroquinazolin-2-yl)ethyl)amino)pyrimidine-5-carbonitrile;

(S)-2,4-diamino-6-((1-(5-(2-morpholino-2-oxoethoxy)-4-oxo-3-phenyl-3,4-dihydroquinazolin-2-yl)ethyl)amino)pyrimidine-5-carbonitrile;

(S)-2,4-diamino-6-((1-(5-(2-(4-methylpiperidin-1-yl)-2-oxoethoxy)-4-oxo-3-phenyl-3,4-dihydroquinazolin-2-yl)ethyl)amino)pyrimidine-5-carbonitrile;

(S)-3-(2-(1-((2,6-diamino-5-cyanopyrimidin-4-yl)amino)ethyl)-4-oxo-3-phenyl-3,4-dihydroquinazolin-5-yl)propanamide;

(S)-3-(2-(1-((2,6-diamino-5-cyanopyrimidin-4-yl)amino)ethyl)-8-fluoro-4-oxo-3-phenyl-3,4-dihydroquinazolin-5-yl)propanamide;

(S)-3-(2-(1-((2,6-diamino-5-cyanopyrimidin-4-yl)amino)ethyl)-3-(3,5-difluorophenyl)-8-fluoro-4-oxo-3,4-dihydroquinazolin-5-yl)propanamide;

(S)-3-(2-(1-((2,6-diamino-5-cyanopyrimidin-4-yl)amino)ethyl)-3-(3,5-difluorophenyl)-4-oxo-3,4-dihydroquinazolin-5-yl)propanamide;

(S)-3-(2-(1-((2,6-diamino-5-chloropyrimidin-4-yl)amino)ethyl)-3-(3,5-difluorophenyl)-8-fluoro-4-oxo-3,4-dihydroquinazolin-5-yl)propanamide;

(S)-3-(2-(1-((2,6-diamino-5-chloropyrimidin-4-yl)amino)ethyl)-3-(3,5-difluorophenyl)-4-oxo-3,4-dihydroquinazolin-5-yl)propanamide;

(S)-3-(2-(1-((2,6-diamino-5-chloropyrimidin-4-yl)amino)ethyl)-4-oxo-3-phenyl-3,4-dihydroquinazolin-5-yl)propanamide;

(S)-3-(2-(1-((2,6-diamino-5-chloropyrimidin-4-yl)amino)ethyl)-8-fluoro-4-oxo-3-phenyl-3,4-dihydroquinazolin-5-yl)propanamide;

(S)-2,4-diamino-6-((1-(4-oxo-3-phenyl-5-(3-(pyrrolidin-1-yl)propyl)-3,4-dihydroquinazolin-2-yl)ethyl)amino)pyrimidine-5-carbonitrile;

(S)-2,4-diamino-6-((1-(4-oxo-3-phenyl-5-(3-(piperidin-1-yl)propyl)-3,4-dihydroquinazolin-2-yl)ethyl)amino)pyrimidine-5-carbonitrile;

(S)-2,4-diamino-6-((1-(5-(3-(3,3-difluoropyrrolidin-1-yl)propyl)-4-oxo-3-phenyl-3,4-dihydroquinazolin-2-yl)ethyl)amino)pyrimidine-5-carbonitrile;

(S)-2,4-diamino-6-((1-(5-(3-(4,4-difluoropiperidin-1-yl)propyl)-4-oxo-3-phenyl-3,4-dihydroquinazolin-2-yl)ethyl)amino)pyrimidine-5-carbonitrile;

2,4-diamino-6-((((1S)-1-(5-(3-(3,5-dimethylmorpholino)propyl)-4-oxo-3-phenyl-3,4-dihydroquinazolin-2-yl)ethyl)amino)pyrimidine-5-carbonitrile;

(S)-2,4-diamino-6-((1-(8-fluoro-4-oxo-3-phenyl-5-(3-(pyrrolidin-1-yl)propyl)-3,4-dihydroquinazolin-2-yl)ethyl)amino)pyrimidine-5-carbonitrile;

(S)-2,4-diamino-6-((1-(3-(3,5-difluorophenyl)-4-oxo-5-(3-(pyrrolidin-1-yl)propyl)-3,4-dihydroquinazolin-2-yl)ethyl)amino)pyrimidine-5-carbonitrile;

(S)-2,4-diamino-6-((1-(5-(3-(2,2-dimethylmorpholino)propyl)-4-oxo-3-phenyl-3,4-dihydroquinazolin-2-yl)ethyl)amino)pyrimidine-5-carbonitrile;

(S)-2,4-diamino-6-((1-(5-(3-(3,3-dimethylmorpholino)propyl)-4-oxo-3-phenyl-3,4-dihydroquinazolin-2-yl)ethyl)amino)pyrimidine-5-carbonitrile;

(S)-2,4-diamino-6-((1-(4-oxo-3-phenyl-5-(3-(2,2,6,6-tetrafluoromorpholino)propyl)-3,4-dihydroquinazolin-2-yl)ethyl)amino)pyrimidine-5-carbonitrile;

(S)-2,4-diamino-6-((1-(5-(3-(3,3-difluoropyrrolidin-1-yl)propyl)-8-fluoro-4-oxo-3-phenyl-3,4-dihydroquinazolin-2-yl)ethyl)amino)pyrimidine-5-carbonitrile;

(S)-2,4-diamino-6-((cyclopropyl(4-oxo-3-phenyl-5-(3-(pyrrolidin-1-yl)propyl)-3,4-dihydroquinazolin-2-yl)methyl)amino)pyrimidine-5-carbonitrile;

(S)-2,4-diamino-6-((cyclopropyl(4-oxo-3-phenyl-5-(3-(piperidin-1-yl)propyl)-3,4-dihydroquinazolin-2-yl)methyl)amino)pyrimidine-5-carbonitrile;

(S)-2,4-diamino-6-((cyclopropyl(8-fluoro-4-oxo-3-phenyl-5-(3-(pyrrolidin-1-yl)propyl)-3,4-dihydroquinazolin-2-yl)methyl)amino)pyrimidine-5-carbonitrile;

(S)-2,4-diamino-6-((cyclopropyl(8-fluoro-4-oxo-3-phenyl-5-(3-(piperidin-1-yl)propyl)-3,4-dihydroquinazolin-2-yl)methyl)amino)pyrimidine-5-carbonitrile;

(S)-2-amino-4-chloro-6-((cyclopropyl(4-oxo-3-phenyl-5-(3-(pyrrolidin-1-yl)propyl)-3,4-dihydroquinazolin-2-yl)methyl)amino)pyrimidine-5-carbonitrile;

(S)-2,4-diamino-6-((1-(5-(3-morpholinopropyl)-4-oxo-3-phenyl-3,4-dihydroquinazolin-2-yl)ethyl)amino)pyrimidine-5-carbonitrile;

(S)-4-((1-(5-(3-(2-oxa-6-azaspiro[3.3]heptan-6-yl)propyl)-4-oxo-3-phenyl-3,4-dihydroquinazolin-2-yl)ethyl)amino)-2,6-diaminopyrimidine-5-carbonitrile;

(S)-4-((1-(5-(3-(2-oxa-6-azaspiro[3.4]octan-6-yl)propyl)-4-oxo-3-phenyl-3,4-dihydroquinazolin-2-yl)ethyl)amino)-2,6-diaminopyrimidine-5-carbonitrile;

(S)-4-((1-(5-(3-(2-oxa-7-azaspiro[3.5]nonan-7-yl)propyl)-4-oxo-3-phenyl-3,4-dihydroquinazolin-2-yl)ethyl)amino)-2,6-diaminopyrimidine-5-carbonitrile;

(S)-2,4-diamino-6-((1-(5-(3-cyclohexylpropyl)-4-oxo-3-phenyl-3,4-dihydroquinazolin-2-yl)ethyl)amino)pyrimidine-5-carbonitrile;

(S)-2-amino-4-chloro-6-((1-(5-chloro-8-fluoro-4-oxo-3-phenyl-3,4-dihydroquinazolin-2-yl)ethyl)amino)pyrimidine-5-carbonitrile;

(S)-2,4-diamino-6-(2-(5-chloro-3-(3,5-difluorophenyl)-4-oxo-3,4-dihydroquinazolin-2-yl)azetidin-1-yl)pyrimidine-5-carbonitrile;

(S)-2,4-diamino-6-(2-(5-chloro-4-oxo-3-phenyl-3,4-dihydroquinazolin-2-yl)azetidin-1-yl)pyrimidine-5-carbonitrile;

(S)-4-(2-(1-((2,6-diamino-5-cyanopyrimidin-4-yl)amino)ethyl)-4-oxo-3-phenyl-3,4-dihydroquinazolin-5-yl)butanoic acid;

(S)-4-(2-(1-(2,6-diamino-5-cyanopyrimidin-4-yl)pyrrolidin-2-yl)-4-oxo-3-phenyl-3,4-dihydroquinazolin-5-yl)butanoic acid;

(S)-4-(2-(1-((2,6-diamino-5-cyanopyrimidin-4-yl)amino)ethyl)-3-(3,5-difluorophenyl)-4-oxo-3,4-dihydroquinazolin-5-yl)butanoic acid;

(S)-2,4-diamino-6-(2-(3-(3-fluorophenyl)-5-(methylsulfonyl)-4-oxo-3,4-dihydroquinazolin-2-yl)pyrrolidin-1-yl)pyrimidine-5-carbonitrile;

(S)-2,4-diamino-6-(2-(3-(2-fluorophenyl)-5-(methylsulfonyl)-4-oxo-3,4-dihydroquinazolin-2-yl)pyrrolidin-1-yl)pyrimidine-5-carbonitrile;

(S)-2,4-diamino-6-(2-(3-(2-fluorophenyl)-5-(methylsulfonyl)-4-oxo-3,4-dihydroquinazolin-2-yl)pyrrolidin-1-yl)pyrimidine-5-carbonitrile;

(S)-2,4-diamino-6-(2-(3-(2,6-difluorophenyl)-5-(methylsulfonyl)-4-oxo-3,4-dihydroquinazolin-2-yl)pyrrolidin-1-yl)pyrimidine-5-carbonitrile;

(S)-2,4-diamino-6-((1-(3-(3-fluorophenyl)-4-oxo-5-(phenylsulfonyl)-3,4-dihydroquinazolin-2-yl)ethyl)amino)pyrimidine-5-carbonitrile;

(S)-2,4-diamino-6-(2-(3-(3-fluorophenyl)-5-(methylsulfonyl)-4-oxo-3,4-dihydroquinazolin-2-yl)pyrrolidin-1-yl)pyrimidine-5-carbonitrile;

(S)-2,4-diamino-6-((1-(3-(3-fluorophenyl)-5-((2-hydroxyethyl)sulfonyl)-4-oxo-3,4-dihydroquinazolin-2-yl)ethyl)amino)pyrimidine-5-carbonitrile;

(S)-2,4-diamino-6-((1-(3-(3-fluorophenyl)-5-((2-hydroxyethyl)thio)-4-oxo-3,4-dihydroquinazolin-2-yl)ethyl)amino)pyrimidine-5-carbonitrile;

(S)-2,4-diamino-6-((1-(5-(cyclopentylsulfonyl)-3-(3-fluorophenyl)-4-oxo-3,4-dihydroquinazolin-2-yl)ethyl)amino)pyrimidine-5-carbonitrile;

(S)-2,4-diamino-6-((1-(3-(3-fluorophenyl)-4-oxo-5-(o-tolylsulfonyl)-3,4-dihydroquinazolin-2-yl)ethyl)amino)pyrimidine-5-carbonitrile;

(S)-2,4-diamino-6-((1-(3-(3-fluorophenyl)-4-oxo-5-((2-(pyrrolidin-1-yl)ethyl)sulfonyl)-3,4-dihydroquinazolin-2-yl)ethyl)amino)pyrimidine-5-carbonitrile;

(S)-2,4-diamino-6-(2-(5-chloro-3-(3,5-difluorophenyl)-4-oxo-3,4-dihydroquinazolin-2-yl)pyrrolidin-1-yl)pyrimidine-5-carbonitrile;

(S)-2,4-diamino-6-(2-(5-chloro-3-(3,5-difluorophenyl)-8-methyl-4-oxo-3,4-dihydroquinazolin-2-yl)pyrrolidin-1-yl)pyrimidine-5-carbonitrile;

(S)-2,4-diamino-6-(2-(8-chloro-3-(3,5-difluorophenyl)-4-oxo-3,4-dihydroquinazolin-2-yl)pyrrolidin-1-yl)pyrimidine-5-carbonitrile;

(S)-2,4-diamino-6-(2-(3-(3,5-difluorophenyl)-8-methyl-4-oxo-3,4-dihydroquinazolin-2-yl)pyrrolidin-1-yl)pyrimidine-5-carbonitrile;

(S)-2,4-diamino-6-(2-(3-(3,5-difluorophenyl)-5-fluoro-4-oxo-3,4-dihydroquinazolin-2-yl)pyrrolidin-1-yl)pyrimidine-5-carbonitrile;

(S)-2,4-diamino-6-(2-(5-chloro-3-(3-cyano-5-fluorophenyl)-4-oxo-3,4-dihydroquinazolin-2-yl)pyrrolidin-1-yl)pyrimidine-5-carbonitrile;

(S)-2-(1-(2,6-diamino-5-cyanopyrimidin-4-yl)pyrrolidin-2-yl)-4-oxo-3-phenyl-3,4-dihydroquinazoline-8-carbonitrile;

(S)-2-(1-(2,6-diamino-5-cyanopyrimidin-4-yl)pyrrolidin-2-yl)-3-(3-(difluoromethyl)phenyl)-4-oxo-3,4-dihydroquinazoline-8-carbonitrile (S)-3-(5,8-dichloro-2-(1-(2,6-diamino-5-cyanopyrimidin-4-yl)pyrrolidin-2-yl)-4-oxoquinazolin-3(4H)-yl)benzenesulfonamide;

(S)-3-(5,8-dichloro-2-(1-(2,6-diamino-5-cyanopyrimidin-4-yl)pyrrolidin-2-yl)-4-oxoquinazolin-3(4H)-yl)benzenesulfonamide;

(S)-2,4-diamino-6-((1-(4-oxo-3-phenyl-5-(1,2,3,6-tetrahydropyridin-4-yl)-3,4-dihydroquinazolin-2-yl)ethyl)amino)pyrimidine-5-carbonitrile;

2,4-diamino-6-((2S,4R)-2-(5-chloro-4-oxo-3-phenyl-3,4-dihydroquinazolin-2-yl)-4-methylpyrrolidin-1-yl)pyrimidine-5-carbonitrile;

2,4-diamino-6-((2S,4R)-2-(5-chloro-3-(3,5-difluorophenyl)-4-oxo-3,4-dihydroquinazolin-2-yl)-4-fluoropyrrolidin-1-yl)pyrimidine-5-carbonitrile;

(S)-2-amino-4-((1-(5-chloro-4-oxo-3-phenyl-3,4-dihydroquinazolin-2-yl)ethyl)amino)-6-methylpyrimidine-5-carbonitrile;

(S)-2-(1-((2-amino-5-iodo-6-methylpyrimidin-4-yl)amino)ethyl)-5-chloro-3-phenylquinazolin-4(3H)-one;

(S)-4-amino-6-((1-(5-chloro-4-oxo-3-phenyl-3,4-dihydroquinazolin-2-yl)ethyl)amino)-2-methylpyrimidine-5-carbonitrile;

(S)-4-amino-6-((1-(5-chloro-3-(3,5-difluorophenyl)-4-oxo-3,4-dihydroquinazolin-2-yl)ethyl)amino)-2-methylpyrimidine-5-carbonitrile (R)-5-chloro-2-(4-(2,6-diamino-5-chloropyrimidin-4-yl)morpholin-3-yl)-3-phenylquinazolin-4(3H)-one (0);

(S)-2-amino-4-chloro-6-((1-(5-chloro-4-oxo-3-phenyl-3,4-dihydroquinazolin-2-yl)ethyl)amino)pyrimidine-5-carbonitrile;

(S)-2-amino-4-chloro-6-((1-(3-(3,5-difluorophenyl)-5-fluoro-4-oxo-3,4-dihydroquinazolin-2-yl)ethyl)amino)pyrimidine-5-carbonitrile;

(S)-2-amino-4-chloro-6-((1-(5-chloro-3-(3,5-difluorophenyl)-4-oxo-3,4-dihydroquinazolin-2-yl)propyl)amino)pyrimidine-5-carbonitrile;

(S)-4-amino-2-chloro-6-((1-(5-chloro-4-oxo-3-phenyl-3,4-dihydroquinazolin-2-yl)ethyl)amino)pyrimidine-5-carbonitrile;

(S)-2-amino-4-chloro-6-((1-(5-chloro-3-(3,5-difluorophenyl)-4-oxo-3,4-dihydroquinazolin-2-yl)ethyl)amino)pyrimidine-5-carbonitrile;

(S)-4-amino-6-((1-(5-chloro-4-oxo-3-phenyl-3,4-dihydroquinazolin-2-yl)ethyl)amino)-2-fluoropyrimidine-5-carbonitrile;

N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2,2-difluoroacetamide;

N-((3S,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2,2,2-trifluoroacetamide;

N-((3R,5S)-5-(5-chloro-3-(3,5-difluorophenyl)-4-oxo-3,4-dihydroquinazolin-2-yl)-1-(2,6-diamino-5-cyanopyrimidin-4-yl)pyrrolidin-3-yl)-2,2-difluoroacetamide;

N-((3R,5S)-5-(5-chloro-3-(3-(difluoromethyl)-5-fluorophenyl)-4-oxo-3,4-dihydroquinazolin-2-yl)-1-(2,6-diamino-5-cyanopyrimidin-4-yl)pyrrolidin-3-yl)-2,2-difluoroacetamide;

N-((3R,5S)-1-(2,6-diamino-5-cyanopyrimidin-4-yl)-5-(3-(3,5-difluorophenyl)-5-fluoro-4-oxo-3,4-dihydroquinazolin-2-yl)pyrrolidin-3-yl)-2,2-difluoroacetamide;

N-((3R,5S)-1-(2,6-diamino-5-cyanopyrimidin-4-yl)-5-(3-(3-(difluoromethyl)-5-fluorophenyl)-5-fluoro-4-oxo-3,4-dihydroquinazolin-2-yl)pyrrolidin-3-yl)-2,2-difluoroacetamide;

N-((3R,5S)-5-(5-chloro-3-(3,5-difluorophenyl)-4-oxo-3,4-dihydroquinazolin-2-yl)-1-(2,6-diamino-5-cyanopyrimidin-4-yl)pyrrolidin-3-yl)-2,2-difluoro-N-methylacetamide;

N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)-2-cyclopropylacetamide;

2-amino-N-((3R,5S)-5-(5-chloro-4-oxo-3-phenyl-3,4-dihydroquinazolin-2-yl)-1-(2,6-diamino-5-cyanopyrimidin-4-yl)pyrrolidin-3-yl)acetamide; and 2-amino-N-((3R,5S)-5-(5-chloro-3-(3,5-difluorophenyl)-4-oxo-3,4-dihydroquinazolin-2-yl)-1-(2,6-diamino-5-cyanopyrimidin-4-yl)pyrrolidin-3-yl)acetamide; or a pharmaceutically acceptable salt thereof.

2. A pharmaceutical composition comprising a compound of claim 1 or a pharmaceutically acceptable salt thereof, and at least one pharmaceutically acceptable vehicle.

* * * * *